US012564661B2

(12) United States Patent
Distefano et al.

(10) Patent No.: US 12,564,661 B2
(45) Date of Patent: Mar. 3, 2026

(54) APPROACH TO REPAIR TISSUE DEFECTS BY BONDING INJECTABLE GELS TO NATIVE SOFT TISSUES

(71) Applicant: Icahn School of Medicine at Mount Sinai, New York, NY (US)

(72) Inventors: Tyler J. Distefano, New York, NY (US); James C. Iatridis, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 895 days.

(21) Appl. No.: 17/772,994

(22) PCT Filed: Oct. 30, 2020

(86) PCT No.: PCT/US2020/058386
§ 371 (c)(1),
(2) Date: Apr. 28, 2022

(87) PCT Pub. No.: WO2021/087378
PCT Pub. Date: May 6, 2021

(65) Prior Publication Data
US 2023/0158210 A1 May 25, 2023

Related U.S. Application Data

(60) Provisional application No. 62/929,682, filed on Nov. 1, 2019.

(51) Int. Cl.
*A61L 27/52* (2006.01)
*A61L 27/26* (2006.01)

(52) U.S. Cl.
CPC ............... *A61L 27/52* (2013.01); *A61L 27/26* (2013.01); *A61L 2400/06* (2013.01); *A61L 2430/06* (2013.01); *A61L 2430/38* (2013.01)

(58) Field of Classification Search
None
See application file for complete search history.

(56) References Cited

U.S. PATENT DOCUMENTS

| 6,288,043 B1 | 9/2001 | Spiro | |
| 2005/0196377 A1 | 9/2005 | Ratcliffe et al. | |
| 2016/0022862 A1 | 1/2016 | Alsberg | |
| 2016/0324888 A1* | 11/2016 | Nicoll | A61L 27/52 |
| 2017/0000923 A1 | 1/2017 | Vernengo et al. | |
| 2019/0083276 A1 | 3/2019 | DiMauro | |
| 2019/0091367 A1* | 3/2019 | Li | A61K 9/7046 |

* cited by examiner

*Primary Examiner* — Dale R Miller

(57) ABSTRACT

Systems, methods, and kits are described for repairing a fibrocartilage defect in a subject. The fibrocartilage defect is contacted with a first composition containing an oxidized and methacrylated glycosaminoglycan to form an imine bond between the glycosaminoglycan and the fibrocartilage defect, thereby coating the fibrocartilage defect with the glycosaminoglycan. The fibrocartilage defect coated with the glycosaminoglycan is then contacted with a mixture of a pre-polymer hydrogel composition containing a first cross-linking unit that, when polymerized, is capable of bonding to methacrylate and a hydrogel polymerization initiator composition, thereby forming a hydrogel that is covalently bonded to the glycosaminoglycan through methacrylate.

16 Claims, 85 Drawing Sheets

Repaired IVD Motion Segment

▨ = Dual-modified Glycosaminoglycan (GAG)

▨ = Interpenetrating Network (IPN) Hydrogel

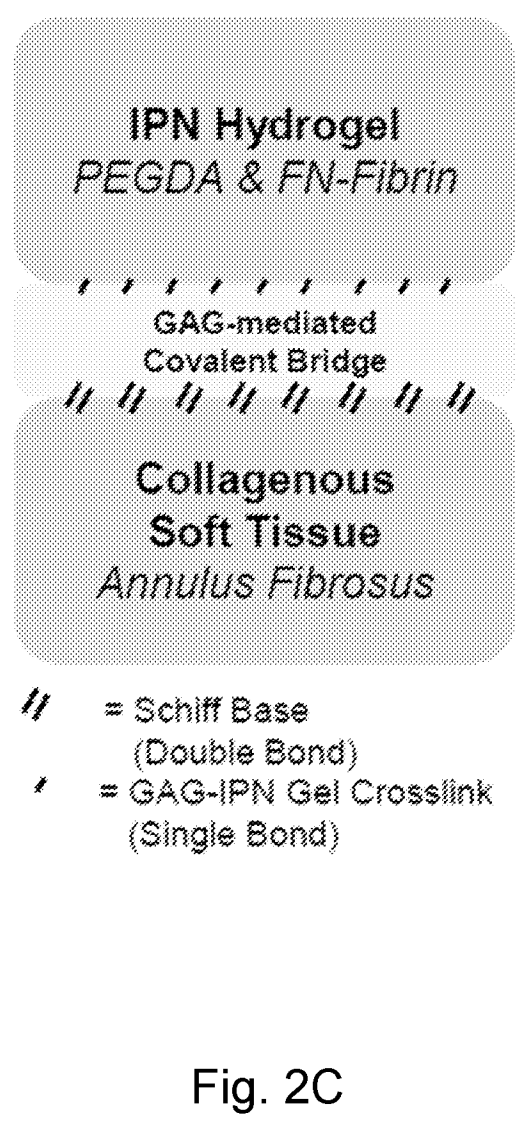

IPN Hydrogel
*PEGDA & FN-Fibrin*

GAG-mediated
Covalent Bridge

**Collagenous
Soft Tissue**
*Annulus Fibrosus*

// = Schiff Base
(Double Bond)

' = GAG-IPN Gel Crosslink
(Single Bond)

Fig. 2C

Chondroitin Sulfate Type A (CS)
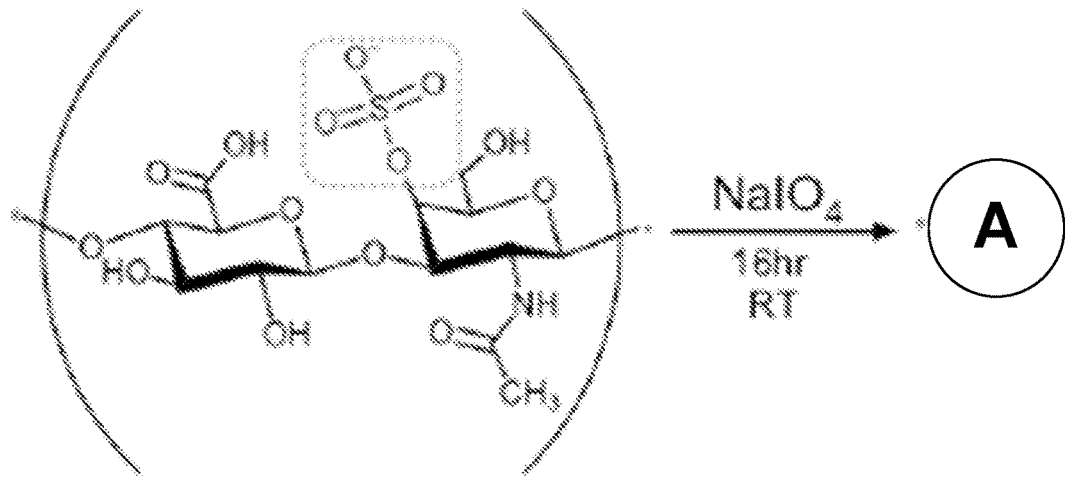
Hyaluronic Acid (HA)
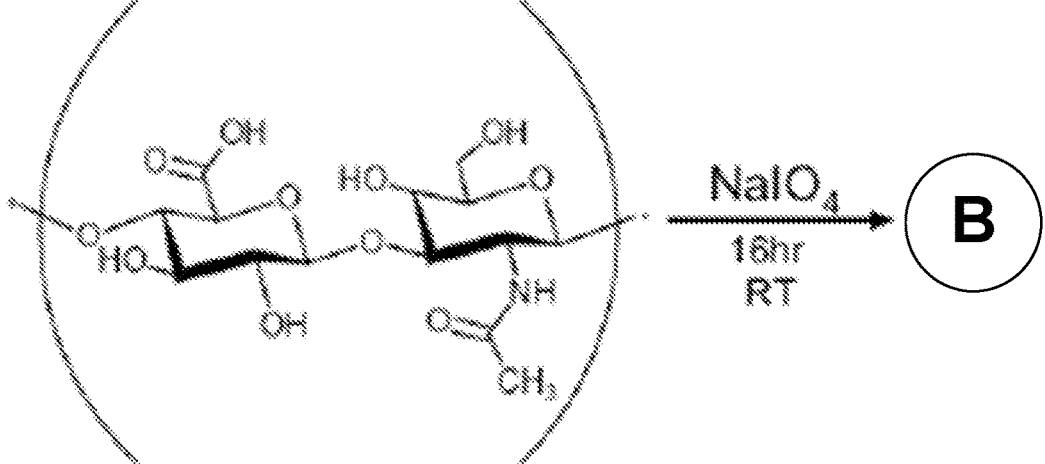
Fig. 3A

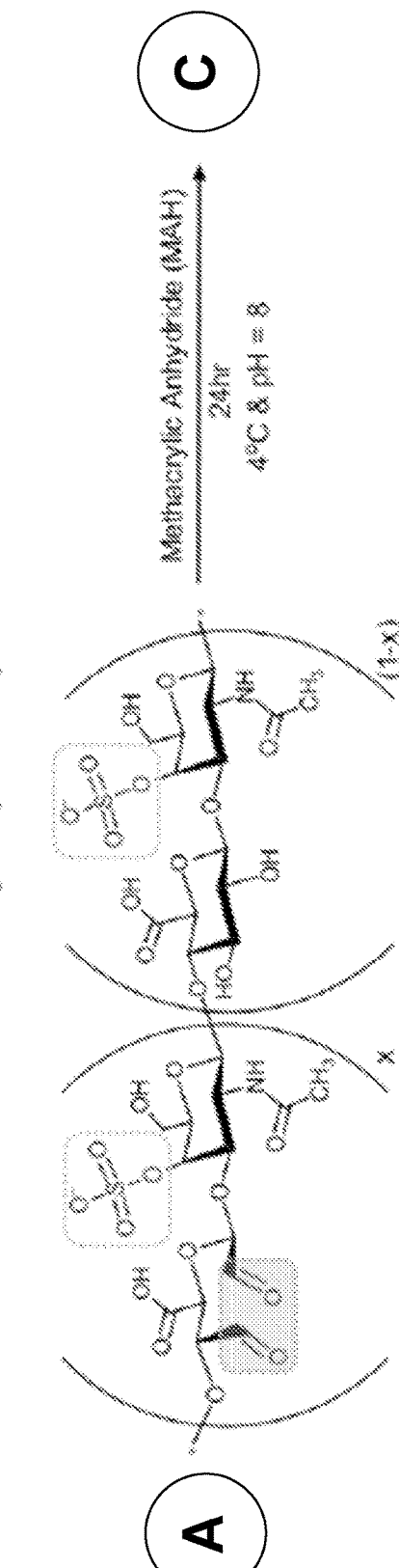
Chondroitin Sulfate Aldehyde (CS Ald)
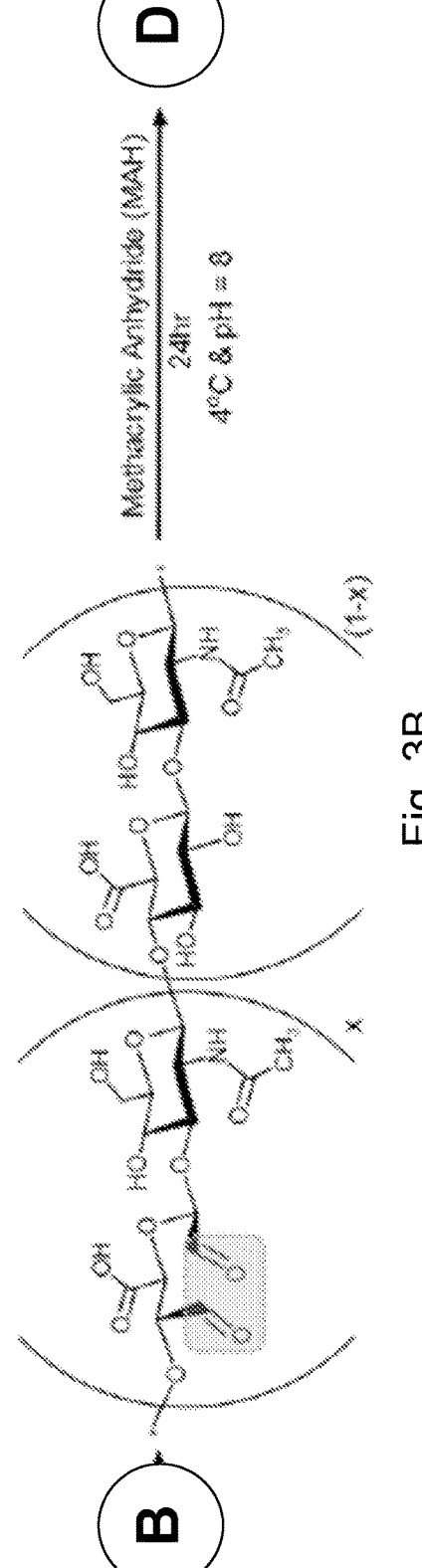
Hyaluronic Acid Aldehyde (HA Ald)
Fig. 3B

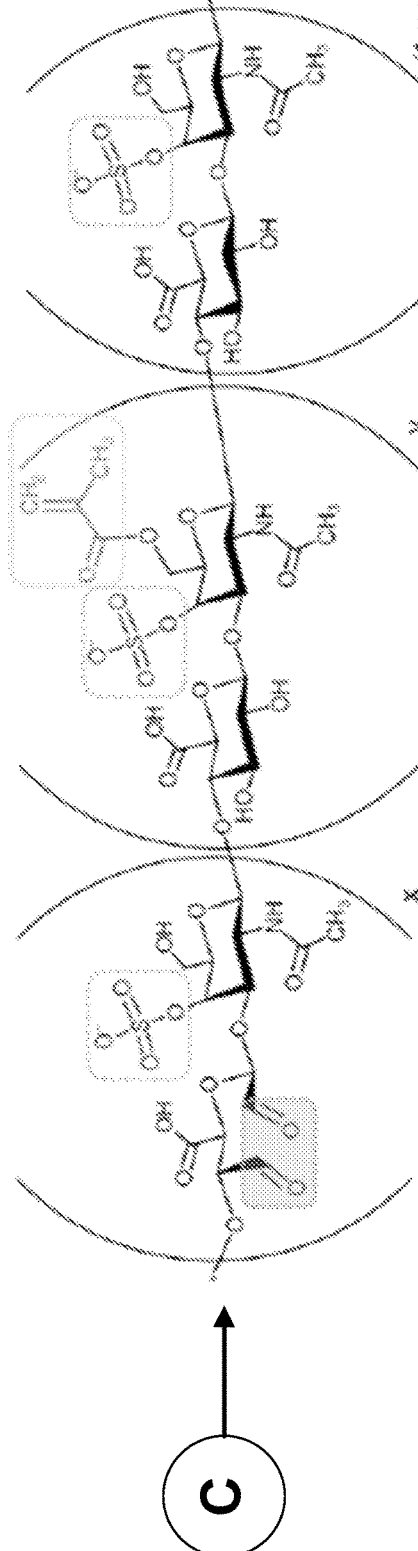
Chondroitin Sulfate Methacrylate Aldehyde (CSMA Ald)
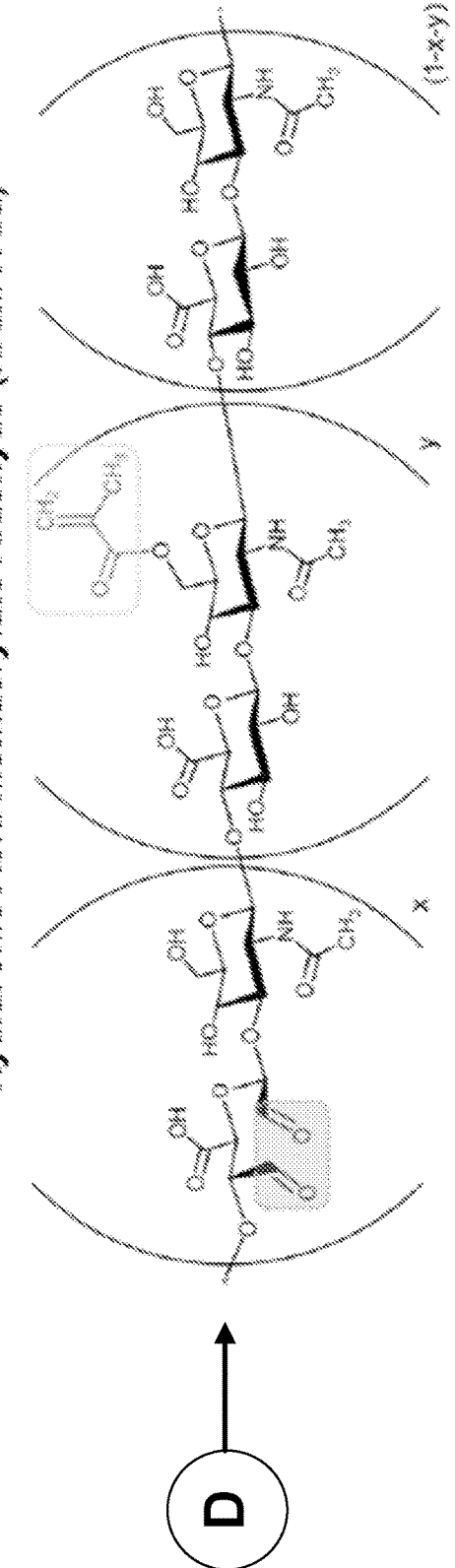
Hyaluronic Acid Methacrylate Aldehyde (HAMA Ald)
Fig. 3C Dual-modified Chondroitin Sulfate (CSMA Ald)

Hydrogel bonding modification

¹H NMR

| CS:MAH Molar Ratio | | |
|---|---|---|
| | 1:10 | 1:20 |
| | CSMA Aldehyde Formulation 1 | CSMA Aldehyde Formulation 2 |
| | CSMA Aldehyde Formulation 3 | CSMA Aldehyde Formulation 4 |

CS:IO₄ Molar Ratio

1:3.5 · 1:2.4

Collagen bonding modification

TNBS

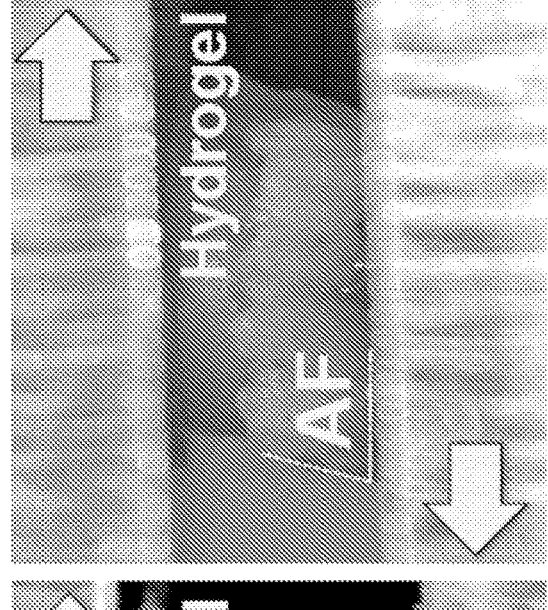
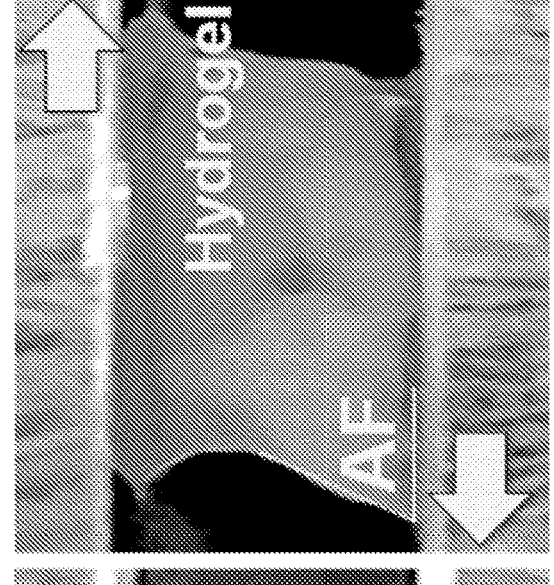
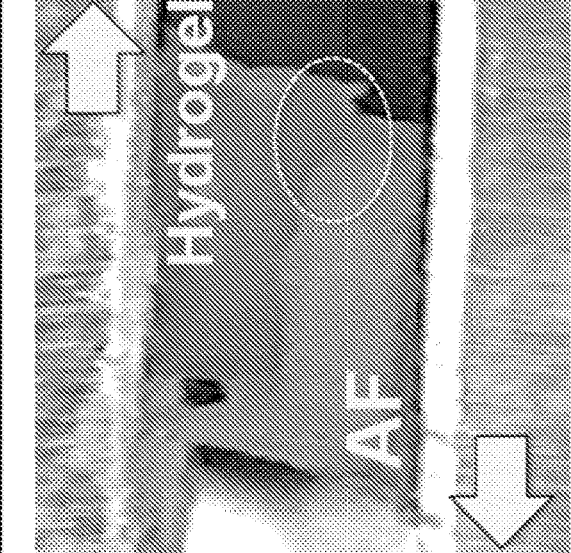
Fig. 9B

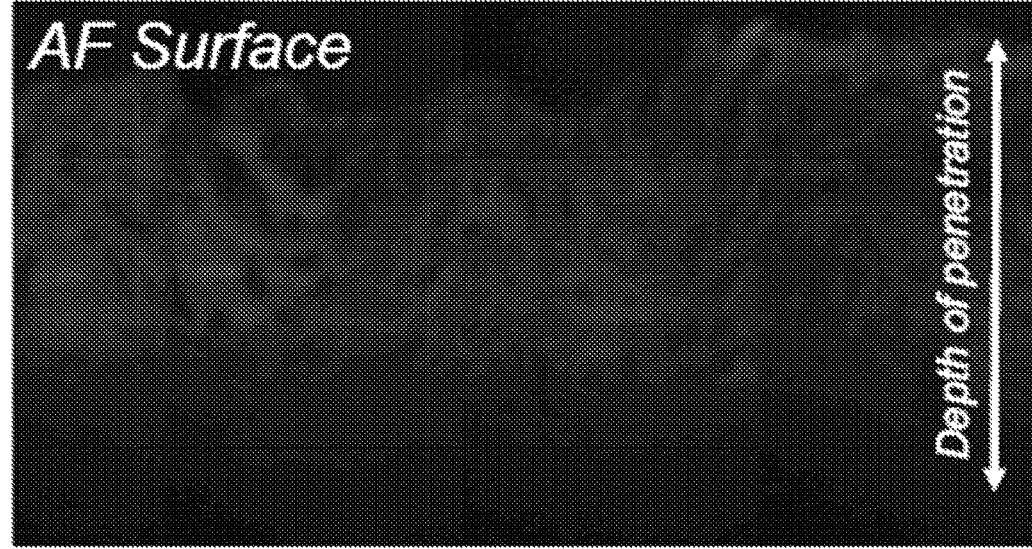
Fig. 12B

Merge
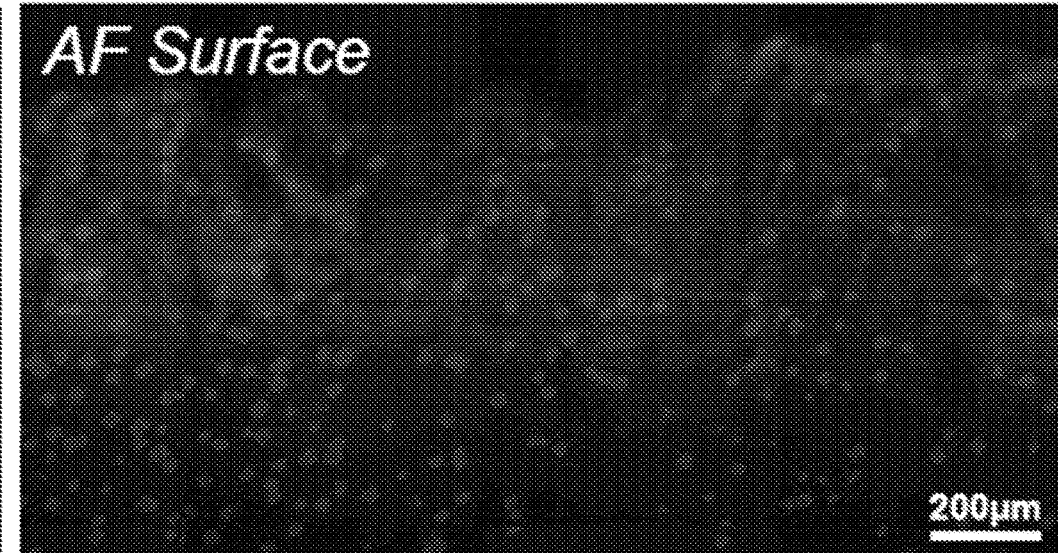
Fig. 12C

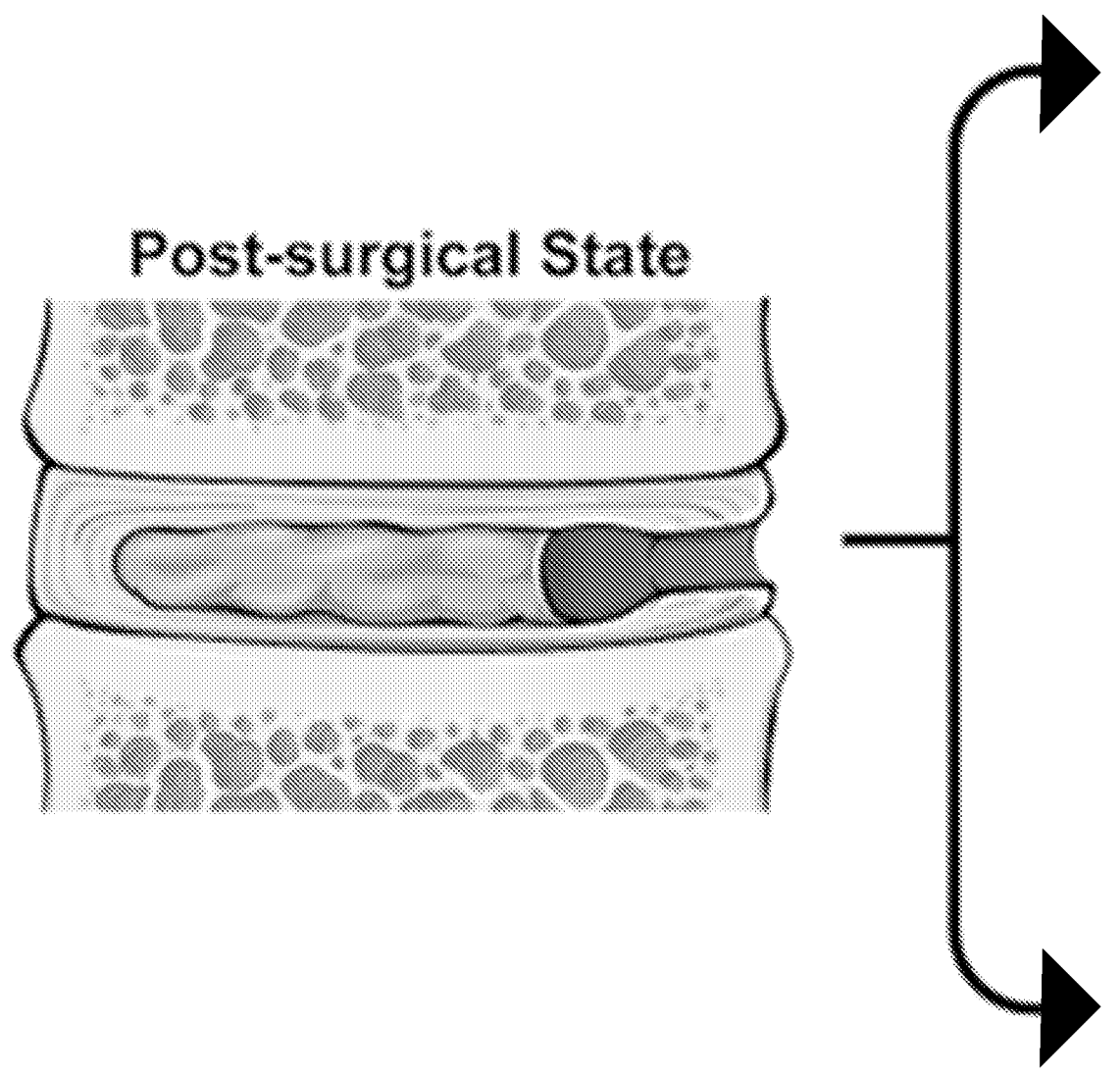
Fig. 15A1

Repaired IVD Motion Segment
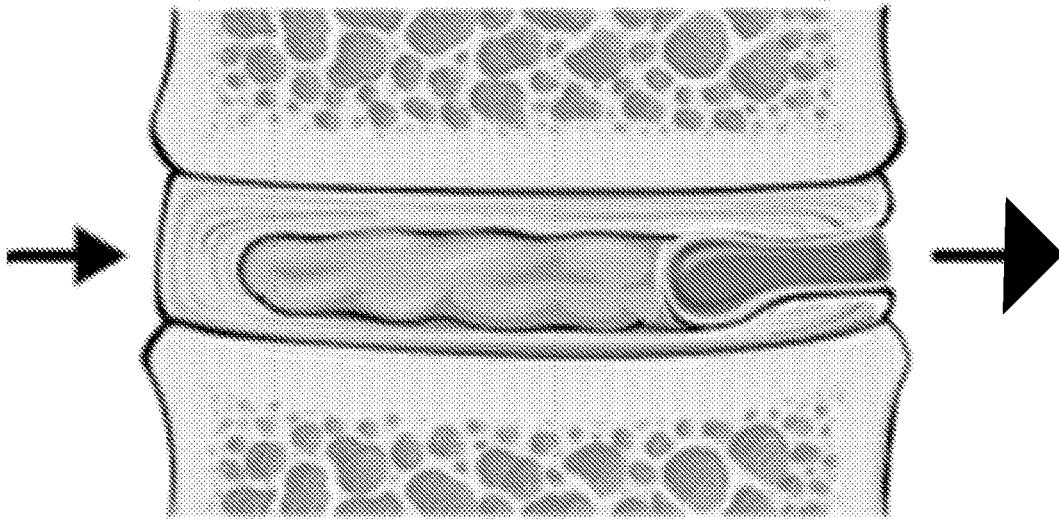
Dual-modified Glycosaminoglycan (GAG)
Interpenetrating Network (IPN) Hydrogel
Current standard of care
Unrepaired IVD Motion Segment
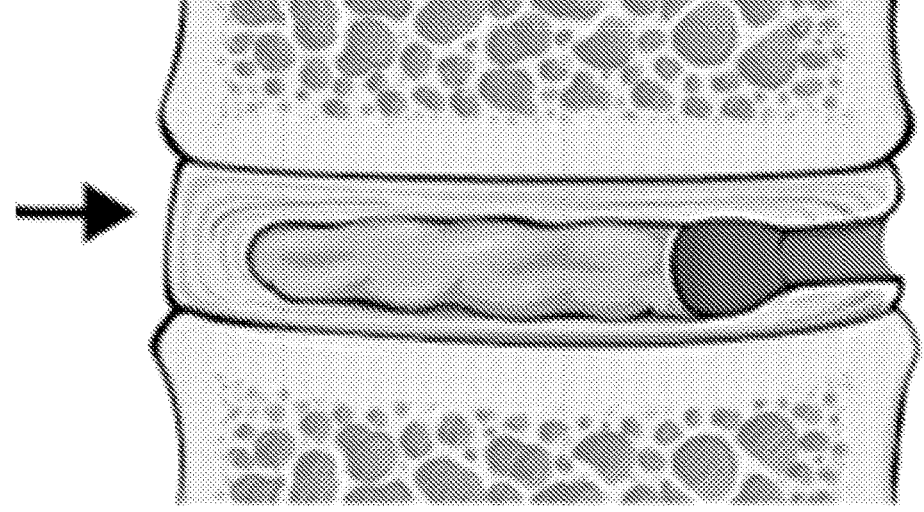
Fig. 15A2

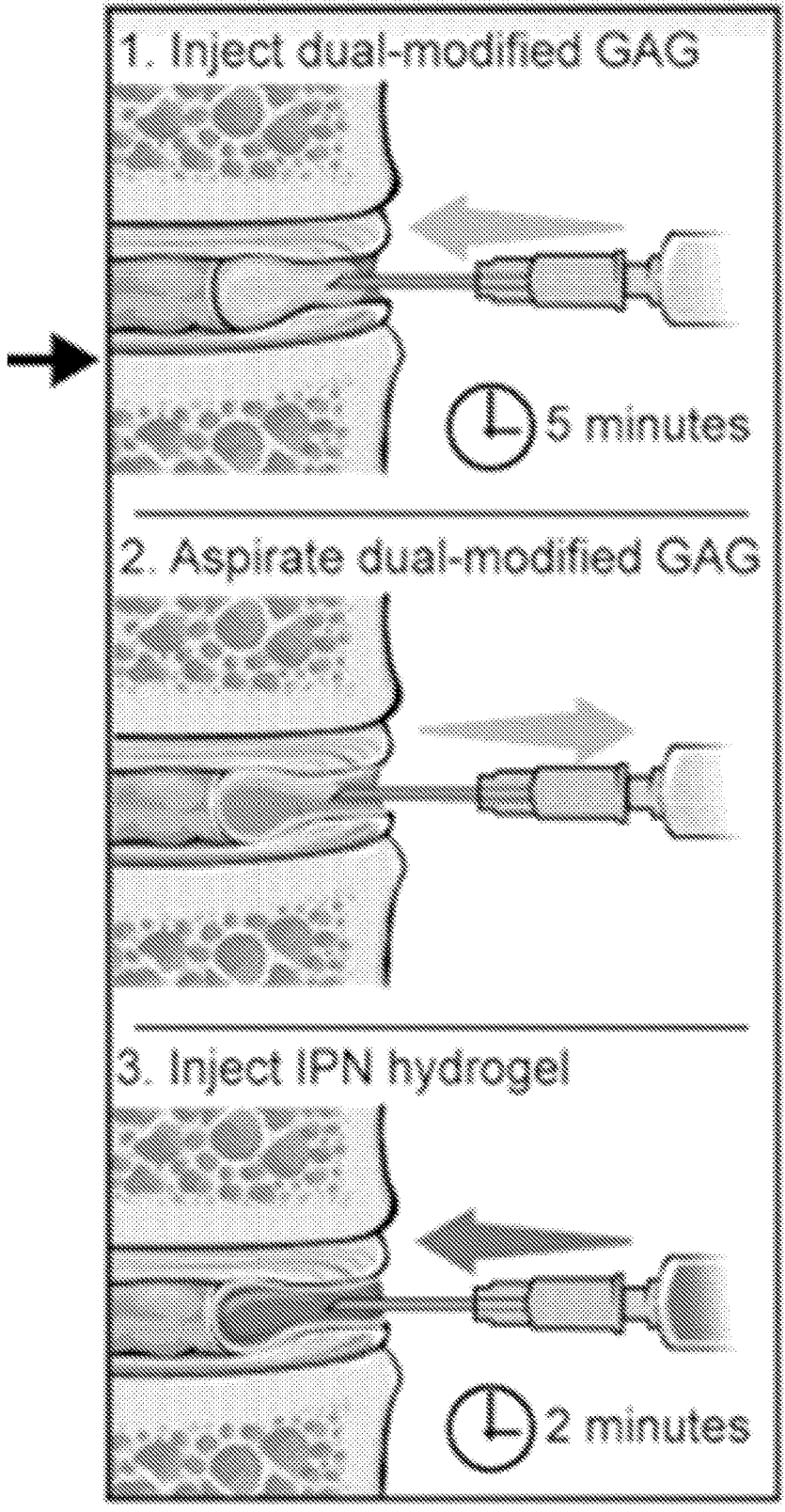
Fig. 15A3

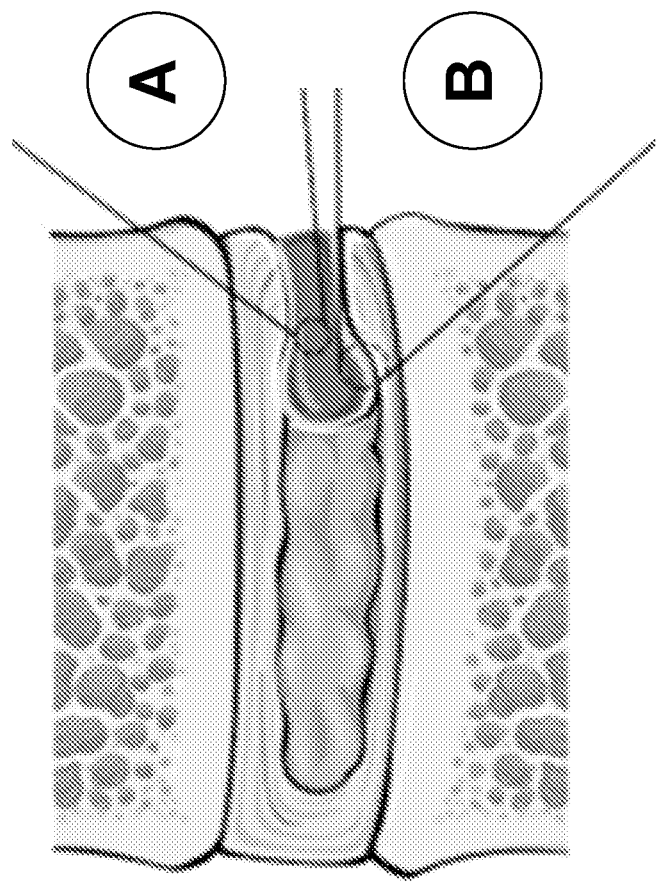
Fig. 15B1

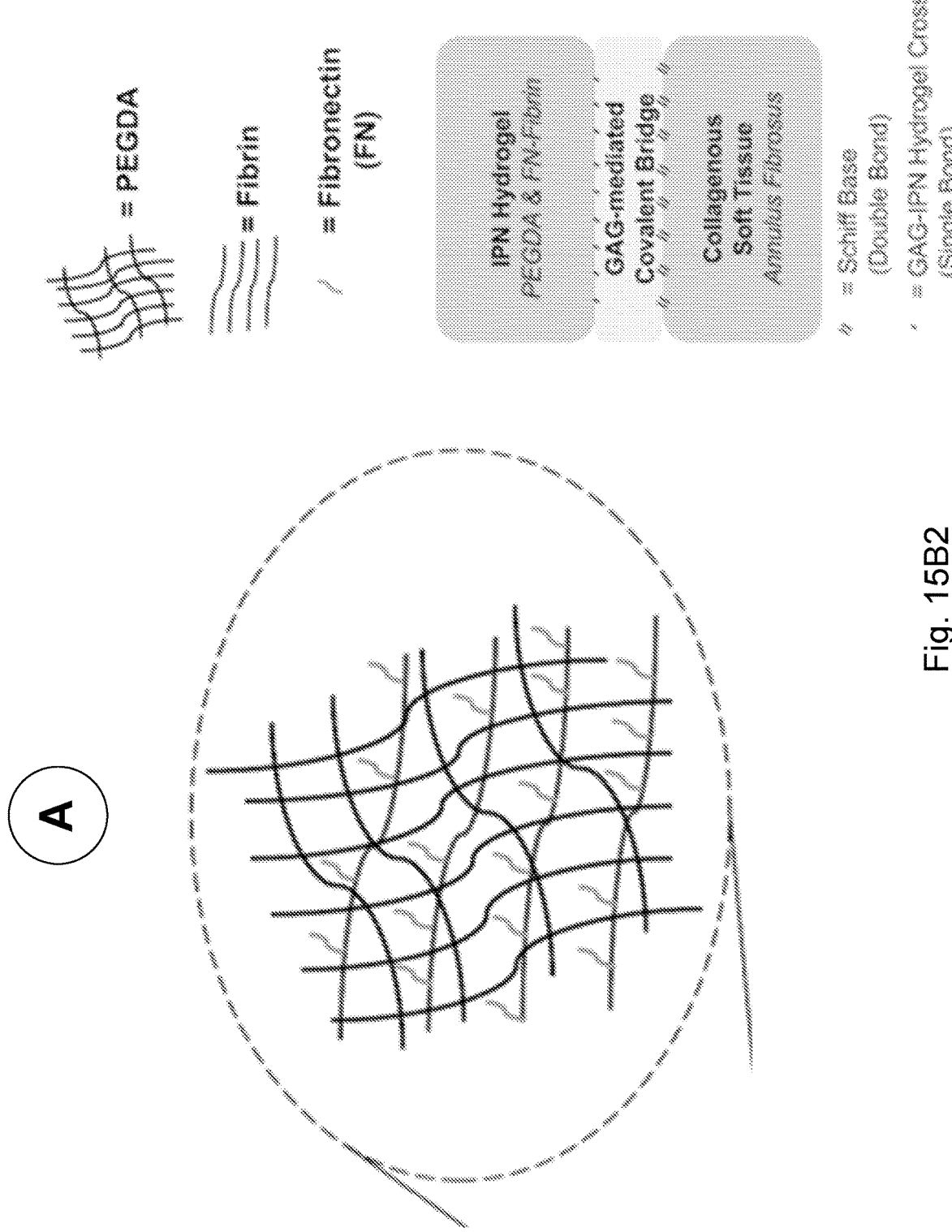
Fig. 15B2

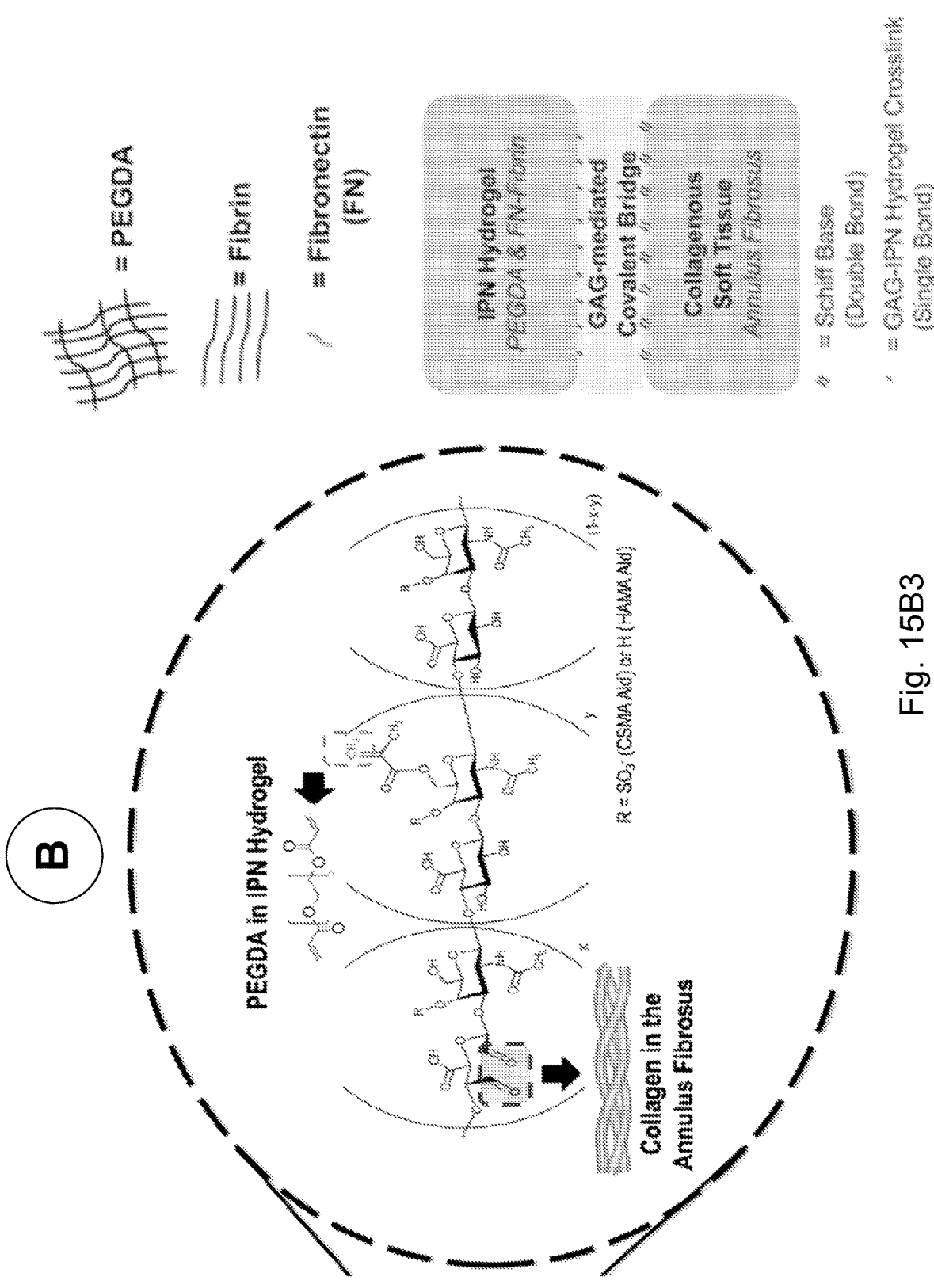
Fig. 15B3

Chondroitin Sulfate Type A (CS)
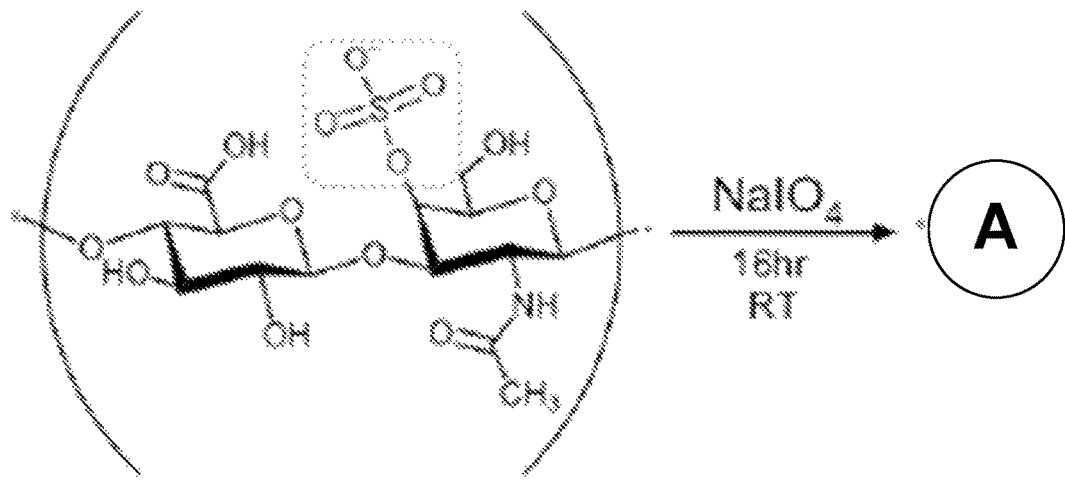
Hyaluronic Acid (HA)
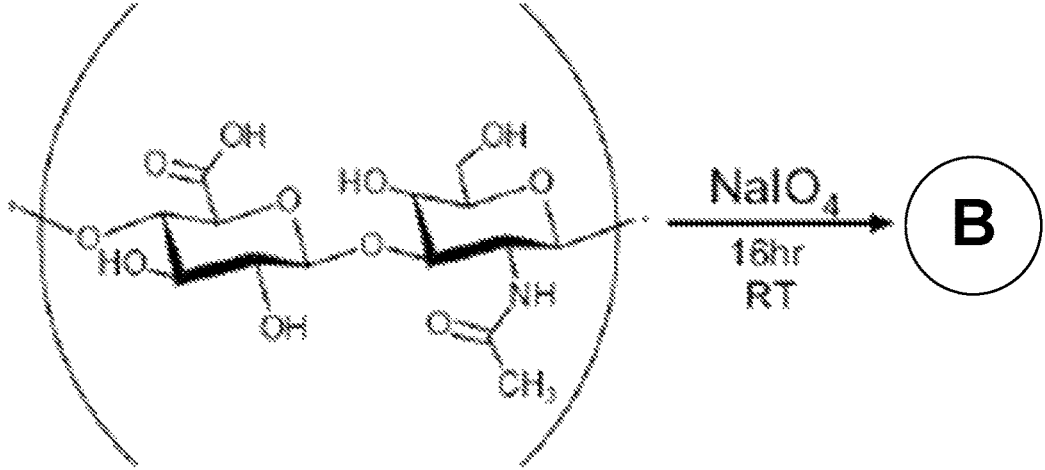
Fig. 16A1

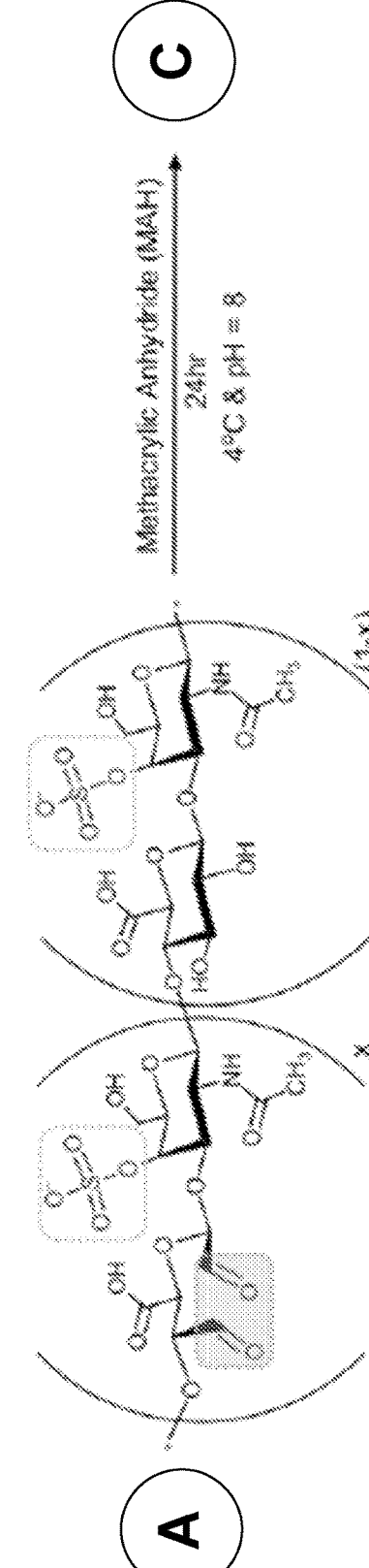
Chondroitin Sulfate Aldehyde (CS Ald)
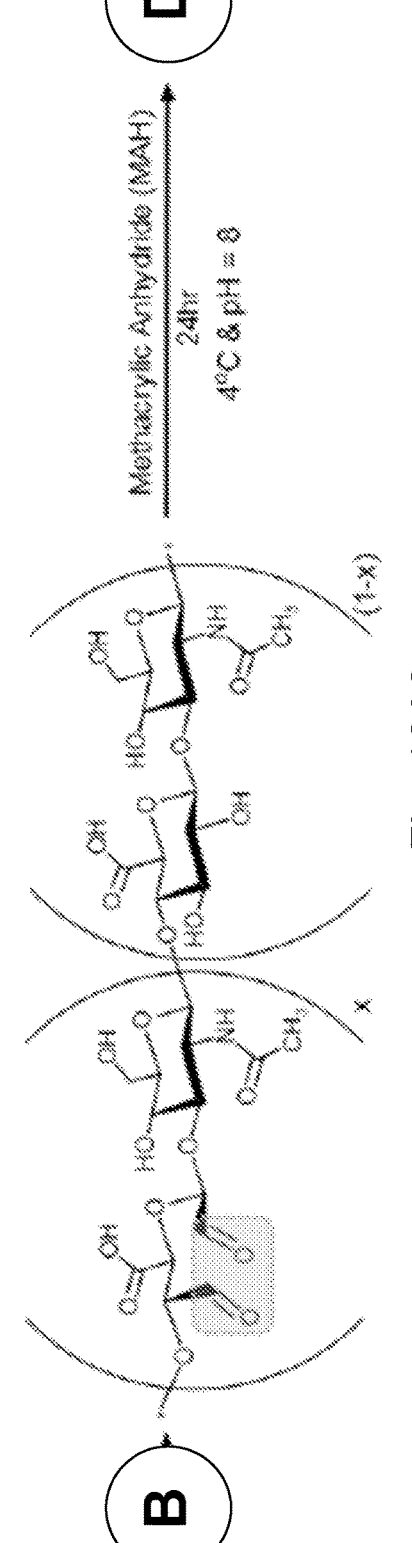
Hyaluronic Acid Aldehyde (HA Ald)
Fig. 16A2

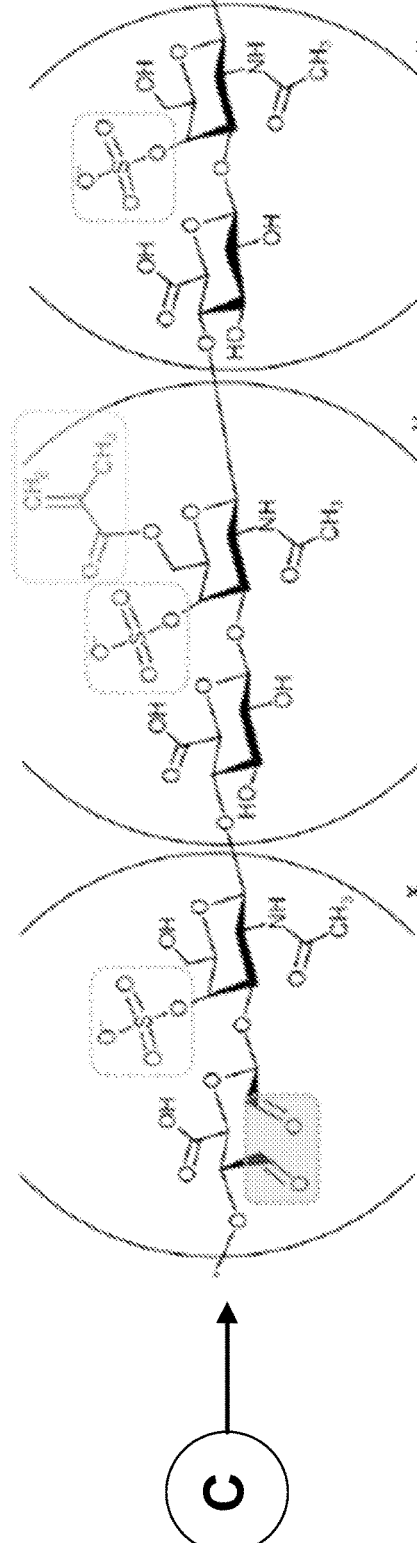
Chondroitin Sulfate Methacrylate Aldehyde (CSMA Ald)
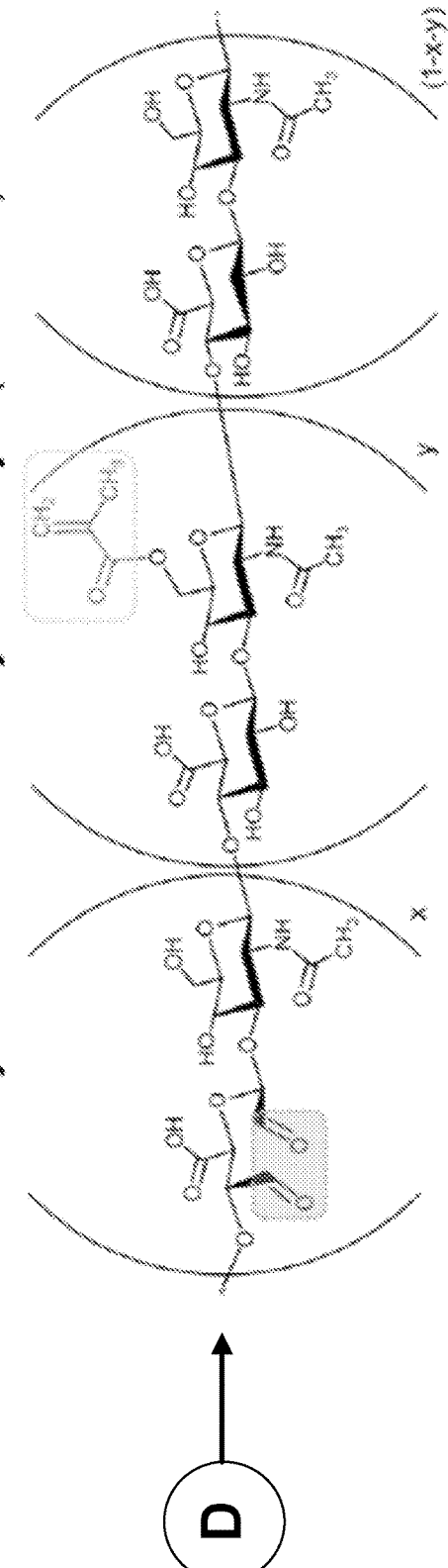
Hyaluronic Acid Methacrylate Aldehyde (HAMA Ald)
Fig. 16A3

HA:MAH Molar Ratio

| HA:IO₄ Molar Ratio | 1:10 | 1:20 |
|---|---|---|
| 1:3.5 | HAMA Aldehyde Formulation 1 | HAMA Aldehyde Formulation 2 |
| 1:2.4 | HAMA Aldehyde Formulation 3 | HAMA Aldehyde Formulation 4 |

CS:MAH Molar Ratio

| CS:IO₄ Molar Ratio | 1:10 | 1:20 |
|---|---|---|
| 1:3.5 | CSMA Aldehyde Formulation 1 | CSMA Aldehyde Formulation 2 |
| 1:2.4 | CSMA Aldehyde Formulation 3 | CSMA Aldehyde Formulation 4 |

Fig. 16B

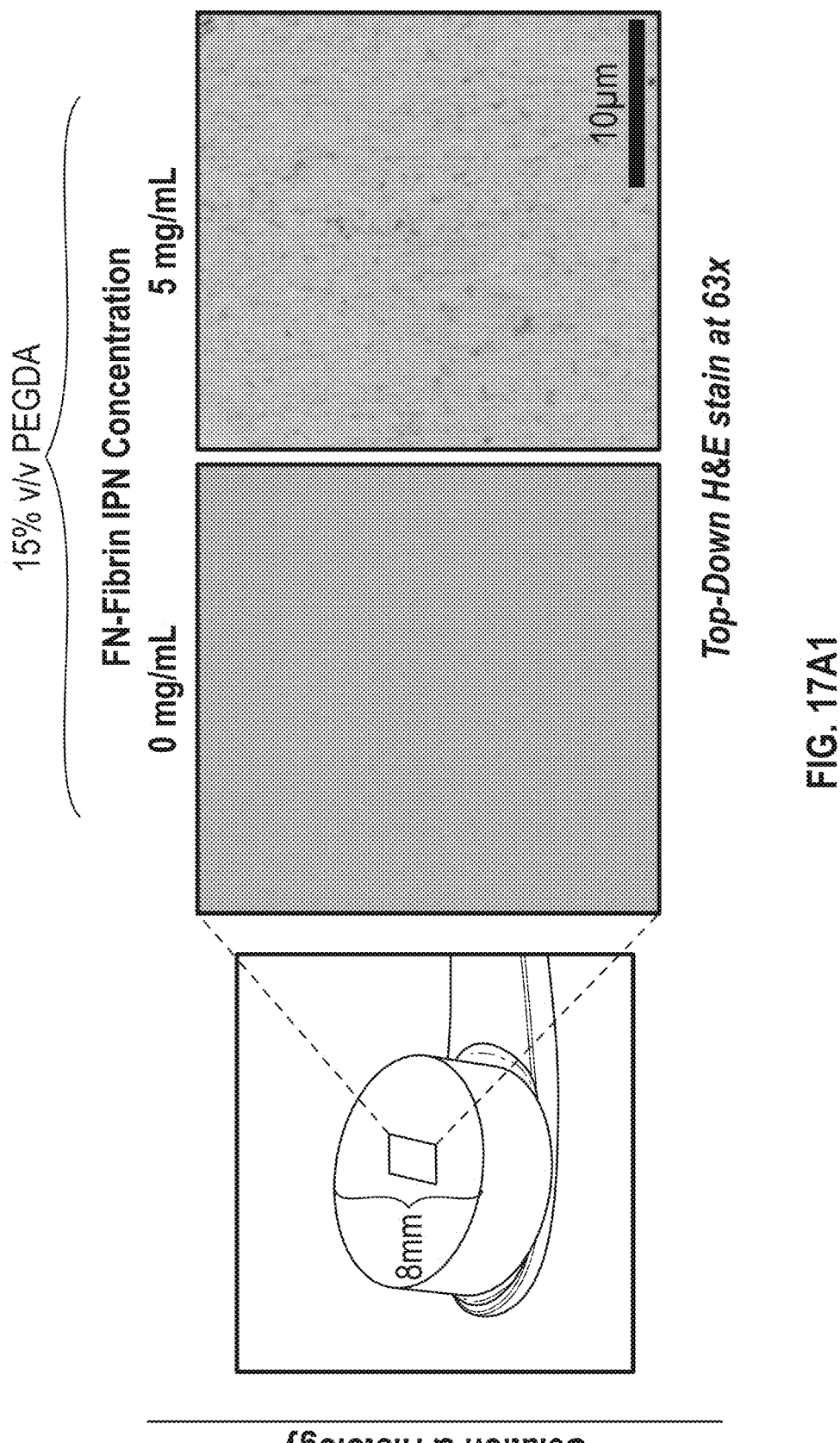
FIG. 17A1

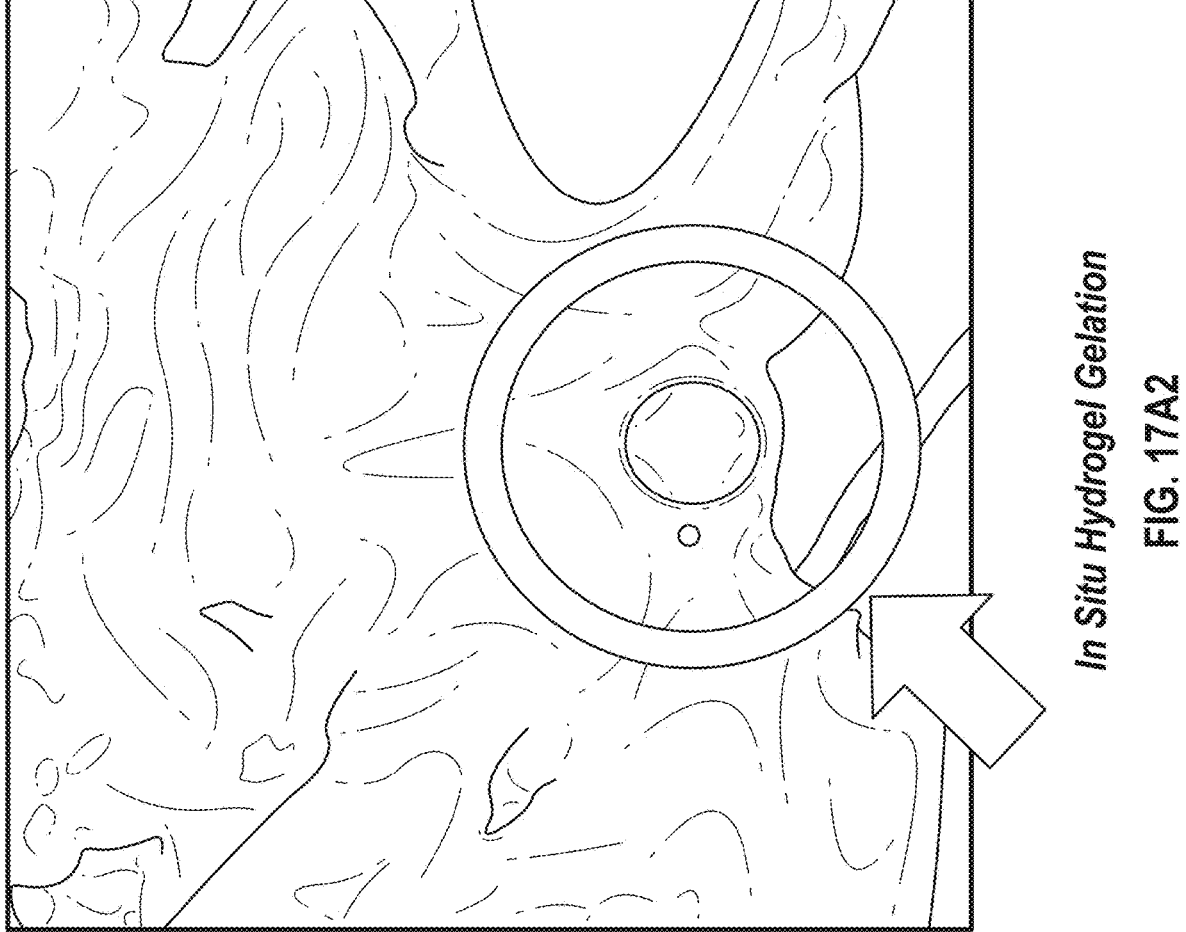
*In Situ Hydrogel Gelation*
FIG. 17A2

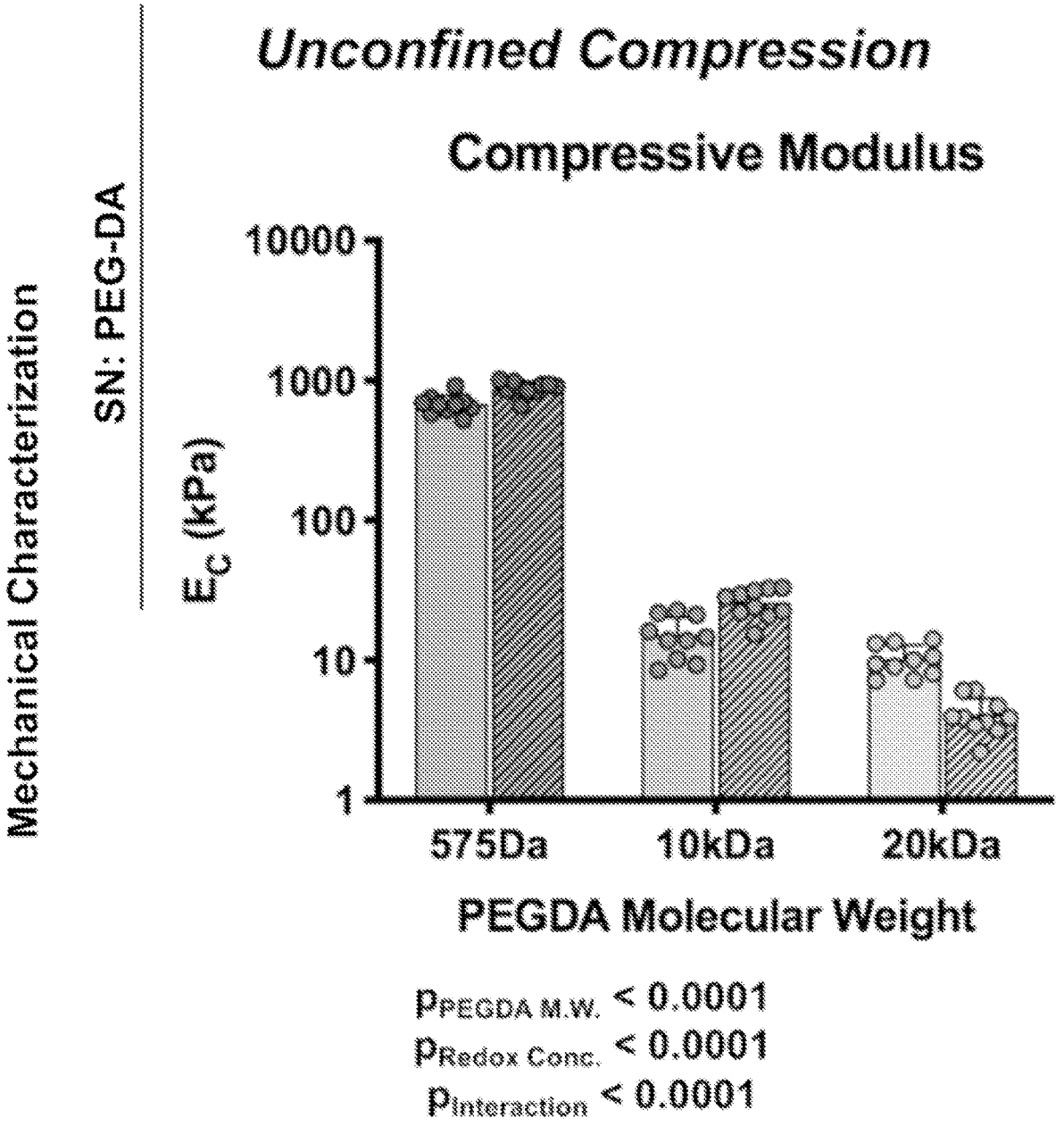
Fig. 17B1

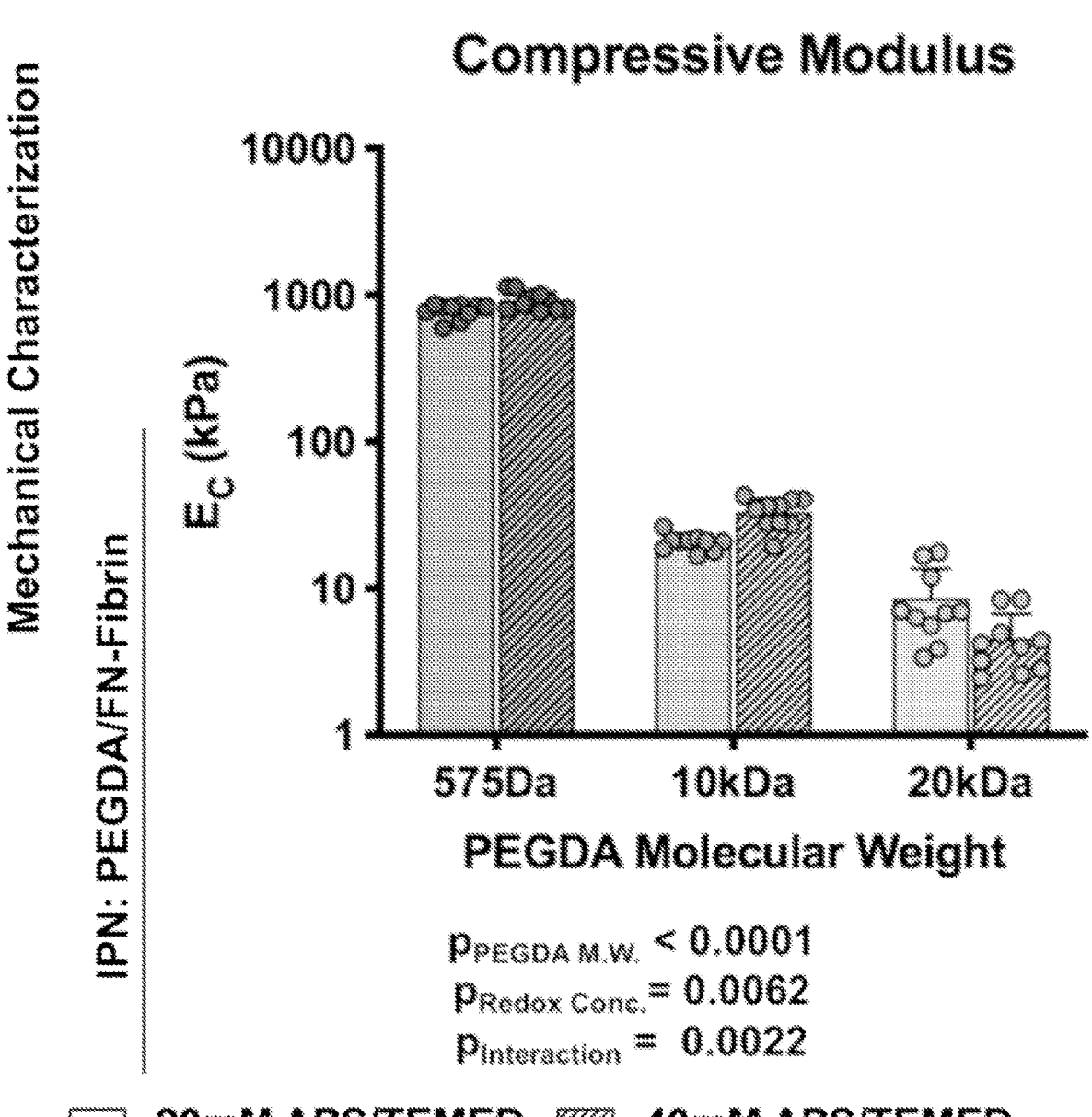
Fig. 17B2

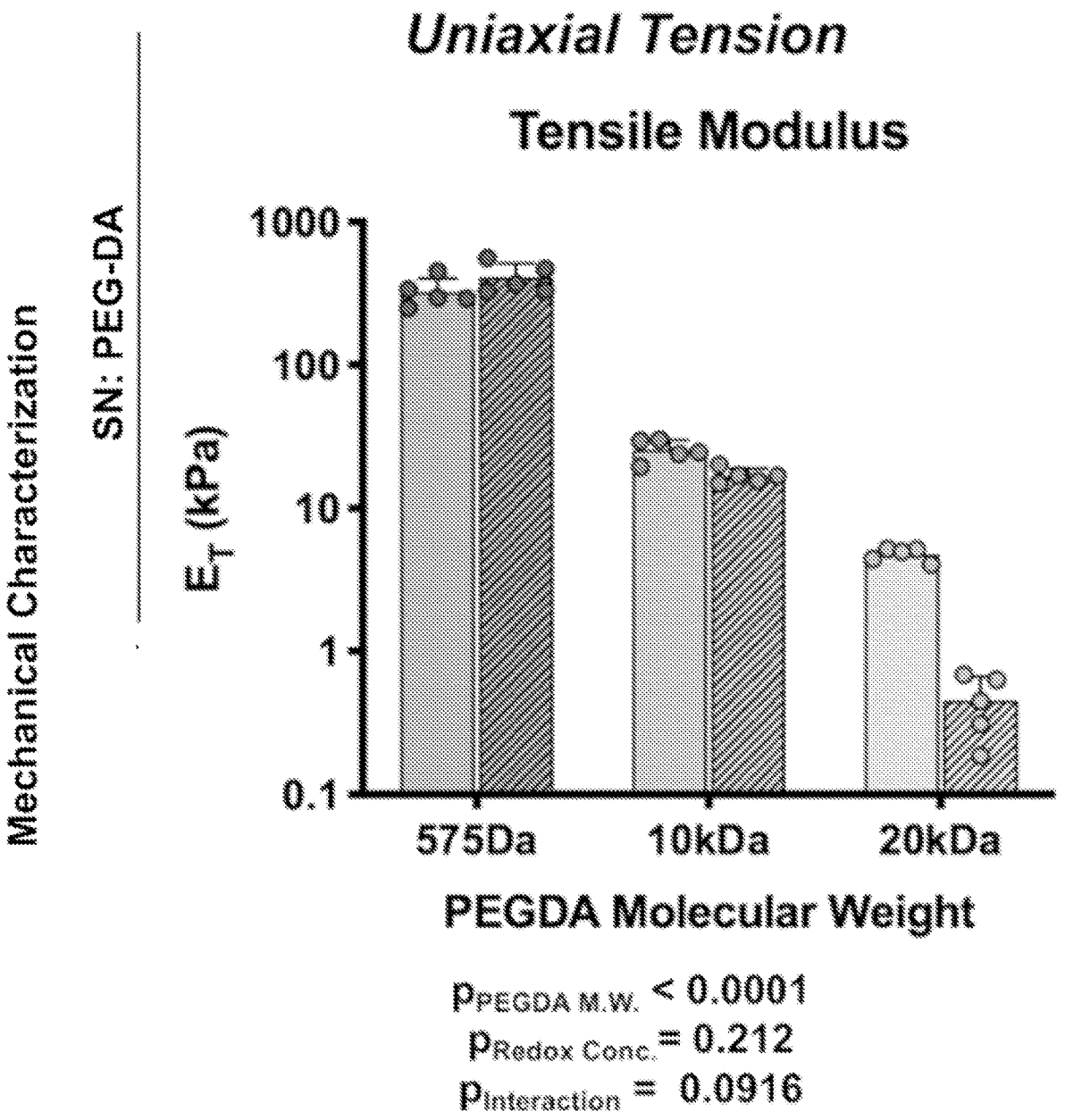
Fig. 17C1

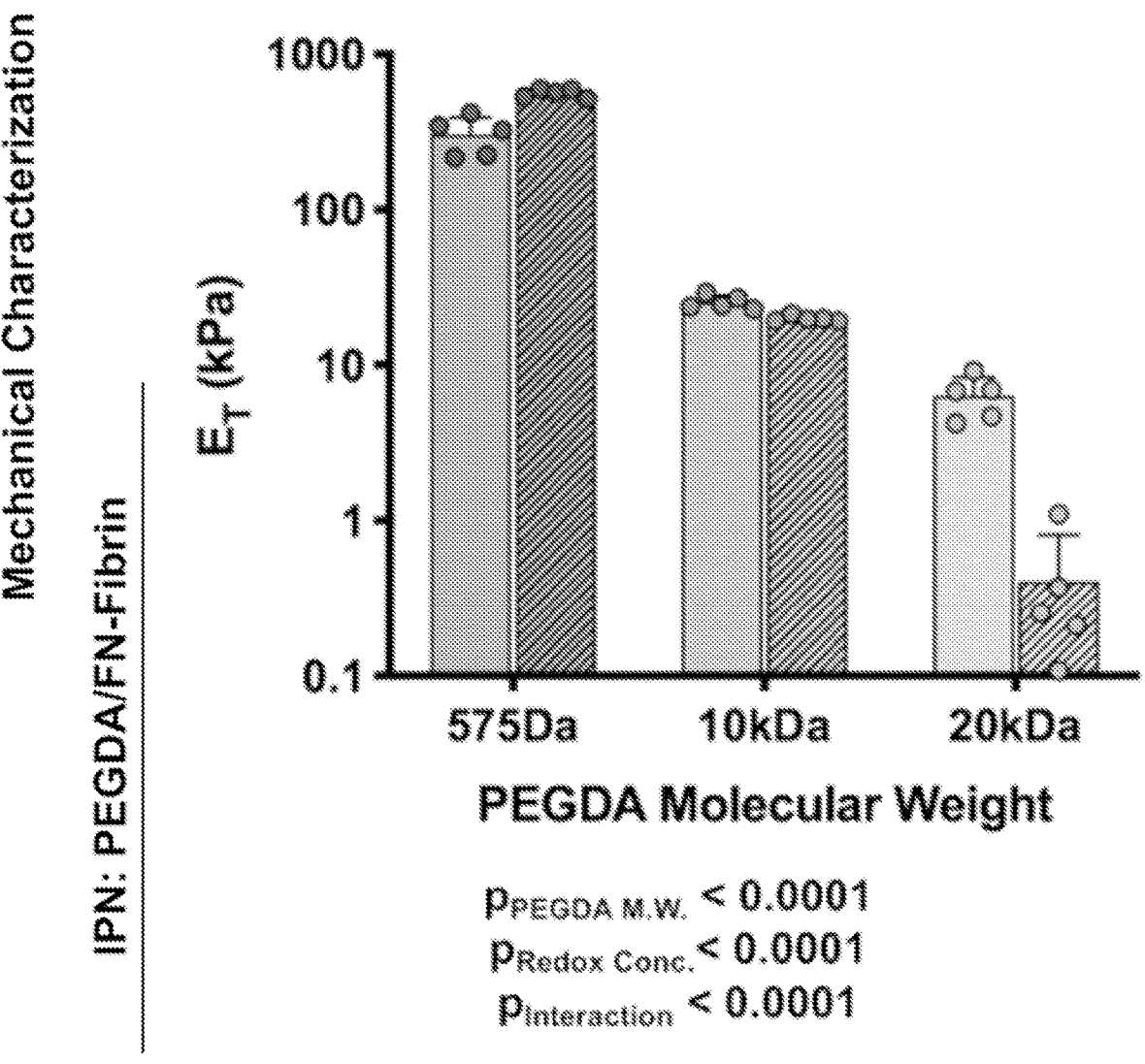
Fig. 17C2

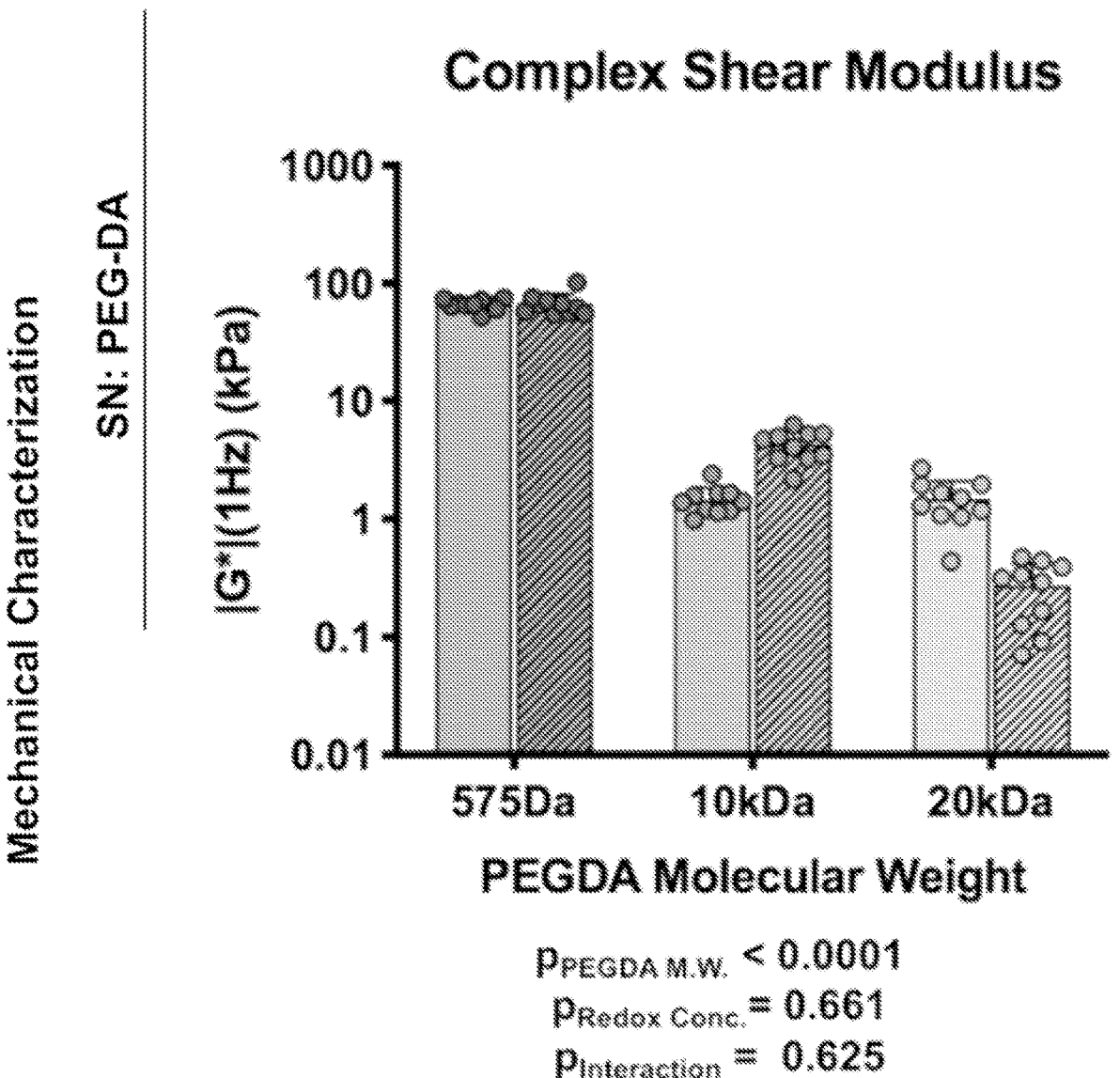
Fig. 17D1

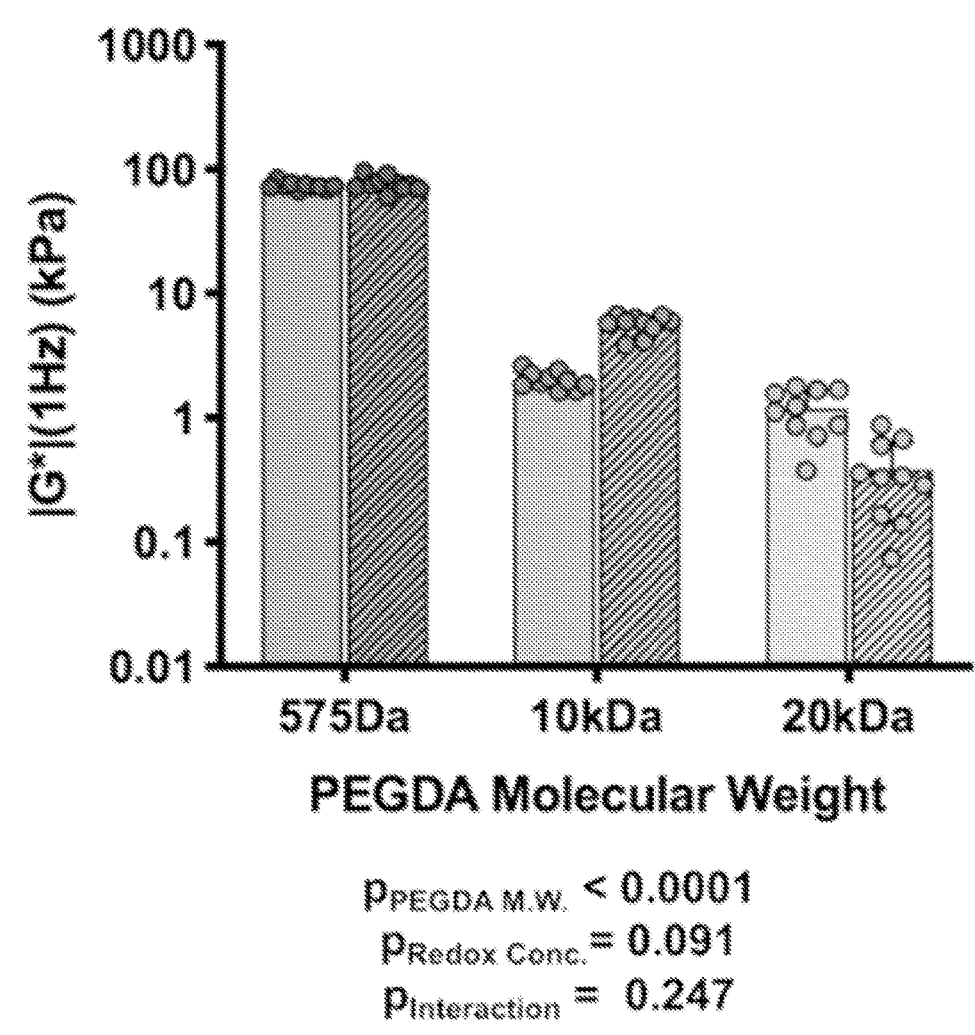
Fig. 17D1

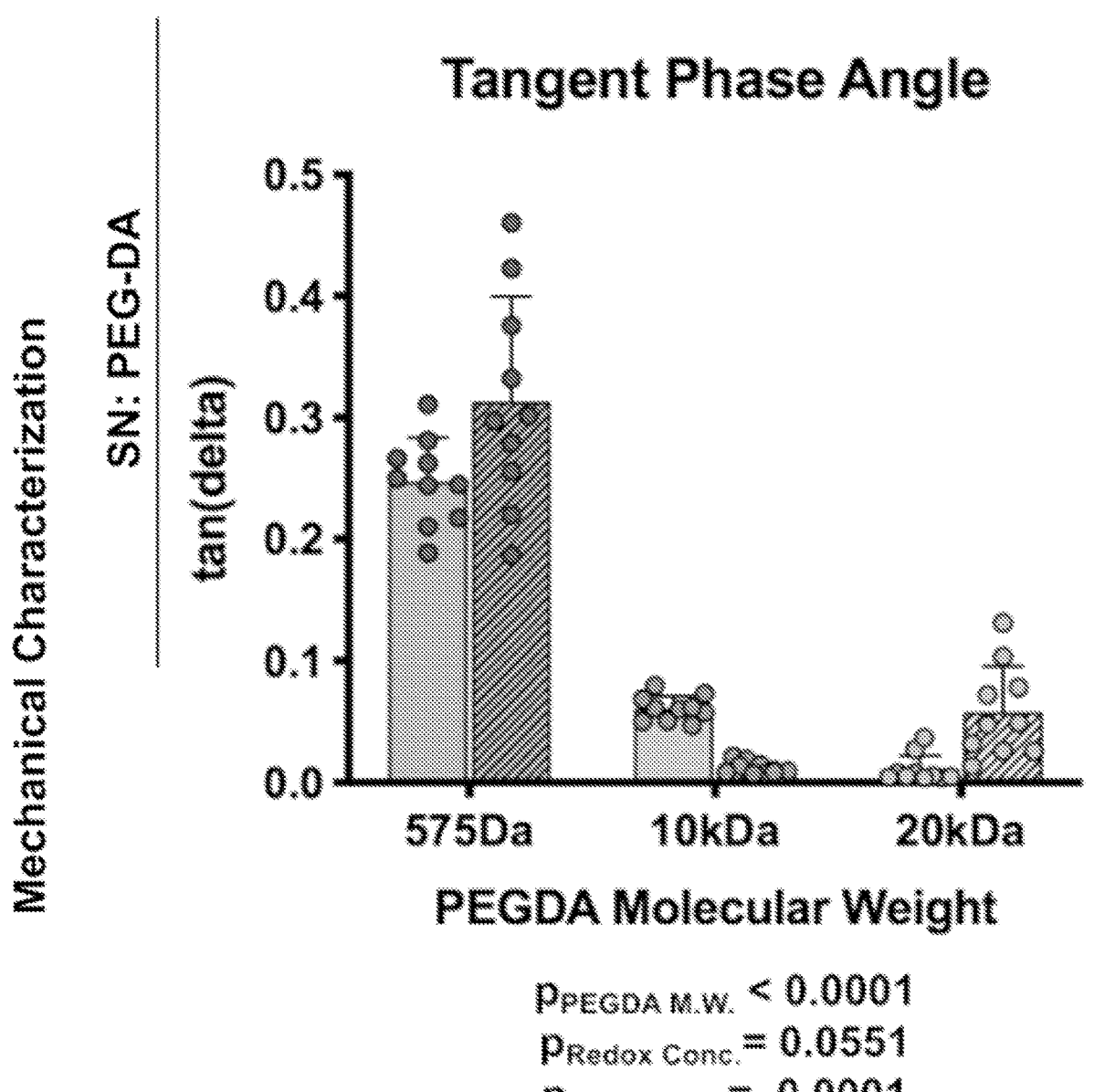
$P_{PEGDA\ M.W.} < 0.0001$
$P_{Redox\ Conc.} = 0.0551$
$P_{Interaction} = 0.0001$
☐ 20mM APS/TEMED ▨ 40mM APS/TEMED
Fig. 17E1

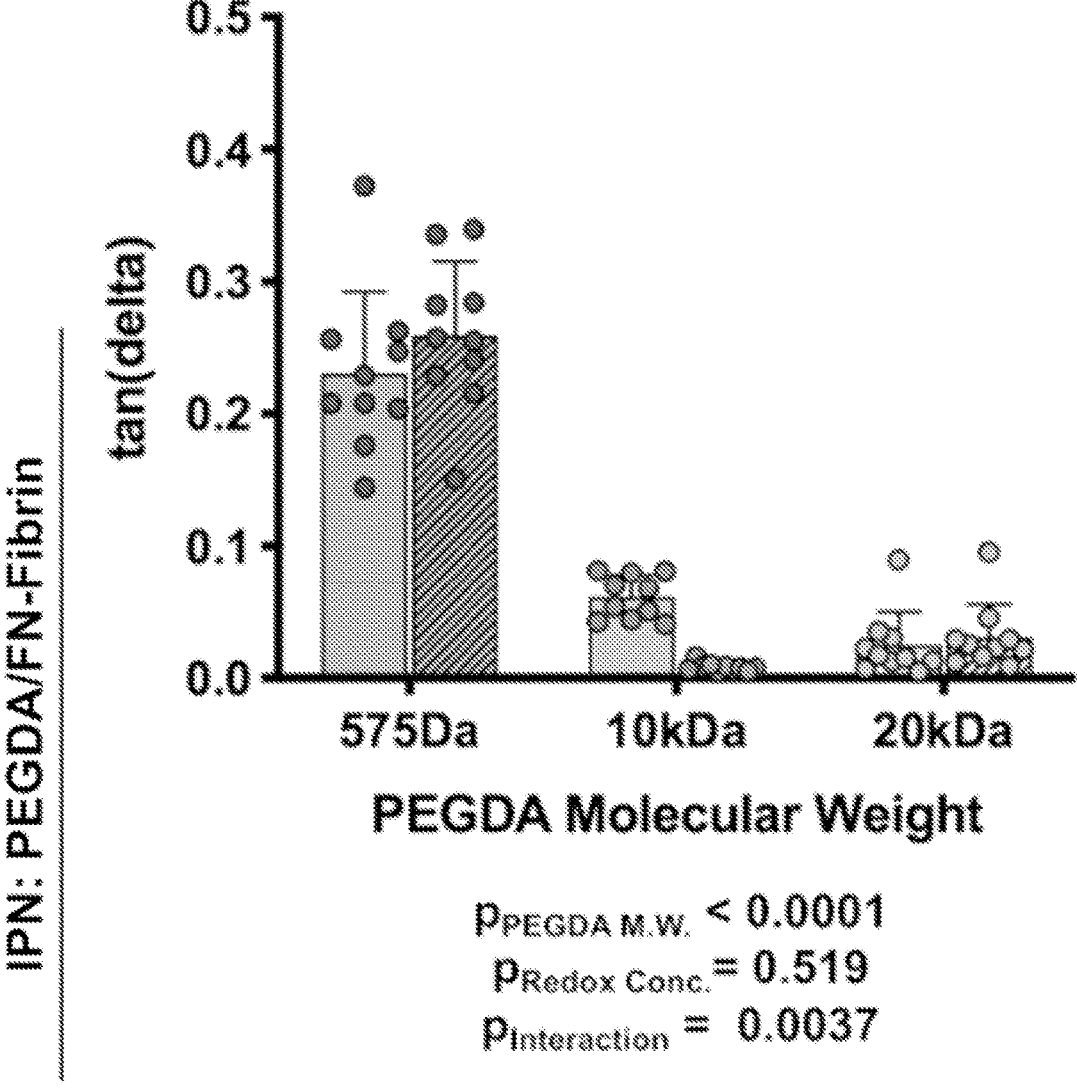
Fig. 17E2

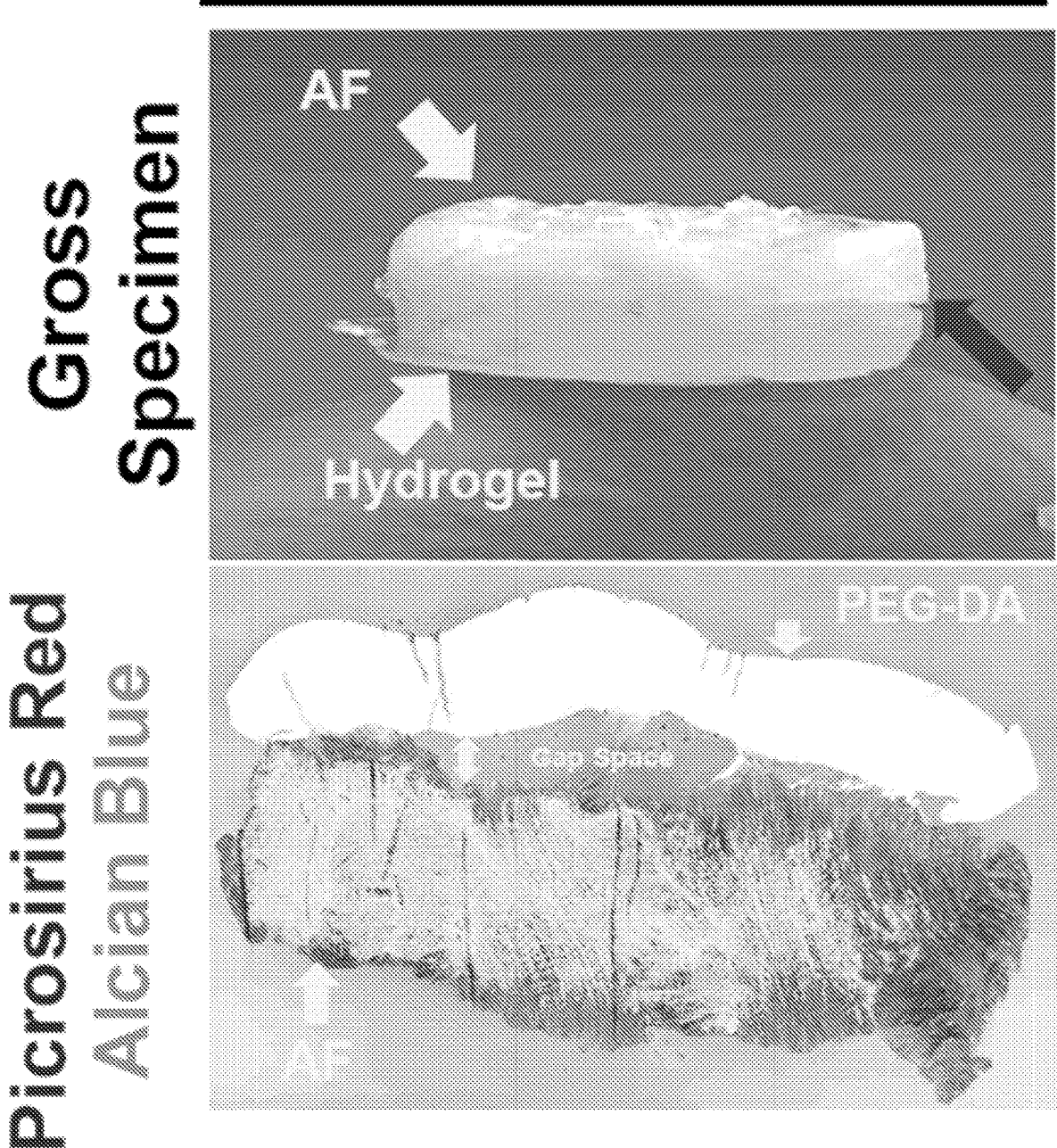
Fig. 18A1

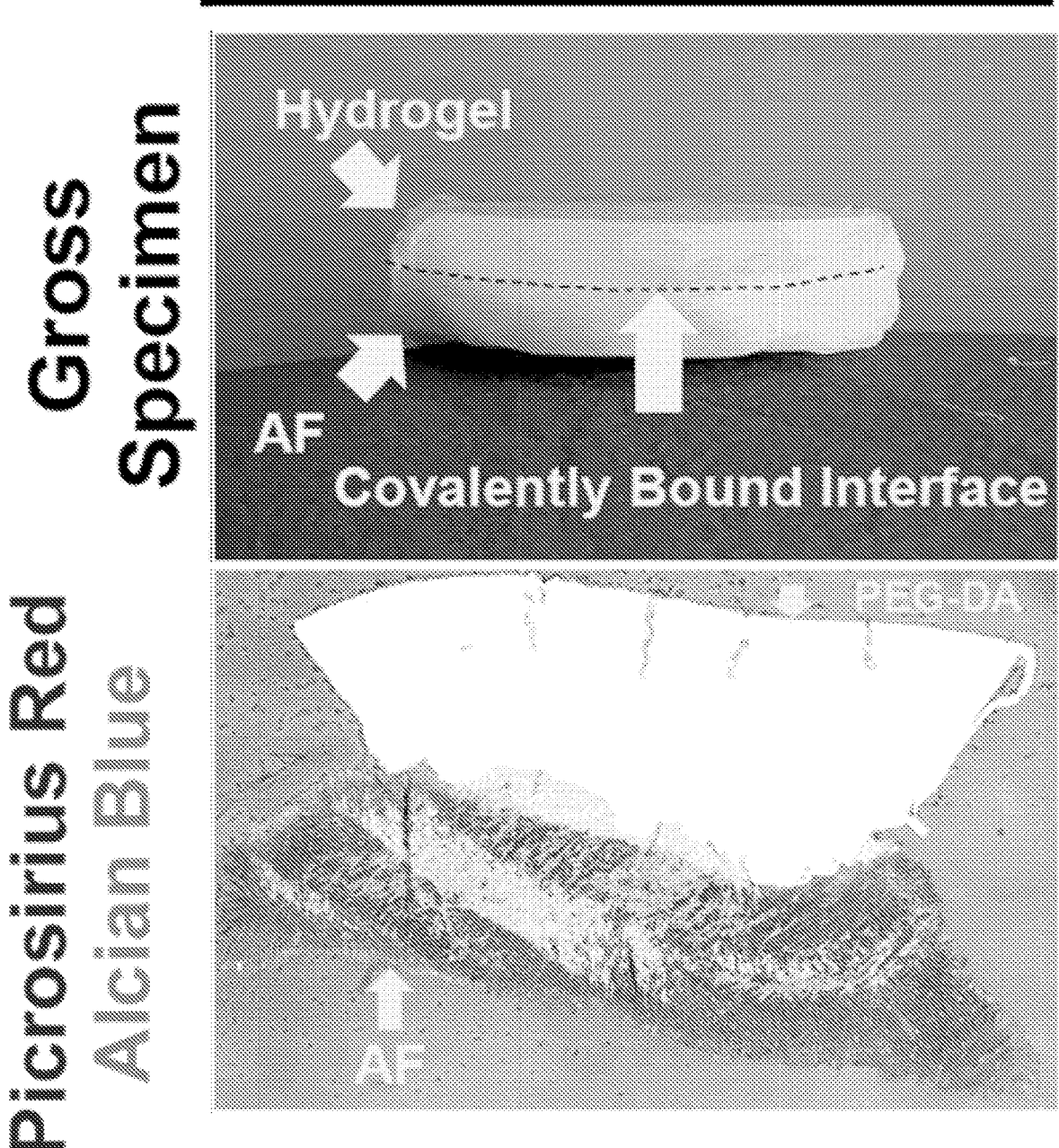
Fig. 18A2

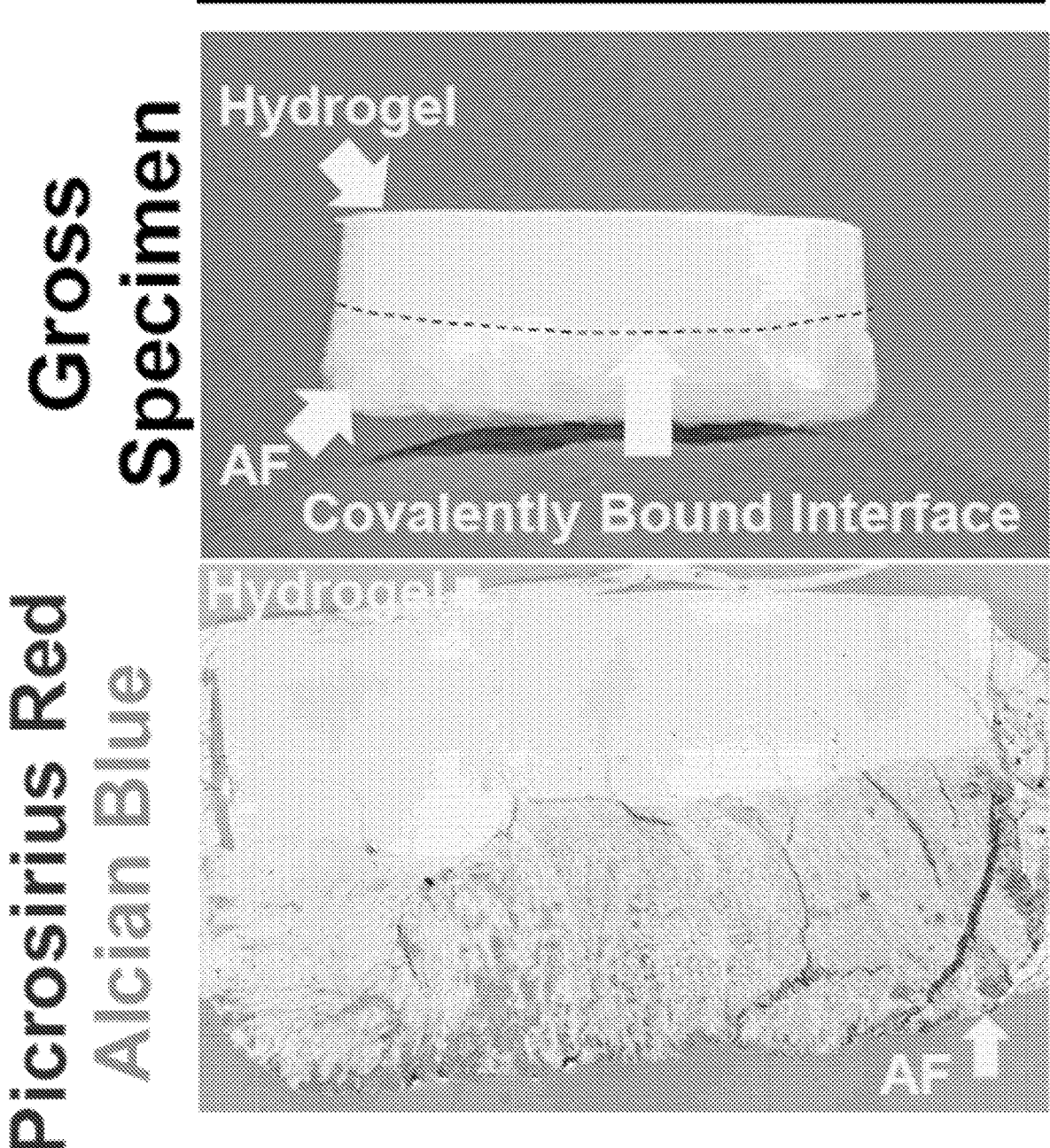
Fig. 18A3

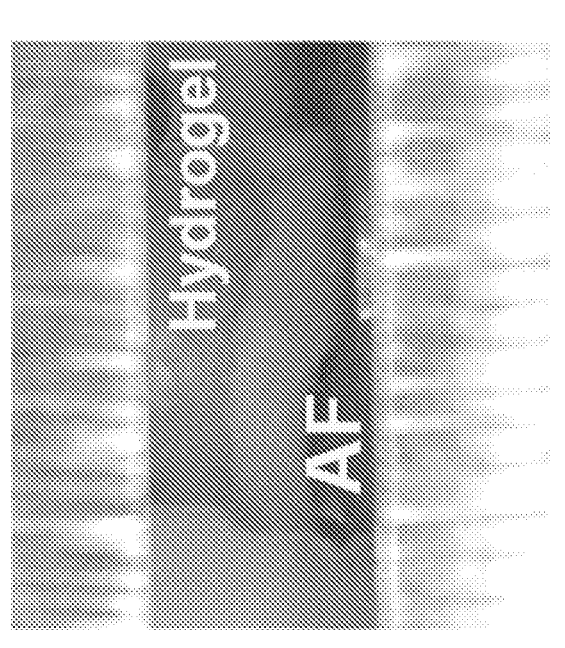
Fig. 18C1

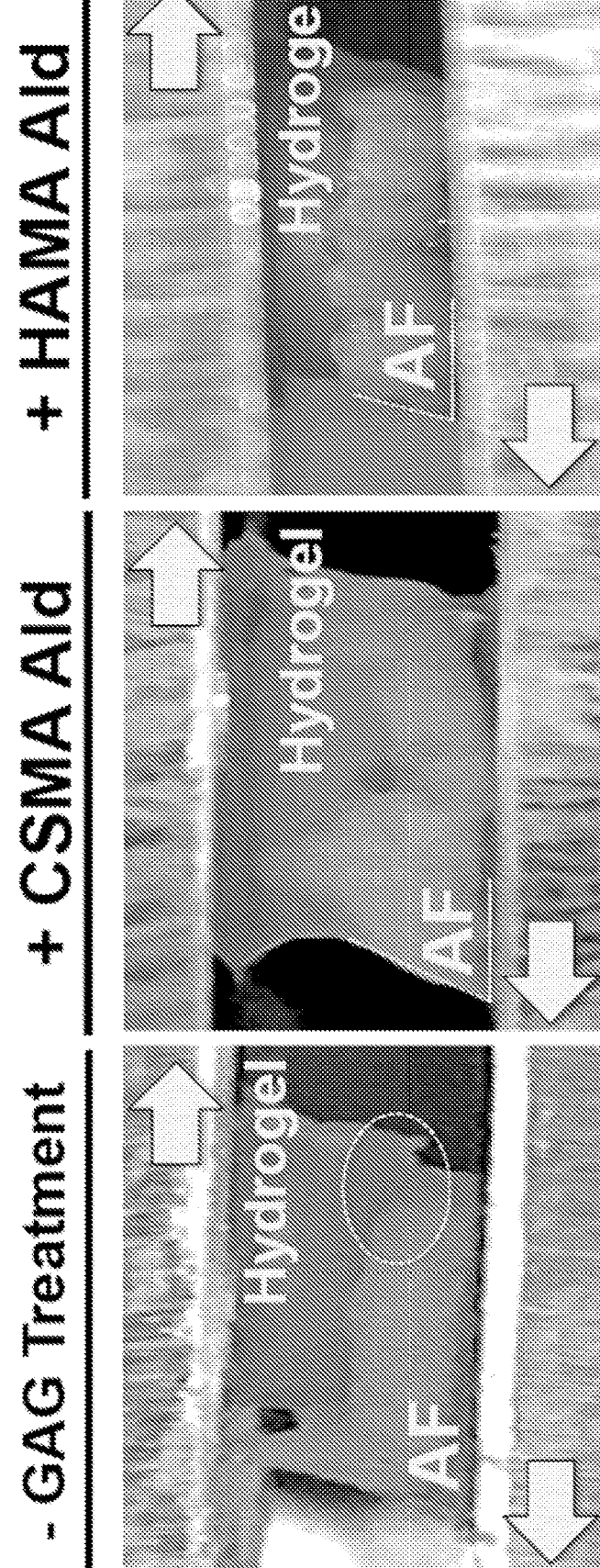
Mid-test
- GAG Treatment   + CSMA Ald   + HAMA Ald
Fig 18C1

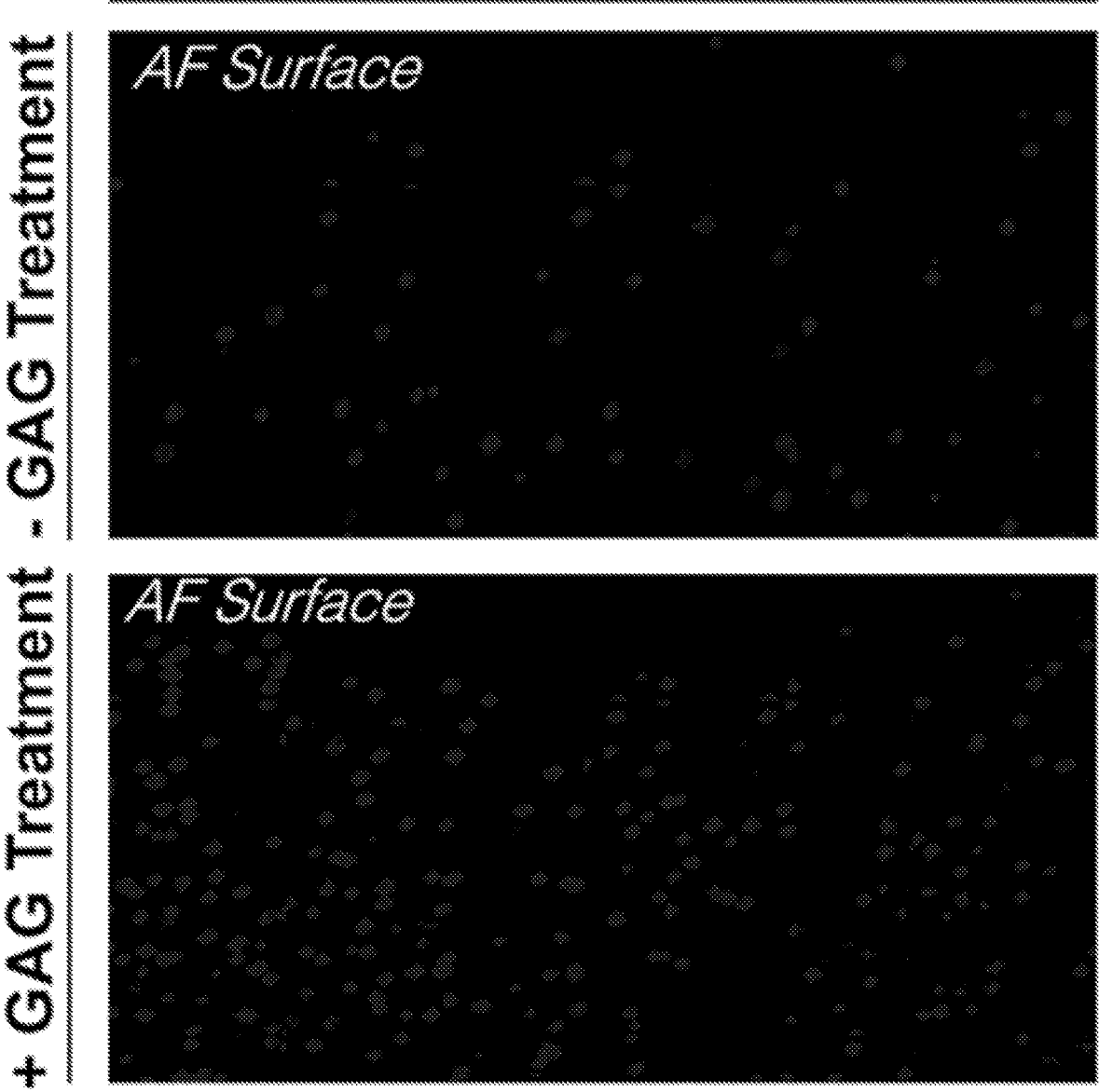
Fig. 19C1

HAMA Aldehyde
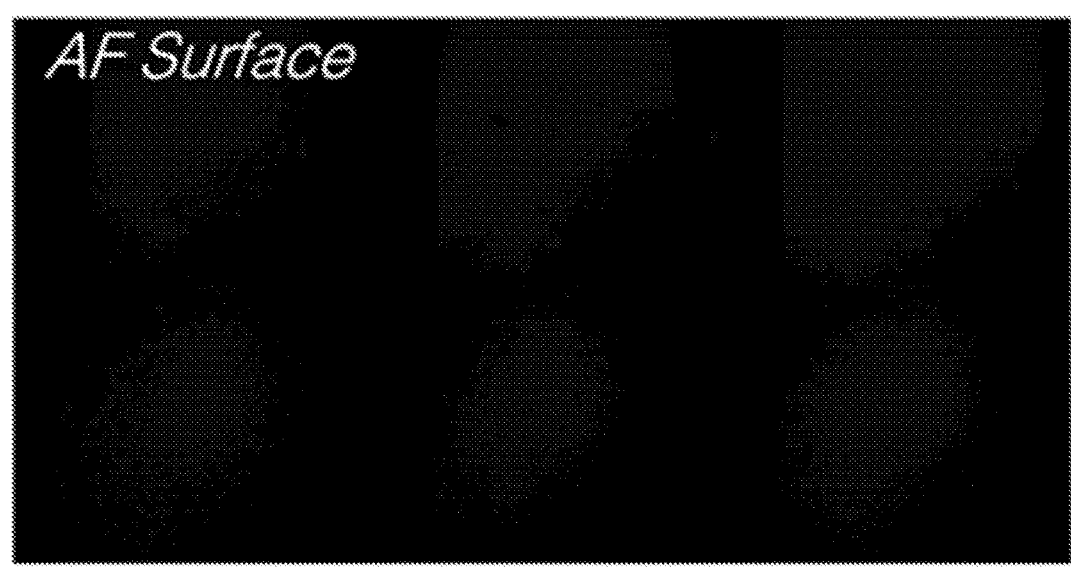
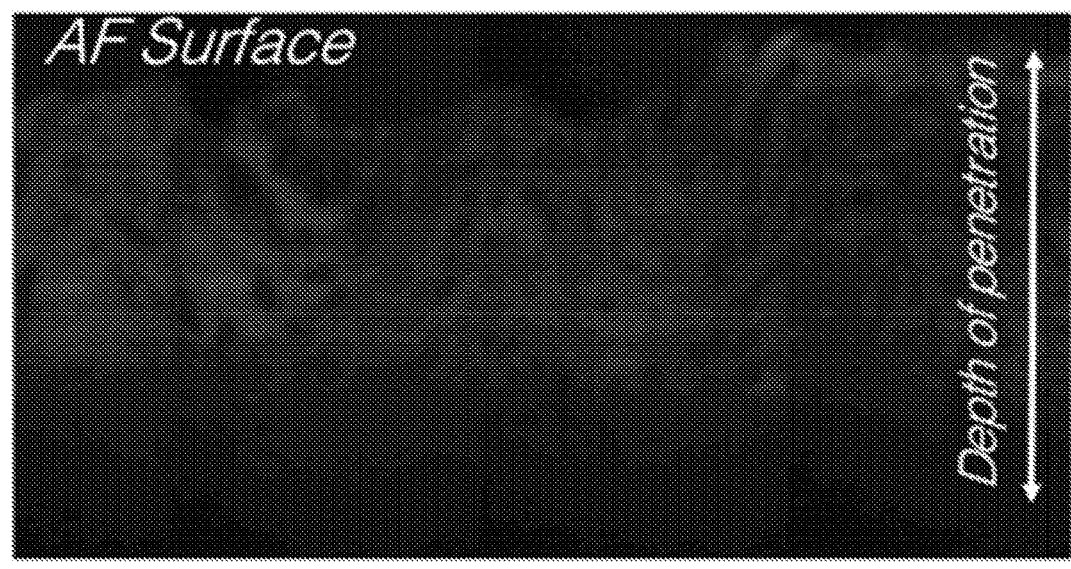
Fig. 19C2

Merge
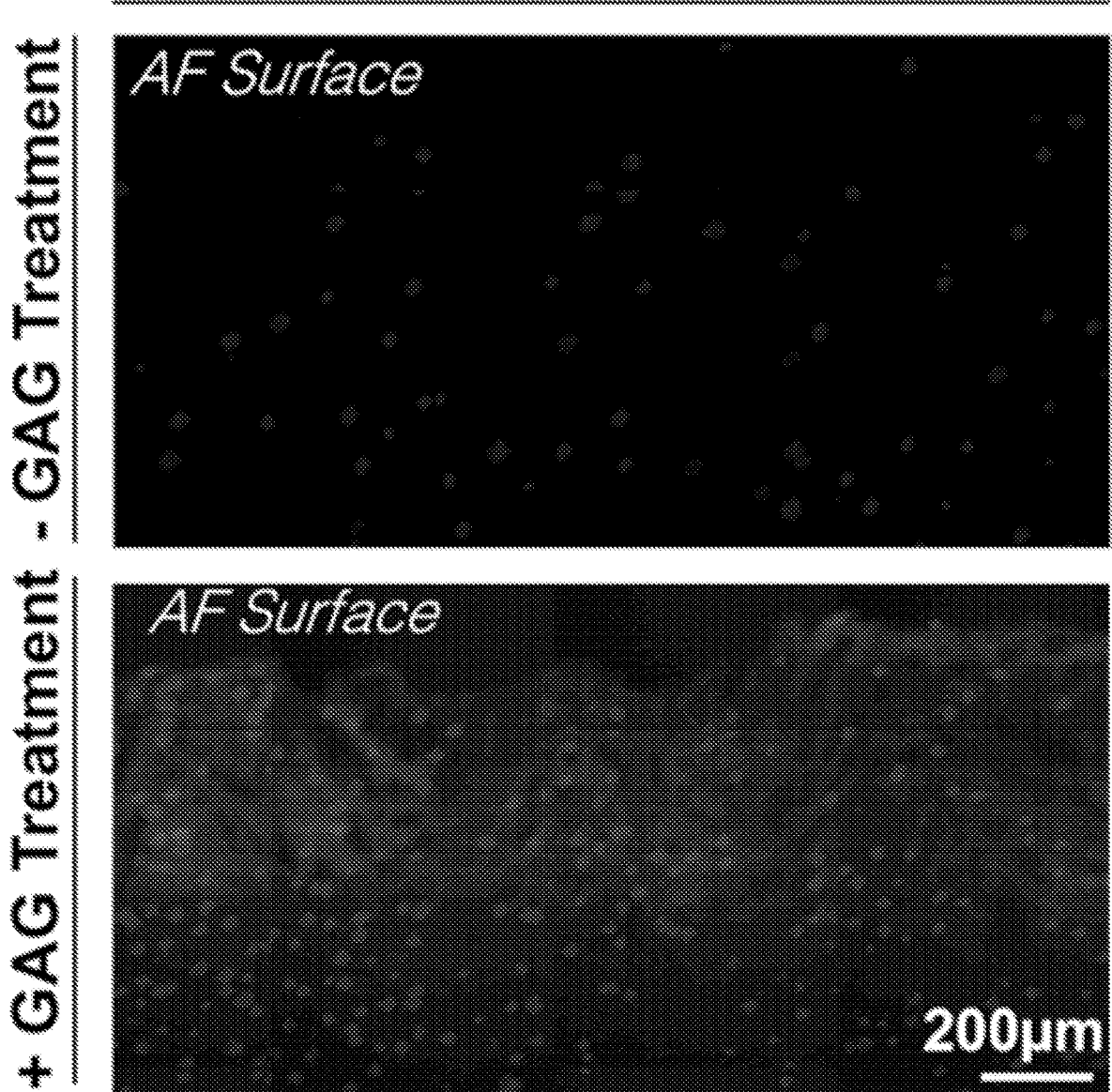
Fig. 19C3

Intact

Discectomy

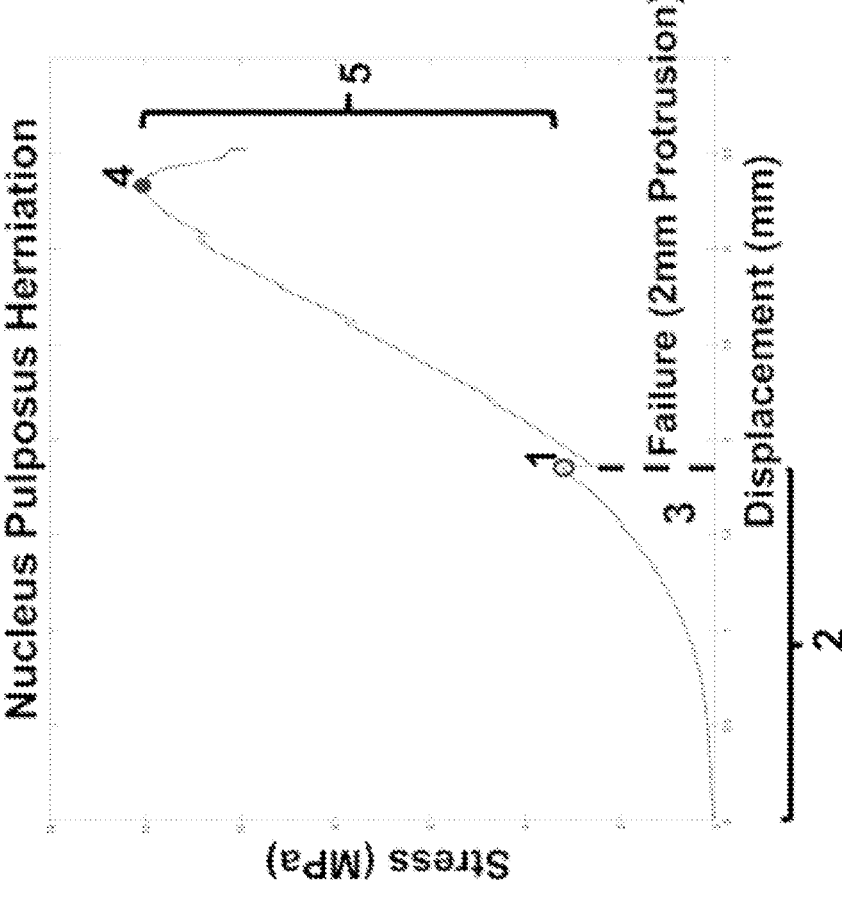
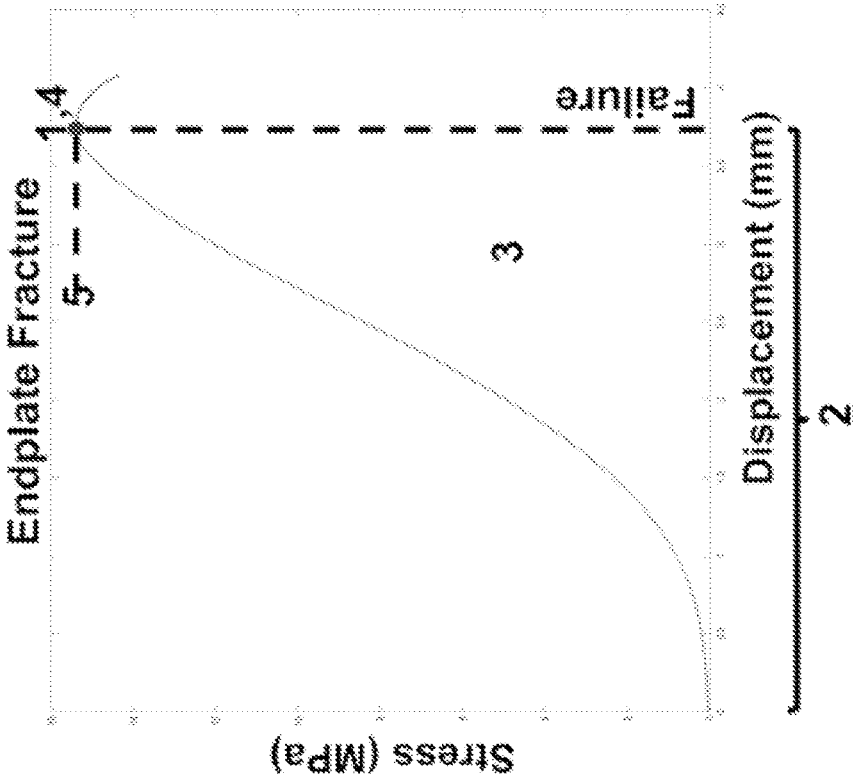
Fig. 22B

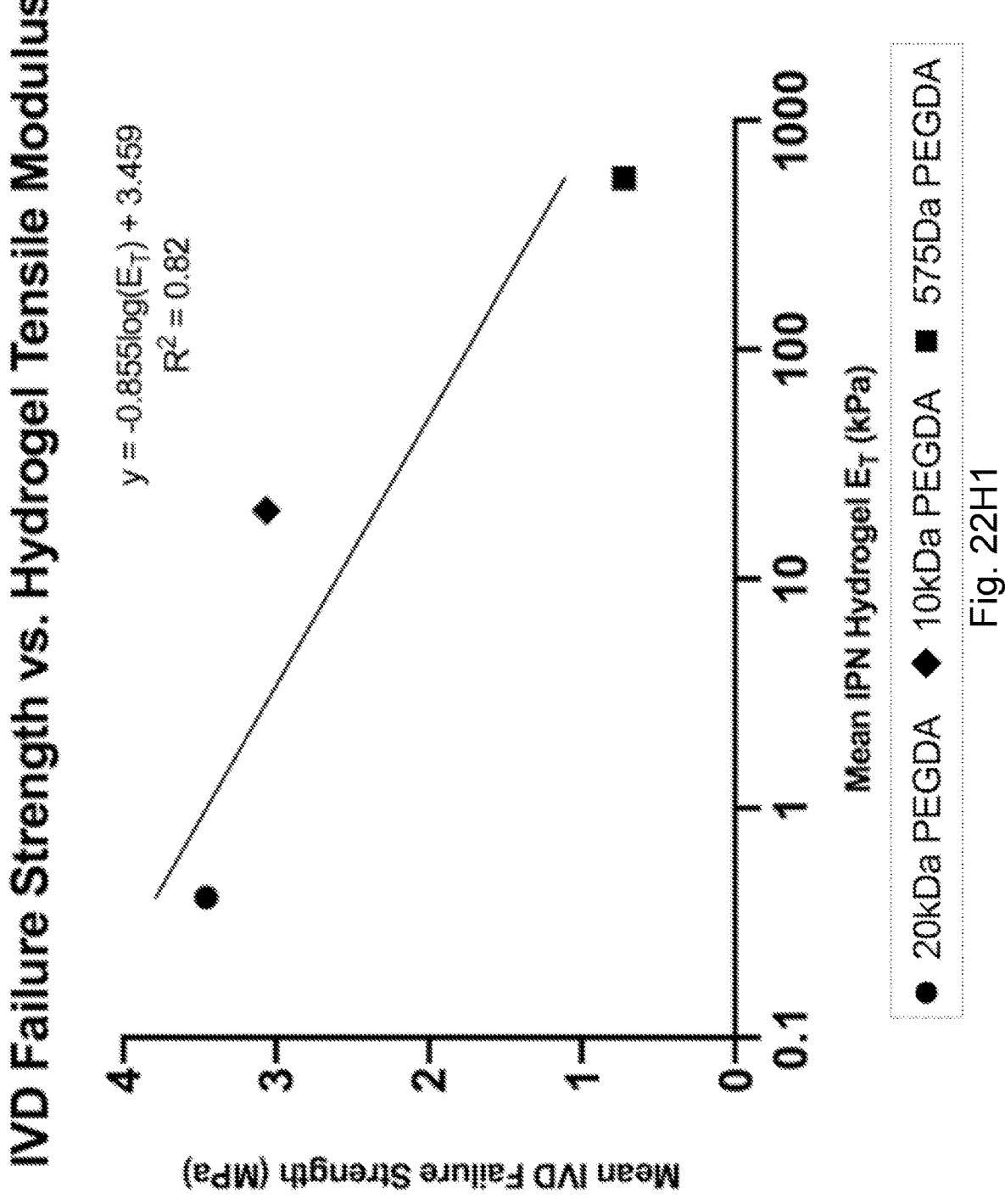
Fig. 22H1

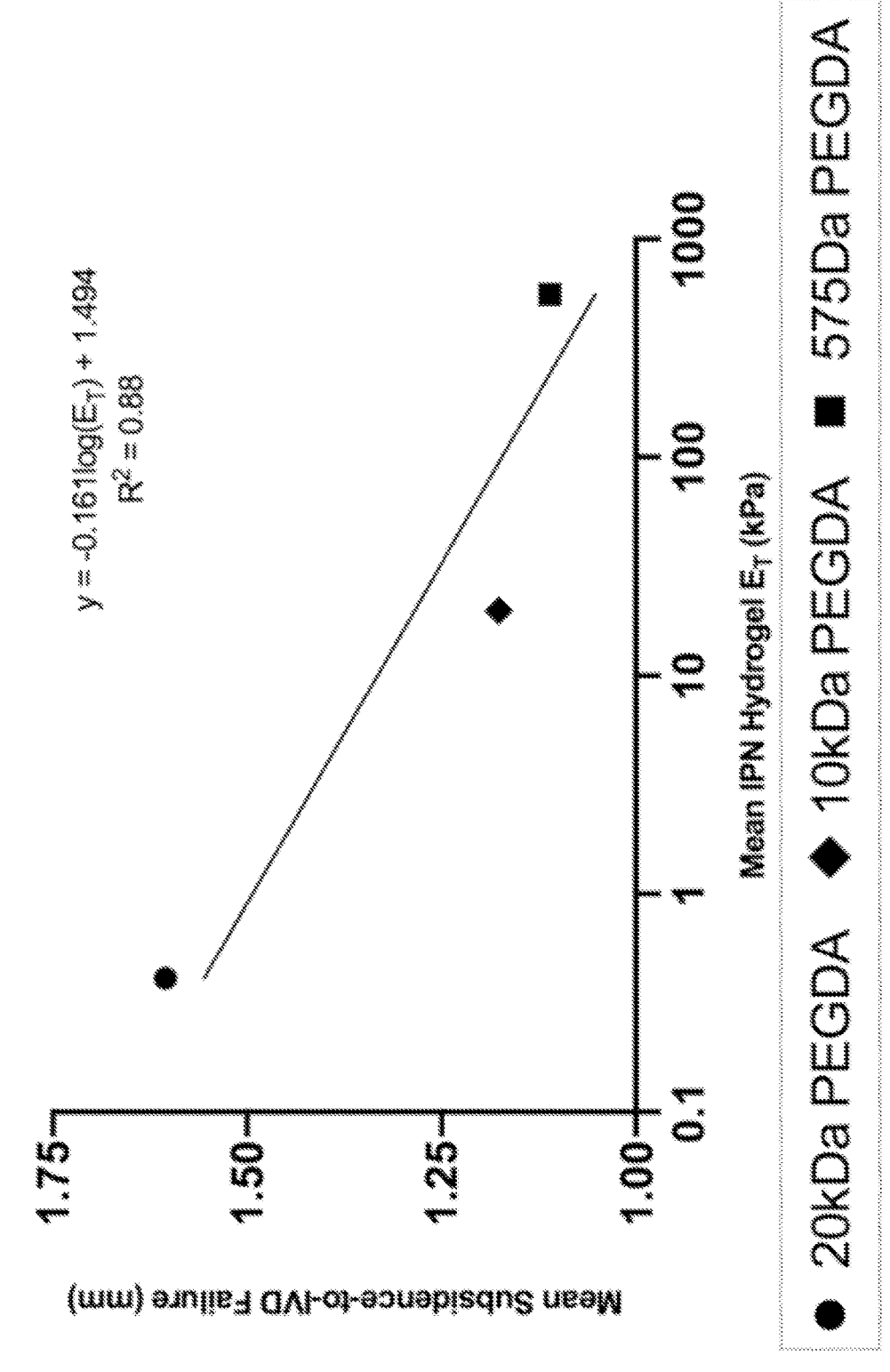
Fig. 22H2

Sample Name: Unmodified HA

Sample Name: Unmodified CS

APPROACH TO REPAIR TISSUE DEFECTS BY BONDING INJECTABLE GELS TO NATIVE SOFT TISSUES

CROSS-REFERENCE TO RELATED APPLICATIONS

This application claims the benefit of U.S. Provisional Application No. 62/929,682, filed on Nov. 1, 2019, which is expressly incorporated by reference herein in its entirety for all purposes.

STATEMENT OF FUNDING

This invention was made with government support under Grant Number NIH RO1 AR057397 awarded by the National Institute of Arthritis and Musculoskeletal and Skin Diseases. The government has certain rights in the invention.

TECHNICAL FIELD

This specification describes implantable hydrogel systems containing a dual-modified (oxidized and methacrylated) glycosaminoglycan for repairing defects in tissues containing fibrocartilage

BACKGROUND

Intervertebral disc (IVD) herniation is one of the most frequent spinal pathologies, with an incidence rate of up to 20 cases per 1000 adults annually. [1] Symptomatic IVD herniation, and IVD defects more generally, results in back and neck pain as well as disability. The tremendous socio-economic costs and diminished quality of life make the burden of chronic low back pain a leading cause of global disability. [2] Defects in the annulus fibrosus (AF) play a critical role in the pathophysiology of symptomatic IVD herniation, where nucleus pulposus (NP) tissue protrudes through AF defects and compresses upon spinal nerve roots leading to neuropathy. [3] Discectomy is the surgical standard-of-care to treat symptomatic IVD herniation, in which a surgeon removes prolapsed NP tissue with a rongeur and relieves mechanical compression of the nerves. [4] Although effective in relieving pain compared to non-operative controls, this procedure does not repair AF defects after NP removal, rendering this treatment option as a palliative response to symptomatic herniation and does not aim to seal IVDs or promote healing to prevent recurrent herniations that may occur after surgery. [5,6]

Recurrent herniation is the leading cause of reoperation following discectomy with a surgical revision rate up to 25%, and is associated with worse clinical outcomes and a greater socioeconomic burden than those who do not require reoperation. [7-11] Large unrepaired AF defects are a significant risk factor for symptomatic reherniation, and due to the poor healing capacity of the IVD, reflect a gap in current surgical practices for patients that bear a high risk of reoperation. [12-14] Next generation treatment strategies incorporate the repair of AF defects to address this critical challenge with primary goals to prevent recurrent herniation, biomechanical dysfunction, and progressive degeneration. [15,16] Mechanical devices such as the Barricaid® Annular Closure Device recently received FDA approval and aims to prevent reherniation following discectomy, however this device lends itself to an invasive approach since it requires anchorage to an adjacent vertebra and bears considerable risk of vertebral subsidence and endplate damage. [17] Additionally, purely mechanical devices do not have the ability to prevent degeneration after surgery. To that end, emerging approaches in regenerative medicine utilize hydrogels as minimally invasive AF repair biomaterials that serve as surgical sealants and void-filling tissue engineering constructs to promote functional restoration. [18-21] These water-swollen polymeric matrices are extraordinarily versatile by design and, depending on composition, have demonstrated ability to restore functionally important biomechanical properties or promote biological repair processes. [21]

Despite their considerable potential as a next generation treatment strategy, hydrogels for AF repair have yet to be translated into the clinic in part due to poor tissue integration with the complex IVD architecture. [22] Integration of polymeric materials is directly related to the adherence to tissue surfaces, which can be imparted by physical and/or chemical interactions at the tissue-hydrogel interface. [23] Strongly adherent surgical sealants employ both physical and chemical means of adsorption to achieve suitable tissue integration, however these materials are often highly cytotoxic and cause damage to treated tissue. [24] Given the high magnitudes of biomechanical loads exerted on the IVD, there is an unmet clinical need to develop an implantable hydrogel system with strong adherence to AF tissue such that it can durably seal AF defects without compromising cellular viability and either match or diminish the risk of herniation compared to current discectomy procedures. [14, 25, 26]

SUMMARY

Accordingly, there is a need for implantable hydrogel systems with strong adherence to tissues containing fibrocartilage such that it can durably seal defects in these tissues without compromising cellular viability and either match or diminish the risk of herniation compared to current discectomy procedures. The present disclosure solves these and other needs by providing a cytocompatible two-part strategy to repair soft tissue defects composed of: (1) a dual-modified (oxidized and methacrylated) glycosaminoglycan molecule and (2) an interpenetrating network (IPN) hydrogel as a void-filling sealant. In some embodiments, this approach enhances hydrogel adhesivity and chemisorption by implementing a non-sulfated glycosaminoglycan, hyaluronic acid (HA), to bond acrylate-based gels to collagen in soft tissues. To date, no group has modified HA in this manner nor has any group systemically optimized biochemical modifications to HA for the purpose of achieving tissue integration.

In some embodiments, a dual-modified HA is disclosed that provides improved hydrogel adhesivity with treated annulus fibrosus tissue, as demonstrated through lap shear tests described herein. This dual-modified HA is versatile in that it can bond with any hydrogel that contains a macromer with acrylate moieties and can covalently bond via photoinitiation or redox initiators. In some embodiments, this approach is applied for intervertebral disc repair, where there is an unmet clinical need to seal defects in the annulus fibrosus. By modulating hydrogel mesh size, soft void-filling hydrogels, e.g., with large mesh size, with dual-modified HA match the performance compared to the current standard-of-care, whereas stiffer hydrogels, e.g., with smaller mesh size, bear a higher risk of implant herniation compared to the current standard-of-care (unrepaired disc after discectomy).

In addition to the high interfacial adhesion strength needed to successfully seal AF defects, the bulk mechanical properties of void-filling hydrogels are also critically important and determine whether the strategy is more amenable to a biomechanical or biological approach for repair. [19] For strategies that aim to restore biomechanical function, AF repair hydrogels should ideally match the native tissue properties so as to re-establish intact IVD behavior under physiological loading, which requires either a high macromer or crosslinking density. [18] However, a tissue engineering construct for the delivery of biologics (i.e. cells and/or bioactive factors) requires a significantly softer gel to maintain high cell viability or sufficient biologic release to elicit regenerative effects. [27,28] Synthetic polymer networks enable highly tunable construct properties; for example the bulk elastic moduli can be adjusted by the macromer molecular weight (MW) to generate either biomechanically-favorable or biologically-favorable strategies. [29-31] However, the effect of elasticity (or inversely, mechanical compliance) on implant herniation risk has yet to be assessed by synthetically tuning macromer MW.

Advantageously, this disclosure is the first to: (1) optimize biomaterial adsorption through the use of oxidized and methacrylated GAGs to seal IVD defects by covalently bonding injectable space-filling hydrogels to native IVD tissue, and (2) determine the effect of construct elasticity on IVD failure mechanics when translating this strategy to a large animal model. Taken together, these results underscore the need to consider interactions at the tissue-hydrogel interface as well as the material properties of void-filling biomaterials in order to mitigate herniation risk. This two-part strategy is amenable to clinical use for AF repair since it is minimally invasive, easily applied to AF defects in a short time span, and demonstrates non-inferiority to the current standard of care. Future studies warrant investigation with an in vivo model of simulated discectomy to further examine endogenous repair processes as well as long-term durability of repair.

Accordingly, in one aspect, the disclosure provides a kit for repairing a fibrocartilage defect. The kit includes a first container holding a first composition comprising an oxidized and methacrylated glycosaminoglycan, a second container holding a pre-polymer hydrogel composition containing a first crosslinking unit that, when polymerized, is capable of bonding to methacrylate, and a third container holding a hydrogel polymerization initiator composition.

In another aspect, the disclosure provides a method for repairing a fibrocartilage defect in a subject. The method includes contacting the fibrocartilage defect with a first composition containing an oxidized and methacrylated glycosaminoglycan to form an imine bond between the glycosaminoglycan and the fibrocartilage defect, thereby coating the fibrocartilage defect with the glycosaminoglycan. The method then includes contacting the fibrocartilage defect coated with the glycosaminoglycan with a mixture of a pre-polymer hydrogel composition containing a first crosslinking unit that, when polymerized, is capable of bonding to methacrylate and a hydrogel polymerization initiator composition, thereby forming a hydrogel that is covalently bonded to the glycosaminoglycan through methacrylate.

INCORPORATION BY REFERENCE

All publications, patents, and patent applications herein are incorporated by reference in their entireties. In the event of a conflict between a term herein and a term in an incorporated reference, the term herein controls.

BRIEF DESCRIPTION OF THE DRAWINGS

The implementations disclosed herein are illustrated by way of example, and not by way of limitation, in the figures of the accompanying drawings. Like reference numerals refer to corresponding parts throughout the several views of the drawings.

FIGS. 3A, 3B and 3C collectively illustrate a schema for oxidation and methacrylation of glycosaminoglycans, in accordance with some embodiments of the present disclosure.

FIGS. 4A and 4B collectively illustrate a schema for titrating oxidation and methacrylation of chondroitin sulfate (4A) and hyaluronic acid (4B), in accordance with some embodiments of the present disclosure.

FIG. 6 illustrates aldehyde quantification, via TNBS assay, of oxidized and methacrylated chondroitin sulfate (5A) and hyaluronic acid (5B) preparations, in accordance with some embodiments of the present disclosure.

FIGS. 15A and 15B are collectively a schematic illustration of AF repair workflow and conceptual model of the two-part repair strategy, in accordance with some embodiments of the present disclosure. (A) Workflow to repair annular defects with this two-part biomaterial system compared to the surgical standard of care. (B) Schematic of hydrogel composition and molecular working principle of dual-modified GAGs that enable covalent bonding of injectable hydrogels to native IVD collagen.

FIGS. 16A, 16B, 16C, 16D, and 16E collectively show the results of synthesis and biochemical characterization of dual-modified GAGs, in accordance with some embodiments of the present disclosure. (A) Two-step reaction scheme used to synthesize dual-modified CS and HA. (B) Dual-modified GAG formulations screened herein categorized by oxidation and methacrylation reaction stoichiometries. (C) TNBS assay optical density measurements, which are used to determine the degree of oxidation for all dual-modified GAG formulations synthesized herein. (D/E) 1H NMR spectra for dual-modified CS and HA, which are used to determine the degree of methacrylation for all formulations synthesized herein.

FIGS. 17A, 17B, 17C, 17D, and 17E collectively show results of fabrication and mechanical characterization of injectable SN and IPN hydrogels, in accordance with some embodiments of the present disclosure. (A) Hydrogels were fabricated in cylindrical molds for mechanical testing and bovine AF defects to demonstrate proof-of-concept in situ gelation. H&E staining of SN and IPN hydrogels demonstrates homogenous incorporation of the FN-Fibrin network up to 5 mg/mL. (B-E) Bulk mechanical characterization of compressive modulus, tensile modulus, complex shear modulus, and tangent phase angle for SN and IPN hydrogel formulations across PEGDA MW and redox initiator concentrations.

FIGS. 18A, 18B, 18C, 18D, 18E, 18F, 18G collectively show that dual-modified HA, in accordance with some embodiments of the present disclosure, imparts greater hydrogel adhesion to AF tissue than dual-modified CS. (A) Gross specimen visualization and picrosirius red/alcian blue staining of samples fabricated for lap shear adhesion testing. (B) Representative load-displacement curve of a lap shear specimen that underwent displacement-controlled ramp-to-failure until the maximum force (Fmax) was reached. (C) Lap shear specimens pre- and mid-test to visualize hydrogel adhesion to AF tissue with and without treatment of dual-modified GAGs. Circled area indicates slippage between the hydrogel and AF tissue during the lap shear test. (D) Lap shear ultimate stress factored by GAG type and formulation number. (E-G) Lap shear ultimate stress as a function of biochemical modifications and linear correlations between ultimate stress and degrees of oxidation and methacrylation, as described with respect to FIG. 11.

FIGS. 19A, 19B, and 19C collectively show that dual-modified HA homogenously covers the surface of AF tissue and penetrates below the tissue surface, in accordance with some embodiments of the present disclosure. (A) Top-down view of lap shear specimens to visualize HAMA Aldehyde coverage on AF tissue. (B) Depth of HAMA Aldehyde fluorescent signal intensity as a function of spatial position. (C) Cross-sectional view of HAMA Aldehyde treated AF to determine depth of biomaterial penetration.

FIGS. 22A, 22B, 22C, 22D, 22E, 22F, 22G, and 22H collectively show demonstrates that repairing AF defects with low-modulus hydrogels, in accordance with some embodiments of the present disclosure, matches the herniation risk of the current surgical standard of care and leads to partial restoration to intact levels. (A) Experimental design to assess implant herniation risk. (B) Representative loading curves for IVD motion segments that failed by vertebral endplate fracture and NP herniation. 1=IVD failure strength, 2=subsidence-to-IVD failure and IVD failure strain, 3=work-to-IVD failure, 4=ultimate strength, and 5=ultimate strength/failure strength ratio. Quantification of (C) IVD failure strength, (D) subsidence-to-IVD failure, (E) failure strain, (F) work-to-IVD failure, and the (G) ultimate strength/failure strength ratio to mechanically characterize in situ implant herniation risk. (H) Nonlinear semi-log correlations between IVD failure strength and hydrogel tensile modulus and subsidence-to-IVD failure and hydrogel tensile modulus. Dashed line in (B) represents physiological upper bound (2.3 MPa) of intradiscal pressure. (NS=Not Significant). *p<0.05; p<0.005; *p<05.

DETAILED DESCRIPTION

Intervertebral disc (IVD) herniation causes pain and disability, but current discectomy procedures alleviate pain without repairing annulus fibrosus (AF) defects. Tissue engineering strategies seal AF defects by utilizing hydrogel systems to prevent recurrent herniation, however current biomaterials are limited by poor adhesion to wetted tissue surfaces or low failure strength resulting in considerable risk of implant herniation upon spinal loading. Here, a two-part repair strategy is provided comprising a dual-modified (oxidized and methacrylated) glycosaminoglycan that can chemically adsorb an injectable interpenetrating network hydrogel composed of fibronectin-conjugated fibrin and poly(ethylene glycol) diacrylate (PEGDA) to covalently bond the hydrogel to AF tissue. The Examples show that dual-modified hyaluronic acid imparts greater adhesion to AF tissue than dual-modified chondroitin sulfate, where the degree of oxidation is more strongly correlated with adhesion strength than methacrylation. The Examples apply this strategy to an ex vivo bovine model of discectomy and demonstrate that PEGDA molecular weight tunes hydrogel mechanical properties and affects herniation risk, where IVDs repaired with low-modulus hydrogels composed of 20 kDa PEGDA failed at levels at or exceeding discectomy, the clinical standard of care. This strategy bonds injectable hydrogels to IVD extracellular matrix proteins, is optimized to seal AF defects, and shows promise for IVD repair.

Figure 15B:
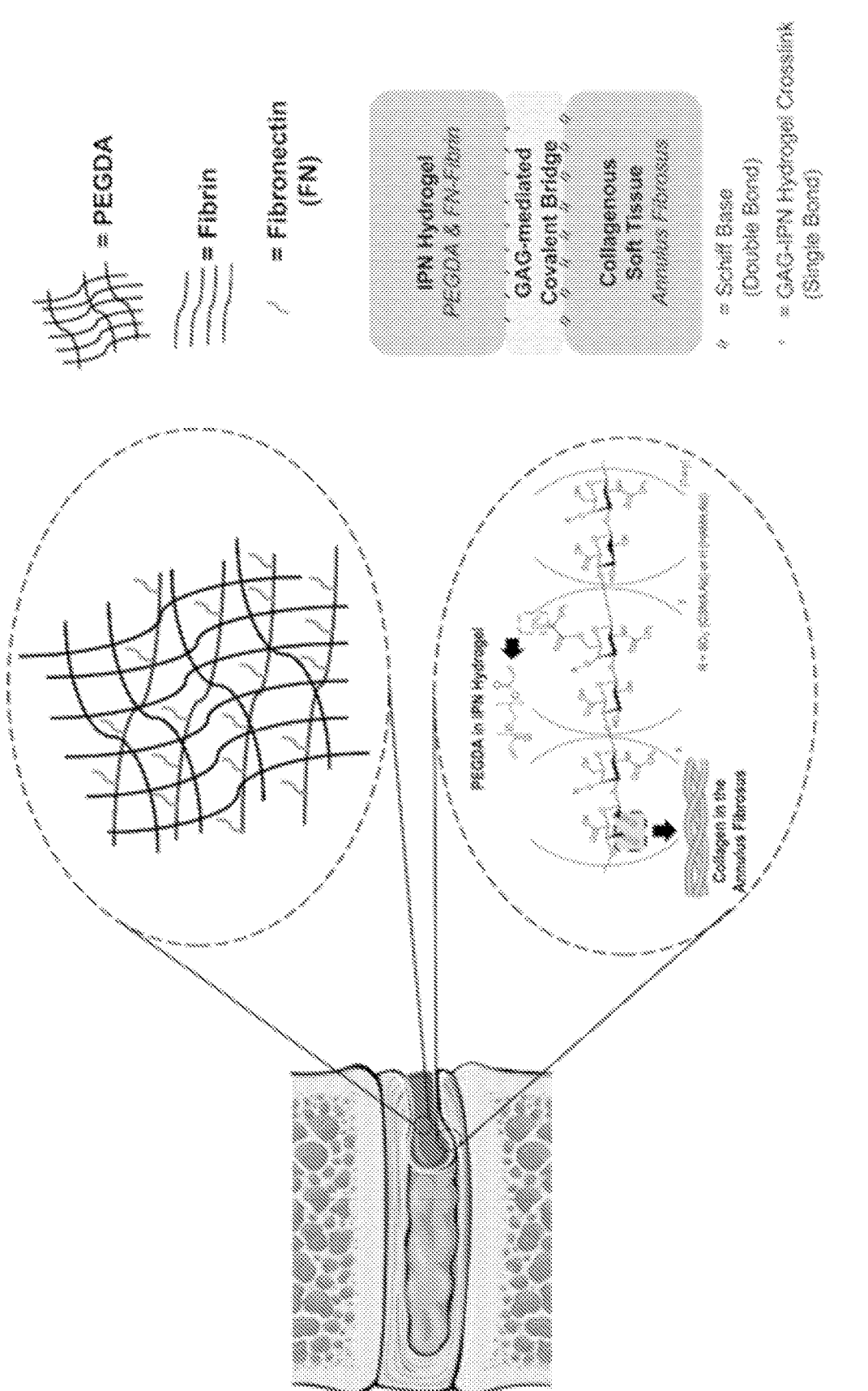
Figure 16C:
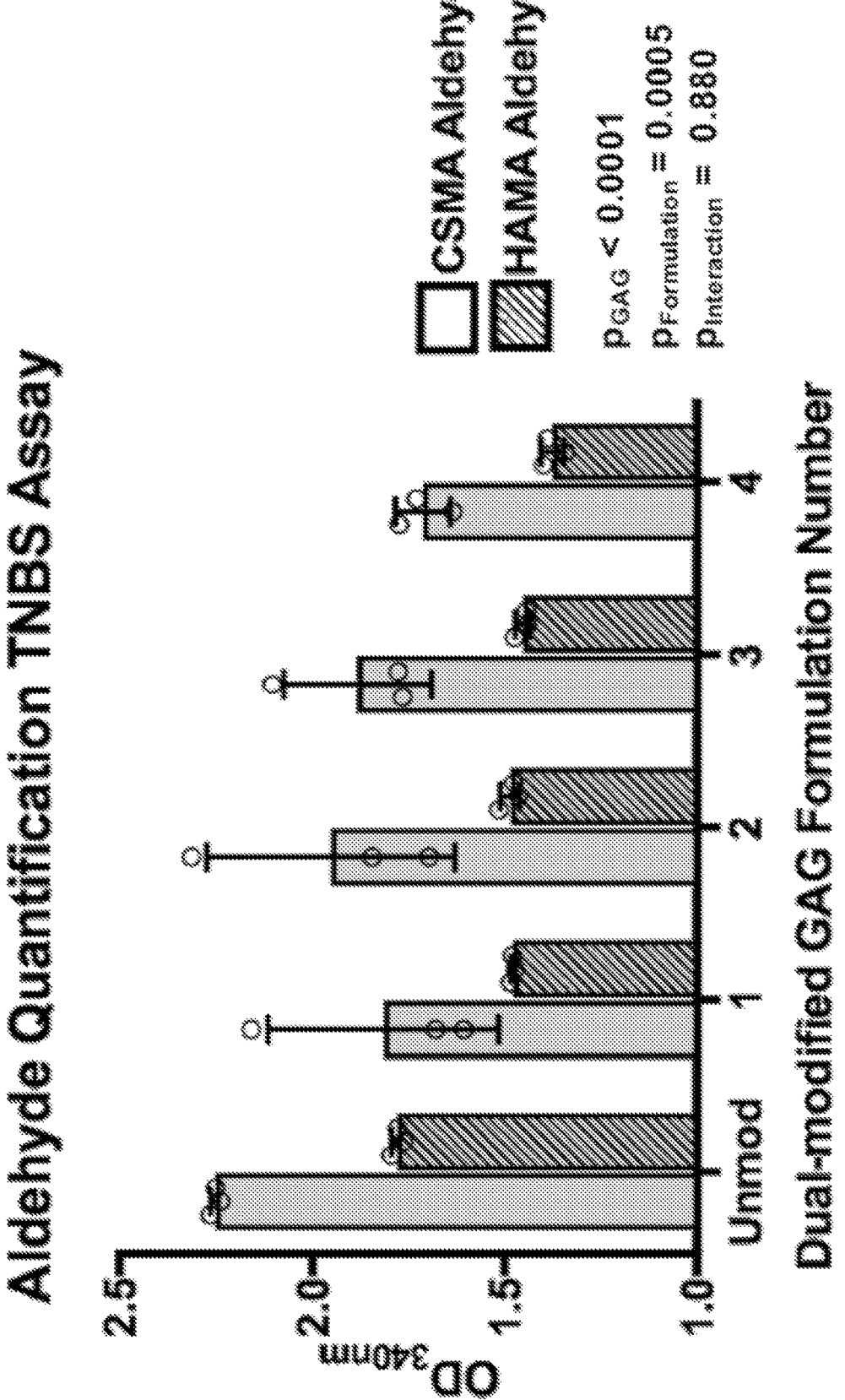
Figure 16D:
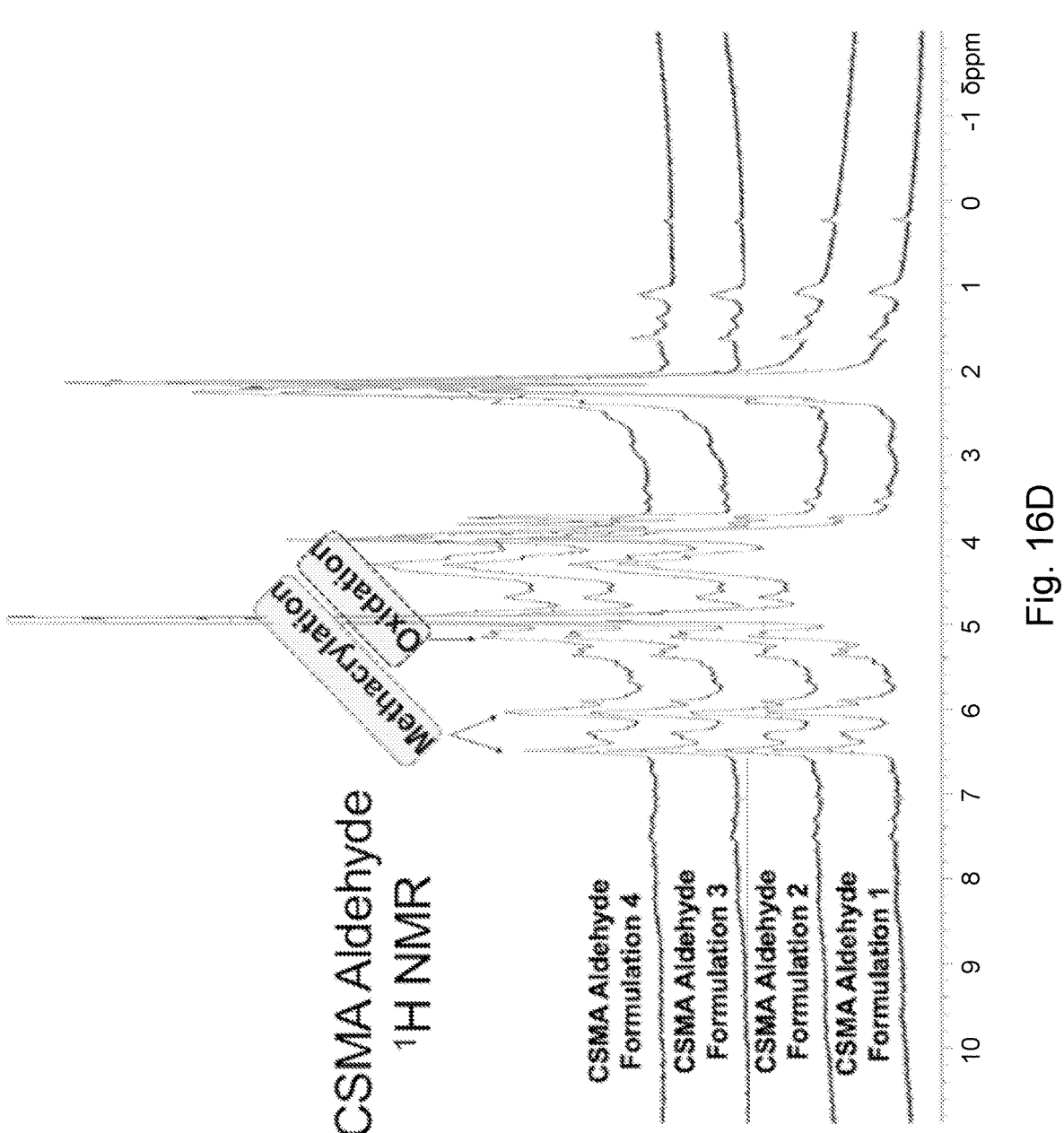
Figure 16E:
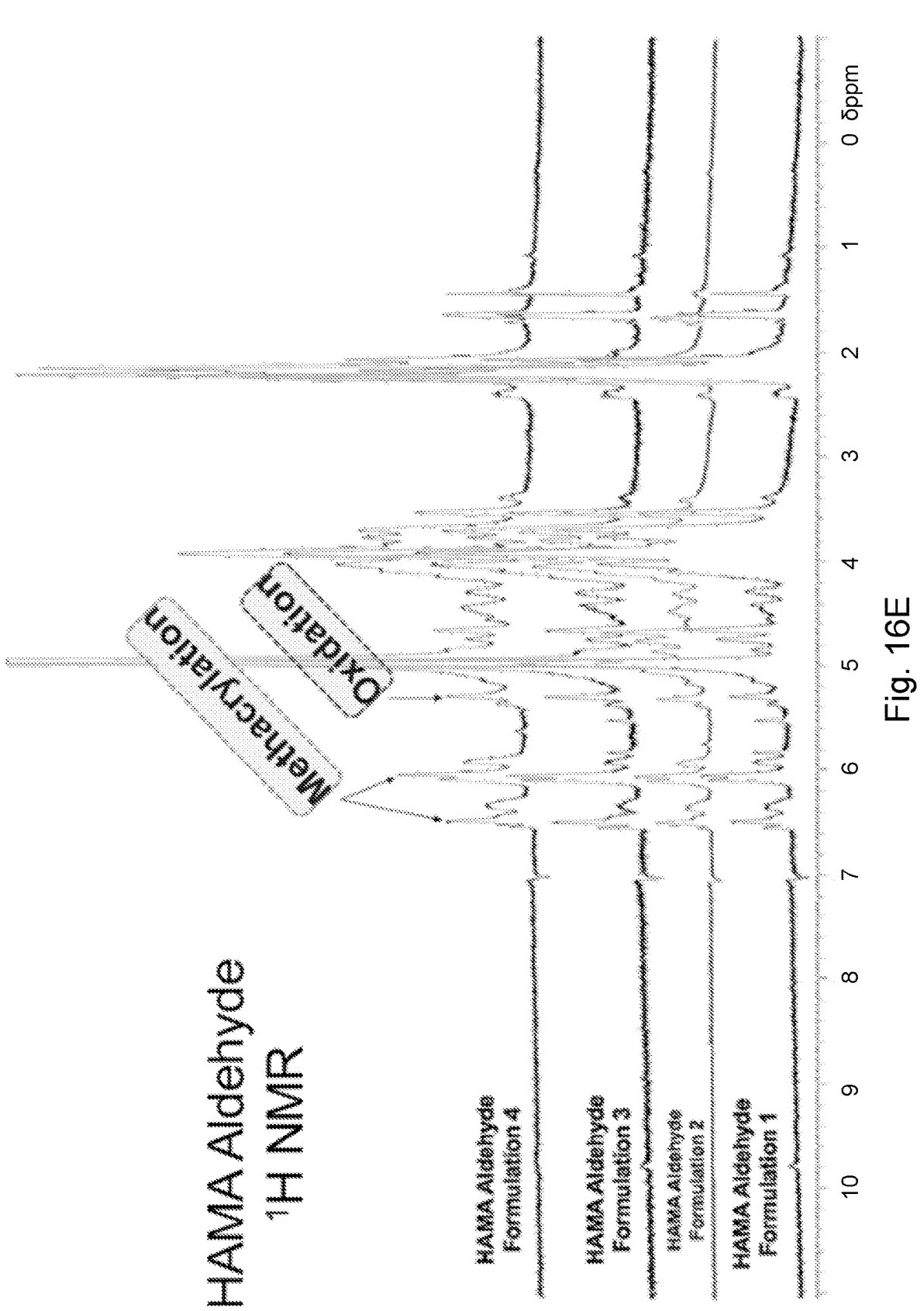

The compositions and methods described herein address adhesion and bulk material properties in IVD tissue engineering by providing a two-part strategy for AF repair composed of: (1) an interpenetrating network (IPN) hydrogel comprising synthetic (poly(ethylene glycol) diacrylate/PEGDA) and natural (fibronectin-conjugated fibrin/FN-Fibrin) polymer networks, and (2) a dual-modified (oxidized and methacrylated) glycosaminoglycan (GAG) that covalently bonds this injectable hydrogel to extracellular matrix proteins in the IVD. (FIG. 15).

As demonstrated in the Examples provided below, a three-part strategy was used to develop the systems and methods disclosed herein: (1) the adhesive properties of the tissue-hydrogel interface were optimized by screening across sulfated and unsulfated GAGs and enhancing degrees of GAG methacrylation and oxidation, (2) cytocompatibility of the optimal dual-modified GAG product used to bond the void-filling hydrogel to AF tissue was assessed, and (3) the method of AF repair was scaled to a large animal model of simulated discectomy ex vivo and determine the effect of hydrogel elasticity on implant herniation risk. Without being bound by any particular theory, dual-modified GAG products with the highest biochemical degrees of modification should impart the greatest hydrogel adhesion strength with no demonstrable cytotoxicity. Furthermore, repairing AF defects with mechanically compliant hydrogels should exhibit a lower risk of implant herniation than stiffer, less compliant hydrogels and match the herniation risk of the clinical standard of care. Accordingly, in some embodiments, chondroitin sulfate (CS) or hyaluronic acid (HA) is oxidized and methacrylated. The Examples provided herein show systematic quantification of these modifications, including their extents of conversion and adhesive strengths to AF tissue, given the same reaction stoichiometries. In some embodiments, this two-part repair strategy is applied to a discectomy model for AF repair. In some embodiments, the effect of hydrogel mesh size is evaluated for its effects on IVD herniation risk.

Accordingly, in some embodiments, the disclosure provides a two-part repair strategy to seal annular defects composed of an interfacial priming agent, a dual-modified GAG, that coats tissue surfaces and a void-filling IPN hydrogel system composed of both natural and synthetic networks that can chemically adsorb to IVD tissue through the dual-modified GAG compound. A similar strategy to bond injectable hydrogels to soft musculoskeletal tissues via dual-modified CS was first developed for articular cartilage repair, but this approach has neither been translated nor optimized with an analogous use of dual-modified HA for AF repair, which requires engineered constructs to endure distinct biomechanical loads and higher deformations for successful translation. [32,49-51] Since outcomes following articular cartilage repair do not inform the likelihood of success in AF repair due to differences in biomechanical behavior, a biomechanical evaluation of construct herniation risk using an ex vivo bovine IVD model of simulated discectomy was necessary in order to determine the integrative strength of this repair strategy after its application to AF defects. [18,52] The Examples show for the first time: (1) unsulfated GAGs (e.g., HA) undergo higher oxidation than sulfated counterparts (e.g., CS) given the same reaction stoichiometry, and impart greater biomaterial adhesion when applied to AF tissue surfaces; (2) the optimized dual-modified GAG, HAMA Aldehyde, was not cytotoxic; and (3) softer/more compliant hydrogel constructs bear a lower herniation risk than stiffer/less compliant constructs of the same material composition. It was surprising that these softer hydrogels had lower herniation risk because the dogma in the literature was that hydrogels should match the native properties of the soft tissue, e.g., the annulus fibrosus being repaired.

When developing this strategy for AF repair, tissue integration of injectable hydrogels was prioritized as the prominent clinical design requirement so as to minimize the risk of reherniation and thereby decrease the probability of reoperation. First, the adhesion strength between the IPN hydrogel and AF tissue was optimized by means of biochemical modifications incorporated on the dual-modified GAG. As shown in the Examples, different reaction stoichiometries produced dual-modified GAG formulations with varying degrees of methacrylation and oxidation, where it was observed that these parameters did not linearly correspond to the GAG:IO$_4^-$ and GAG:MAH molar ratios. When comparing lap shear adhesion strength across GAG type, treatment of AF tissue with dual-modified HA yielded significantly greater hydrogel adhesion than treating AF tissue with dual-modified CS across all formulations screened herein. Relating this outcome to the biochemical degrees of modification, dual-modified HA had an equal or greater degree of oxidation compared to dual-modified CS whereas dual-modified CS had an equal or greater degree of methacrylation compared to dual-modified HA across all formulations screened herein. Additionally, when comparing the coefficients of determination (R$^2$) between ultimate stress and degrees of modification, the ultimate stress was more strongly correlated with the degree of oxidation than the degree of methacrylation (R$^2_{HA}$, Oxidation=0.88 versus R$^2_{HA}$, Methacrylation=0.76, and R$^2_{CS}$, Oxidation=0.63 versus R$^2_{CS}$, Methacrylation=0.49), irrespective of GAG type. This outcome suggests that GAG oxidation has a greater influence on biomaterial adsorption to tissue surfaces than GAG methacrylation.

Without being bound by any particular theory, this may be explained by the formation of two covalent double bonds via Schiff base formation between the two aldehyde moieties per GAG repeat unit of the dual-modified GAG and primary amines on extracellular matrix proteins in the IVD, versus the single covalent bond formed between the methacrylate group per GAG repeat unit and acrylate end group on the PEGDA macromer in the hydrogel when exposed to APS/TEMED redox initiators. A potential biochemical factor that may explain why HA exhibited greater degrees of oxidation than CS following the two-step reaction scheme, given the same stoichiometries, is the presence of sulfate groups at the C4 position on the GalNAc subunit of CS; sulfate groups may limit the extent of conversion in the first reaction step, where other studies demonstrated greater oxidation for HA compared to a similar carbohydrate, dextran sulfate. [33] Notably, this is the first disclosure of combining simultaneous impart these two biochemical modifications to the HA backbone and implementing this system for bioadhesive tissue engineering applications. Advantageously, the disclosure provides improved methods and systems using simultaneous oxidation and methacrylation with analogous polysaccharides by quantifying and systematically comparing the biochemical degrees of oxidation and methacrylation as well as bioadhesivity between dual-modified HA and dual-modified CS. [32, 49, 50, 53]

When contextualizing these results to other studies that use bioadhesive hydrogels for AF repair, this approach yields comparatively higher lap shear adhesion strengths than riboflavin-crosslinked collagen and genipin-crosslinked fibrin. [54,55] When compared to studies that use oxidized and/or methacrylated materials, it is demonstrated in the Examples that this method matches or exceeds lap shear adhesion strengths with respect to single-crosslinked OMA-9/PEG (2 kPa), dual-crosslinked OMA-20/PEG (15 kPa), PNIPAAm-g-CS+CS aldehyde (≤2 kPa), but is lower than that in the original Wang et al. study reporting the use of CSMA Aldehyde as a tissue adhesive (46 kPa). [32,38,56] It should be noted that the stoichiometries used to synthesize dual-modified CS Formulation 1 in the Examples correspond to theoretical degrees of methacrylation higher than that reported in Wang et al., given the higher efficiency of methacrylic anhydride versus glycidyl methacrylate reported by Bryant et al., yet it was observed that this product of CSMA Aldehyde only imparts an average adhesion strength of 9.51 kPa with AF tissue. [35] These differences in observed outcomes might be attributed to dissimilarities in tissue composition and surface topography between cartilage and the AF, which are known to affect bonding at the tissue-biomaterial interface and thus impact adhesion strength values. [57]

Following the optimization of interfacial adhesion strength, the Examples assess motion segment herniation risk with hydrogel implants of varying mechanical molecular weight to test the hypothesis that hydrogel elasticity is a critical factor impacting herniation strength in situ. It was found that compliance of the hydrogel system, while keeping material composition constant, plays a considerable role in failure mechanics of the motion segment as well as the mechanism by which the motion segment fails. Surprisingly, mechanically compliant hydrogels (low Young's modulus and high PEGDA MW) bear a lower herniation risk than less compliant implants (high Young's modulus and low PEGDA MW). While modifying MW, PEGDA concentration was maintained constant at 15% (v/v) in the IPN hydrogel system to eliminate volumetric concentration as a confounder. For IVDs that were repaired with IPN hydrogels comprising 20 kDa PEGDA, there was no statistical difference when compared to intact failure properties with respect to subsidence-to-IVD failure and failure strain, suggesting that partial restoration was achieved with this two-part repair strategy. Moreover, there was no statistical difference between this repair group and the discectomy condition for all mechanical output measures, suggesting that non-inferiority to the surgical standard of care was demonstrated. For IVD motion segments that were repaired with either 575 Da or 10 kDa PEGDA in the IPN hydrogel, it was observed that failure occurred at the tissue-hydrogel interface and the entire hydrogel would dislodge from the defect space upon NP pressurization. IVD motion segments that were repaired with IPN hydrogels containing 20 kDa PEGDA had a distinctly different failure mechanism, where the hydrogel would deform and NP tissue gradually displaced through pores of the polymeric network, eventually inducing a mid-substance failure that led to NP protrusion from the outer AF. In the post-failure state, these specimens retained the IPN hydrogel within the repair site and the hydrogel was still adherent to the AF, indicating that the interfacial bonding was not compromised during motion segment ramp-to-failure. Taken together, these outcomes show that AF repair with a soft (e.g., high MW) hydrogel mitigates IVD herniation risk compared to stiff (e.g., low MW) hydrogels since the construct has the ability to continuously deform with the motion segment under loading, whereas stiff hydrogels that match AF properties cannot deform with the motion segment and quickly herniate from the repair site. Since mesh size of the construct is proportional to the MW of the macromer, the IPN hydrogel with the largest MW PEGDA (20 kDa) tested allowed for displacement of NP tissue through the pores of the hydrogel, reducing stresses at the interface and resulting in mid-substance failure. In contrast, IPN hydrogels of 575 Da and 10 kDa PEGDA had mesh sizes too small to support physical dislocation of NP through the biomaterial, giving rise to interface failure and hydrogel extrusion with comparatively higher risk of herniation. Moreover, this unexpected finding that hydrogel mesh size has a larger influence in mitigating herniation risk than matching native AF properties has critical implications for AF repair. Matching native AF tissue properties is historically thought to be the gold standard of AF tissue engineering with the primary goal of restoring biomechanical function. This disclosure identifies that soft-deformable hydrogels feature a comparatively lower herniation risk and are more effective as sealants to prevent recurrent herniation with potential uses as a delivery vehicle for cells and/or bioactive factors.

Functionally important biological assessments, such as annulocyte cytocompatibility with the biomaterials comprising this repair strategy, were completed following biomechanical tests. Since fibronectin and fibrin are natural biopolymers, they are inherently cytocompatible and used in FDA-approved sealants that are commercially available, including TISSEEL. [58,59] In addition to synthetic tunability and functional moieties that enable hydrogel bonding, PEGDA was employed in this strategy because PEG-based materials have extensively been shown to be biocompatible and are FDA-approved for use in humans as well. [60] Although the constitutive polymer networks of the hydrogel are biocompatible, it has yet to be determined if the oxidized and methacrylated HA priming agent in this repair strategy is non-cytotoxic to AF cells. Results from the cell viability assay suggest that there is no demonstrable cytotoxicity to AF cells when exposed to HAMA Aldehyde product at the working concentrations (and lower) used in this repair. 1 hour of exposure was chosen as the timepoint for AF cell viability measurements, since it is substantially longer than the 5-minute application period in our workflow and would account for both acute and relatively long-term exposure to the dual-modified HA product. It was observed that there was a significant increase in viability measured at 10 μM and 20 μM, indicating some benefit of HAMA Aldehyde for cell survival. These findings may be attributed to an increase in cell proliferation when exposed to HAMA Aldehyde at these concentrations, which can be elicited downstream through CD44 (homing cell adhesion molecule) intracellular signaling. [61] CD44 is a non-kinase transmembrane glycoprotein that binds to unconverted regions of HAMA Aldehyde and can promote a proliferative response through the PI3K/AKT pathway. [62] Moreover, it was observed that there was a significant decrease in viability at a concentration of 100 μM HAMA Aldehyde, which may suggest that the culture conditions were too acidic for AF cell survival, as indicated by a change in the phenol red indicator of culture media from red to yellow.

With respect to clinical utility, the ease-of-application and required time for repair were prominent factors of consideration when developing this strategy. The injectability of the prepolymer solutions lends itself to a minimally invasive approach for AF repair, in which the biomaterials can be easily applied to defect spaces of human or large animal model IVDs. When considering clinical utility in the context of the simulated discectomy model described herein, 25% of NP tissue was removed to enhance biomaterial delivery to the repair site as well as mitigate the risk of recurrent herniation following repair, since NP removal is known to increase IVD failure strength. [44] This outcome is validated by Carragee et al., in which patients that undergo a more aggressive discectomy procedure with NP removal demonstrate a lower reherniation rate (9%) than those without any NP removal (18%). [63] Moreover, the APS/TEMED redox initiator system used for macromer crosslinking can overcome issues regarding cure depth for UV-catalyzed photopolymerization in situ. [64] The current repair workflow takes approximately 7 minutes to apply this two-part biomaterial adhesive given the timescales of HAMA Aldehyde bonding and hydrogel gelation (FIG. 15), and considering the average length of discectomy procedures is approximately 78 minutes, this procedure would only extend surgical time by approximately 9%. [65] Taken together, this strategy is expected to be an effective, cytocompatible method of repairing AF defects within a reasonable timeframe.

Definitions

Unless defined otherwise, all technical and scientific terms used herein have the meaning commonly understood by a person skilled in the art to which this invention belongs. The following references provide one of ordinary skill in the art with a general definition of many of the terms used herein: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Mahram, The Harper Collins Dictionary of Biology (1991); Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the presently disclosed subject matter. As used herein, the following terms have the meanings ascribed to them below, unless specified otherwise.

As used herein, "fibrocartilage" refers to a mixture of white fibrous tissue and cartilaginous tissue. Generally, fibrocartilage contains both type I and type II collagen. Fibrocartilage is found in various locations in the human body including, without limitation, secondary cartilaginous joints (such as the pubic symphysis, the annulus fibrosus of intervertebral discs, and the manubriosternal joint), the glenoid labrum of shoulder joints, the acetabular labrum of hip joints, the medial and lateral menisci of knee joints, and generally where tendons and ligaments attach to bone.

As used herein, "glycosaminoglycan" refers to a molecule having a linear polysaccharide of repeating disaccharide (double sugar) units. Accordingly, as used herein, a glycosaminoglycan includes both linear polysaccharides of repeating disaccharide units and larger molecules that include linear polysaccharides of repeating disaccharide units, such as proteoglycans. Non-limiting classes of glycosaminoglycans, as defined herein, include keratin sulfate type glycosaminoglycans (such as keratin sulfate and derivatives thereof), hyaluronic type glycosaminoglycans (such as hyaluronic acid and derivatives thereof), Heparin/heparan sulfate type glycosaminoglycans (HSGAGs; such as heparin, heparan sulfate, and derivatives thereof), chondroitin sulfate/dermatan sulfate type glycosaminoglycans (CSGAGs; such as chondroitin sulfate, dermatan sulfate, and derivatives thereof), and proteoglycans thereof (e.g., decorin, biglycan, testican, bikunin, fibromodulin, lumican, and derivatives thereof). In some embodiments, the glycosaminoglycan is a natural glycosaminoglycan, e.g., that is purified from a biological source. In some embodiments, the glycosaminoglycan is a synthetic glycosaminoglycan, e.g., that is chemically synthesized.

As used herein, the term "subject" refers to any animal (e.g., a mammal), including, but not limited to, humans, and non-human animals (including, but not limited to, non-human primates, dogs, cats, rodents, horses, cows, pigs, mice, rats, hamsters, rabbits, and the like (e.g., which is to be the recipient of a particular treatment, or from whom cells are harvested). In preferred embodiments, the subject is a human. The terms "subject" and "patient" are used interchangeably herein.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease condition, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

System for Repairing a Fibrocartilage Defect

The ability of a hydrogel to function as a surgical sealant and adhesive is contingent on the extent of integration with the native tissue, where integration is formally defined as the connectivity between two materials of homogenous or disparate composition. Integration is conceptually focused on the biological interface between the tissue in need of repair and an implantable hydrogel system. Although large efforts have been spent on the development of hydrogel systems as viable substrates for tissue engineering applications in vitro, far less scientific attention has been directed at the interface between these hydrogel systems and tissue of interest. Yet, the potential for clinical translation is dependent on establishing a durable connection at the tissue-biomaterial interface so as to ensure construct longevity and satisfactory postoperative performance. As tissue engineering and regenerative medicine strategies advance towards clinical applications in orthopaedics, emphasis should be placed on the role of biomaterial-tissue interfaces to ensure translational success. Given the musculoskeletal system's primary roles in providing structural support, distributing internal loads, and enabling locomotion, it is critical to form and maintain a robust interface between the biomaterial and tissue surface. Successful integration should render sturdy biological fixation that manifests in hydrogel immobilization in situ, thereby enabling immediate tissue functionality upon implantation. Advantageously, the present disclosure provides hydrogel systems with robust biomaterial-tissue interfaces mediated through a polymer that chemical bonds to both the tissue being repaired and the hydrogel.

Accordingly, in one aspect, the disclosure provides a system for repairing a fibrocartilage defect. The system includes an oxidized and methacrylated polymer, e.g., a glycosaminoglycan, that bridges a damaged tissue with a hydrogel by covalently bonding to each. Specifically, the oxidized and methacrylated glycosaminoglycan is applied to the damaged tissue and forms Schiff bases with accessible primary amines on extracellular matrix proteins in the tissue. The system also includes a pre-polymer hydrogel composition containing at least one cross-linking unit, e.g., at least one macromer, having a vinyl group that is amenable to polyacrylamide polymerization with the methyacrylate group of the modified glycosaminoglycan, e.g., in the presence of redox initiators or photocrosslinked w/UV light. Accordingly, the pre-polymer hydrogel composition forms a hydrogel at the site of the fibrocartilage damage, which is held in place through covalent bonds to the anchored glycosaminoglycan.

In some embodiments, the systems, methods, and kits described herein facilitate repair of damaged soft tissue within the musculoskeletal system, such as damage at annulus fibrosus of intervertebral discs. However, these systems, methods, and kits are not limited to these applications and can be used to repair damage at any location containing fibrocartilage, including at secondary cartilaginous joints (such as the pubic symphysis, the annulus fibrosus of intervertebral discs, and the manubriosternal joint), the glenoid labrum of shoulder joints, the acetabular labrum of hip joints, the medial and lateral menisci of knee joints, and generally where tendons and ligaments attach to bone.

Generally, any glycosaminoglycan can be used in the systems, methods, and kits described herein to link the hydrogel to the soft tissue, e.g., to tissue containing fibrocartilage. Moreover, in some embodiments, the glycosaminoglycan is a glycosaminoglycan composition containing two or more types of glycosaminoglycan. The only requirement is that a glycosaminoglycan is oxidized and methacrylated, to facilitate bonding to both the soft tissue and the hydrogel. In some embodiments, the glycosaminoglycan composition includes a keratin sulfate type glycosaminoglycan. In some embodiments, the keratin sulfate type glycosaminoglycan is keratin sulfate. In some embodiments, the glycosaminoglycan composition includes a hyaluronic type glycosaminoglycan. In some embodiments, the hyaluronic type glycosaminoglycan is hyaluronic acid. In some embodiments, the glycosaminoglycan composition includes a Heparin/heparan sulfate type glycosaminoglycan. In some embodiments, the Heparin/heparan sulfate type glycosaminoglycan is heparin. In some embodiments, the Heparin/heparan sulfate type glycosaminoglycan is heparan sulfate. In some embodiments, the glycosaminoglycan composition includes a chondroitin sulfate/dermatan sulfate type glycosaminoglycan. In some embodiments, the chondroitin sulfate/dermatan sulfate type glycosaminoglycan is chondroitin sulfate. In some embodiments, the chondroitin sulfate/dermatan sulfate type glycosaminoglycan is dermatan sulfate. In some embodiments, the glycosaminoglycan composition includes a proteoglycan. In some embodiments, the proteoglycan is decorin. In some embodiments, the proteoglycan is biglycan. In some embodiments, the proteoglycan is testican. In some embodiments, the proteoglycan is bikunin. In some embodiments, the proteoglycan is fibromodulin. In some embodiments, the proteoglycan is lumican.

Further, in some embodiments, a polysaccharide/carbohydrate other than a glycosaminoglycan can be used in place of, or in addition to, a glycosaminoglycan to chemically bridge the soft tissue to the hydrogel. Thus, in some embodiments, the systems described herein include an oxidized and methacrylated polysaccharide/carbohydrate to bridge a damaged tissue with a hydrogel by covalently bonding to each, in an analogous fashion to that described above for glycosaminoglycan.

Generally, the dual-modified polymers e.g., a glycosaminoglycan or other polysaccharide/carbohydrate, used in the systems, methods, and kits described herein must be sufficiently oxidized to facilitate binding to the damaged tissue. Accordingly, in some embodiments, the dual modified polymer is at least 10% oxidized. In some embodiments, the dual modified polymer is at least 20% oxidized. In some embodiments, the dual modified polymer is at least 30% oxidized. In some embodiments, the dual modified polymer is at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% oxidized. In some embodiments, the degree of oxidation of the oxidized and methacrylated polymer, e.g., glycosaminoglycan, is from 10% to 80%. In some embodiments, the degree of oxidation of the oxidized and methacrylated polymer, e.g., glycosaminoglycan, is from 15% to 70%. In some embodiments, the degree of oxidation of the oxidized and methacrylated polymer, e.g., glycosaminoglycan, is from 15% to 60%. In some embodiments, the degree of oxidation of the oxidized and methacrylated polymer, e.g., glycosaminoglycan, is from 15% to 50%. In some embodiments, the degree of oxidation of the oxidized and methacrylated polymer, e.g., glycosaminoglycan, is from 15% to 45%. In some embodiments, the degree of oxidation of the oxidized and methacrylated polymer, e.g., glycosaminoglycan, is from 20% to 50%. In some embodiments, the degree of oxidation of the oxidized and methacrylated polymer, e.g., glycosaminoglycan, is from 20% to 45%. Methods for oxidizing suitable polymers are known in the art. See, for example, Wang D A, et al., Nat. Mater., 6:385-92 (2007); and Purcell B P, et al., Nat. Mater., 13:653-61 (2014), the contents of which are disclosed herein by reference, in their entireties, for all purposes. Example 2 describes a particular method for oxidizing a glycosaminoglycan.

Generally, the dual-modified polymers e.g., a glycosaminoglycan or other polysaccharide/carbohydrate, used in the systems, methods, and kits described herein must be sufficiently methacrylated to facilitate binding to the damaged tissue. Accordingly, in some embodiments, the dual modified polymer is at least 20% methacrylated. In some embodiments, the dual modified polymer is at least 30% methacrylated. In some embodiments, the dual modified polymer is at least 40% methacrylated. In some embodiments, the dual modified polymer is at least 20%, at least 25%, at least 30%, at least 35%, at least 40%, at least 45%, at least 50%, at least 55%, at least 60%, at least 65%, at least 70%, at least 75%, or at least 80% methacrylated. In some embodiments, the degree of methacrylated of the oxidized and methacrylated polymer, e.g., glycosaminoglycan, is from 20% to 80%. In some embodiments, the degree of methacrylated of the oxidized and methacrylated polymer, e.g., glycosaminoglycan, is from 25% to 80%. In some embodiments, the degree of methacrylated of the oxidized and methacrylated polymer, e.g., glycosaminoglycan, is from 30% to 80%. Example 3 describes a particular method for methacrylating a glycosaminoglycan. However, other methods for methacrylating suitable polymers are known in the art. See, for example, Burdick J A et al., Biomacromolecules, 6:386-91 (2005); and Bryant S J et al., Macromolecules, 37:6726-33 (2004), the contents of which are disclosed herein by reference, in their entireties, for all purposes.

The pre-polymer hydrogel compositions used in the systems described herein include a crosslinking unit suitable for forming a hydrogel in situ. In some embodiments, hydrogels are formed by cross-linking crosslinking units, e.g., macro (mono)mers, forming hydrophilic macromolecules, which typically do not form mechanically strong intermolecular bonds due to a lack of strong disperse interactions. In some embodiments, the pre-polymer hydrogel composition includes a single type of crosslinking unit. In other embodiments, the pre-polymer hydrogel composition includes multiple types of crosslinking units, e.g., at least 2, 3, 4, 5, 6, 7, 8, 9, 10, or more different types of crosslinking units. For a review of multi-functional macromers useful for hydrogel formation see, for example, Hacker M C and Nawaz H A, Int J Mol Sci., 16(11):27677-706 (2015), the content of which is disclosed herein by reference, in its entirety, for all purposes.

Many such hydrogel compositions are known in the art, any of which may be used in the methods, systems, and kits described herein. Generally, the only requirement of the pre-polymer hydrogel composition, is that at least one crosslinking unit in the composition has a vinyl group that is amenable to bonding to a pendant methacrylate group in the methacrylated polymer, e.g., the dual-modified glycosaminoglycan or dual-modified polysaccharide/carbohydrate. For a review of hydrogel compositions, preparatory methodology, and application see, for example, Ahmed E M, J Adv Res., 6(2):105-21 (2015), the content of which is disclosed herein by reference, in its entirety, for all purposes.

Non-limiting examples of hydrogels known in the art are provided below in Table 1. Generally, any one of these hydrogels can be implemented in the methods, systems, and kits provided herein for soft tissue repair, provided that they were modified to include a vinyl group for bonding to a pendant methacrylate group in the methacrylated polymer, e.g., dual-modified glycosaminoglycan, as does poly(ethylene glycol) diacrylate. Otherwise, the skilled artisan will know how to modify a hydrogel provided below in order to incorporate such a vinyl group for bonding to the methacrylated polymer.

TABLE 1

Example hydrogels

| Hydrogel Composition | Abbreviation |
|---|---|
| Genipin-crosslinked fibrin | FibGen |
| Riboflavin-crosslinked collagen | RF-Collagen |
| Rose Bengal-crosslinked collagen | RB-Collagen |
| poly(ethylene glycol)-poly(trimethylene carbonate)-hexamethylene diisocyanate | PEG400-TMC3-HDI |
| Albumin/Glutaraldehyde | BioGlue ® |
| n-butyl cyanoacrylate (n-BCA) and octyl cyanoacrylate (OCA) | Cyanoacrylate/ LiquiBand ® |
| citric acid-1-ethyl-3-(3-dimethylaminopropyl) carbodiimide/N-hydroxysuccinimide type I collagen | CA-EDC/NHS collagen |
| 1-(3-dimethylaminopropyl)-3-ethyl-carbodiimide hydrochloride-crosslinked gelatin/poly(γ-glutamic acid) | EDC-Gelatin-γPGA |
| Fibrin | Fibrin |
| poly(lactic-co-glycolic acid)/fibrin | PLGA/Fibrin |
| poly(lactic-co-glycolic acid) | PLGA |
| Alginate/Collagen | Alginate-Collagen |
| Alginate | Alginate |
| Hyaluronic acid | HA |
| Hyaluronic acid/Albumin | HA/Albumin |
| Ultrapurified alginate | UPAL |
| Cellulose nanofiber-reinforced chitosan | CNF/CHI |
| poly(ethylene glycol) diacrylate | PEGDA |

Other examples of suitable hydrogel compositions for use in the systems, methods, and kits described herein include gelatin methacrylate (GelMA)-based hydrogels, which contain vinyl groups that are available for bonding to a pendant methacrylate group in the methacrylated polymer, e.g., dual-modified glycosaminoglycan. For review, see, Xiao S. et al., Stem Cell Rev Rep., 15(5):664-79 (2019), the content of which is incorporated herein by reference, in its entirety, for all purposes. Other multi-functional macromers suitable for use in the systems, methods, and kits described herein, including those containing vinyl groups that are available for bonding to a pendant methacrylate group in the methacrylated polymer, e.g., dual-modified glycosaminoglycan, are described in Hacker M C and Nawaz H A, Int J Mol Sci., 16(11):27677-706 (2015), the content of which is incorporated herein by reference, in its entirety, for all purposes. Similarly, human protein-based hydrogels may find use in the systems, methods, and kits described herein. See, for example, Annabi N. et al., Sci Transl Med., 9(410):eaai7466 (2017), the content of which is incorporated herein by reference, in its entirety, for all purposes. Yet other examples of cross-linked hydrogels that can be used for the systems, methods, and kits described herein are described in Parhi R., Adv Pharm Bull., 7(4):515-30 (2017), the content of which is incorporated herein by reference, in its entirety, for all purposes.

In some embodiments, the pre-polymer hydrogel composition includes a macromer having an average molecular weight of from 250 Da to 80 kDa. In some embodiments, the macromer has an average molecular weight of from 250 Da to 40 kDa. In some embodiments, the macromer has an average molecular weight of from 500 Da to 40 kDa. In some embodiments, the macromer has an average molecular weight of from 1 kDa to 40 kDa. In some embodiments, the macromer has an average molecular weight of from 5 kDa to 40 kDa. In some embodiments, the macromer has an average molecular weight of from 10 kDa to 40 kDa. In some embodiments, the macromer has an average molecular weight of from 1 kDa to 25 kDa. In some embodiments, the macromer has an average molecular weight of from 5 kDa to 25 kDa. In some embodiments, the macromer has an average molecular weight of from 10 kDa to 25 kDa. In some embodiments, the macromer has an average molecular weight of from 15 kDa to 25 kDa. In some embodiments, the macromer has a molecular weight of about 20 kDa. In some embodiments, the macromer has an average molecular weight of about 250 Da, about 500 DA, about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, or another value within the range of 250 Da to 80 kDa. Generally, the properties of the hydrogel formed by cross-linking of the macromer is dependent upon both the material properties of the mocromer and the average molecular weight of the macromer.

In one embodiment, the pre-polymer hydrogel composition includes poly(ethylene glycol) diacrylate (PEGDA). In some embodiments, the PEGDA has an average molecular weight of from 250 Da to 80 kDa. In some embodiments, the PEGDA has an average molecular weight of from 250 Da to 40 kDa. In some embodiments, the PEGDA has an average molecular weight of from 500 Da to 40 kDa. In some embodiments, the PEGDA has an average molecular weight of from 1 kDa to 40 kDa. In some embodiments, the PEGDA has an average molecular weight of from 5 kDa to 40 kDa. In some embodiments, the PEGDA has an average molecular weight of from 10 kDa to 40 kDa. In some embodiments, the PEGDA has an average molecular weight of from 1 kDa to 25 kDa. In some embodiments, the PEGDA has an average molecular weight of from 5 kDa to 25 kDa. In some embodiments, the PEGDA has an average molecular weight of from 10 kDa to 25 kDa. In some embodiments, the PEGDA has an average molecular weight of from 15 kDa to 25 kDa. In some embodiments, the PEGDA has a molecular weight of about 20 kDa. In some embodiments, the PEGDA has an average molecular weight of about 250 Da, about 500 DA, about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, or another value within the range of 250 Da to 80 kDa.

In some embodiments, the macromer is present in the hydrogel at a final concentration of about 15% (v/v). In some embodiments, the macromer is present in the hydrogel at a final concentration of from 10% (v/v) to 20% (v/v). In some embodiments, the macromer is present in the hydrogel at a final concentration of from 12.5% (v/v) to 17.5% (v/v). In some embodiments, the macromer is present in the hydrogel at a final concentration of 8%, 9%, 10%, 11%, 12%, 13%, 14%, 16%, 17%, 18%, 19%, 20%, 21%, 22%, 23%, 24%, 25%, 26%, 27%, 28%, 29%, 30%, or higher.

In some embodiments, the pre-polymer hydrogel composition includes poly(ethylene glycol) diacrylate (PEGDA) having an average molecular weight of from 15 kDa to 25 kDa and is present in the hydrogel at a final concentration of from 12.5% (v/v) to 17.5% (v/v).

In some embodiments, upon cross-linking, the pre-polymer hydrogel composition forms a single network hydrogel. In other embodiments, upon cross-linking, the pre-polymer hydrogel composition forms an interpenetrating network hydrogel. In some embodiments, the interpenetrating network hydrogel is incorporated to integrate integrin recognition sites that facilitate cellular migration into the construct. For example, in some embodiments, the interpenetrating network hydrogel includes a fibronectin-conjugated fibrin network. This can be achieved, for example, by including fibronectin, Factor XIII, and thrombin in the pre-polymer hydrogel composition. However, any secondary network can serve as the interpenetrating network to achieve this purpose if cells can bind to that network. For a review of interpenetrating network hydrogels, see, for example, Matricardi P. et al., Adv Drug Deliv Rev., 65(9):1172-87 (2013); Zoratto N and Matricardi P, Adv Exp Med Biol., 1059:155-88 (2018); and Dragan E S, Chemical Engineering Journal, 243:572-90 (2014), the content of which is disclosed herein by reference, in its entirety, for all purposes.

In some embodiments, the systems, methods, and kits described herein include a hydrogel polymerization initiator that is mixed with the pre-polymer hydrogel composition to form the hydrogel, e.g., in situ. Many hydrogel polymerization initiator systems are known in the art. In some embodiments, because schiff base formation is reversible, and in acidic environments favors the reverse reaction, redox pairs that act in the physiological pH range or higher, e.g., at least pH 7.4, are selected to ensure the fidelity of bonds formed between the dual-modified polymer and the soft tissue. In some embodiments, the hydrogel polymerization initiator composition includes ammonium persulfate (APS) and N,N,N',N'-tetramethylethylenediamine (TEMED). However, many hydrogel polymerization initiator systems suitable for use in the systems, methods, and kits described herein are known in the art. In yet other embodiments, the hydrogel is formed by photo-polymerization, e.g., using UV irradiation to initiate hydrogel formation.

In some embodiments, the systems described herein are applied to a tissue defect in a two-step process. First, the soft tissue defect is coated with the composition containing the oxidized and methacrylated polymer, e.g., glycosaminoglycan or other polysaccharide/carbohydrate, to cause bonding between the polymer and the soft tissue, i.e., through Schiff base formation. In some embodiments, the contacting includes filling or partially filling, e.g., injecting, a soft tissue cavity comprising the defect, waiting for a sufficient time to allow formation of imine bonds between the polymer and the soft tissue, and then removing, e.g., aspirating, excess polymer that has not bonded to the soft tissue, e.g., to make room for the hydrogel. Generally, the dual-modified polymer sufficiently bonds with the soft tissue in less than five minutes. Second, the coated tissue defect is then filled with the pre-polymer hydrogel composition, which forms a hydro gel in situ that covalently bonds to the polymer, i.e., through polyacrylamide polymerization with the methyacrylate group of the polymer. In some embodiments, where a chemical activator is used to initiate hydrogel formation, a dual-barrel syringe, e.g., containing a volumetric mixing cap is used to inject a newly formed mixture of the pre-polymer hydrogel composition and a hydrogel polymerization initiator composition into the coated tissue defect.

Methods for Repairing a Fibrocartilage Defect

In one aspect, the disclosure provides methods for repairing a fibrocartilage defect by applying a two-part hydrogel system described herein at the defect sight. Generally, any system described above, including any combination of elements described above and modifications thereof, may be used in these methods.

In one embodiment, the method includes contacting the fibrocartilage defect with a first composition containing an oxidized and methacrylated polymer, e.g., a dual-modified glycosaminoglycan or other polysaccharide/carbohydrate, to form an imine bond between the glycosaminoglycan and the fibrocartilage defect, thereby coating the fibrocartilage defect with the polymer. The method then includes contacting the fibrocartilage defect coated with the polymer with a pre-polymer hydrogel composition containing a first cross-linking unit that, when cross-linked, e.g., polymerized, is capable of bonding to methacrylate, and initiating cross-linking, thereby forming a hydrogel that is covalently bonded to the polymer, e.g., glycosaminoglycan, through methacrylate. In this fashion, the hydrogel formed in situ is covalently linked to the site of the fibrocartilage defect through the polymer intermediate. In some embodiments, where cross-linking is initiated through chemical means, the fibrocartilage defect coated with the polymer is contacted with a mixture of the pre-polymer hydrogel composition and a hydrogel polymerization initiator composition, e.g., by using a dual-barrel syringe and volumetric mixing cap to form the mixture in situ.

In some embodiments, as described above, the method facilitates repair of damaged soft tissue within the musculoskeletal system, such as damage at annulus fibrosus of intervertebral discs. However, these methods are not limited to these applications and can be used to repair damage at any location containing fibrocartilage, including at secondary cartilaginous joints (such as the pubic symphysis, the annulus fibrosus of intervertebral discs, and the manubriosternal joint), the glenoid labrum of shoulder joints, the acetabular labrum of hip joints, the medial and lateral menisci of knee joints, and generally where tendons and ligaments attach to bone.

In some embodiments, as described above, the oxidized and methacrylated polymer is an oxidized and methacrylated glycosaminoglycan. Generally, any glycosaminoglycan can be used in these methods to link the hydrogel to the soft tissue, e.g., to tissue containing fibrocartilage. Moreover, in some embodiments, the glycosaminoglycan is a glycosaminoglycan composition containing two or more types of glycosaminoglycan. The only requirement is that a glycosaminoglycan is oxidized and methacrylated, to facilitate bonding to both the soft tissue and the hydrogel. In some embodiments, the glycosaminoglycan composition includes a keratin sulfate type glycosaminoglycan. In some embodiments, the keratin sulfate type glycosaminoglycan is keratin sulfate. In some embodiments, the glycosaminoglycan composition includes a hyaluronic type glycosaminoglycan. In some embodiments, the hyaluronic type glycosaminoglycan is hyaluronic acid. In some embodiments, the glycosaminoglycan composition includes a Heparin/heparan sulfate type glycosaminoglycan. In some embodiments, the Heparin/heparan sulfate type glycosaminoglycan is heparin. In some embodiments, the Heparin/heparan sulfate type glycosaminoglycan is heparan sulfate. In some embodiments, the glycosaminoglycan composition includes a chondroitin sulfate/dermatan sulfate type glycosaminoglycan. In some embodiments, the chondroitin sulfate/dermatan sulfate type glycosaminoglycan is chondroitin sulfate. In some embodiments, the chondroitin sulfate/dermatan sulfate type glycosaminoglycan is dermatan sulfate. In some embodiments, the glycosaminoglycan composition includes a proteoglycan. In some embodiments, the proteoglycan is decorin. In some embodiments, the proteoglycan is biglycan. In some embodiments, the proteoglycan is testican. In some embodiments, the proteoglycan is bikunin. In some embodiments, the proteoglycan is fibromodulin. In some embodiments, the proteoglycan is lumican.

Further, in some embodiments, a polysaccharide/carbohydrate other than a glycosaminoglycan can be used in place of, or in addition to, a glycosaminoglycan to chemically bridge the soft tissue to the hydrogel. Thus, in some embodiments, the methods use an oxidized and methacrylated polysaccharide/carbohydrate to bridge a damaged tissue with a hydrogel by covalently bonding to each, in an analogous fashion to that described above for glycosaminoglycan.

Generally, the dual-modified polymers e.g., a glycosaminoglycan or other polysaccharide/carbohydrate, used in these methods must be sufficiently oxidized to facilitate binding to the damaged tissue. Accordingly, in some embodiments, the dual modified polymer is at least 10% oxidized. In some embodiments, the dual modified polymer is at least 20% oxidized. In some embodiments, the dual modified polymer is at least 30% oxidized. In some embodiments, the dual modified polymer is at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% oxidized. In some embodiments, the degree of oxidation of the oxidized and methacrylated polymer, e.g., glycosaminoglycan, is from 10% to 80%. In some embodiments, the degree of oxidation of the oxidized and methacrylated polymer, e.g., glycosaminoglycan, is from 15% to 70%. In some embodiments, the degree of oxidation of the oxidized and methacrylated polymer, e.g., glycosaminoglycan, is from 15% to 60%. In some embodiments, the degree of oxidation of the oxidized and methacrylated polymer, e.g., glycosaminoglycan, is from 15% to 50%. In some embodiments, the degree of oxidation of the oxidized and methacrylated polymer, e.g., glycosaminoglycan, is from 15% to 45%. In some embodiments, the degree of oxidation of the oxidized and methacrylated polymer, e.g., glycosaminoglycan, is from 20% to 50%. In some embodiments, the degree of oxidation of the oxidized and methacrylated polymer, e.g., glycosaminoglycan, is from 20% to 45%. Methods for oxidizing suitable polymers are known in the art. See, for example, Wang D A, et al., Nat. Mater., 6:385-92 (2007); and Purcell B P, et al., Nat. Mater., 13:653-61 (2014), the contents of which are disclosed herein by reference, in their entireties, for all purposes. Example 2 describes a particular method for oxidizing a glycosaminoglycan.

Generally, the dual-modified polymers e.g., a glycosaminoglycan or other polysaccharide/carbohydrate, used in these methods must by sufficiently methacrylated to facilitate binding to the damaged tissue. Accordingly, in some embodiments, the dual modified polymer is at least 20% methacrylated. In some embodiments, the dual modified polymer is at least 30% methacrylated. In some embodiments, the dual modified polymer is at least 40% methacrylated. In some embodiments, the dual modified polymer is at least 20%, at least 25%, at least 30%, at least 35%, at least 40%, at least 45%, at least 50%, at least 55%, at least 60%, at least 65%, at least 70%, at least 75%, or at least 80% methacrylated. In some embodiments, the degree of methacrylated of the oxidized and methacrylated polymer, e.g., glycosaminoglycan, is from 20% to 80%. In some embodiments, the degree of methacrylated of the oxidized and methacrylated polymer, e.g., glycosaminoglycan, is from 25% to 80%. In some embodiments, the degree of methacrylated of the oxidized and methacrylated polymer, e.g., glycosaminoglycan, is from 30% to 80%. Example 3 describes a particular method for methacrylating a glycosaminoglycan. However, other methods for methacrylating suitable polymers are known in the art. See, for example, Burdick J A et al., Biomacromolecules, 6:386-91 (2005); and Bryant S J et al., Macromolecules, 37:6726-33 (2004), the contents of which are disclosed herein by reference, in their entireties, for all purposes.

The pre-polymer hydrogel compositions used in these methods include a crosslinking unit suitable for forming a hydrogel in situ. In some embodiments, hydrogels are formed by cross-linking crosslinking units, e.g., macro (mono)mers, forming hydrophilic macromolecules, which typically do not form mechanically strong intermolecular bonds due to a lack of strong disperse interactions. In some embodiments, the pre-polymer hydrogel composition includes a single type of crosslinking unit. In other embodiments, the pre-polymer hydrogel composition includes multiple types of crosslinking units, e.g., at least 2, 3, 4, 5, 6, 7, 8, 9, 10, or more different types of crosslinking units. For a review of multi-functional macromers useful for hydrogel formation see, for example, Hacker M C and Nawaz H A, Int J Mol Sci., 16(11):27677-706 (2015), the content of which is disclosed herein by reference, in its entirety, for all purposes.

Many such hydrogel compositions are known in the art, any of which may be used in the methods described herein. Generally, the only requirement of the pre-polymer hydrogel composition, is that at least one crosslinking unit in the composition has a vinyl group that is amenable to bonding to a pendant methacrylate group in the methacrylated polymer, e.g., the dual-modified glycosaminoglycan or dual-modified polysaccharide/carbohydrate. For a review of hydrogel compositions, preparatory methodology, and application see, for example, Ahmed E M, J Adv Res., 6(2):105-21 (2015), the content of which is disclosed herein by reference, in its entirety, for all purposes.

Non-limiting examples of hydrogels known in the art are provided below in Table 1. Generally, any one of these hydrogels can be implemented in these methods for soft tissue repair, assuming that they include a vinyl group that is amenable to bonding to a pendant methacrylate group in the methacrylated polymer (e.g., dual-modified glycosaminoglycan. Otherwise, the skilled artisan will know how to modify a hydrogel provided below in order to incorporate such a vinyl group for bonding to the methacrylated polymer. In some embodiments, the hydrogel used in the methods described herein is a hydrogel composition selected from those hydrogels listed in Table 1.

In some embodiments, the pre-polymer hydrogel composition includes a macromer having an average molecular weight of from 250 Da to 80 kDa. In some embodiments, the macromer has an average molecular weight of from 250 Da to 40 kDa. In some embodiments, the macromer has an average molecular weight of from 500 Da to 40 kDa. In some embodiments, the macromer has an average molecular weight of from 1 kDa to 40 kDa. In some embodiments, the macromer has an average molecular weight of from 5 kDa to 40 kDa. In some embodiments, the macromer has an average molecular weight of from 10 kDa to 40 kDa. In some embodiments, the macromer has an average molecular weight of from 1 kDa to 25 kDa. In some embodiments, the macromer has an average molecular weight of from 5 kDa to 25 kDa. In some embodiments, the macromer has an average molecular weight of from 10 kDa to 25 kDa. In some embodiments, the macromer has an average molecular weight of from 15 kDa to 25 kDa. In some embodiments, the macromer has a molecular weight of about 20 kDa. In some embodiments, the macromer has an average molecular weight of about 250 Da, about 500 DA, about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, or another value within the range of 250 Da to 80 kDa. Generally, the properties of the hydrogel formed by cross-linking of the macromer is dependent upon both the material properties of the mocromer and the average molecular weight of the macromer.

In one embodiment, the pre-polymer hydrogel composition includes poly(ethylene glycol) diacrylate (PEGDA). In some embodiments, the PEGDA has an average molecular weight of from 250 Da to 80 kDa. In some embodiments, the PEGDA has an average molecular weight of from 250 Da to 40 kDa. In some embodiments, the PEGDA has an average molecular weight of from 500 Da to 40 kDa. In some embodiments, the PEGDA has an average molecular weight of from 1 kDa to 40 kDa. In some embodiments, the PEGDA has an average molecular weight of from 5 kDa to 40 kDa. In some embodiments, the PEGDA has an average molecular weight of from 10 kDa to 40 kDa. In some embodiments, the PEGDA has an average molecular weight of from 1 kDa to 25 kDa. In some embodiments, the PEGDA has an average molecular weight of from 5 kDa to 25 kDa. In some embodiments, the PEGDA has an average molecular weight of from 10 kDa to 25 kDa. In some embodiments, the PEGDA has an average molecular weight of from 15 kDa to 25 kDa. In some embodiments, the PEGDA has a molecular weight of about 20 kDa. In some embodiments, the PEGDA has an average molecular weight of about 250 Da, about 500 DA, about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, or another value within the range of 250 Da to 80 kDa.

In some embodiments, the macromer is present in the hydrogel at a final concentration of about 15% (v/v). In some embodiments, the macromer is present in the hydrogel at a final concentration of from 10% (v/v) to 20% (v/v). In some embodiments, the macromer is present in the hydrogel at a final concentration of from 12.5% (v/v) to 170.5% (v/v). In some embodiments, the macromer is present in the hydrogel at a final concentration of 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or higher.

In some embodiments, the pre-polymer hydrogel composition includes poly(ethylene glycol) diacrylate (PEGDA) having an average molecular weight of from 15 kDa to 25 kDa and is present in the hydrogel at a final concentration of from 12.5% (v/v) to 170.5% (v/v).

In some embodiments, upon cross-linking, the pre-polymer hydrogel composition forms a single network hydrogel. In other embodiments, upon cross-linking, the pre-polymer hydrogel composition forms an interpenetrating network hydrogel. In some embodiments, the interpenetrating network hydrogel is incorporated to integrate integrin recognition sites that facilitate cellular migration into the construct. For example, in some embodiments, the interpenetrating network hydrogel includes a fibronectin-conjugated fibrin network. This can be achieved, for example, by including fibronectin, Factor XIII, and thrombin in the pre-polymer hydrogel composition. However, any secondary network can serve as the interpenetrating network to achieve this purpose if cells can bind to that network. For a review of interpenetrating network hydrogels, see, for example, Matricardi P. et al., Adv Drug Deliv Rev., 65(9):1172-87 (2013); Zoratto N and Matricardi P, Adv Exp Med Biol., 1059:155-88 (2018); and Dragan E S, Chemical Engineering Journal, 243:572-90 (2014), the content of which is disclosed herein by reference, in its entirety, for all purposes.

In some embodiments, the methods described herein include a hydrogel polymerization initiator that is mixed with the pre-polymer hydrogel composition to form the hydrogel, e.g., in situ. Many hydrogel polymerization initiator systems are known in the art. In some embodiments, because schiff base formation is reversible, and in acidic environments favors the reverse reaction, redox pairs that act in the physiological pH range or higher, e.g., at least pH 7.4, are selected to ensure the fidelity of bonds formed between the dual-modified polymer and the soft tissue. In some embodiments, the hydrogel polymerization initiator composition includes ammonium persulfate (APS) and N,N,N',N'-tetramethylethylenediamine (TEMED). However, many hydrogel polymerization initiator systems suitable for use in the methods described herein are known in the art. In yet other embodiments, the hydrogel is formed by photo-polymerization, e.g., using UV irradiation to initiate hydrogel formation.

In some embodiments, the methods described herein are performed in a two-step process. First, the soft tissue defect is coated with the composition containing the oxidized and methacrylated polymer, e.g., glycosaminoglycan or other polysaccharide/carbohydrate, to cause bonding between the polymer and the soft tissue, i.e., through Schiff base formation. In some embodiments, the contacting includes filling or partially filling, e.g., injecting, a soft tissue cavity comprising the defect, waiting for a sufficient time to allow formation of imine bonds between the polymer and the soft tissue, and then removing, e.g., aspirating, excess polymer that has not bonded to the soft tissue, e.g., to make room for the hydrogel. Generally, the dual-modified polymer sufficiently bonds with the soft tissue in less than five minutes. Second, the coated tissue defect is then filled with the pre-polymer hydrogel composition, which forms a hydro gel in situ that covalently bonds to the polymer, i.e., through polyacrylamide polymerization with the methyacrylate group of the polymer. In some embodiments, where a chemical activator is used to initiate hydrogel formation, a dual-barrel syringe, e.g., containing a volumetric mixing cap is used to inject a newly formed mixture of the pre-polymer hydrogel composition and a hydrogel polymerization initiator composition into the coated tissue defect.

In one embodiment, the disclosure provides a method for repairing a fibrocartilage defect in a subject. The method includes contacting the fibrocartilage defect with a first composition containing an oxidized and methacrylated glycosaminoglycan to form an imine bond between the glycosaminoglycan and the fibrocartilage defect, thereby coating the fibrocartilage defect with the glycosaminoglycan. The method then includes contacting the fibrocartilage defect coated with the glycosaminoglycan with a pre-polymer hydrogel composition containing a first crosslinking unit that is capable of bonding to methacrylate, to form a hydrogel that is covalently bonded to the glycosaminoglycan through methacrylate.

Generally, any known methodology can be used to form a hydrogel in situ from a pre-polymer hydrogel composition. For instance, in some embodiments, covalent crosslinking of a macromer, e.g., the first crosslinking unit, can be imparted by visible or UV-catalyzed irradiation, e.g., using a photoinitiator like Irgacure 2959. In some embodiments, the photoinitiator is included in the pre-polymer hydrogel composition and the cross-linking is initiated in situ by exposure of the pre-polymer hydrogel composition to visible or UV activating irradiation at the tissue damage site. In some embodiments, e.g., where the photoinitiator is not highly soluble in the solvent used for the pre-polymer hydrogel composition, the photoinitiator is included in a separate hydrogel polymerization initiator composition, that is mixed with the pre-polymer hydrogel composition immediately before or while being applied to the damage tissue coated with the dual-modified polymer, e.g., using a dual-barrel syringe and volumetric mixing cap. In other embodiments, crosslinking is achieved through redox initiator pairs, such as APS/TEMED, etc. Accordingly, in some embodiments, one or both agents in the redox initiator pairs is included in a separate hydrogel polymerization initiator composition, that is mixed with the pre-polymer hydrogel composition immediately before or while being applied to the damage tissue coated with the dual-modified polymer, e.g., using a dual-barrel syringe and volumetric mixing cap. In yet other embodiments, a thermogelation polymer, with the ability to undergo a sol-gel transition at body temperature (but are a pre-polymer solution at Room Temp) is used to form the hydrogel. In this case, no crosslinking agent is required for in situ hydrogel formation. Non-limiting examples of thermogelling polymers for use in the systems, methods, and kits described herein are described, for example, in Alexander A. et al., J Control Release, 172(3):715-29 (2013); Supper S. et al., Expert Opin Drug Deliv., 11(2):249-67 (2014); and Dou Q Q et al., Adv Healthc Mater., 3(7):977-88 (2014), the contents of which are incorporated herein by reference, in their entireties, for all purposes.

In one embodiment, the disclosure provides a method for repairing a fibrocartilage defect in a subject. The method includes contacting the fibrocartilage defect with a first composition containing an oxidized and methacrylated glycosaminoglycan to form an imine bond between the glycosaminoglycan and the fibrocartilage defect, thereby coating the fibrocartilage defect with the glycosaminoglycan. The method also includes contacting the fibrocartilage defect coated with the glycosaminoglycan with a mixture of (i) a pre-polymer hydrogel composition containing a first crosslinking unit that, when polymerized, is capable of bonding to methacrylate and (ii) a hydrogel polymerization initiator composition, thereby forming a hydrogel that is covalently bonded to the glycosaminoglycan through methacrylate. In some embodiments, the fibrocartilage defect is an annulus fibrosus defect in an intervertebral disk.

In some embodiments, contacting the fibrocartilage defect with the first composition includes filling a cavity comprising the fibrocartilage defect with the first composition containing the glycosaminoglycan, waiting for a sufficient time to allow formation of imine bonds between the glycosaminoglycan and the fibrocartilage defect, and aspirating excess glycosaminoglycan that has not bonded to the fibrocartilage defect from the cavity.

In some embodiments, the oxidized and methacrylated glycosaminoglycan is oxidized and methacrylated hyaluronic acid. In some embodiments, the oxidized and methacrylated glycosaminoglycan is oxidized and methacrylated chondroitin sulfate. In some embodiments, the glycosaminoglycan is selected from keratin sulfate, decorin sulfate, heparin sulfate, and biglycan.

In some embodiments, the degree of oxidation of the oxidized and methacrylated glycosaminoglycan is from 20% to 45%. In some embodiments, the degree of methacrylation of the oxidized and methacrylated glycosaminoglycan is from 30% to 80%.

In some embodiments, contacting the fibrocartilage defect coated with the glycosaminoglycan includes using a dual-barrel syringe and volumetric mixing tip to inject a newly formed mixture of the pre-polymer hydrogel composition and hydrogel polymerization initiator composition into the coated fibrocartilage defect.

In some embodiments, the first crosslinking unit has an average molecular weight of from 250 Da to 40 kDa. In some embodiments, the first crosslinking unit is poly(ethylene glycol) diacrylate (PEGDA). In some embodiments, the PEGDA has an average molecular weight of from 15 kDA to 25 kDA.

In some embodiments, mixing of the pre-polymer hydrogel composition and the hydrogel polymerization initiator composition forms a single network hydrogel. In some embodiments, mixing of the pre-polymer hydrogel composition and the hydrogel polymerization initiator composition forms an interpenetrating network hydrogel. In some embodiments, the interpenetrating network hydrogel includes a fibronectin-conjugated fibrin network.

In some embodiments, the hydrogel polymerization initiator composition comprises ammonium persulfate (APS) and N,N,N',N'-tetramethylethylenediamine (TEMED).

Kits for Repairing a Fibrocartilage Defect

In one aspect, the disclosure provides kits of a soft tissue repair system, as described above, for repairing a fibrocartilage defect. Generally, any system described above, including any combination of elements described above and modifications thereof, may be used to form such a kit. In one embodiment, the kit includes a first container holding a first composition containing an oxidized and methacrylated glycosaminoglycan, a second container holding a pre-polymer hydrogel composition containing a first crosslinking unit that, when polymerized, is capable of bonding to methacrylate, and a third container holding a hydrogel polymerization initiator composition.

In one embodiment, the kit is for use in a method described herein, e.g., that includes contacting a fibrocartilage defect with a first composition containing an oxidized and methacrylated polymer, e.g., a dual-modified glycosaminoglycan or other polysaccharide/carbohydrate, to form an imine bond between the glycosaminoglycan and the fibrocartilage defect, thereby coating the fibrocartilage defect with the polymer. The fibrocartilage defect coated with the polymer is then contacted with a pre-polymer hydrogel composition containing a first crosslinking unit that, when cross-linked, e.g., polymerized, is capable of bonding to methacrylate, and initiating cross-linking, thereby forming a hydrogel that is covalently bonded to the polymer, e.g., glycosaminoglycan, through methacrylate. In this fashion, the hydrogel formed in situ is covalently linked to the site of the fibrocartilage defect through the polymer intermediate. In some embodiments, where cross-linking is initiated through chemical means, the fibrocartilage defect coated with the polymer is contacted with a mixture of the pre-polymer hydrogel composition and a hydrogel polymerization initiator composition, e.g., by using a dual-barrel syringe and volumetric mixing cap to form the mixture in situ.

In some embodiments, as described above, the kit enables repair of damaged soft tissue within the musculoskeletal system, such as damage at annulus fibrosus of intervertebral discs. However, these kits are not limited to these applications and can be used to repair damage at any location containing fibrocartilage, including at secondary cartilaginous joints (such as the pubic symphysis, the annulus fibrosus of intervertebral discs, and the manubriosternal joint), the glenoid labrum of shoulder joints, the acetabular labrum of hip joints, the medial and lateral menisci of knee joints, and generally where tendons and ligaments attach to bone.

In some embodiments, as described above, the oxidized and methacrylated polymer is an oxidized and methacrylated glycosaminoglycan. Generally, any glycosaminoglycan can be included in these kits to link the hydrogel to the soft tissue, e.g., to tissue containing fibrocartilage. Moreover, in some embodiments, the glycosaminoglycan is a glycosaminoglycan composition containing two or more types of glycosaminoglycan. The only requirement is that a glycosaminoglycan is oxidized and methacrylated, to facilitate bonding to both the soft tissue and the hydrogel. In some embodiments, the glycosaminoglycan composition includes a keratin sulfate type glycosaminoglycan. In some embodiments, the keratin sulfate type glycosaminoglycan is keratin sulfate. In some embodiments, the glycosaminoglycan composition includes a hyaluronic type glycosaminoglycan. In some embodiments, the hyaluronic type glycosaminoglycan is hyaluronic acid. In some embodiments, the glycosaminoglycan composition includes a Heparin/heparan sulfate type glycosaminoglycan. In some embodiments, the Heparin/heparan sulfate type glycosaminoglycan is heparin. In some embodiments, the Heparin/heparan sulfate type glycosaminoglycan is heparan sulfate. In some embodiments, the glycosaminoglycan composition includes a chondroitin sulfate/dermatan sulfate type glycosaminoglycan. In some embodiments, the chondroitin sulfate/dermatan sulfate type glycosaminoglycan is chondroitin sulfate. In some embodiments, the chondroitin sulfate/dermatan sulfate type glycosaminoglycan is dermatan sulfate. In some embodiments, the glycosaminoglycan composition includes a proteoglycan. In some embodiments, the proteoglycan is decorin. In some embodiments, the proteoglycan is biglycan. In some embodiments, the proteoglycan is testican. In some embodiments, the proteoglycan is bikunin. In some embodiments, the proteoglycan is fibromodulin. In some embodiments, the proteoglycan is lumican.

Further, in some embodiments, a polysaccharide/carbohydrate other than a glycosaminoglycan can be included in place of, or in addition to, a glycosaminoglycan to chemically bridge the soft tissue to the hydrogel. Thus, in some embodiments, the kits include an oxidized and methacrylated polysaccharide/carbohydrate to bridge a damaged tissue with a hydrogel by covalently bonding to each, in an analogous fashion to that described above for glycosaminoglycan.

Generally, the dual-modified polymers e.g., a glycosaminoglycan or other polysaccharide/carbohydrate, included in these kits must be sufficiently oxidized to facilitate binding to the damaged tissue. Accordingly, in some embodiments, the dual modified polymer is at least 10% oxidized. In some embodiments, the dual modified polymer is at least 20% oxidized. In some embodiments, the dual modified polymer is at least 30% oxidized. In some embodiments, the dual modified polymer is at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% oxidized. In some embodiments, the degree of oxidation of the oxidized and methacrylated polymer, e.g., glycosaminoglycan, is from 10% to 80%. In some embodiments, the degree of oxidation of the oxidized and methacrylated polymer, e.g., glycosaminoglycan, is from 15% to 70%. In some embodiments, the degree of oxidation of the oxidized and methacrylated polymer, e.g., glycosaminoglycan, is from 15% to 60%. In some embodiments, the degree of oxidation of the oxidized and methacrylated polymer, e.g., glycosaminoglycan, is from 15% to 50%. In some embodiments, the degree of oxidation of the oxidized and methacrylated polymer, e.g., glycosaminoglycan, is from 15% to 45%. In some embodiments, the degree of oxidation of the oxidized and methacrylated polymer, e.g., glycosaminoglycan, is from 20% to 50%. In some embodiments, the degree of oxidation of the oxidized and methacrylated polymer, e.g., glycosaminoglycan, is from 20% to 45%. Methods for oxidizing suitable polymers are known in the art. See, for example, Wang D A, et al., Nat. Mater., 6:385-92 (2007); and Purcell B P, et al., Nat. Mater., 13:653-61 (2014), the contents of which are disclosed herein by reference, in their entireties, for all purposes. Example 2 describes a particular method for oxidizing a glycosaminoglycan.

Generally, the dual-modified polymers e.g., a glycosaminoglycan or other polysaccharide/carbohydrate, included in these kits must by sufficiently methacrylated to facilitate binding to the damaged tissue. Accordingly, in some embodiments, the dual modified polymer is at least 20% methacrylated. In some embodiments, the dual modified polymer is at least 30% methacrylated. In some embodiments, the dual modified polymer is at least 40% methacrylated. In some embodiments, the dual modified polymer is at least 20%, at least 25%, at least 30%, at least 35%, at least 40%, at least 45%, at least 50%, at least 55%, at least 60%, at least 65%, at least 70%, at least 75%, or at least 80% methacrylated. In some embodiments, the degree of methacrylated of the oxidized and methacrylated polymer, e.g., glycosaminoglycan, is from 20% to 80%. In some embodiments, the degree of methacrylated of the oxidized and methacrylated polymer, e.g., glycosaminoglycan, is from 25% to 80%. In some embodiments, the degree of methacrylated of the oxidized and methacrylated polymer, e.g., glycosaminoglycan, is from 30% to 80%. Example 3 describes a particular method for methacrylating a glycosaminoglycan. However, other methods for methacrylating suitable polymers are known in the art. See, for example, Burdick J A et al., Biomacromolecules, 6:386-91 (2005); and Bryant S J et al., Macromolecules, 37:6726-33 (2004), the contents of which are disclosed herein by reference, in their entireties, for all purposes.

The pre-polymer hydrogel compositions included in these kits include a crosslinking unit suitable for forming a hydrogel in situ. In some embodiments, hydrogels are formed by cross-linking crosslinking units, e.g., macro (mono)mers, forming hydrophilic macromolecules, which typically do not form mechanically strong intermolecular bonds due to a lack of strong disperse interactions. In some embodiments, the pre-polymer hydrogel composition includes a single type of crosslinking unit. In other embodiments, the pre-polymer hydrogel composition includes multiple types of crosslinking units, e.g., at least 2, 3, 4, 5, 6, 7, 8, 9, 10, or more different types of crosslinking units. For a review of multi-functional macromers useful for hydrogel formation see, for example, Hacker M C and Nawaz H A, Int J Mol Sci., 16(11):27677-706 (2015), the content of which is disclosed herein by reference, in its entirety, for all purposes.

Many such hydrogel compositions are known in the art, any of which may be included in the kits described herein. Generally, the only requirement of the pre-polymer hydrogel composition, is that at least one crosslinking unit in the composition has a vinyl group that is amenable to bonding to a pendant methacrylate group in the methacrylated polymer, e.g., the dual-modified glycosaminoglycan or dual-modified polysaccharide/carbohydrate. For a review of hydrogel compositions, preparatory methodology, and application see, for example, Ahmed E M, J Adv Res., 6(2):105-21 (2015), the content of which is disclosed herein by reference, in its entirety, for all purposes.

Non-limiting examples of hydrogels known in the art are provided below in Table 1. Generally, any one of these hydrogels can be included in these kits for soft tissue repair, assuming that they include a vinyl group that is amenable to bonding to a pendant methacrylate group in the methacrylated polymer (e.g., dual-modified glycosaminoglycan. Otherwise, the skilled artisan will know how to modify a hydrogel provided below in order to incorporate such a vinyl group for bonding to the methacrylated polymer. In some embodiments, the hydrogel included in the kits described herein is a hydrogel composition selected from those hydrogels listed in Table 1.

In some embodiments, the pre-polymer hydrogel composition includes a macromer having an average molecular weight of from 250 Da to 80 kDa. In some embodiments, the macromer has an average molecular weight of from 250 Da to 40 kDa. In some embodiments, the macromer has an average molecular weight of from 500 Da to 40 kDa. In some embodiments, the macromer has an average molecular weight of from 1 kDa to 40 kDa. In some embodiments, the macromer has an average molecular weight of from 5 kDa to 40 kDa. In some embodiments, the macromer has an average molecular weight of from 10 kDa to 40 kDa. In some embodiments, the macromer has an average molecular weight of from 1 kDa to 25 kDa. In some embodiments, the macromer has an average molecular weight of from 5 kDa to 25 kDa. In some embodiments, the macromer has an average molecular weight of from 10 kDa to 25 kDa. In some embodiments, the macromer has an average molecular weight of from 15 kDa to 25 kDa. In some embodiments, the macromer has a molecular weight of about 20 kDa. In some embodiments, the macromer has an average molecular weight of about 250 Da, about 500 DA, about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, or another value within the range of 250 Da to 80 kDa. Generally, the properties of the hydrogel formed by cross-linking of the macromer is dependent upon both the material properties of the mocromer and the average molecular weight of the macromer.

In one embodiment, the pre-polymer hydrogel composition includes poly(ethylene glycol) diacrylate (PEGDA). In some embodiments, the PEGDA has an average molecular weight of from 250 Da to 80 kDa. In some embodiments, the PEGDA has an average molecular weight of from 250 Da to 40 kDa. In some embodiments, the PEGDA has an average molecular weight of from 500 Da to 40 kDa. In some embodiments, the PEGDA has an average molecular weight of from 1 kDa to 40 kDa. In some embodiments, the PEGDA has an average molecular weight of from 5 kDa to 40 kDa. In some embodiments, the PEGDA has an average molecular weight of from 10 kDa to 40 kDa. In some embodiments, the PEGDA has an average molecular weight of from 1 kDa to 25 kDa. In some embodiments, the PEGDA has an average molecular weight of from 5 kDa to 25 kDa. In some embodiments, the PEGDA has an average molecular weight of from 10 kDa to 25 kDa. In some embodiments, the PEGDA has an average molecular weight of from 15 kDa to 25 kDa. In some embodiments, the PEGDA has a molecular weight of about 20 kDa. In some embodiments, the PEGDA has an average molecular weight of about 250 Da, about 500 DA, about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, or another value within the range of 250 Da to 80 kDa.

In some embodiments, the macromer is present in the hydrogel at a final concentration of about 15% (v/v). In some embodiments, the macromer is present in the hydrogel at a final concentration of from 10% (v/v) to 20% (v/v). In some embodiments, the macromer is present in the hydrogel at a final concentration of from 12.5% (v/v) to 170.5% (v/v). In some embodiments, the macromer is present in the hydrogel at a final concentration of 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, or higher.

In some embodiments, the pre-polymer hydrogel composition includes poly(ethylene glycol) diacrylate (PEGDA) having an average molecular weight of from 15 kDa to 25 kDa and is present in the hydrogel at a final concentration of from 12.5% (v/v) to 17.5% (v/v).

In some embodiments, upon cross-linking, the pre-polymer hydrogel composition forms a single network hydrogel. In other embodiments, upon cross-linking, the pre-polymer hydrogel composition forms an interpenetrating network hydrogel. In some embodiments, the interpenetrating network hydrogel is incorporated to integrate integrin recognition sites that facilitate cellular migration into the construct. For example, in some embodiments, the interpenetrating network hydrogel includes a fibronectin-conjugated fibrin network. This can be achieved, for example, by including fibronectin, Factor XIII, and thrombin in the pre-polymer hydrogel composition. However, any secondary network can serve as the interpenetrating network to achieve this purpose if cells can bind to that network. For a review of interpenetrating network hydrogels, see, for example, Matricardi P. et al., Adv Drug Deliv Rev., 65(9):1172-87 (2013); Zoratto N and Matricardi P, Adv Exp Med Biol., 1059:155-88 (2018); and Dragan E S, Chemical Engineering Journal, 243:572-90 (2014), the content of which is disclosed herein by reference, in its entirety, for all purposes.

In some embodiments, the kits described herein include a hydrogel polymerization initiator that is mixed with the pre-polymer hydrogel composition to form the hydrogel, e.g., in situ. Many hydrogel polymerization initiator systems are known in the art. In some embodiments, because Schiff base formation is reversible, and in acidic environments favors the reverse reaction, redox pairs that act in the physiological pH range or higher, e.g., at least pH 7.4, are selected to ensure the fidelity of bonds formed between the dual-modified polymer and the soft tissue. In some embodiments, the hydrogel polymerization initiator composition includes ammonium persulfate (APS) and N,N,N',N'-tetramethylethylenediamine (TEMED). However, many hydrogel polymerization initiator systems suitable for inclusion in the kits described herein are known in the art. In yet other embodiments, the hydrogel is formed by photo-polymerization, e.g., using UV irradiation to initiate hydrogel formation.

In one embodiment, a kit is provided for repairing a fibrocartilage defect. The kit includes a first container holding a first composition containing an oxidized and methacrylated glycosaminoglycan and a second container holding a pre-polymer hydrogel composition containing a first crosslinking unit that is capable of bonding to methacrylate.

Generally, any known methodology can be used to form a hydrogel in situ from a pre-polymer hydrogel composition. For instance, in some embodiments, covalent crosslinking of a macromer, e.g., the first crosslinking unit, can be imparted by visible or UV-catalyzed irradiation, e.g., using a photoinitiator like Irgacure 2959. In some embodiments, the photoinitiator is included in the pre-polymer hydrogel composition and the cross-linking is initiated in situ by exposure of the pre-polymer hydrogel composition to visible or UV activating irradiation at the tissue damage site. In some embodiments, e.g., where the photoinitiator is not highly soluble in the solvent used for the pre-polymer hydrogel composition, the photoinitiator is included in a separate hydrogel polymerization initiator composition, that is mixed with the pre-polymer hydrogel composition immediately before or while being applied to the damage tissue coated with the dual-modified polymer, e.g., using a dual-barrel syringe and volumetric mixing cap. In other embodiments, crosslinking is achieved through redox initiator pairs, such as APS/TEMED, etc. Accordingly, in some embodiments, one or both agents in the redox initiator pairs is included in a separate hydrogel polymerization initiator composition, that is mixed with the pre-polymer hydrogel composition immediately before or while being applied to the damage tissue coated with the dual-modified polymer, e.g., using a dual-barrel syringe and volumetric mixing cap. In yet other embodiments, a thermogelation polymer, with the ability to undergo a sol-gel transition at body temperature (but are a pre-polymer solution at Room Temp) is used to form the hydrogel. In this case, no crosslinking agent is required for in situ hydrogel formation. Non-limiting examples of thermogelling polymers for use in the systems, methods, and kits described herein are described, for example, in Alexander A. et al., J Control Release, 172(3):715-29 (2013); Supper S. et al., Expert Opin Drug Deliv., 11(2):249-67 (2014); and Dou Q Q et al., Adv Healthc Mater., 3(7):977-88 (2014), the contents of which are incorporated herein by reference, in their entireties, for all purposes.

In one embodiment, a kit is provided for repairing a fibrocartilage defect. The kit includes a first container holding a first composition containing an oxidized and methacrylated glycosaminoglycan, a second container holding a pre-polymer hydrogel composition containing a first crosslinking unit that, when polymerized, is capable of bonding to methacrylate, and a third container holding a hydrogel polymerization initiator composition. In some embodiments, the kit is for repairing an annulus fibrosus defect in an intervertebral disk.

In some embodiments, the oxidized and methacrylated glycosaminoglycan is oxidized and methacrylated hyaluronic acid. In some embodiments, the oxidized and methacrylated glycosaminoglycan comprises oxidized and methacrylated chondroitin sulfate. In some embodiments, the glycosaminoglycan is selected from the group consisting of keratin sulfate, decorin sulfate, heparin sulfate, and biglycan.

In some embodiment, the degree of oxidation of the oxidized and methacrylated glycosaminoglycan is from 20% to 45%. In some embodiments, the degree of methacrylation of the oxidized and methacrylated glycosaminoglycan is from 30% to 80%.

In some embodiments, the first container includes a syringe that is pre-loaded with the first composition.

In some embodiments, the first crosslinking unit has an average molecular weight of from 250 Da to 40 kDa. In some embodiments, the first crosslinking unit is poly(ethylene glycol) diacrylate (PEGDA). In some embodiments, the PEGDA has an average molecular weight of from 15 kDA to 25 kDA.

In some embodiments, mixing of the pre-polymer hydrogel composition and the hydrogel polymerization initiator composition forms a single network hydrogel. In some embodiments, mixing of the pre-polymer hydrogel composition and the hydrogel polymerization initiator composition forms an interpenetrating network hydrogel. In some embodiments, the interpenetrating network hydrogel comprises a fibronectin-conjugated fibrin network.

In some embodiments, the hydrogel polymerization initiator composition contains ammonium persulfate (APS) and N,N,N',N'-tetramethylethylenediamine (TEMED).

In some embodiments, the second and third containers comprise a dual-barrel syringe and volumetric mixing tip. In some embodiments, the volumetric mixing tip is a 1:1 volumetric mixing tip. In other embodiments, the volumetric mixing tip is a 1:10, 1:9, 1:8, 1:7, 1:6, 1:5, 1:4, 1:3, 1:2, 2:1, 3:1, 4:1, 5:1, 6:1, 7:1, 8:1, 9:1, or 10:1 volumetric mixing tip.

EXAMPLES

Figure 1:
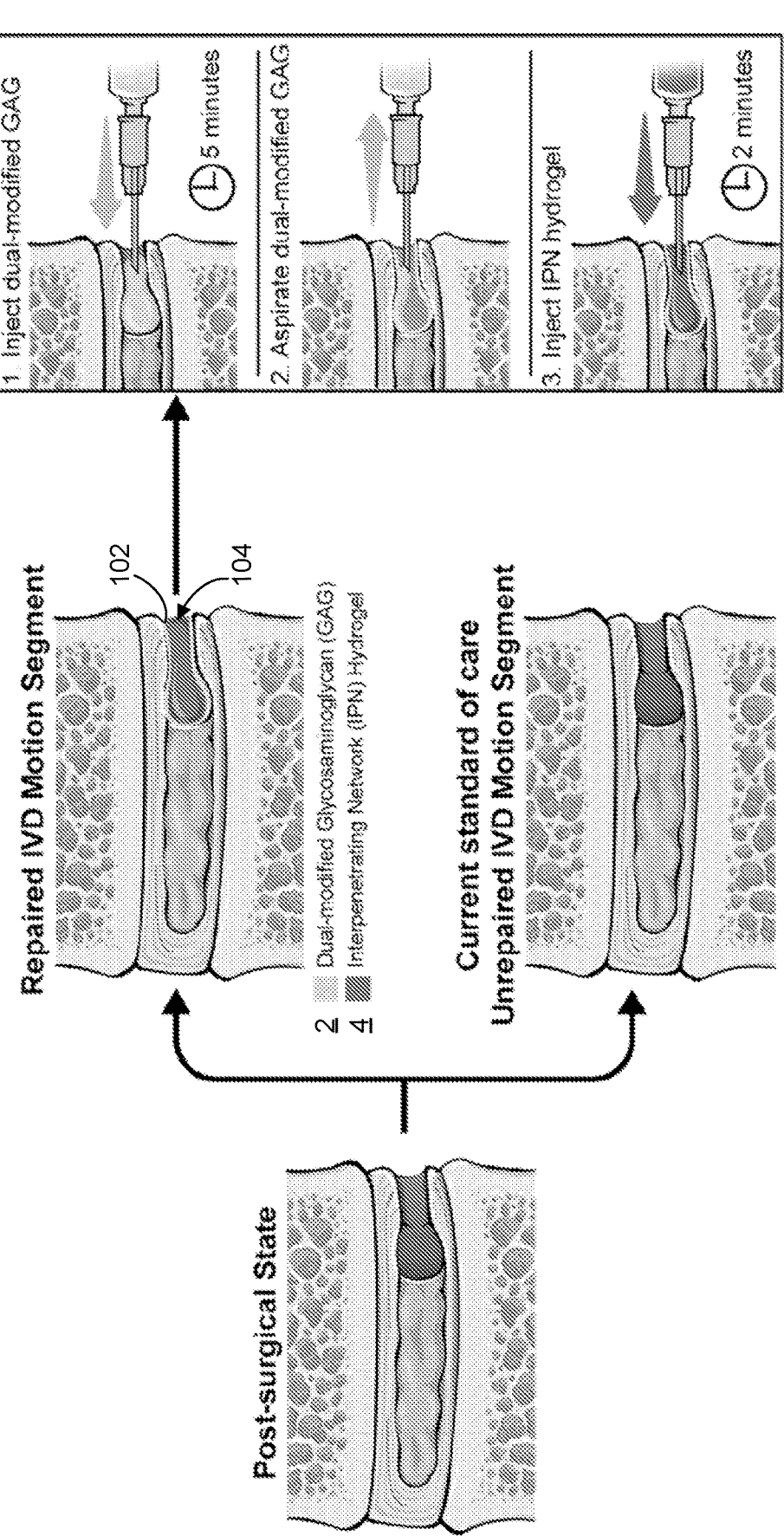
FIG. 1 illustrates a three-step process for repairing annulus fibrosus defects, in accordance with some embodiments of the present disclosure.
Figure 2A:
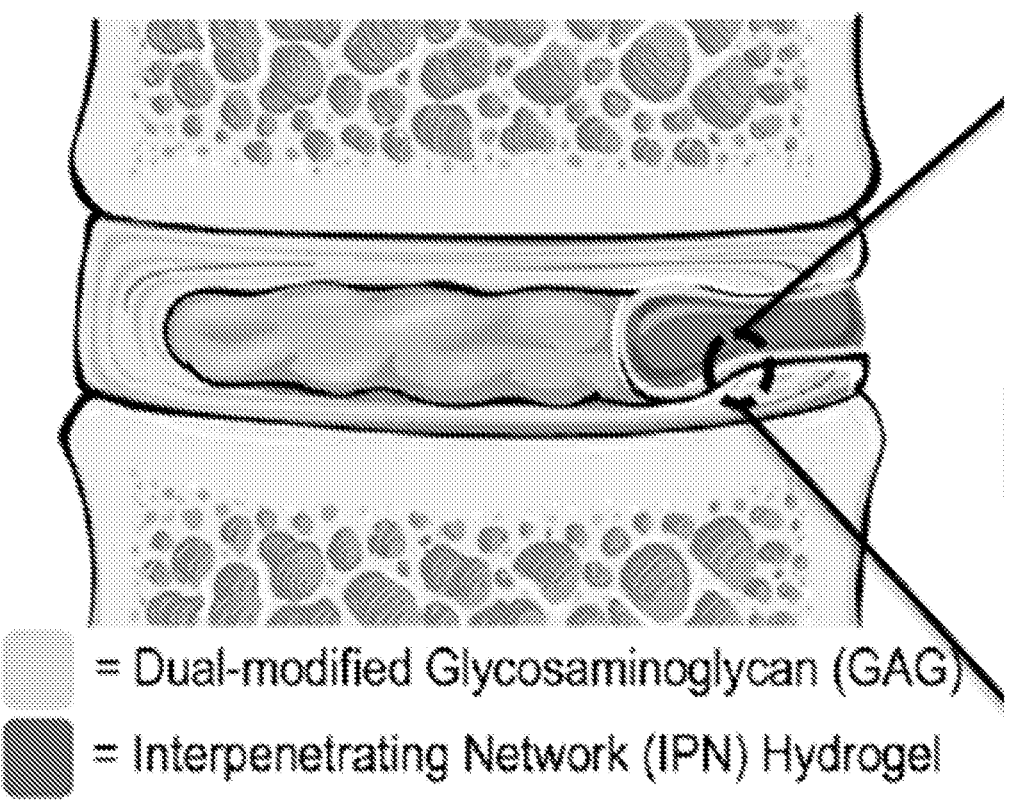
FIG. 2 illustrates a two-part biomaterial adhesive strategy for coating defect surfaces with modified GAGs that covalently bonds injectable hydrogels to intervertebral disc tissue, in accordance with some embodiments of the present disclosure.
Figure 2B:
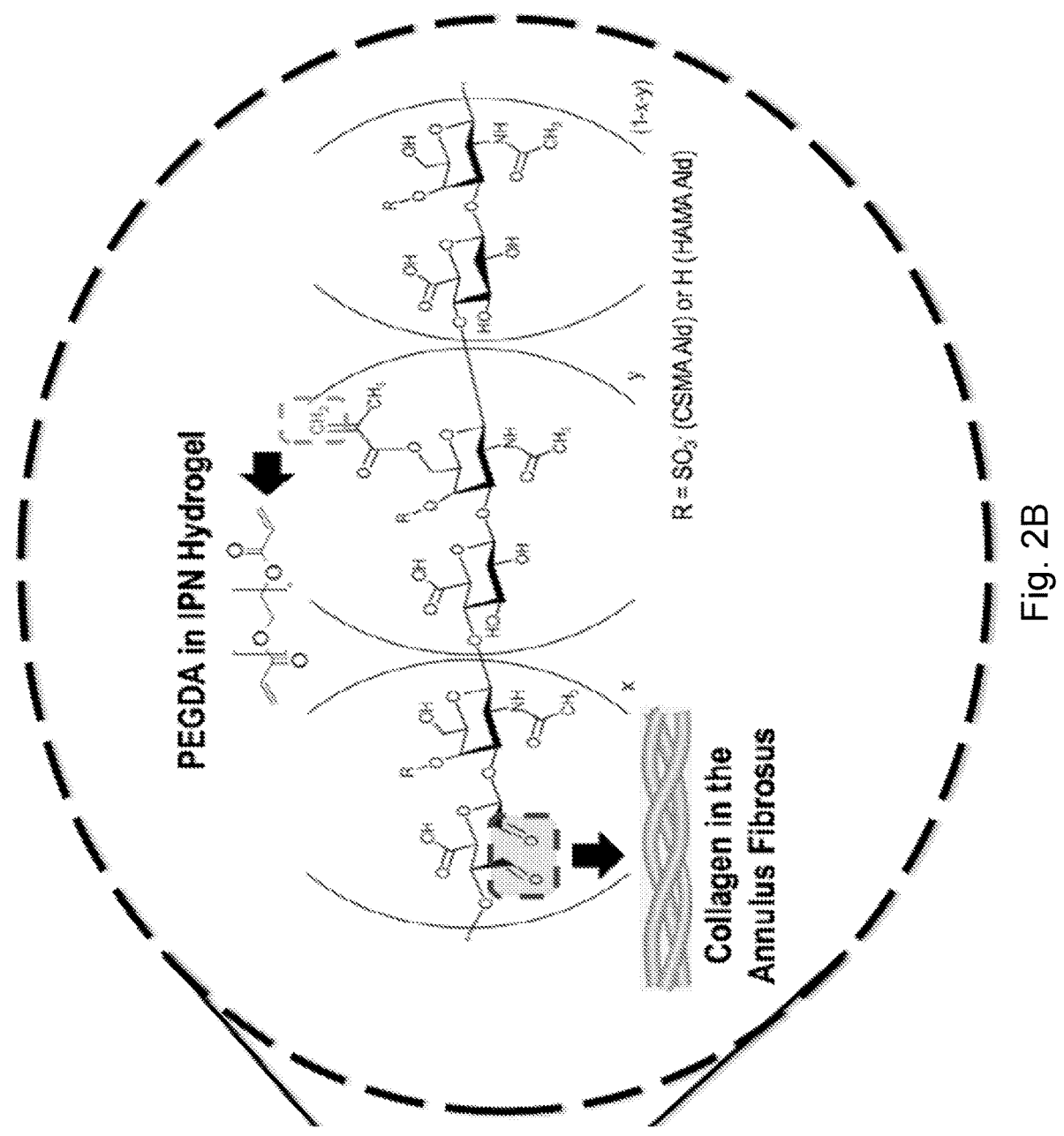

Example 1—Bioadhesive Optimization and Cytocompatibility Assessment of a Novel Two-Part Strategy for Annular Repair Reherniation is the leading cause of reoperation following discectomy, underscoring the unmet clinical need to seal annulus fibrosus (AF) defects with a durable and strong adhesive that can withstand the complex mechanical behavior of the spinal column. Synthetic and composite surgical sealants can achieve relatively large adhesion strength compared to natural sealants, but are frequently plagued by demonstrable cytotoxicity and high herniation risk, thereby motivating the development of a cytocompatible AF sealant with high adhesivity so as to prevent recurrent herniation. To that end, we developed a novel two-part AF repair strategy composed of: (1) an interpenetrating network (IPN) hydrogel comprising synthetic (poly(ethylene glycol) diacrylate/ PEGDA) and natural (fibronectin-conjugated Fibrin/FN-Fibrin) polymer networks, and (2) a dual-modified (oxidized and methacrylated) glycosaminoglycan (GAG) that covalently bonds this injectable hydrogel to collagen in the IVD (outlined in FIGS. 1 and 2). Although constitutive networks of the IPN hydrogel system are biocompatible, cytocompatibility of the dual-modified GAG component has yet to be characterized. Additionally, proof-of-concept bonding was demonstrated with this system in vitro, but hydrogel adhesion could be further improved with the primary goal of minimizing implant herniation risk after scaling this approach up for in situ AF repair with a large animal model. Therefore, the objectives of the studies disclosed in the Examples are threefold: (1) Optimize hydrogel adhesion with AF tissue by enhancing biochemical degrees of modification for dual-modified chondroitin sulfate (CS) and hyaluronic acid (HA) polymers in order to select the optimal dual-modified GAG formulation; (2) Assess biomaterial depth of penetration in AF tissue after treatment and correspondingly quantify cell viability upon exposure to the optimal dual-modified GAG product; (3) Scale-up this approach to repair AF defects in situ using a large animal bovine coccygeal IVD model and assess construct integration.

Figure 4B:
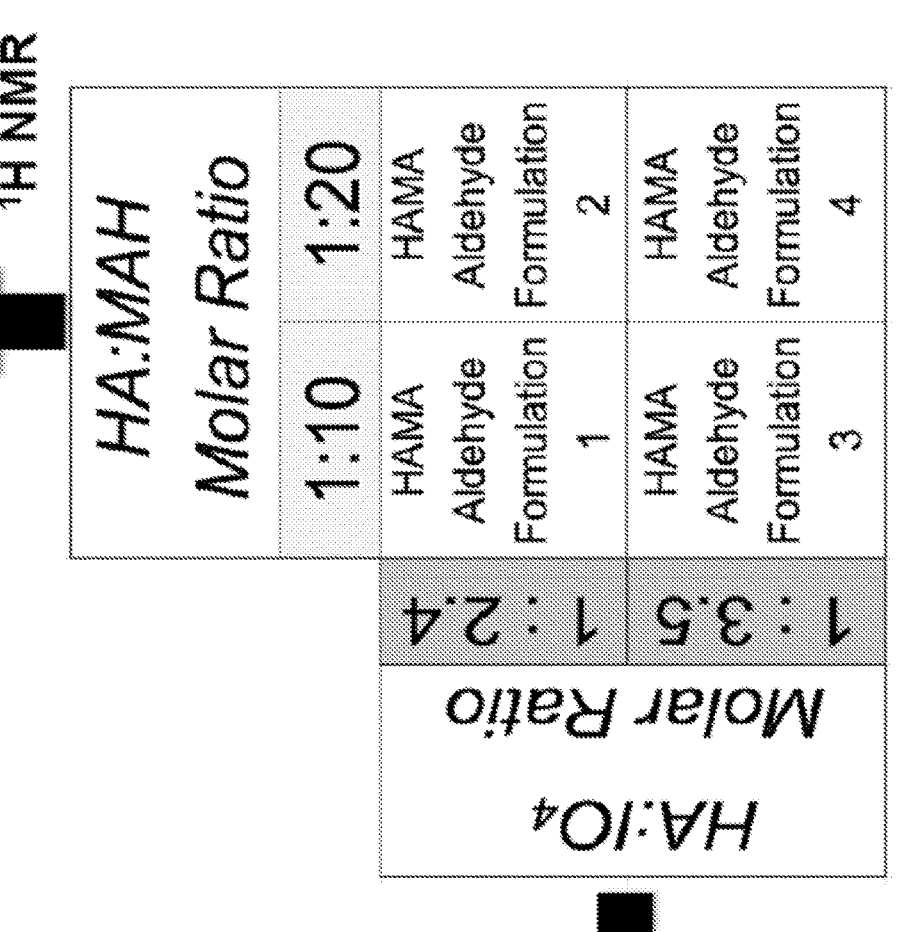
Figure 5A:
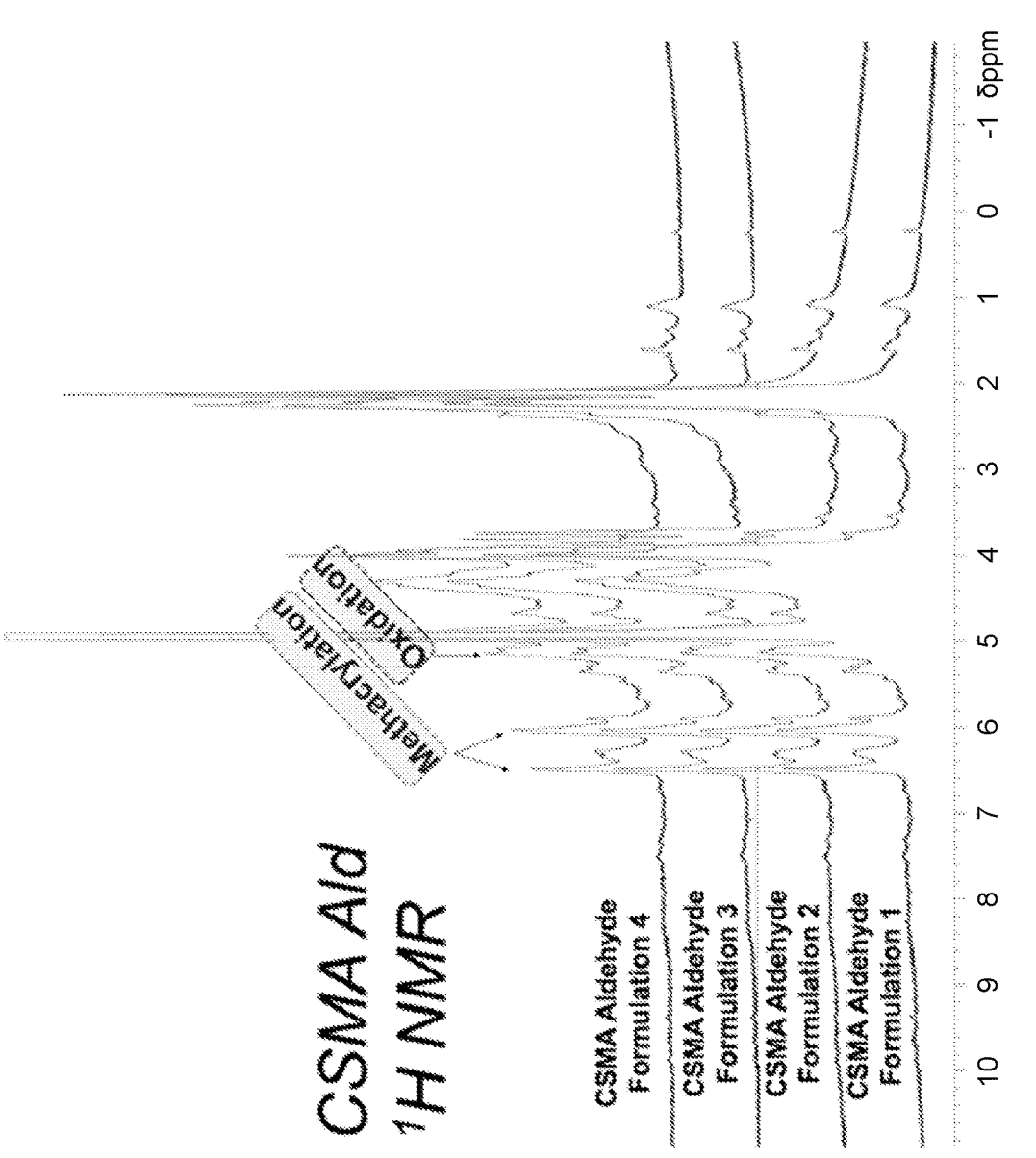
FIGS. 5A and 5B illustrate $^1$H NMR spectra for dual-modified GAG formulations of oxidized and methacrylated chondroitin sulfate (5A) and hyaluronic acid (5B) indicating successful functionalization, in accordance with some embodiments of the present disclosure. The downfield vinyl peaks at approximately 6.2 ppm (chondroitin sulfate) and 6.5 ppm (hyaluronic acid) were used to calculate the degree of methacrylation for each of the preparations.
Figure 5B:
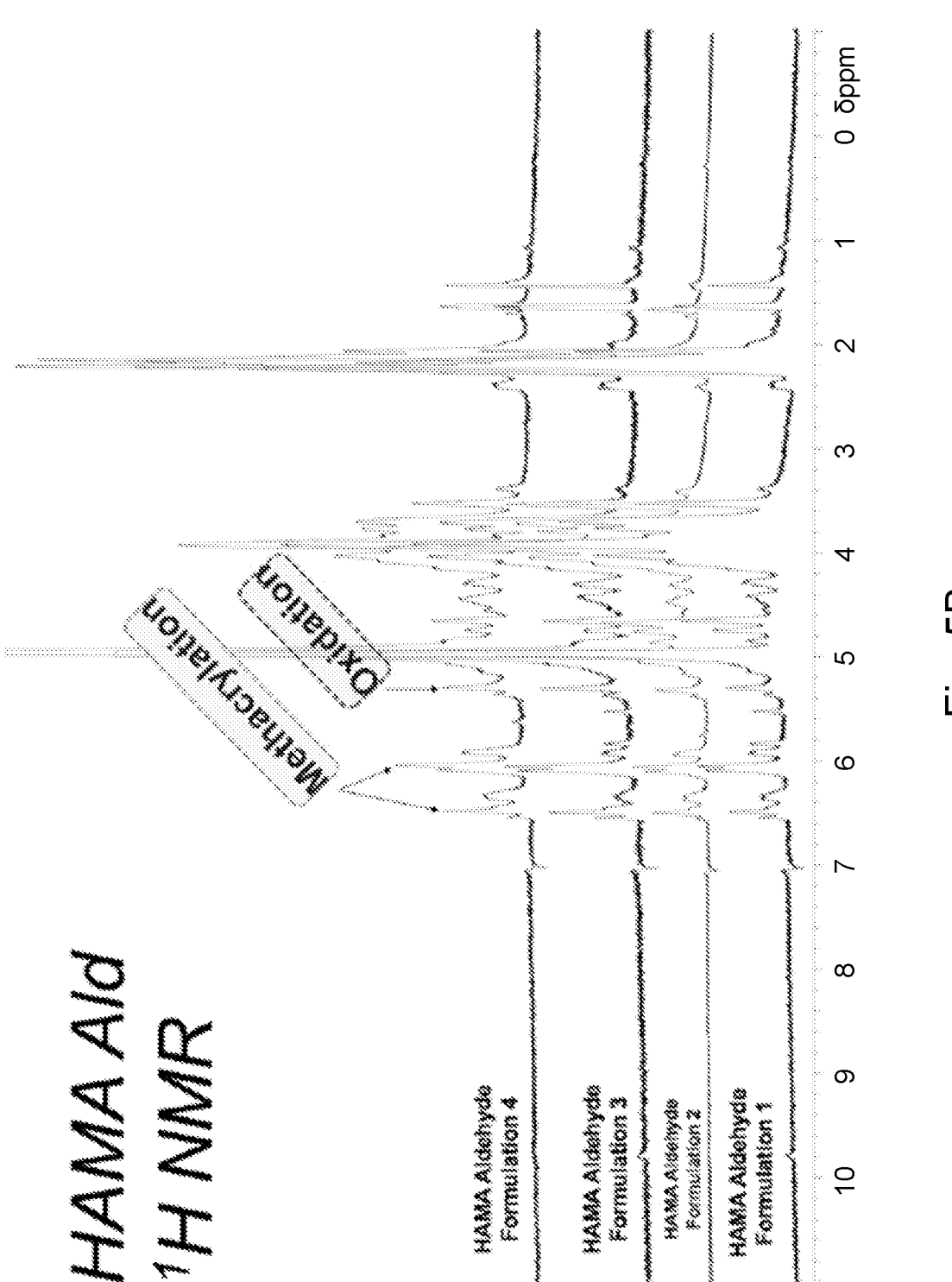
Figure 6:
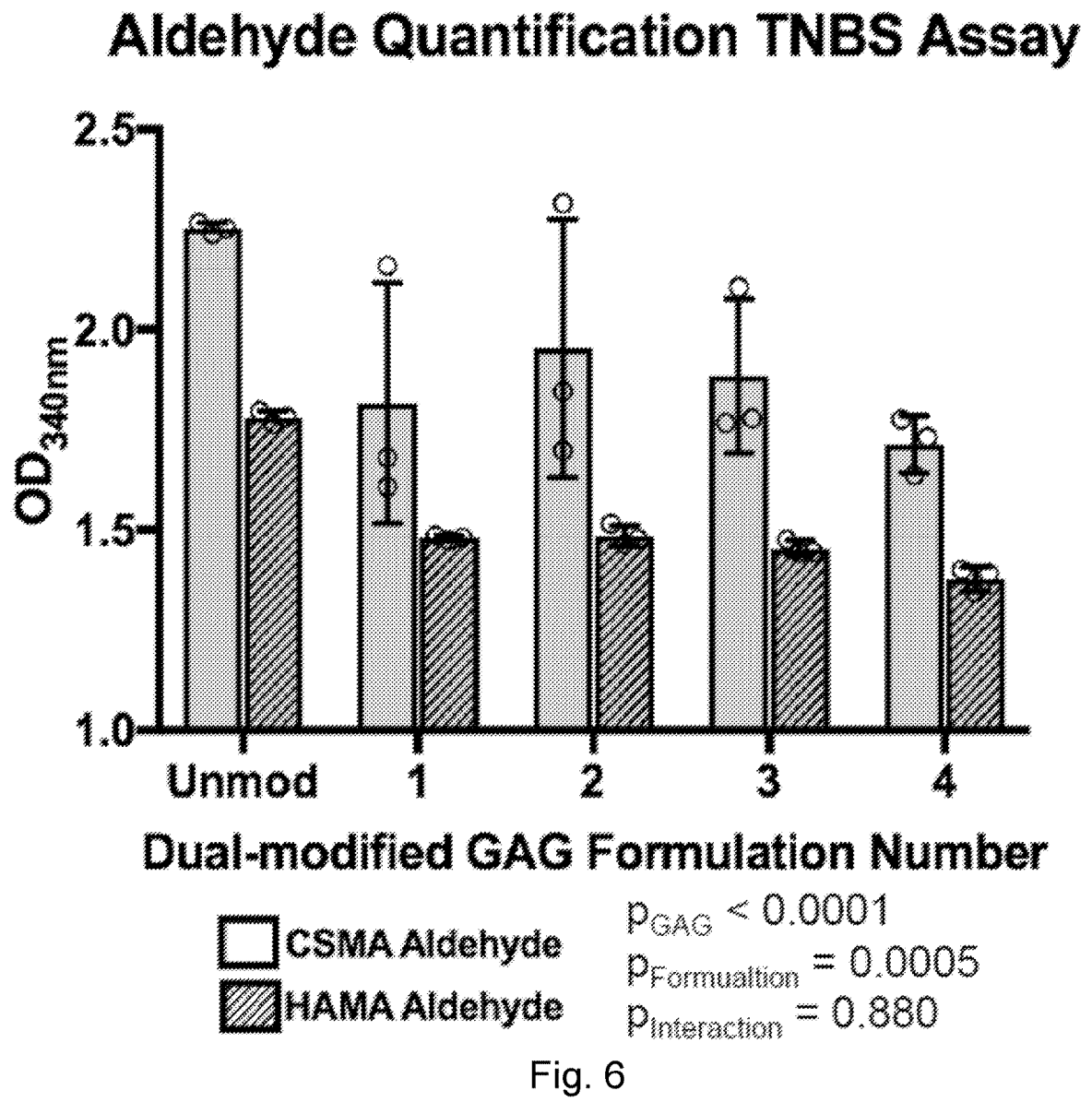
Figure 7A:
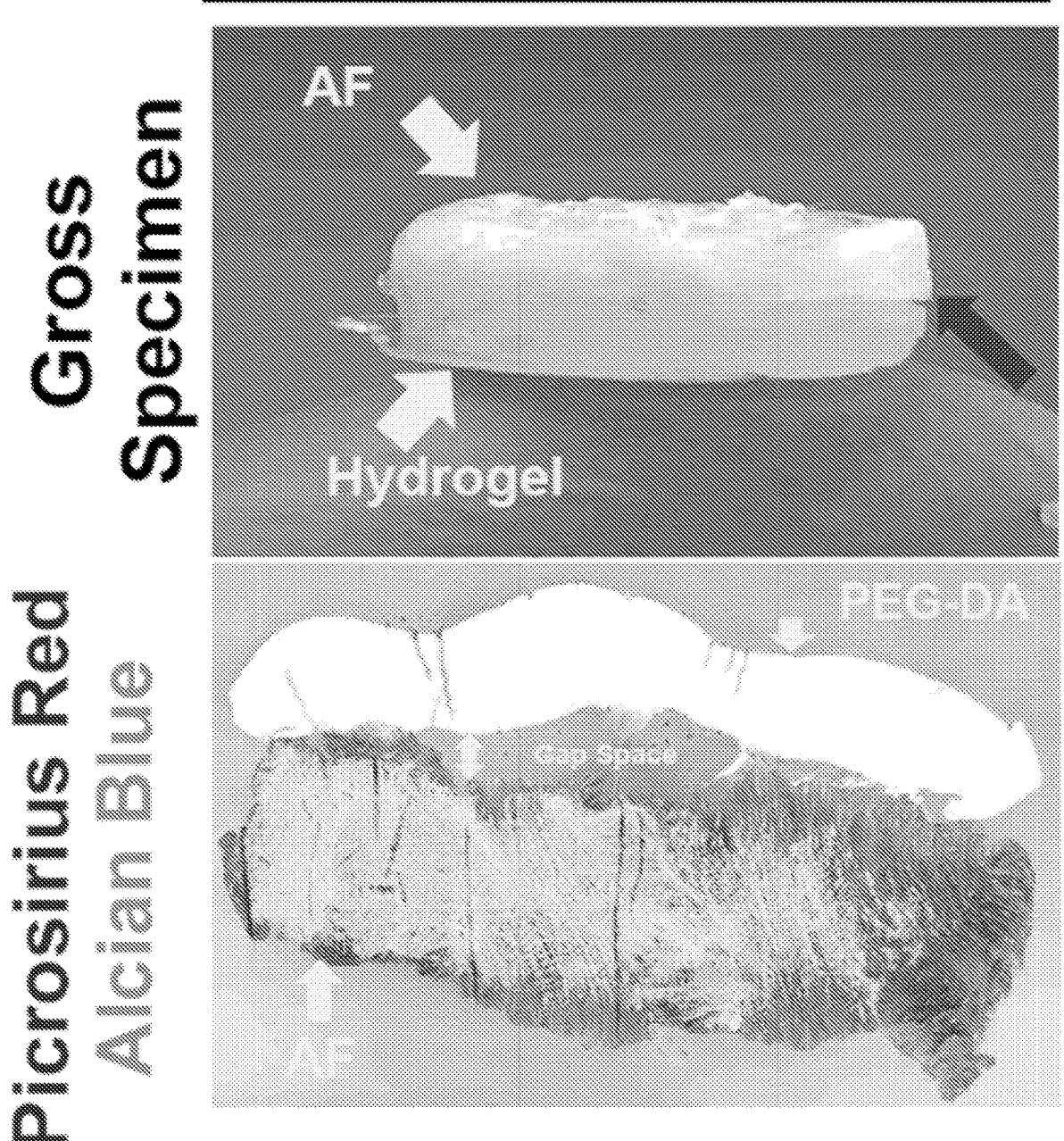
FIG. 7 shows that oxidation and methacrylation of chondroitin sulfate (middle panels) and hyaluronic acid (right panels) facilitates covalent bonding between annulus fibrosus and a hydrogel, in accordance with some embodiments of the present disclosure.
Figure 7B:
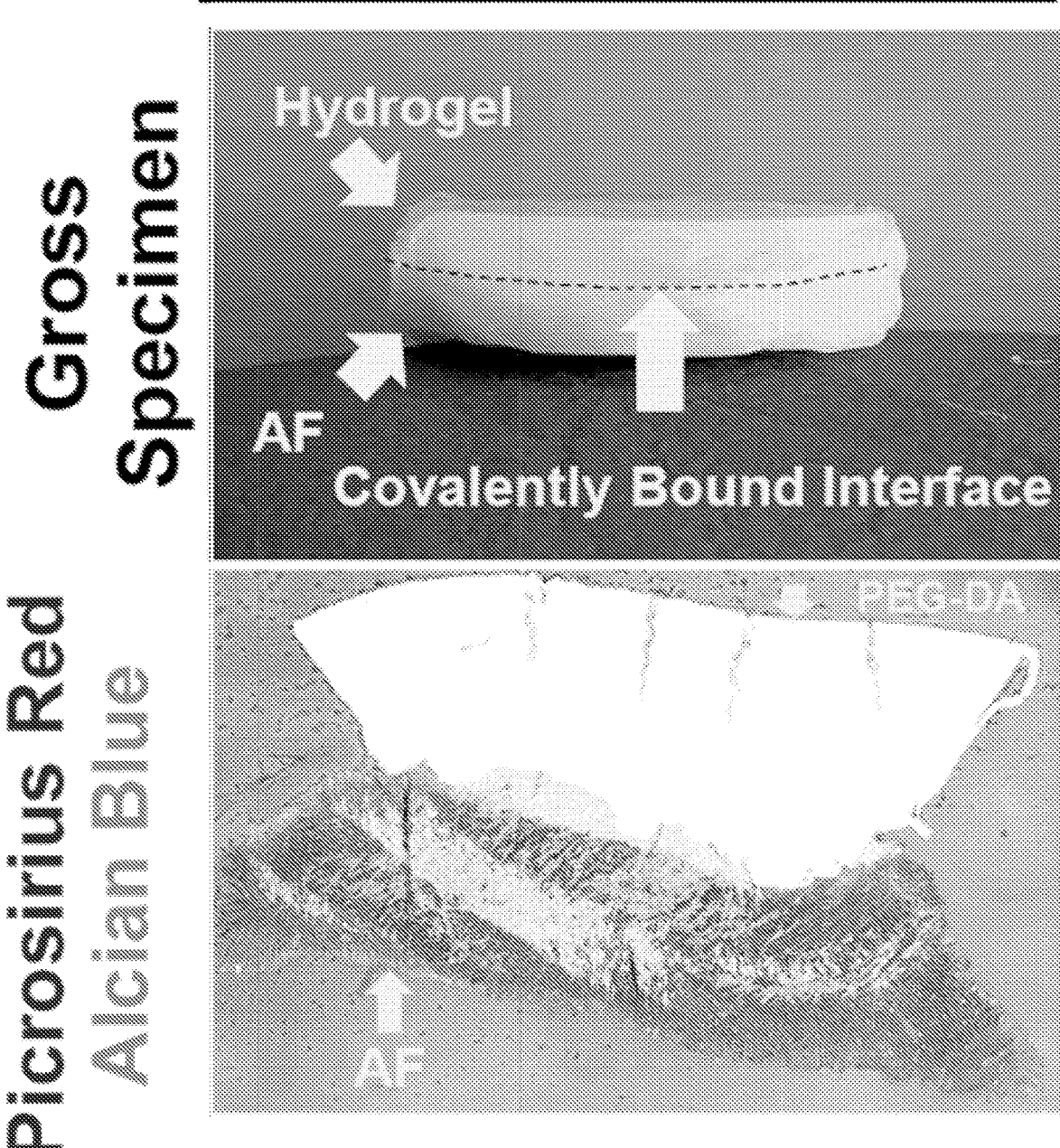
Figure 7C:
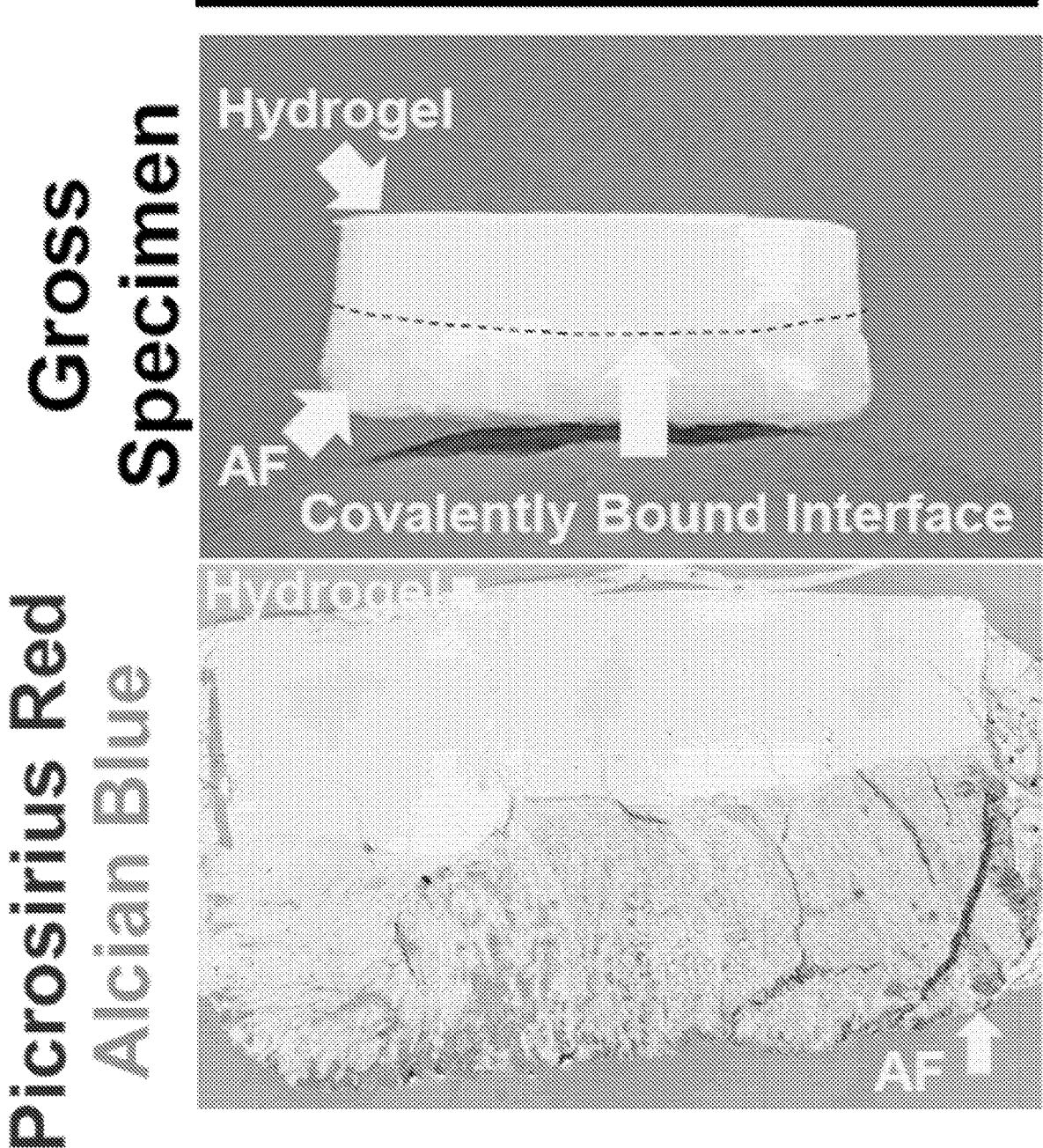
Figure 8A:
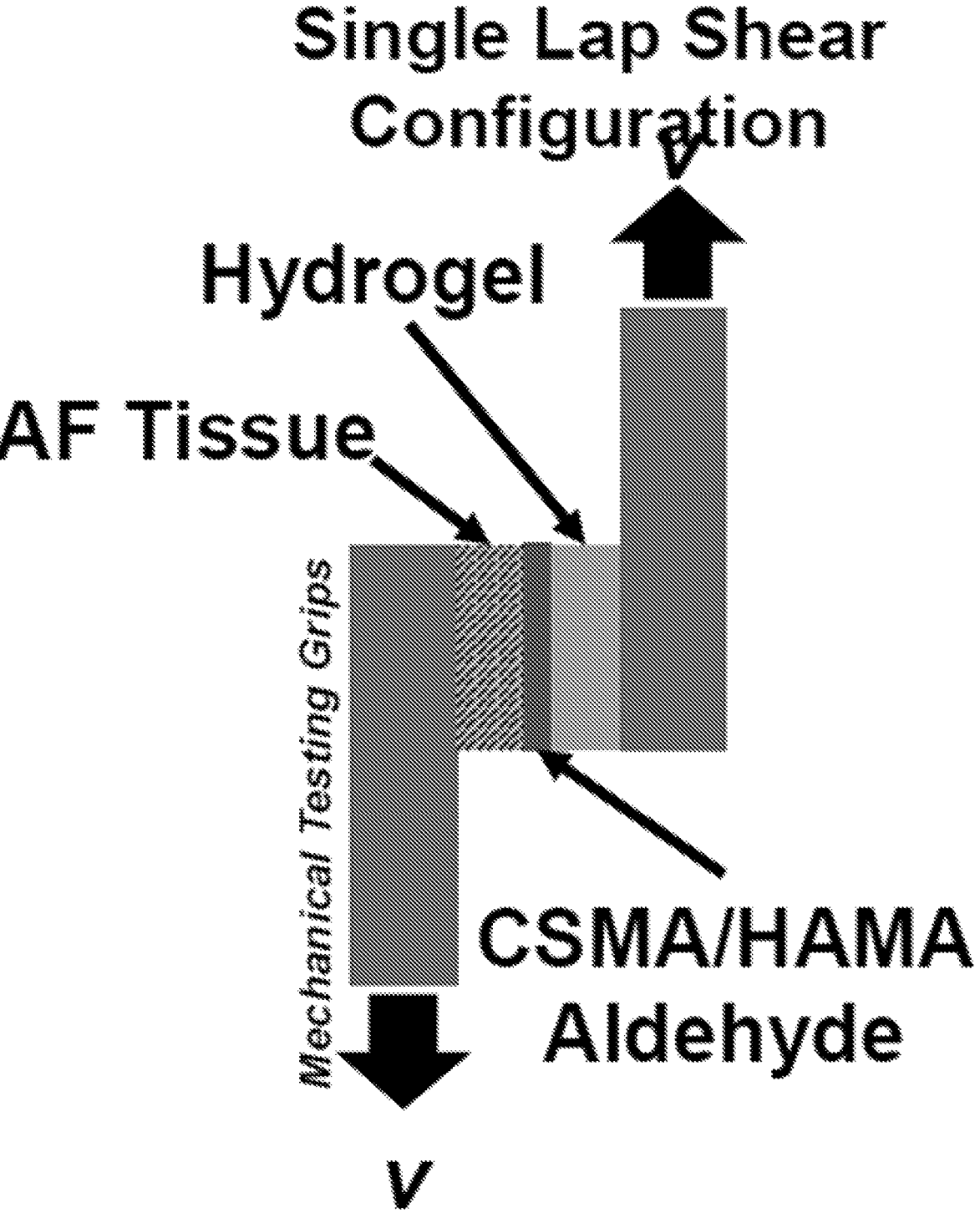
FIGS. 8A and 8B collectively illustrate theory and representative results of an assay assessing adhesion strength between annulus fibrosus tissue and hydrogel, according to some embodiments of the present disclosure. Specimens underwent displacement-controlled shear at 0.2% strain per second, according to adapted ASTM standard until failure to assess adhesion strength.
Figure 8B:
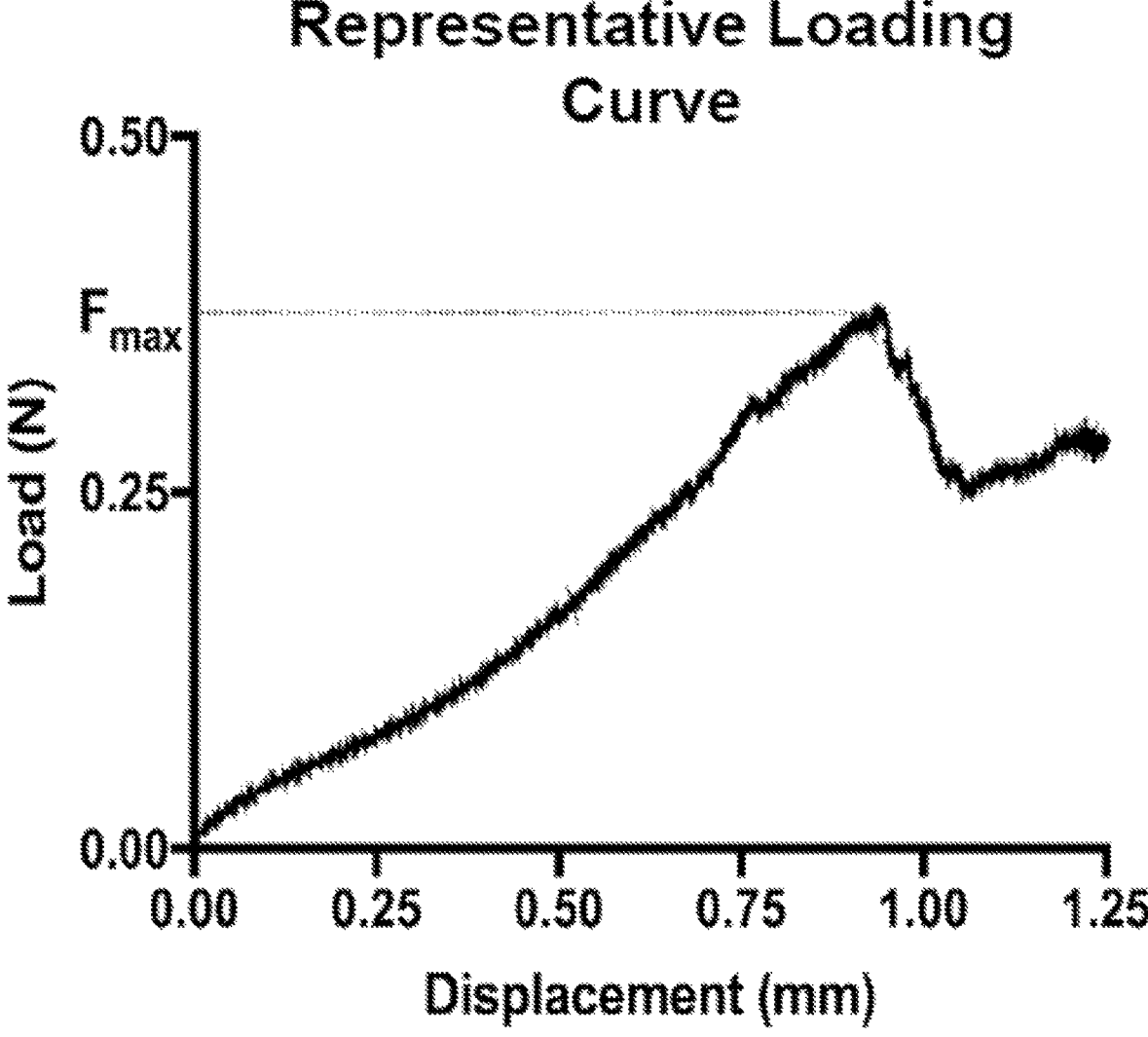
Figure 9A:
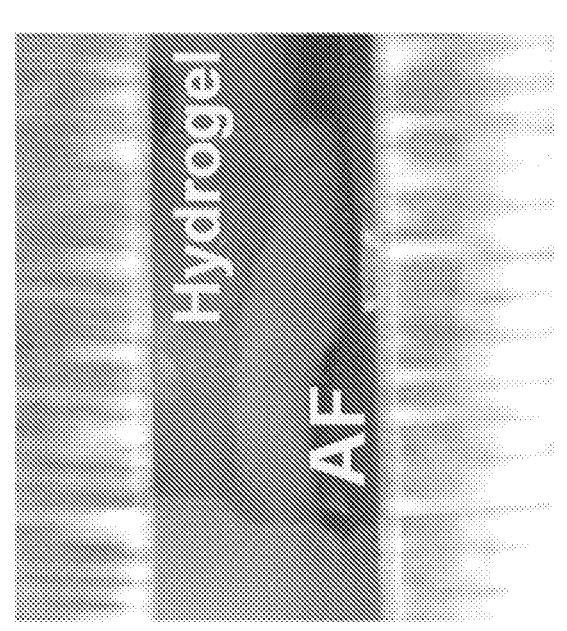
FIG. 9 shows mid-test images of hydrogel bound to annulus fibrosus specimen through dual-modified and unmodified glycosaminoglycans in displacement-controlled shear assays.
Figure 12A:
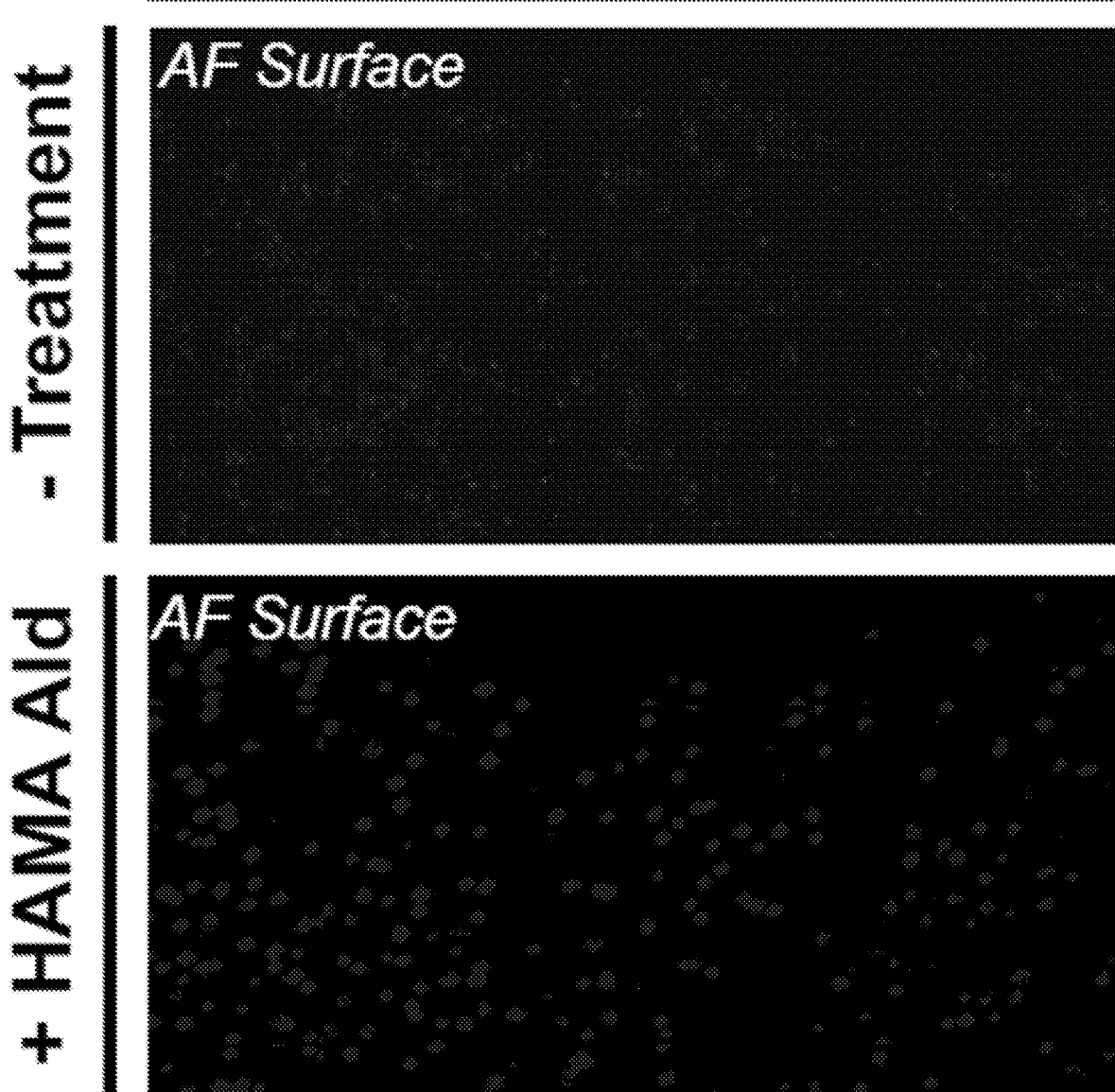
FIG. 12 shows images of hyaluronic acid localization near the tissue surface in hydrogel-annulus fibrosus specimen containing dual-modified (bottom panels) and unmodified (top panels) hyaluronic acid after a five minute treatment, in accordance with some embodiments of the present disclosure. Visualization of HAMA Aldehyde within
Figure 13A:
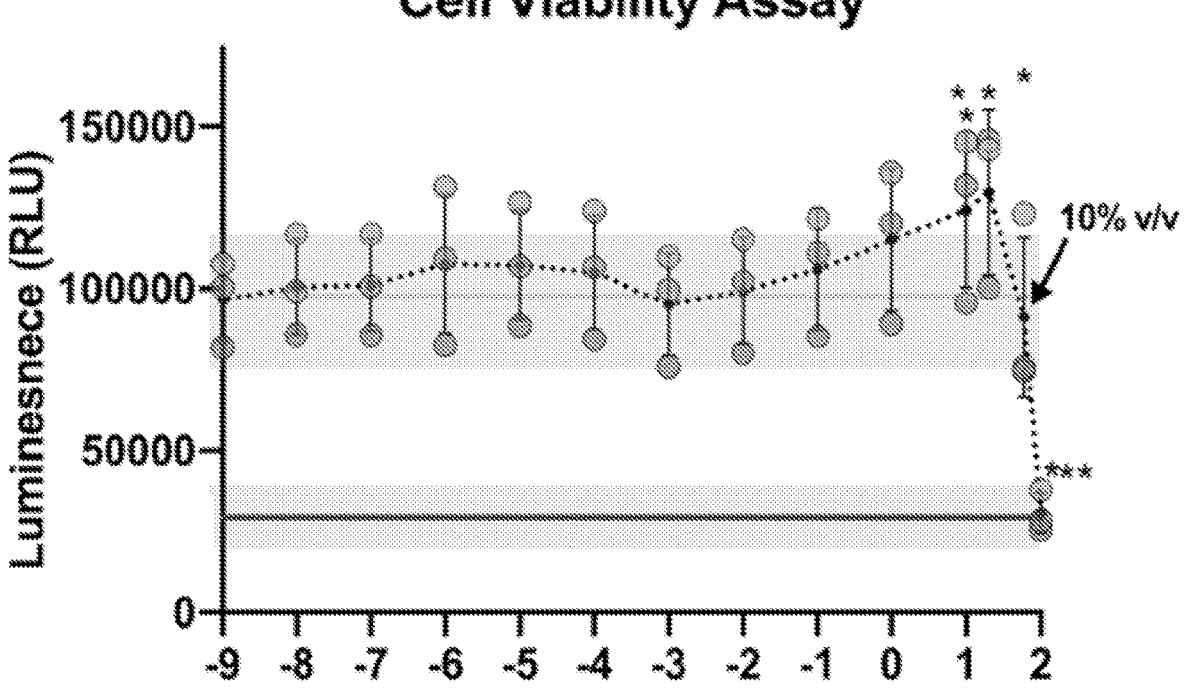
FIGS. 13A and 13B show the results of cell viability assays upon challenge with oxidized and methacrylated hyaluronic acid, in accordance with various embodiments of the present disclosure. Average=dotted line; live cell control=top unbroken line; 20% ethanol treated=bottom unbroken line.
Figure 13B:
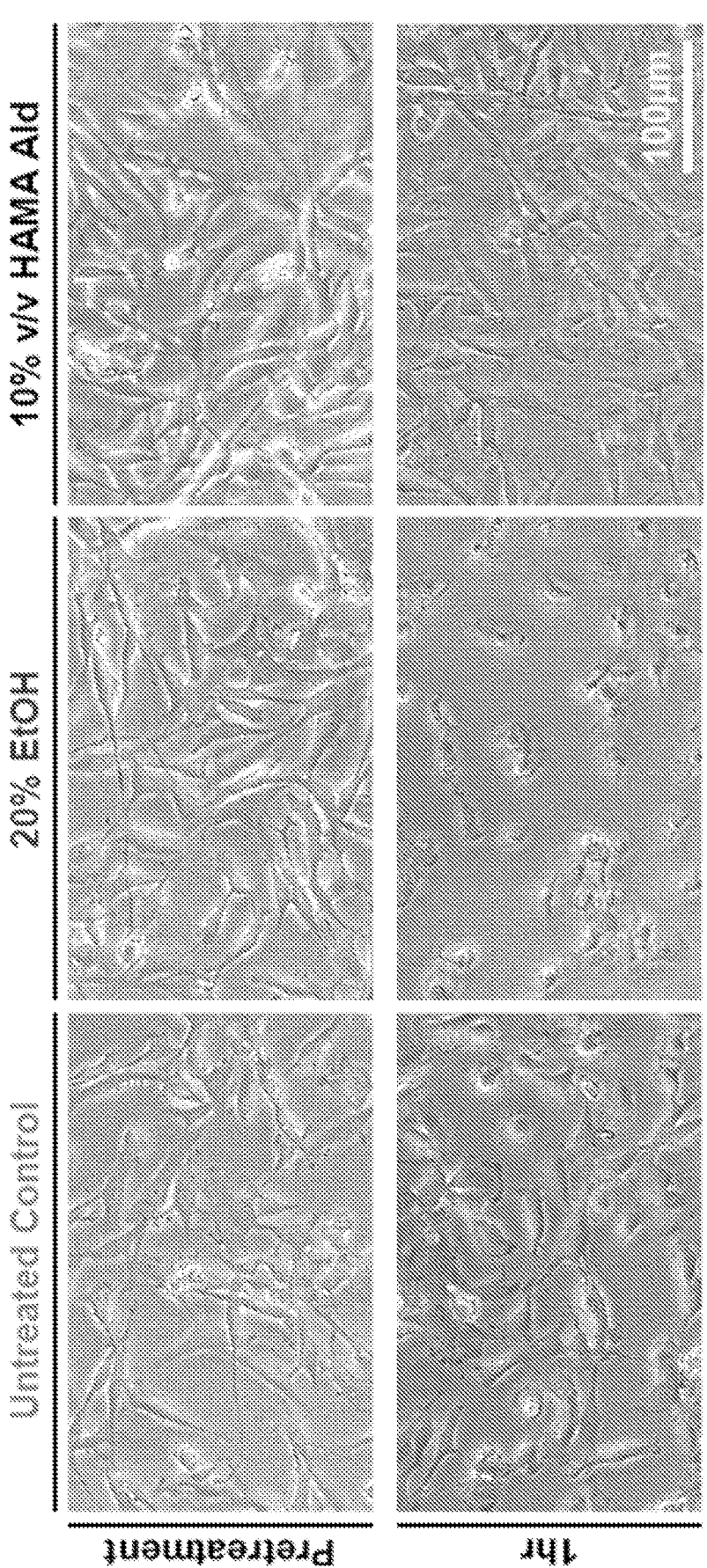

Dual-modified GAG Synthesis & Biochemical Analysis CS and HA were first oxidized with $NaIO4$ at a 1:2.4 or 1:3.5 ($GAG:IO_4^{-1}$) molar ratio followed by methacrylation via Methacrylic Anhydride (MAH) at a 1:10 or 1:20 (GAG: MAH) molar ratio, resulting in eight total products screened (outlined in FIGS. 3 and 4). All intermediate and final products were purified by dialysis for 3 days (MWCO=6-8 kDa), frozen down at −80° C., and recovered by lyophilization after 1 week. $^1H$ NMR was used to verify GAG methacrylation (δ~6.0 & 6.5 ppm) and compute Degree of Methacrylation using the downfield vinyl peak (FIG. 5). TNBS assay was used to verify GAG oxidation and compute Degree of Oxidation compared to unmodified controls (FIG. 6). Adhesion Testing Hydrogel adhesion was determined using an adapted lap shear test according to ASTM 2255-05 (outlined in FIG. 8). Briefly, 1.5 mm thick IPN hydrogels composed of a synthetic network (15% v/v PEGDA, Mn=575 Da) and natural polymer network (FN-Fibrin; 10 g/mL FN and 5 mg/mL Fibrin) were casted over 1.5 mm thick punches of AF tissue treated with dual-modified GAG for 5 mins prior to gel casting (shown in FIG. 7). Lap shear by tension loading was performed on specimens (3 mm composite thickness, 8 mm diameter) at 0.2% strain/sec. HAMA Aldehyde Tissue Distribution Alexa Fluor 594 Cadaverine was conjugated to the carboxylic moiety on HAMA Aldehyde polymer and subsequently applied to AF tissue (8 mm diameter by 1 mm thick biopsy punches) for 5 mins (mid-test images shown in FIG. 9). Constructs were sectioned and imaged using a Zeiss LSM 880 Microscope to visualize GAG depth of penetration. Cell Viability Bovine AF cell viability was measured after 1 hr of culture with HAMA Aldehyde (−9≤log [HAMA Aldehyde]≤2 (μM)) using the CellTiter-Glo® 2.0 assay for AF cells isolated from 3 biological donors (FIG. 13). Histological Analyses In situ hydrogel integration was histologically assessed using picrosirius red/alcian blue (PR/AB) staining on bovine coccygeal IVDs (FIG. 12). Statistics One-way and Two-way ANOVA with Tukey's post-hoc were used where appropriate. Significance labels are as follows: *p<0.05 p<0.01 *p<0.0001.

Figure 10:
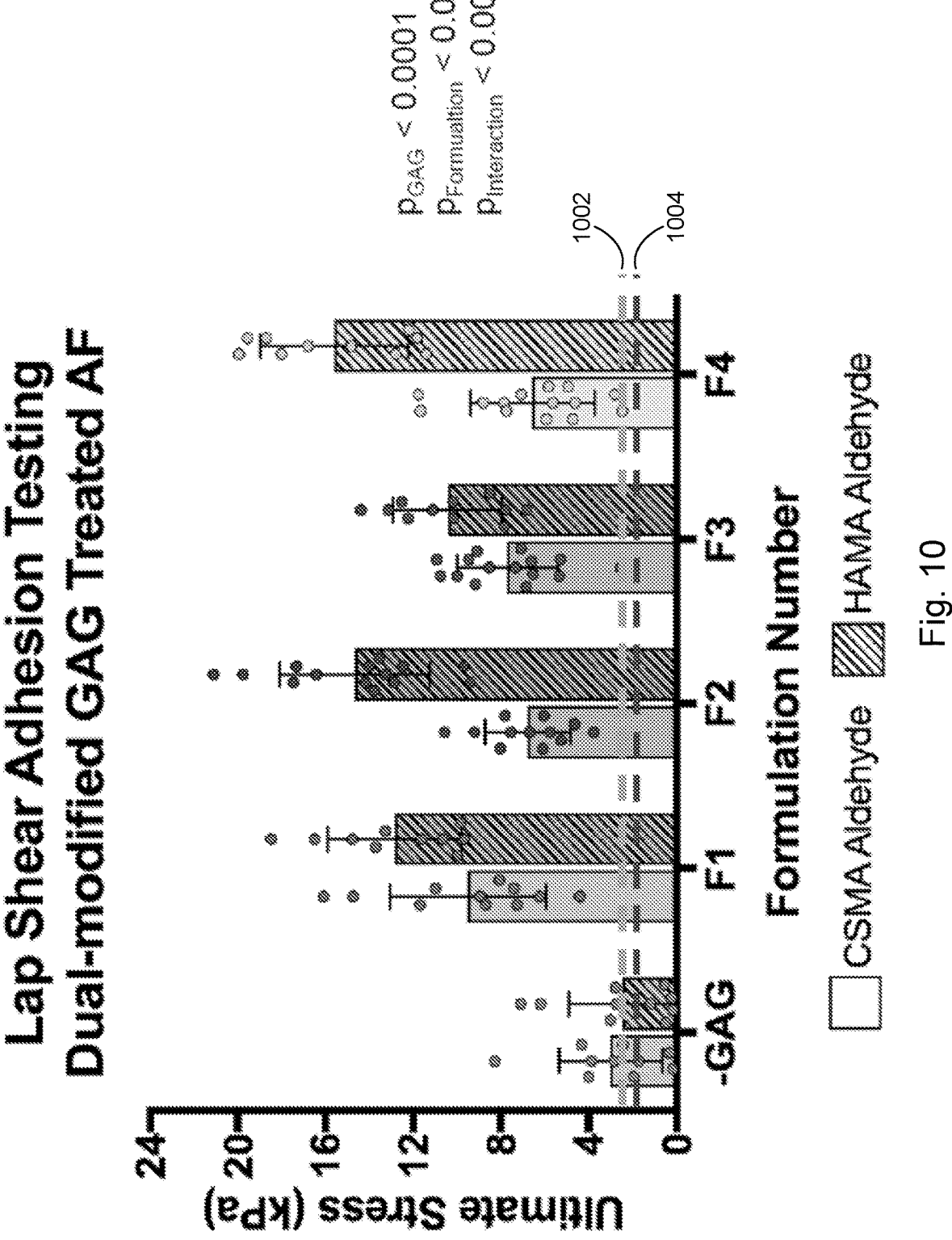
FIG. 10 illustrates adhesion strength between hydrogel and annulus fibrosus after treatment with dual-modified glycosaminoglycans oxidated and methacrylated at different stoichiometries, relative to unmodified glycosaminoglycans, fibrin adhesive specimen (102), and riboflavin-crosslinked collagen hydrogels (104).
Figure 11A:
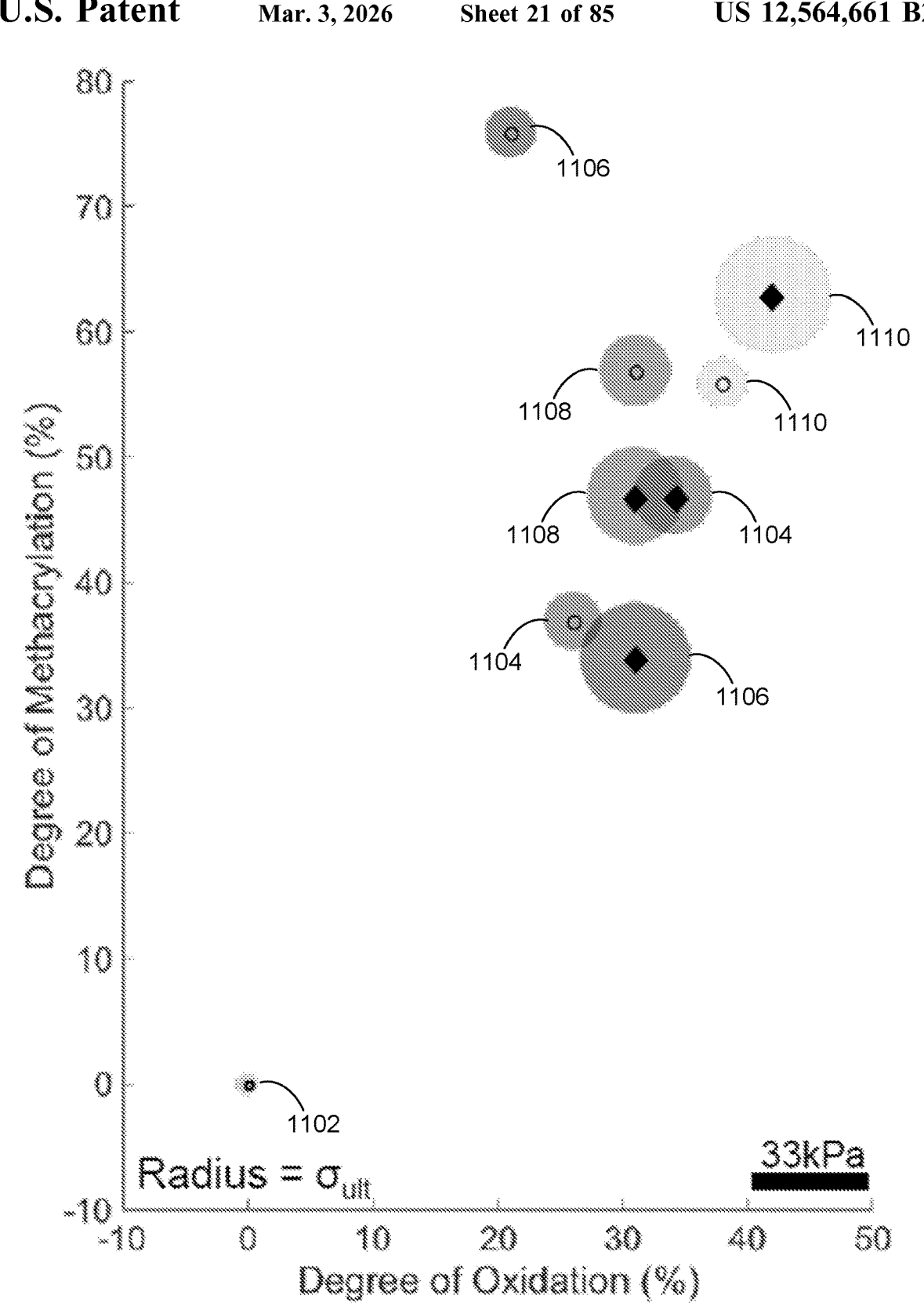
FIGS. 11A, 11B, and 11C collectively show the results of maximum lap shear as a function of glycosaminoglycan methacrylation and oxidation for dual-modified chondroitin sulfate (circles) and hyaluronic acid (diamonds). Unmodified glycosaminoglycan (1102); formulation 1 (1104); formulation 2 (1106); formulation 3 (1108); and formulation 4 (1110).
Figures 11B, 11C:
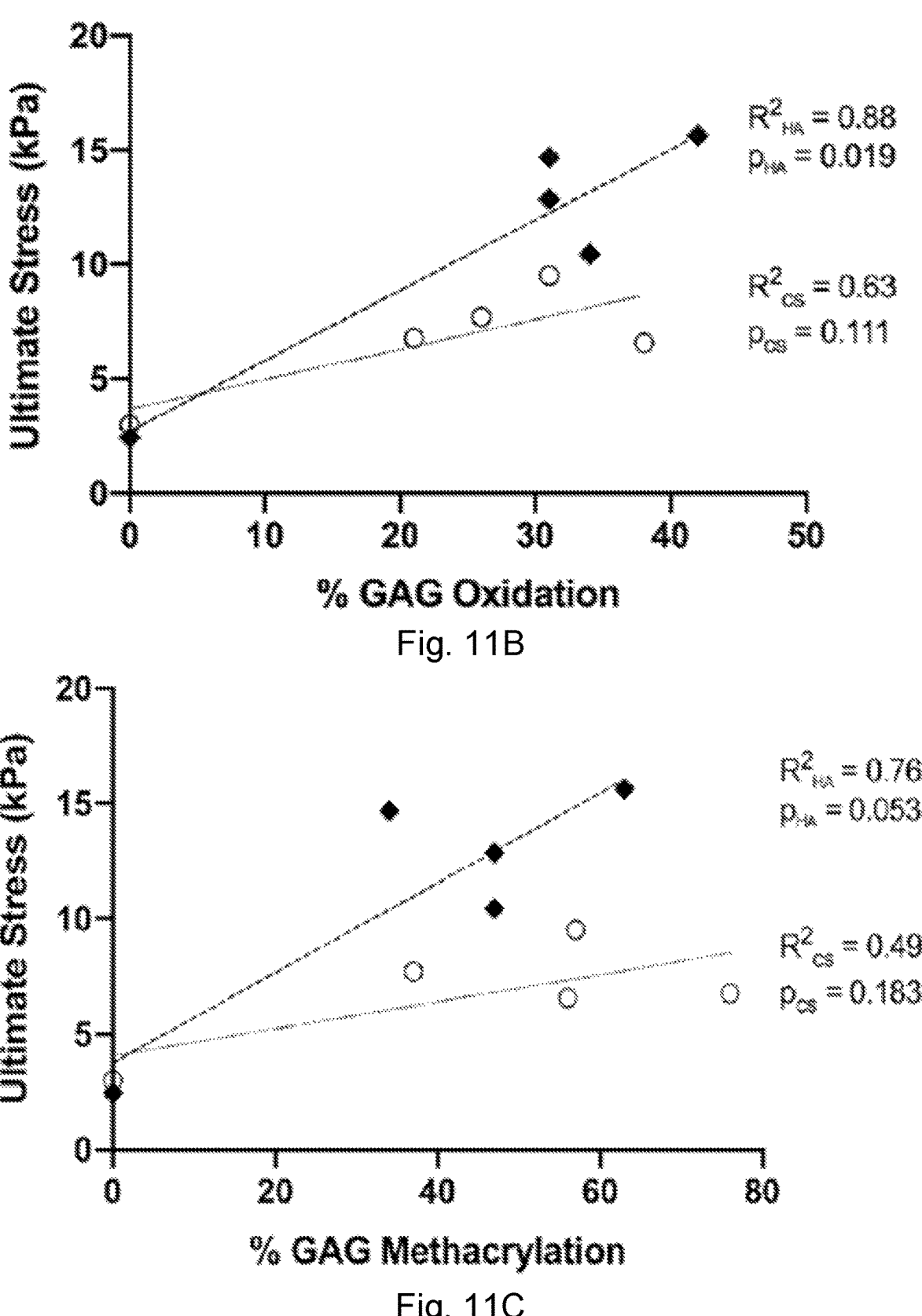
Figure 14A:
FIGS. 14A and 14B show staining of injured (14A) and repaired (14B) bovine coccygeal intervertebral disk tissue.
Figure 14B:
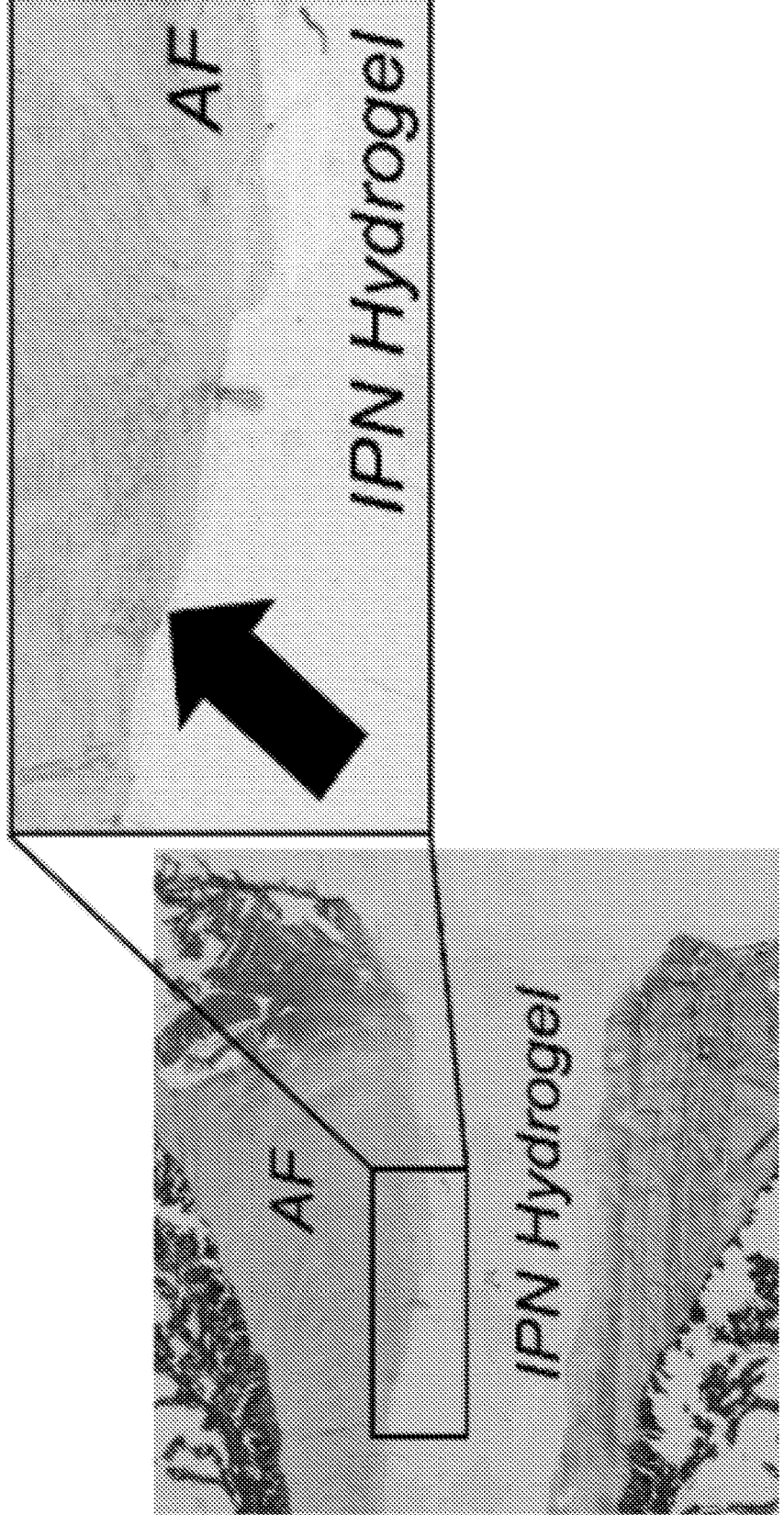

Lap shear tests indicate that treatment of AF tissue with dual-modified GAGs led to a significant increase in hydrogel adhesion strength compared to untreated controls. Additionally, dual-modified HA imparted significantly higher adhesion strength than dual-modified CS. (FIG. 10) These functional differences in adhesion strength are likely related to GAG aldehydation since degree of oxidation of dual-modified HA was greater than or equal to that of dual-modified CS for all formulations screened. (FIG. 11) Screening of dual-modified GAG formulations in lap shear suggest that HAMA Aldehyde Formulation 4 was the optimal product for downstream applications. After 5 min treatment of 10% v/v (6 μM) HAMA Aldehyde, the biomaterial was retained within 500 m from the tissue surface, with a number of AF cells exposed to the dual-modified GAG product. (FIG. 12) CellTiter-Glo 2.0@assay demonstrated that HAMA Aldehyde is non-cytotoxic at or below the 10% v/v (6 μM) working concentration. (FIG. 13) PR/AB staining demonstrates that in situ application of this two-part repair strategy leads to successful covalent bonding and tissue integration of the IPN hydrogel within an AF defect compared to unrepaired IVD control. (FIG. 14)

The present disclosure provides a cytocompatible two-part AF repair strategy that achieves adhesion strengths greater than that of commercial fibrin sealants (e.g., Tisseel) and other hydrogels for AF repair (e.g., riboflavin-cross-linked collagen and PNIPAAm-g-CS). Previous studies that characterize aldehydation of sulfated and unsulfated polysaccharides motivated us to systematically compare dual-modified CS and HA in relation to lap shear performance. We demonstrate here that oxidation of unsulfated GAGs (e.g., HA) yields greater adhesive strength compared to sulfated analogues (e.g., CS). This disclosure therefore advances the dual-modified CS previously used to repair cartilage defects by showing dual-modified HA has greater adhesive strength to integrate tissue engineering constructs, and also uniquely repurposes and optimizes this approach for IVD repair. When applied to AF defects in a large animal model of simulated discectomy, this repair strategy was well-integrated in situ as evidenced by a contiguous boundary between the AF and hydrogel with no cytotoxic responses. Together, these results suggest this repair strategy warrants future work to assess its success in maintaining IVD height and decreasing herniation risk after repair.

Discectomy does not repair residual AF defects, thereby posing a high risk of reoperation for a large patient population (~120,000 annually). Novel repair strategies utilize injectable gels to seal AF defects, which aim to address this unmet clinical need by reducing the risk of reherniation and preventing progressive degeneration.

Example 2—Glycosaminoglycan Oxidation

In order to synthesize the dual-modified GAG products, unmodified GAGs first underwent an oxidation reaction to produce an oxidized intermediate. Chondroitin sulfate Type A (CS) (Alfa Aesar, Haverhill, MA) and hyaluronic acid (HA) (Acros Organics, Fair Lawn, NJ) were dissolved in ddH$_2$O at a concentration of 6% (w/v) and 0.25% (w/v), respectively. Once fully dissolved, GAGs were oxidized by adding sodium periodate (NaIO$_4$) (Sigma-Aldrich, St. Louis, MO) to solution at a 1:2.4 or 1:3.5 GAG:IO$_4^{-1}$ molar ratio for 16 hours devoid of light with vigorous stirring at room temperature. [32,33] The reaction was stopped by adding 10% (v/v) ethylene glycol (Sigma-Aldrich, St. Louis, MO) to the reaction mixture and subsequently purified by dialyzing against ddH$_2$O for 3 days using Spectra/Por® 1 dialysis membranes (MWCO=6-8 kDa) (Spectrum Laboratories, Rancho Dominguez, CA). During the dialysis period, solutions were transferred to a new dialysis membrane once a day and ddH$_2$O was changed twice a day. After dialysis, intermediate products were frozen down at −80° C. for 24 hours and subsequently recovered by lyophilization for 7 days.

Example 3—Glycosaminoglycan Methacrylation

Following oxidation, e.g., as described in Example 2, intermediate products then underwent a methacrylation reaction to produce the final dual-modified GAG products. Upon recovery, CS aldehyde and HA aldehyde intermediates were dissolved in ddH$_2$O at a concentration of 25% (w/v) and 0.5% (w/v), respectively. The pH of solution was first raised to 8.00 with the addition of 1M NaOH prior to the start of the methacrylation reaction. Oxidized GAGs then underwent methacryloyl substitution by adding methacrylic anhydride (MAH) (Sigma-Aldrich, St. Louis, MO) to the reaction mixture at a 1:10 or 1:20 GAG:MAH molar ratio. [34,35] The pH of the reaction mixture was maintained at 8.00 by the addition of 1M NaOH and proceeded for 24 hours at 4° C. devoid of light with vigorous stirring. Final products were purified by dialyzing against ddH$_2$O for 3 days using Spectra/Por® 1 dialysis membranes (MWCO=6-8 kDa) (Spectrum Laboratories, Rancho Dominguez, CA). During the dialysis period, solutions were transferred to a new dialysis membrane once a day and ddH$_2$O was changed twice a day. After dialysis, final products were frozen down at −80° C. for 24 hours and subsequently recovered by lyophilization for 7 days to obtain all dual-modified GAG products (CSMA Aldehyde and HAMA Aldehyde).

Example 4—Quantifcation of Dual-Modified GAG Degree of Oxidation

A 2,4,6-trinitrobenzenesulphonic acid (TNBS) assay was used to determine the degree of oxidation for dual-modified GAG products. [36] tert-Butyl carbazate (t-BC) (Sigma-Aldrich, St. Louis, MO) reacts with aldehyde moieties forming a stable carbazone in a similar manner to imine formation, enabling the quantification of aldehyde modification. A standard calibration curve from aqueous t-BC solutions (0-50 mM) was used to determine the amount of unreacted t-BC and in turn compute aldehyde content for each of the eight dual-modified GAG formulations screened herein. First, a 2% (w/v) solution of dual-modified CS, 0.25% (w/v) solution of dual-modified HA, and 1% (w/v) solution of trichloroacetic acid (TCA) (Fisher Chemical, Fair Lawn, NJ) was prepared in ddH$_2$O. Differences in weight by volume concentrations account for the difference between molecular weight and solubility between the two GAG types. Additionally, 0.1M sodium borate buffer was prepared by dissolving sodium tetraborate decahydrate (Fisher Chemical, Fair Lawn, NJ) in ddH$_2$O and the pH was adjusted down to 8.0 with 0.5N HCl (Fisher Chemical, Fair Lawn, NJ). A stock 50 mM t-BC solution for standards and experimental samples was made with 1% TCA as the solvent. 25 μL of the 2% (w/v) dual-modified CS solution (0.5 mg of dual-modified CS product) was mixed with 25 μL of the 50 mM t-BC in TCA solution, and the reaction mixtures were vigorously agitated on an orbital shaker devoid of light for 16 hours. In order to keep stoichiometry consistent between the total molecular weight of CS and HA reacted with t-BC, 200 μL of the 0.25% (w/v) dual-modified HA solution (0.5 mg of dual-modified HA product) was mixed with 25 μL of the 50 mM t-BC in TCA solution, and the reaction mixtures were vigorously agitated on an orbital shaker devoid of light for 16 hours. Following incubation, 0.5 mL of 6 mM TNBS solution in 0.1M borate buffer was added to standard and experimental samples and the reaction mixtures were vigorously agitated on an orbital shaker devoid of light for 1 hour. After incubation, 20 μL of each experimental and standard sample was added into wells of a 96 well plate in triplicate, and 180 μL of 0.5N HCl was added to each well. Optical density measurements were taken at 340 nm using a SpectraMax i3x Multi-Mode Microplate Reader (Molecular Devices, San Jose, CA).

Example 5—Quantification of Dual-Modified GAG Degree of Methacrylation

Figure 23A:
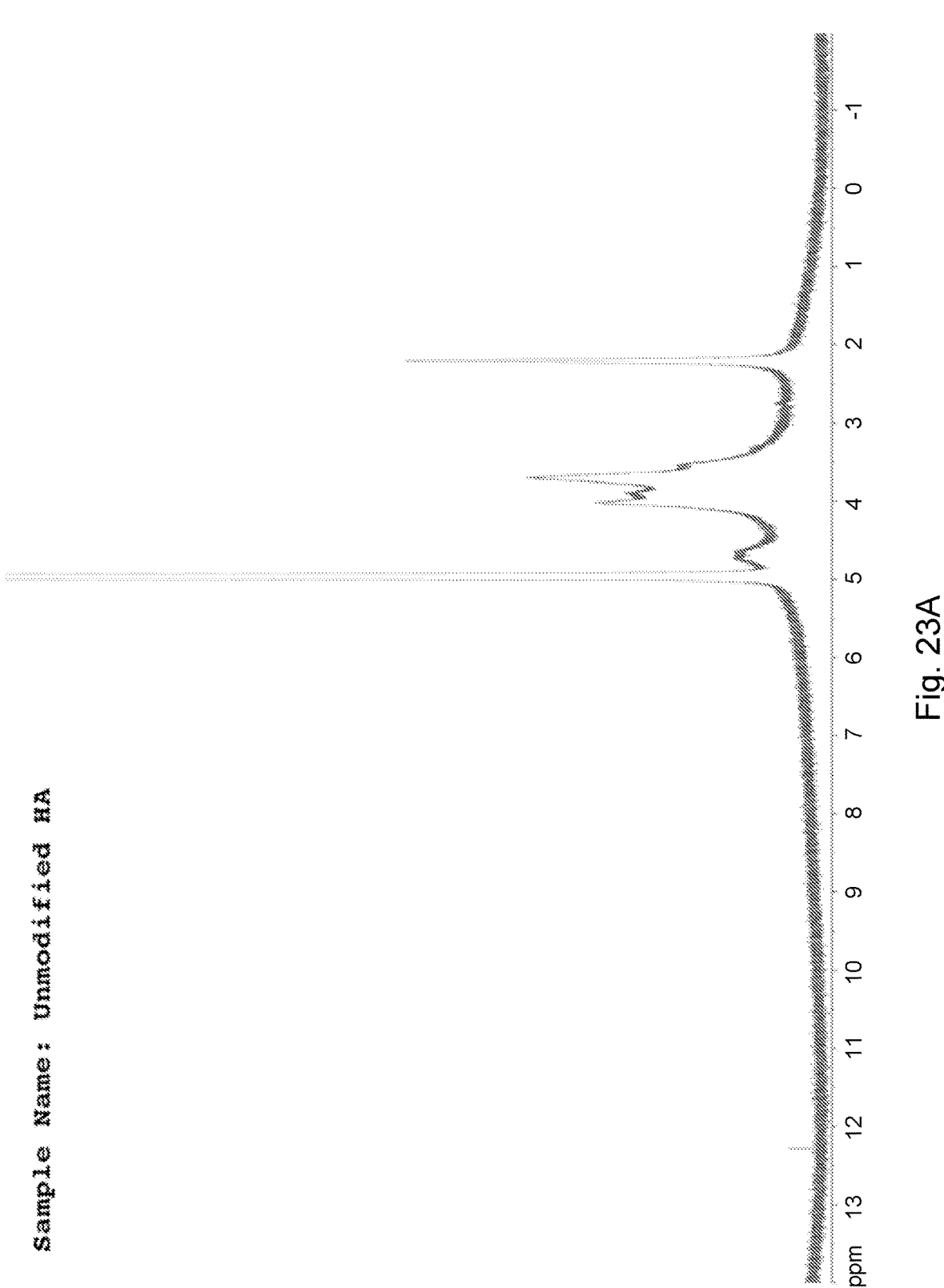
FIGS. 23A and 23B show 1H NMR spectra of unmodified hyaluronic acid (HA) and chondroitin sulfate (CS).
Figure 23B:
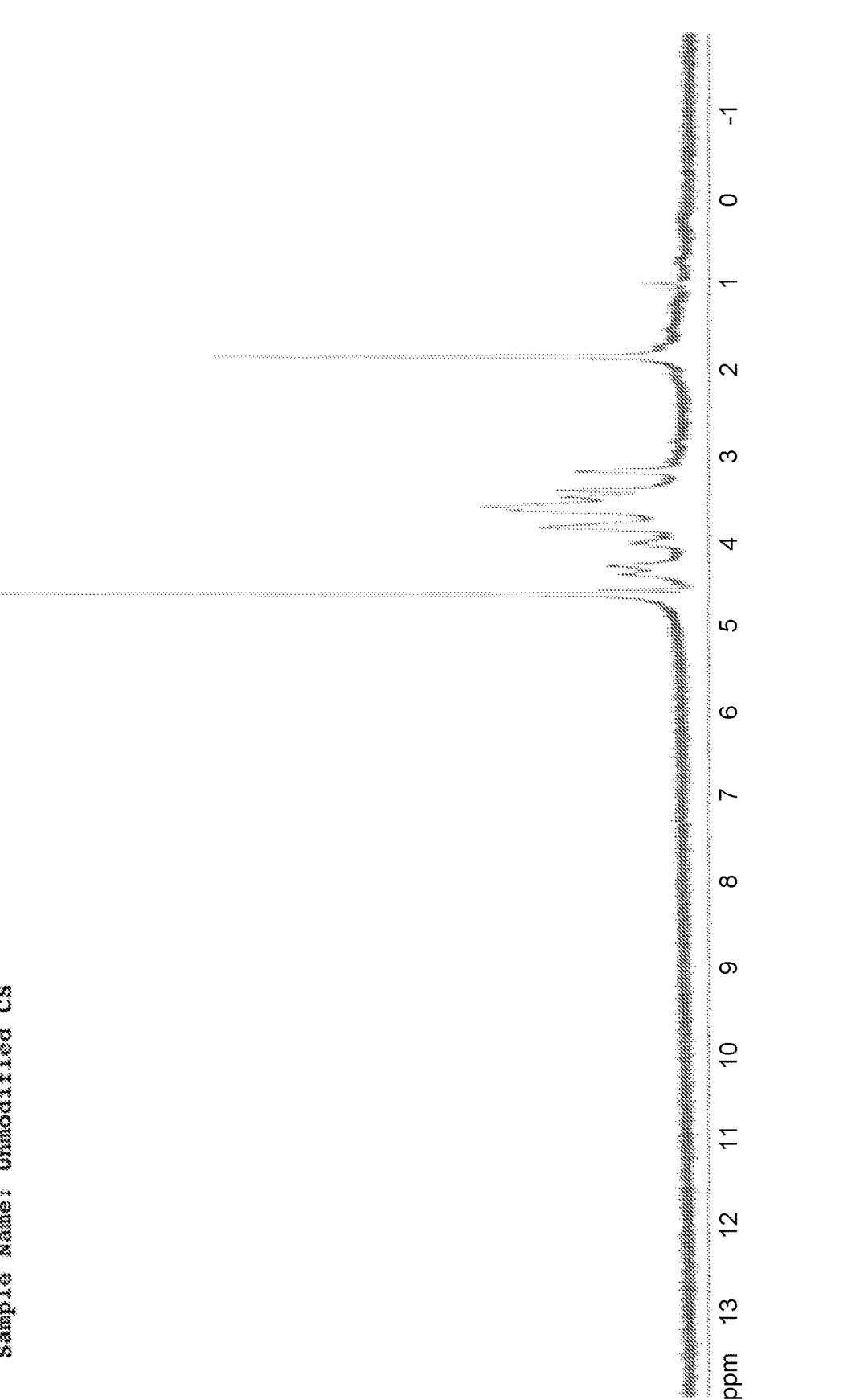

Proton nuclear magnetic resonance (H NMR) spectroscopy (500 MHz Varian Mercury 300, Agilent Technologies, Santa Clara, CA) was used to verify oxidation and methacrylation of dual-modified GAG products when compared to the unmodified polymer (FIG. 23). [37,38] Additionally, $^1$H NMR was used to compute the degree of methacrylation for each formulation by determining the integration of the downfield vinyl peak at δ=6.5 ppm relative to the integration of the HA or CS backbone δ=3.20-4.45 ppm on iNMR software. [35,39-41]

Example 6—Hydrogel Fabrication

Figure 24A:
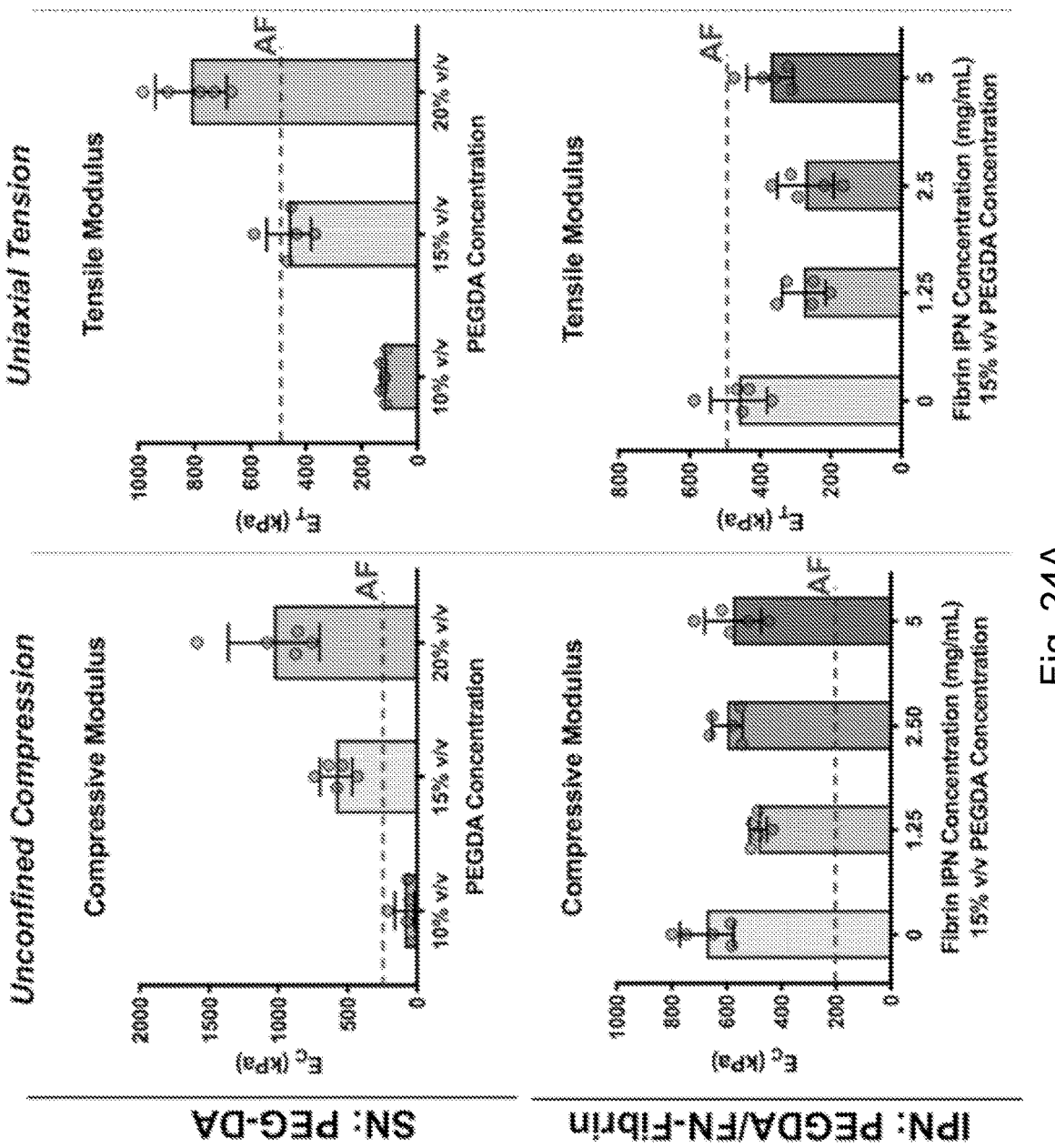
FIGS. 24A and 24B show material properties of single network (SN) and interpenetrating network (IPN) hydrogels composed of PEGDA Mw=575 Da and crosslinked with the AA/Oxone initiator pair at 11 mM, in accordance with some embodiments of the present disclosure.
Figure 24B:
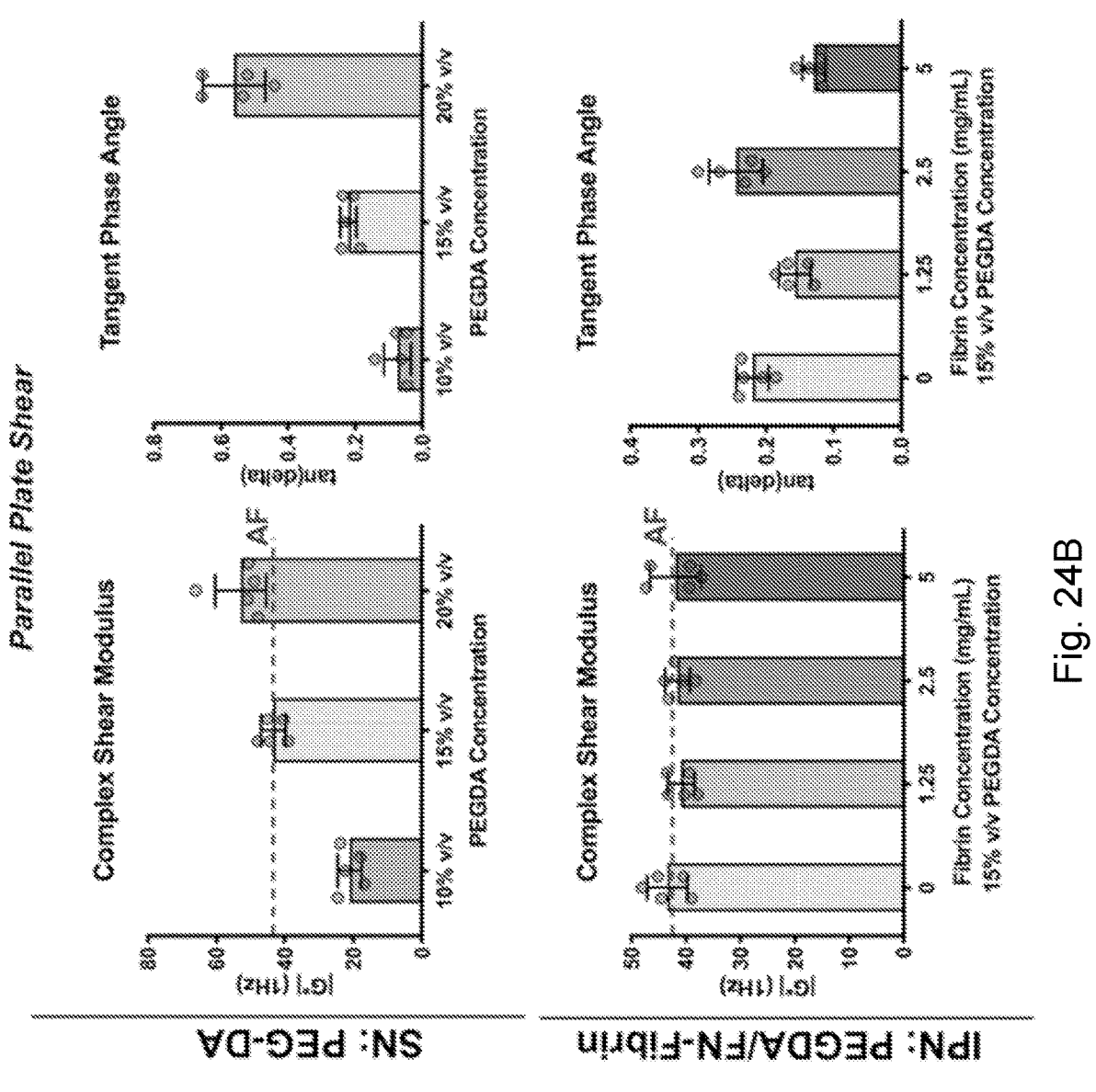

Single Network (SN) and Interpenetrating Network (IPN) hydrogels were initially fabricated using 575 Da PEGDA (Sigma Aldrich, St. Louis, MO) across a volumetric concentration range of 10-20% (v/v) for mechanical characterization using 11 mM L-Ascorbic Acid (AA) (Fisher Scientific, Fair Lawn, NJ) and Oxone monopersulfate (Alfa Aesar, Haverhill, MA) as a redox initiation system to crosslink acrylate end groups. (FIG. 24) Due to the pH sensitivity of the Schiff base reaction, the redox initiation system was changed to ammonium persulfate (APS) (Acros Organics, Fair Lawn, NJ) and N,N,N',N'-tetramethylethylenediamine (TEMED) (Bio-Rad Laboratories, Hercules, CA) at either 20 mM or 40 mM for hydrogel mechanical testing, lap shear tests, and downstream in situ experiments.

SN hydrogels were fabricated using three MWs of PEGDA at 15% (v/v): 575 Da (Sigma Aldrich, St. Louis, MO), 10 kDa (Polysciences Inc., Warrington, PA), and 20 kDa (Polysciences Inc., Warrington, PA) with 3.3% (v/v) (1.17 U/mL) of Oxyrase-EC (Oxyrase®, Mansfield, OH) as an oxygen scavenger and either 20 mM or 40 mM APS/TEMED redox initiators. IPN hydrogels incorporated a fibronectin-conjugated fibrin network by the inclusion of 10 μg/mL human fibronectin (Sigma Aldrich, St. Louis, MO), 0.5 U/mL Factor XIII (EMD Millipore, Darmstadt, Germany), 10 U/mL thrombin (Sigma Aldrich, St. Louis, MO), and 5 mg/mL human fibrin (Sigma Aldrich, St. Louis, MO) into the prepolymer solution.

All constructs were fabricated by using a 1:1 dual-barrel syringe and 1:1 volumetric mixing tip (PacDent International, Walnut, CA) to cast prepolymer solution into cylindrical acrylic molds (8 mm diameter by 3 mm height) for rheological and compression testing or "dog-bone" ASTM D638-02a type V molds for tensile testing, and coverslipped for at least 5 minutes to ensure full gelation.

Example 7—Hydrogel Mechanical Testing

After a 3-day swelling period in PBS to reach equilibrium, hydrogel specimens underwent unconfined compression (N=10/group), parallel plate shear (N=10/group), and uniaxial tensile (N=5/group) testing to characterize the material properties across all SN and IPN hydrogel formulations according to ASTM F2150-19. [42] Unconfined compression tests were conducted on an Electroforce 3220 (TA Instruments, New Castle, DE), where specimens underwent a displacement-controlled ramp at 1% strain/sec to a total of 20% strain. Data was collected on WinTest 7 software (TA Instruments, New Castle, DE) and post-processed on Microsoft Excel, where the slope of the force-displacement curve at the top 10% of the linear region was used to obtain stiffness values for each specimen and normalized by cross-sectional area to convert stiffness to the unconfined compressive modulus. Parallel plate shear testing was conducted on a TA Instruments AR2000ex rheometer (TA Instruments, New Castle, DE), where specimens underwent a frequency sweep from 0.1-10 Hz at 1% strain, and the complex modulus (|G*|) and tangent phase angle (tan δ) values were obtained at 1 Hz, which is a physiologically-relevant loading frequency. [43] Rheometry data was collected on Rheology Advantage software (TA Instruments, New Castle, DE). Uniaxial tensile testing was conducted on an Instron 8872 Fatigue Testing System (Instron, Norwood, MA), where specimens underwent displacement-controlled ramp at 0.2% strain/sec to either 50% strain for SN and IPN hydrogels composed of 10 kDa PEGDA and 20 kDa PEGDA, or failure for SN and IPN hydrogels composed of 575 Da PEGDA since failure occurred below 50% strain for this MW. For SN and IPN hydrogels fabricated with 40 mM APS/TEMED and 20 kDa PEGDA, smaller rectangular casting molds of 9.5 mm×27 mm were used to ensure complete gelation and minimize material usage. Data was collected and processed with Microsoft Excel software to compute stiffness values from the linear region of the force-displacement curves and converted to tensile modulus by normalizing to cross-sectional area.

Example 8—Lap Shear Adhesion Testing

Hydrogel adhesion imparted by the dual-modified GAG products was quantitatively determined using a lap shear configuration according to the ASTM 2255-05 testing protocol (N=10-15/group). Prior to testing, lap shear specimens were fabricated in 8 mm diameter by 3 mm height acrylic molds. First, 8 mm diameter biopsy punches of AF tissue were obtained from skeletally mature and healthy bovine IVDs from coccygeal IVD levels cc1/2, cc2/3, cc3/4, and cc4/5 (Springfield Meat Co., Richlandtown, PA) using an axial orientation of the punch. AF tissue punches were then sliced into 1.5 mm thick sections with Tissue Matrix (ASI Instruments, Warren, MI) and placed in the base of the acrylic mold. AF tissue punches were coated with either 25% (w/v) solution of the CSMA Aldehyde products or 10% (w/v) solution of the HAMA Aldehyde products for 5 minutes to enable Schiff base formation to occur. Differences in weight-by-volume concentrations between CSMA Aldehyde and HAMA Aldehyde were to control for the total weight of polymer applied to AF tissue samples. Negative control (–GAG) samples were treated with 1×PBS for 5 minutes instead of dual-modified GAG products to control for the effect of GAG treatment. After 5 minutes, the dual-modified GAG product or PBS was aspirated off AF tissue, and the IPN hydrogel prepolymer solution (20 mM APS/TEMED) was casted directly over the specimens followed by coverslipping to create a 3 mm thick AF tissue/dual-modified GAG/IPN Hydrogel specimens with parallel faces. PEGDA MW in the IPN hydrogel formulation was held constant ($M_n$=575 Da) in order to screen for differences in adhesion strength imparted by dual-modified GAG formulation. Specimens were then glued to custom aluminum platens with Loctite® 401 adhesive and fixed within Bose Electroforce 3220 equipped with a 5 N load cell. Specimens underwent displacement-controlled ramp-to-failure at a shear strain rate of 0.2% strain/sec, and the maximum force at which interfacial failure occurred was used to determine the ultimate strength of the specimen. All data were collected on WinTest 7 software and post-processed on Microsoft Excel. The dual-modified GAG that imparted the highest average biomaterial adhesion strength (HAMA Aldehyde Formulation 4) was chosen for all downstream experimentation.

Example 9—Dual-Modified HA Visualization in AF Tissue

To visualize the depth of HAMA Aldehyde penetration into the AF, Alexa Fluor Cadaverine-594 (Thermo Fisher Scientific, Rochester, NY) was conjugated to the carboxylic moiety of the dual-modified HA via 1-ethyl-3-(-3-dimethylaminopropyl) carbodiimide hydrochloride/N-hydroxysuccinimide (EDC/NHS) chemistry. Prior to the reaction, sodium hydrogen phosphate heptahydrate (Alfa Aesar, Ward Hill, MA) and sodium phosphate monobasic monohydrate (Fisher Chemical, Fair Lawn, NJ) were dissolved in ddH$_2$O to prepare phosphate buffer with a pH of 8.2 and buffer strength of 100 mM. A 10 mg/mL solution of HAMA Aldehyde and 100 mg/mL solution of EDAC was prepared in 0.1 M BupH™ MES buffered saline (Thermo Fisher Scientific, Rochester, NY) prior to the reaction as well. 4 μL of 100 mg/mL EDAC was added to 1 mL of the 10 mg/mL HAMA Aldehyde solution to generate the unstable o-acylisourea ester intermediate. 6 μL of 100 mg/mL NHS solution was then added into the reaction mixture and incubated on an orbital shaker for 15 minutes at room temperature to produce the semi-stable amine-reactive ester. Following incubation, 3500 μL of phosphate buffer was added to the reaction mixture to bring the pH of solution above 7.0. After the addition of buffer, 100 μL of Alexa Fluor Cadaverine-594 at a concentration of 0.002 mg/mL was added to the reaction mixture and incubated on an orbital shaker for 2 hours at room temperature. After 2 hours, the final product was collected using Amicon® Ultra-0.5 centrifugal filter devices (Ultracel®—3,000 NMWL) (Merck Millipore Ltd., Darmstadt, Germany). Briefly, 500 μL of the final product was aliquoted into Amicon® filter devices and spun down at 14,000 g for 20 minutes using an Eppendorf centrifuge. The concentrated solute was recovered by inverting the filter device in a clean microcentrifuge tube and spinning the sample down at 1000 g for 2 minutes.

A 10% w/v solution of HAMA Aldehyde with the conjugated Alexa Fluor Cadaverine-594 probe was cast over 8 mm diameter punches of AF tissue for 5 minutes. Following incubation, the solution was aspirated off the AF and tissue specimens were either embedded in Tissue-Tek® O.C.T. Compound (Sakura Finetek USA, Torrance, CA) for cryosectioning to visualize cross-sectional depth-of-penetration or imaged on a Zeiss LSM 880 confocal microscope (Carl Zeiss Microscopy LLC, White Plains, NY) to assess spatial homogeneity of HAMA Aldehyde. Nine consecutive z-stacks from confocal imaging were imported into MATLAB (Release 2018b MathWorks, Natick, MA) and each pixel underwent thresholding according to fluorescent signal intensity. Pixel fluorescence data was smoothed across each z-stack using the MATLAB smoothdata function, and cumulatively added together at each spatial location to generate a surface topography map that visually represents HAMA Aldehyde depth across the entire area of the specimen. OCT-embedded tissues were sectioned on a cryotome to produce 12 μm thick sections mounted on charged slides. Sections were then stained with a 1:1000 dilution of 1 μg/mL stock solution of 4',6-diamidino-2-phenylindole (DAPI) for 5 minutes to visualize AF cell nuclei. After coverslipping with Fluoro-Gel mounting medium (Electron Microscopy Sciences, Hatfield, PA), slides were imaged on a Zeiss AxioImager Z2 (Carl Zeiss Microscopy LLC, White Plains, NY).

Example 10—Cell Viability Assay

Cytotoxicity of the optimal dual-modified GAG product (i.e. HAMA Aldehyde Formulation 4) was assessed using a cell viability assay across a large range of HAMA Aldehyde concentrations. Primary bovine AF cells were isolated from three healthy and skeletally mature biological donors (B21, B24, and B26) (Springfield Meat Co., Richlandtown, PA) from coccygeal levels cc1/2, cc2/3, cc3/4, and cc4/5 using a collagenous digestion protocol. Briefly, isolated IVDs were first dipped in 70% ethanol followed by a thorough rinse in washing solution containing 1.5% Amphotericin B (Fisher Scientific, Pittsburgh, PA), and 3% penicillin/streptomycin (Life Technologies Corporation, Grand Island, NY), and 1×PBS. After washing, the AF was dissected off of the NP and finely cut into ~3 mm$^3$ pieces. AF tissue was then sterilely transferred to a T75 Nunc™ EasYFlask™ (Thermo Fisher Scientific, Rochester, NY) with 25 mL of 0.2% pronase (Fisher Scientific, Pittsburgh, PA) in Dulbecco's Modified Eagle's Medium (DMEM) (Thermo Fisher Scientific, Rochester, NY) and incubated at 37° C., 5% CO2 for 90 minutes on a rocker plate. Partially digested AF tissue was washed twice with 1×PBS to remove pronase, and 25 mL of DMEM with 200 U/mL collagenase I (Fisher Scientific, Pittsburgh, PA) was added to the flasks for 13 hours. Digested AF tissue was then filtered through a 70 μm filter (Fisher Scientific, Pittsburgh, PA), centrifuged at 500 g for 10 minutes, and the collected cells were analyzed for cell count and viability. AF cells (p0) were expanded to 90% confluence to obtain the appropriate yield for experimentation and used at p1 after TrypLE™ Express dissociation (Fisher Scientific, Pittsburgh, PA). AF cells (p1) were plated into Nunc™ MicroWell™ 96-Well Optical Bottom Plates with Polymer Base (Thermo Fisher Scientific, Rochester, NY) at a density of 4.4×103 cells/cm$^2$. Cells were cultured at 37° C., 5% CO2 with 100 μL of growth medium per well, where the growth medium was composed of high glucose (4.5 g/L) DMEM, 10% FBS (Gemini Bio-Products, West Sacramento, CA), 1% penicillin/streptomycin (Life Technologies Corporation, Grand Island, NY), and 0.2% L-Ascorbic Acid (Fisher Scientific, Fair Lawn, NJ). When AF cells reached 80% confluency, cell viability upon exposure to HAMA Aldehyde was assessed using the CellTiter-Glo® 2.0 assay (Promega Corporation, Madison, WI). Growth medium was first aspirated and 100 μL of medium supplemented with HAMA Aldehyde at concentration range of $10^{-9}$ to $10^2$ μM was applied to AF cells for 1 hour. Live cell and dead cell controls were included by replacing medium with 0 μM HAMA Aldehyde (Untreated) and 20% v/v EtOH, respectively. Blank wells were used to determine background luminescence readings. Prior to use, CellTiter-Glo® 2.0 reagent was thawed to room temperature and at the 1-hour time-point, 100 μL of CellTiter-Glo® 2.0 reagent was added to each well and incubated for 2 minutes on an orbital shaker devoid of light to induce cell lysis. After 2 minutes, well plates were taken off the orbital shaker and incubated at room temperature for 10 minutes to stabilize luminescent signal. After 10 minutes, luminescence in relative luminescence units (RLUs) was recorded on a SpectraMax i3x Multi-Mode Microplate Reader (Molecular Devices, San Jose, CA). All conditions were performed in triplicate for three biological donors.

Example 11—Motion Segment Preparation

Bovine tails from healthy and skeletally mature animals were procured from a local abattoir (Springfield Meat Co., Richlandtown, PA) and coccygeal motion segments (vertebrae-disc-vertebrae) were isolated from levels cc2/3, cc3/4, and cc4/5 to histologically assess biomaterial integration and evaluate implant herniation risk. All facet and transverse processes were removed with a bone band saw (Mar-Med Inc., Strongsville, OH) in addition to the removal of extraneous musculature and ligaments with a scalpel, and motion segment samples were stored at −20° C. until further use.

Example 12—Histological Analysis

A subset of specimens prepared for hydrogel characterization, lap shear, and herniation risk tests were allotted for histological analysis. Specimens were first fixed in aqueous buffered zinc formalin fixative (Anatech Ltd., Battle Creek, MI) for 48 hours and subsequently infiltrated with a hydrophilic resin, 2-hydroxypropyl methacrylate (Sigma-Aldrich, St. Louis, MO), for 48 hours with two changes of monomer solution to avoid dehydration and clearing of specimens. The monomer solution was then polymerized by the slow addition of heat at 37° C. to form blocks for sectioning. Histological sections were prepared by 5 µm slices and mounted on silane slides (Matsunami Glass, Osaka, Japan). Sections from slides were first deplasticized by placing slides in toluene (Sigma-Aldrich, St. Louis, MO) for 30 minutes and changed with fresh toluene for another 30 minutes. Toluene was then replaced with a 50% volumetric mix of toluene and petroleum ether (Sigma-Aldrich, St. Louis, MO) for 5 minutes. Slides were then dipped in ethylene glycol mono ethyl ether (EGME) (Sigma-Aldrich, St. Louis, MO) five times and rinsed with three changes of ddH₂O.

Sections from lap shear and motion segment specimens underwent tinctorial staining with picrosirius red and alcian blue dyes to visualize collagen and proteoglycan content, respectively, assess hydrogel integration, as well as observe overall specimen structure. After deplasticizing, sections were stained with Gomori's Hematoxylin (Fisher Healthcare, Houston, TX) for 15 minutes and rinsed with ddH₂O three times. Sections were then stained with alcian blue (pH=2.5) (Poly Scientific R&D, Bay Shore, NY) for 30 minutes and rinsed with ddH₂O three times. Following alcian blue staining, sections were then stained with picrosirius red (Sigma-Aldrich, St. Louis, MO) for 1 hour and rinsed with 1% acid water for 2 minutes. Following staining, sections were dehydrated with EGME, cleared with Xylenes (Sigma-Aldrich, St. Louis, MO), and coverslipped with Eukitt mounting media (Electron Microscopy Sciences, Hatfield, PA).

Hydrogel-only sections (FIG. 17) were stained with Gomori's Hematoxylin (Fisher Healthcare, Houston, TX) for 10 minutes and subsequently rinsed with ddH₂O three times. Slides were then stained with Protocol Eosin Y for 2 minutes (Fisher Healthcare, Houston, TX), followed by three rinses of ddH₂O. Following staining, sections were dehydrated with EGME, cleared with Xylenes (Sigma-Aldrich, St. Louis, MO), and coverslipped with Eukitt mounting media. All slides were imaged on a Leica DM6B Upright Microscope (Leica Microsystems GmbH, Wetzlar, Germany).

Example 13—Assessment of Herniation Risk

IVDs were isolated from motion segments by using an IsoMet® 1000 Precision Cutter (Buehler, Lake Bluff, IL) to make parallel cuts approximately 3 mm from the superior and inferior vertebral end plates. Biomaterial implant herniation risk was characterized by a displacement-controlled (2 mm/min) ramp-to-failure mechanical tests at a 5° incline to maximize stress at the repair site, as previously described. [44-48]50 IVDs from bovine coccygeal levels cc2/3, cc3/4, and cc4/5 were systematically assigned to three cohorts to account for potential level effects: 'Intact', 'Discectomy', and 'Repair', where IVDs in the 'Repair' cohort were split into three separate groups in which AF defects were primed with HAMA Aldehyde Formulation 4 and subsequently sealed with IPN hydrogels of the three PEGDA molecular weights considered herein (575 Da, 10 kDa, and 20 kDa) (N=10/group). All motion segments assigned to 'Discectomy' or 'Repair' groups first underwent a clinically-relevant injury of a 4 mm biopsy punch (Integra LifeSciences, Princeton, NJ) with 200 mg (~25%) of NP removal. To simulate a clinically-relevant AF defect, a 4 mm biopsy punch was inserted 7 mm deep into the posterolateral face of the AF and the resulting plug of tissue was removed using a rongeur. Following initial tissue removal, the NP was then disrupted for 2 minutes with a curette and 200 mg of fragmented NP tissue was removed from the IVD with a rongeur. For IVDs undergoing repair, ~150 µL HAMA Aldehyde solution (10% w/v) was slowly injected into the AF defect using a 5 mL syringe with a 20 G×1-1/2" BD PrecisionGlide™ Needle (Beckton, Dickinson and Company, Franklin Lakes, NJ) at a controlled rate to coat the tissue surface for 5 minutes to allow the Schiff base formation to occur. After 5 minutes, HAMA Aldehyde solution was aspirated and IPN hydrogel prepolymer solution was injected into the AF defect with a 1:1 dual-barrel syringe and 1:1 volumetric mixing tip (PacDent International, Walnut, CA) and covered with parafilm. Specimens were set for 15 minutes prior to mechanical testing to allow full gelation (~2 minutes) and bonding with HAMA Aldehyde. The following mechanical output parameters that assess herniation risk were computed from the force-displacement curves using a custom MATLAB code and normalized to IVD cross-sectional area when necessary: failure strength, subsidence-to-IVD failure, failure strain, work-to-IVD failure, and ultimate strength to failure strength ratio. IVD failure occurred either by endplate fracture or NP herniation, where NP herniation was defined as 2 mm of NP or implant protrusion from the outer radius of the AF. In the case of endplate fracture, IVD failure always coincided with the ultimate strength of the specimen (i.e. global maximum stress). IVD failure strength was defined as the stress at which endplate fracture or NP herniation occurred. Subsidence-to-IVD failure was defined as the displacement to which the point of failure for a given specimen occurred. Failure strain was defined as the percent deformation at the point of failure with respect to the original IVD height, where the IVD height prior to testing was measured in triplicate between parallel superior and inferior faces of the motion segment using a caliper. Work-to-IVD failure was defined as the area under the force-displacement trace until IVD failure occurred. The ultimate strength to failure strength ratio was computed by identifying the global maximum strength of a given specimen and normalizing that value to the failure strength of the same specimen.

Example 14—Statistical Analyses

All quantitative data are presented as mean±standard deviation. One-way ANOVA with Tukey's post-hoc test was used to assess significant differences for quantitative data pertaining to cell viability measurements. Two-way ANOVA was used to assess significant differences for quantitative data pertaining to the degree of GAG oxidation (TNBS assay), hydrogel mechanical properties, and lap shear adhesion strengths. Simple linear regression was used to assess the correlative relationship between GAG degree of oxidation and GAG degree of methacrylation with lap shear ultimate stress. Due to inhomogeneity of variance, Kruskal-Wallis nonparametric test with Dunn's post-hoc was used to analyze all quantitative output measures corresponding to the in situ herniation risk experiment. Statistical outliers were identified by the ROUT method (Q=1%) and consequentially excluded as necessary for output measures corresponding to the in situ herniation risk experiment. A non-linear semi-log fit was used to correlate failure strength and subsidence-to-failure to the tensile modulus of IPN hydrogels comprising different PEGDA MWs. Statistical analyses were performed using GraphPad Prism 8.0 (GraphPad Software, San Diego, CA) with threshold for significance across all experiments set to α=0.05.

Example 15—Synthesis and Biochemical Characterization of Dual-Modified GAGs

Dual-modified CS and HA were successfully synthesized according to a two-step reaction scheme, where unmodified GAGs are first oxidized by sodium periodate (as described in Example 2) and the intermediate product is subsequently methacrylated by methacrylic anhydride (as described in Example 3). (FIG. 15A) Using this two-step reaction scheme, four products (Formulations 1-4) were synthesized per GAG type for stoichiometries that enhance the degree of oxidation as well as methacrylation. (FIG. 15B) The degree of oxidation for dual-modified GAG products was computed by calculating the percent difference between $OD_{340}$ measurements between a given formulation and the unmodified GAG polymer (as described in Example 4). Significant differences were detected for the main effects of formulation number ($p_{Formulation}$=0.0005) and GAG type ($p_{GAG}$<0.0001), but no significant interaction between these effects ($p_{interaction}$=0.880). The degree of oxidation for all dual-modified HA formulations were equal to or greater than the degree of oxidation for dual-modified CS formulations. (FIG. 15C) $^1$H NMR (performed as described in Example 5) indicated that all dual-modified GAG products were methacrylated, indicated by the presence of vinylic peaks at 6.0 ppm and 6.5 ppm. The degree of methacrylation for dual-modified GAG products was computed by calculating the integral of the downfield vinyl peak, in which all dual-modified CS formulations had a degree of methacrylation greater than or equal to that of dual-modified HA. Peaks at 5.2 ppm additionally indicate that all dual-modified GAG formulations were oxidized, as these chemical shifts correspond adjacent protons to the aldehyde moiety. [37](FIG. 15D)$^1$H NMR of unmodified GAG polymers were used to ensure that all chemical shifts correspond to functionalization of the HA or CS backbone. (FIG. 23) All computed biochemical degrees of modification for a given formulation of dual-modified HA and CS are specified in Table 2.

TABLE 2

| Biochemical Degrees of Modification for Dual-modified GAGFormulations | | | | |
| | For-mulation | GAG: MAH | GAG: $IO_4^-$ | Degree of Oxidation (x) | Degree of Methacrylation (y) |
|---|---|---|---|---|---|
| CSMA Aldehyde | 1 | 1:10 | 1:2.4 | 31% | 57% |
| | 2 | 1:20 | 1:2.4 | 21% | 76% |
| | 3 | 1:10 | 1:3.5 | 26% | 37% |
| | 4 | 1:20 | 1:3.5 | 38% | 56% |
| HAMA Aldehyde | 1 | 1:10 | 1:2.4 | 31% | 47% |
| | 2 | 1:20 | 1:2.4 | 31% | 34% |
| | 3 | 1:10 | 1:3.5 | 34% | 47% |
| | 4 | 1:20 | 1:3.5 | 42% | 63% |

Example 16—Synthesis and Mechanical Characterization of SN and IPN Hydrogels

All SN and IPN hydrogels underwent a sol-gel transition in the presence of APS/TEMED redox initiators, and the FN-Fibrin natural polymer network was homogenously incorporated within the synthetic PEGDA network as histologically visualized by H&E staining. Gels were fabricated in geometric molds for mechanical testing and could also be injected directly into clinically-relevant AF defects. (FIG. 17A) The compressive, tensile, and shear moduli for SN and IPN hydrogel formulations employed herein were characterized to determine the effects of redox initiator concentration and hydrogel mesh size on construct stiffness. After initially screening across volumetric concentrations with 575 Da PEGDA, it was found that a concentration of 15% v/v approximately matches AF properties in unconfined compression, uniaxial tension, and parallel plate shear. (FIG. 24) To determine the effect of hydrogel mesh size on construct stiffness and in situ herniation risk, hydrogel formulations of higher PEGDA MW (10 k Da and 20 k Da) were considered herein while holding the 15% v/v PEGDA concentration constant. Across all mechanical parameters, there was a significant decrease in the modulus as the PEGDA MW increases ($p_{PEGDA}$ MW<0.001), where gels composed of 10 kDa and 20 kDa PEGDA were comparably less stiff than AF tissue in compression, tension, and shear. There was a significant effect of redox initiator concentration on the unconfined compressive modulus for SN (p<0.0001) and IPN (p<0.0001) hydrogels and IPN hydrogels in uniaxial tension (p<0.0001) but had no significant effect on other mechanical properties (p>0.05). (FIG. 17B)

Example 17—Lap Shear Adhesion Testing

Figure 18B:
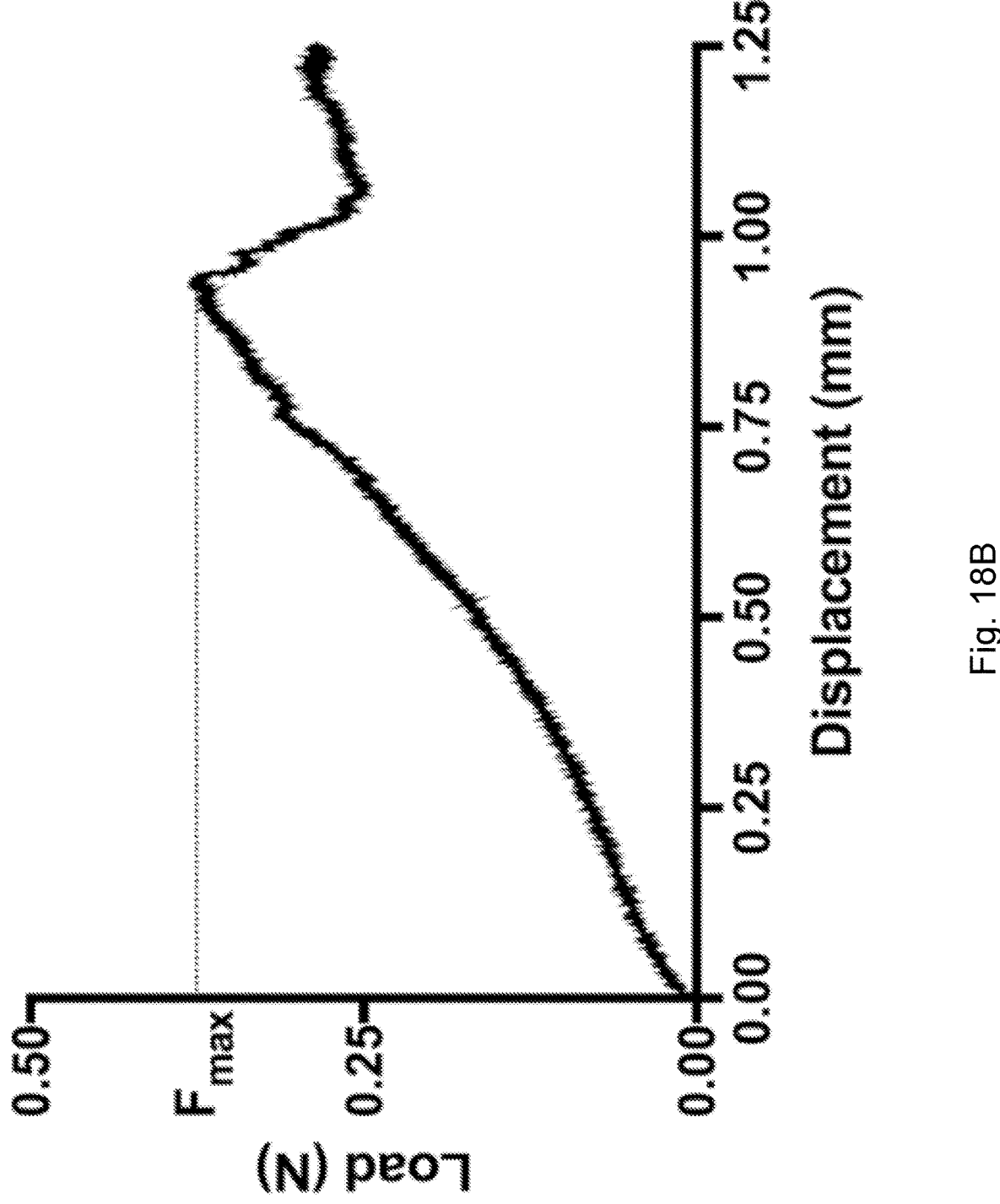

When treating AF tissue with either dual-modified CS or HA, hydrogel bonding with AF tissue was visually achieved when comparing gross specimens with negative controls after sample preparation. Histologically, this was observed through picrosirius red and alcian blue staining, where dual-modified GAG treated samples had a contiguous boundary between the IPN hydrogel and AF tissue (as described in Example 12). Negative control samples (−GAG treatment) featured a considerable gap space between hydrogel and AF tissue, indicating no chemical adsorption amongst the gel and AF. (FIG. 18A) Displacement-controlled lap shear tests indicated functional covalent bonding

US 12,564,661 B2

Figure 18D:
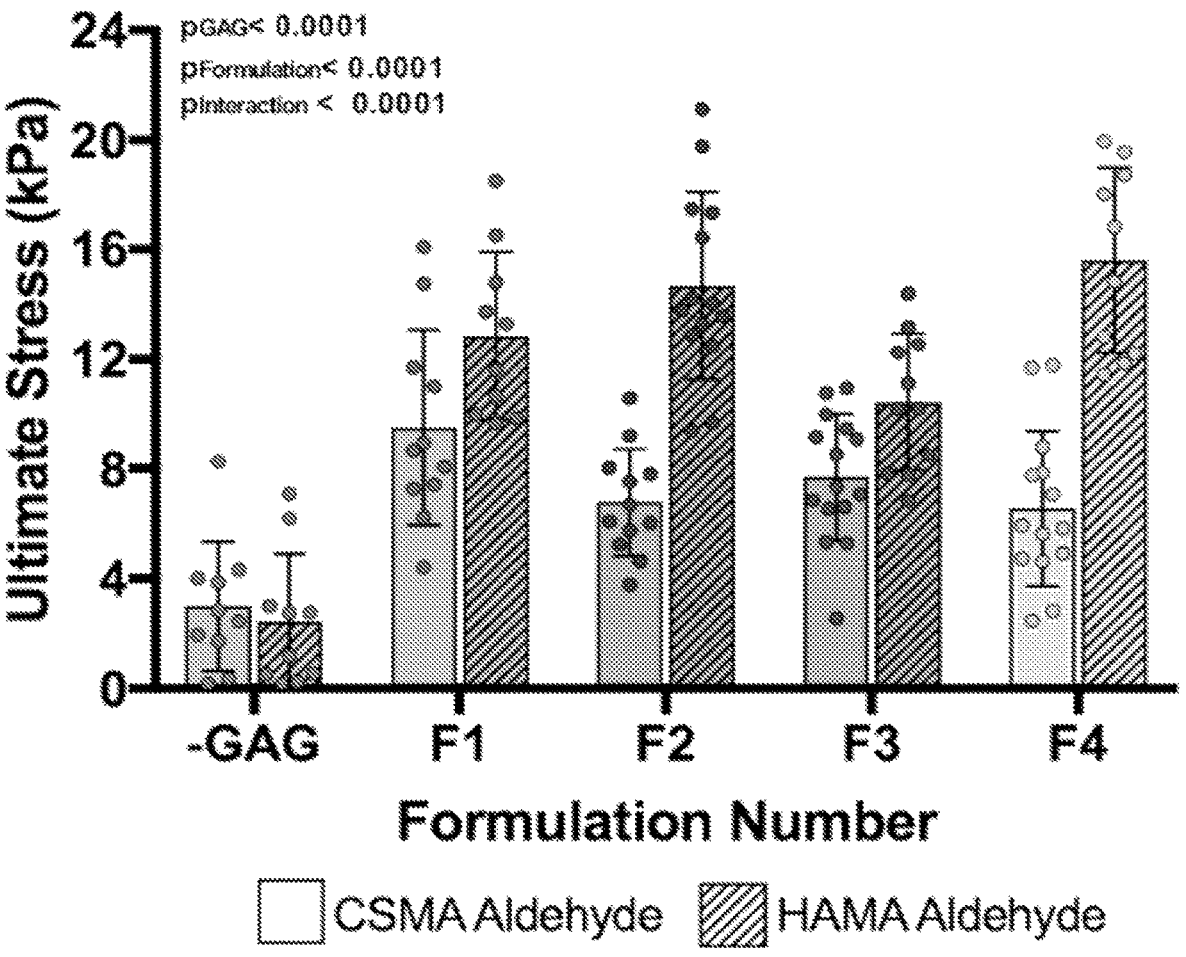
Figure 18E:
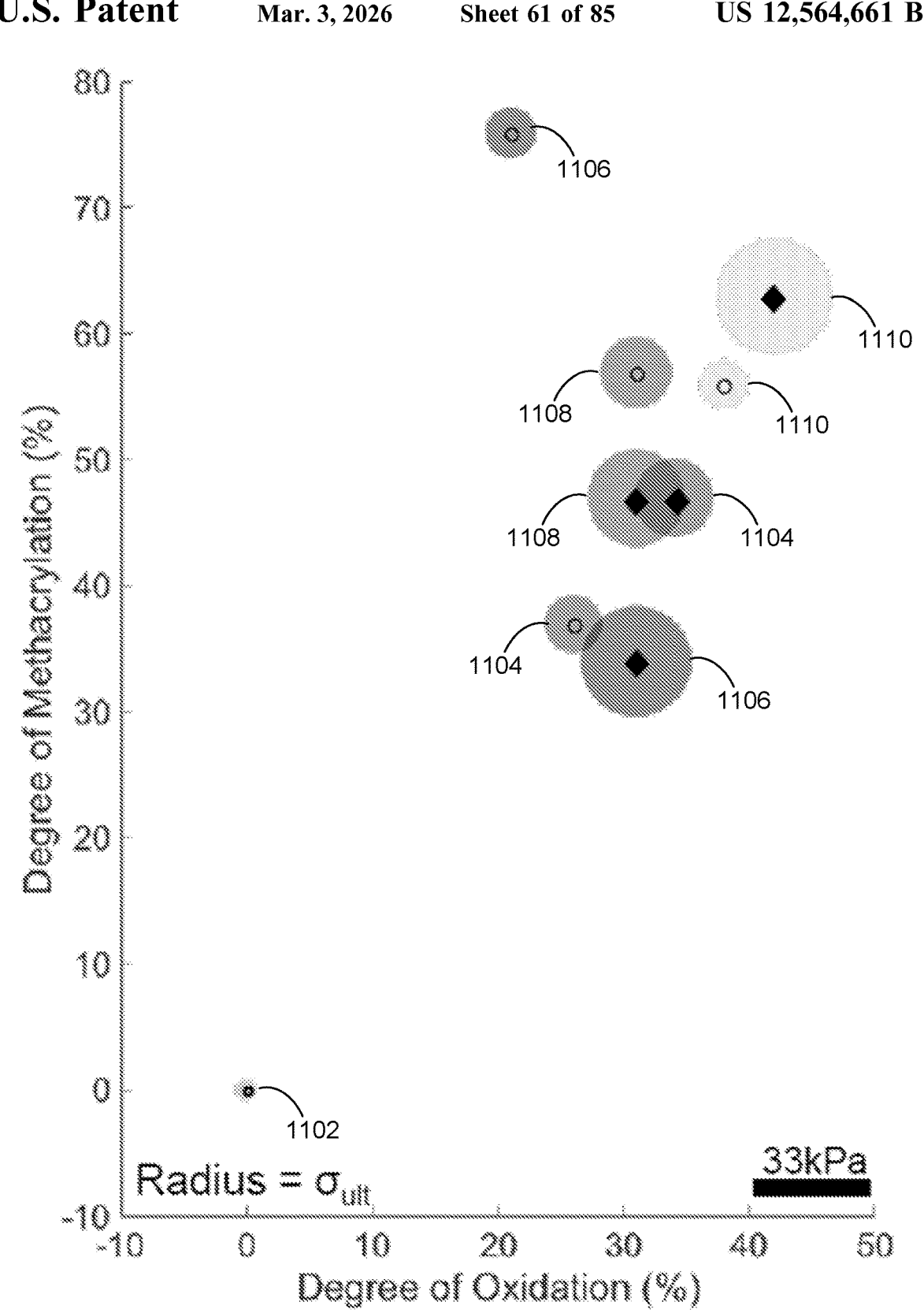
Figures 18F, 18G:
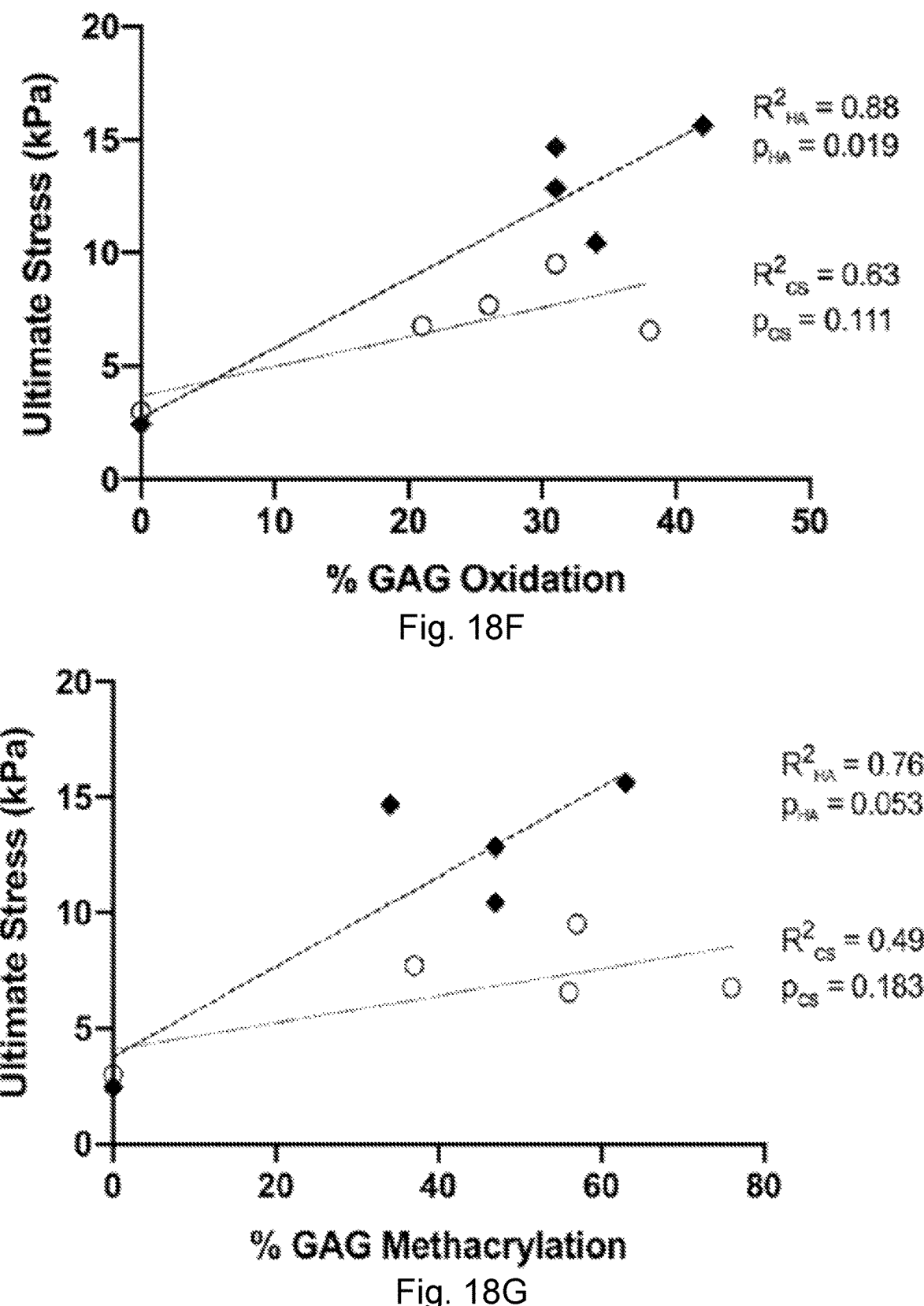

43                                                                                                      44 between the hydrogel and AF tissue, demonstrated by a continuous rise in force over time until failure occurred as shown in a representative loading curve. (FIG. 18B) These force-displacement traces corroborate with visual observations during lap shear tests, where treated specimens slid together until failure occurred at the interface, whereas untreated controls slid over one another for the entire duration of the test. (FIG. 18C) Quantitative assessments of specimen ultimate strength indicated that there were significant main effects of GAG type (p<0.0001) and formulation number (p<0.0001), as well as a significant interaction (p<0.0001). (FIG. 18D) When corresponding the ultimate strength to the biochemical degrees of GAG modification, there was a significant positive correlation between HA oxidation and ultimate strength ($R^2$=0.88, p=0.019), but the positive correlation between CS oxidation and ultimate strength did not reach statistical significance ($R^2$=0.63, p=0.111). Moreover, the positive correlation between HA methacrylation and ultimate strength trended towards significance ($R^2$=0.76, p=0.053) and the positive correlation between CS methacrylation and ultimate strength did not reach statistical significance ($R^2$=0.49, p=0.183). (FIG. 18E)

Example 18—HAMA Aldehyde Tissue Distribution

Figure 19A:
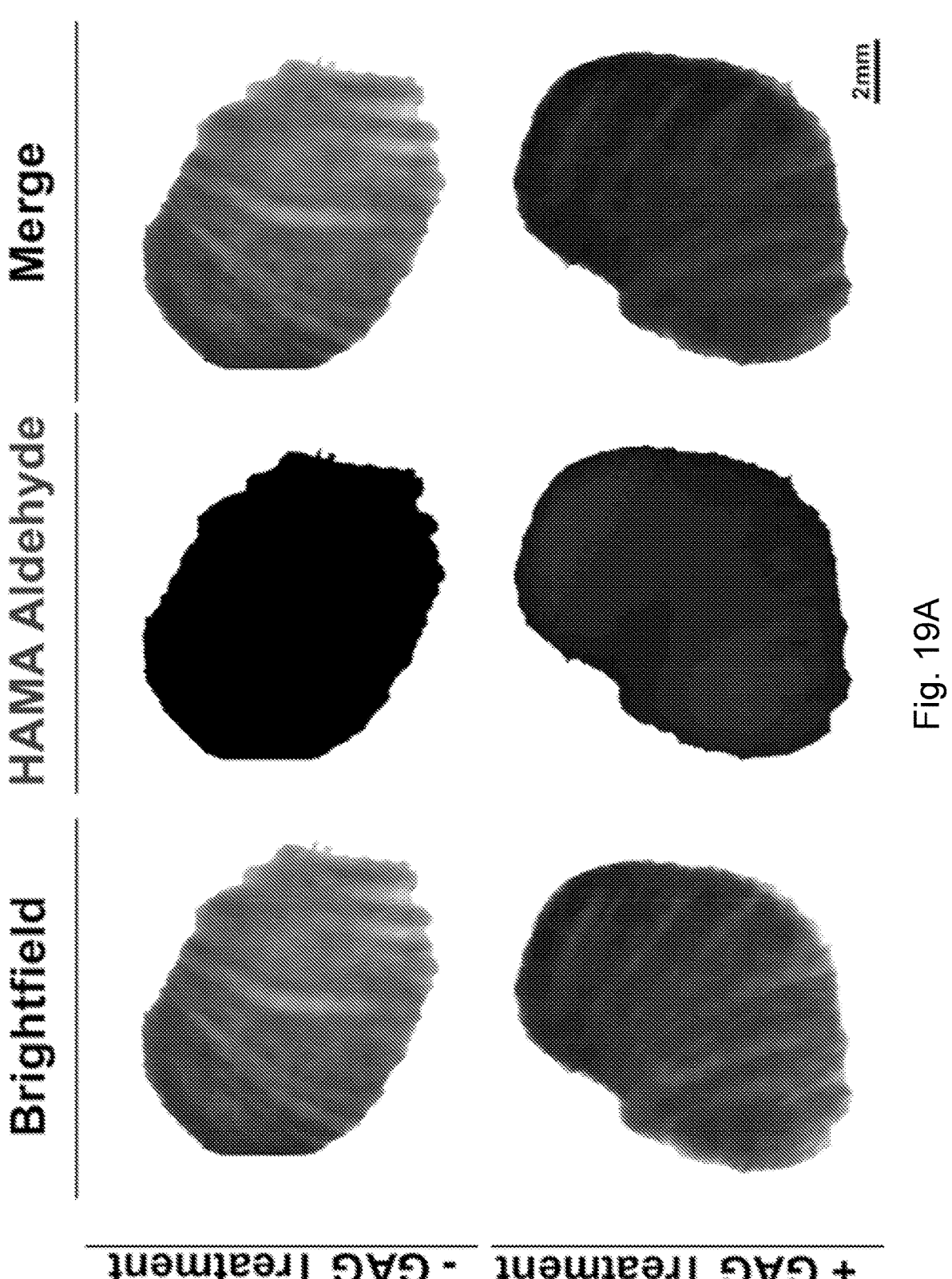
Figure 19B:
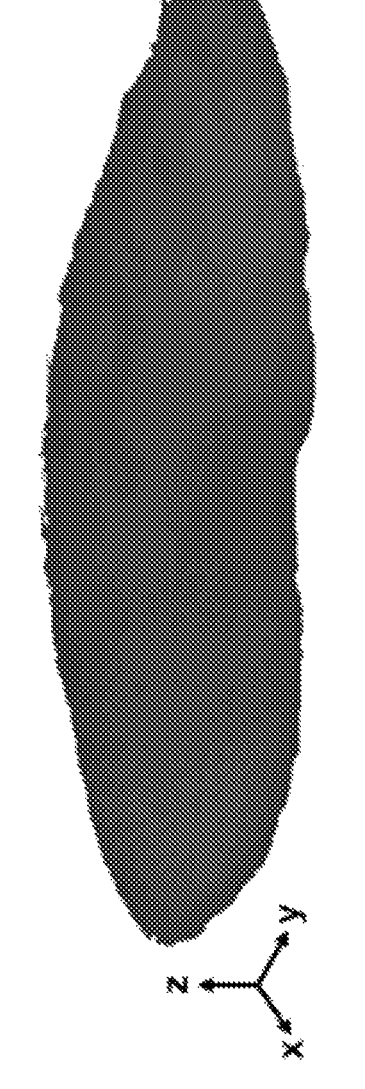

The spatial distribution of HAMA Aldehyde product in AF tissue after 5 minutes of treatment was histologically assessed and used to semi-quantitatively determine the maximum depth-of-penetration (as described in Example 9). A top-down view of HAMA Aldehyde-treated AF tissue shows that the biomaterial product homogenously covered the surface of the specimen. (FIG. 19A) When mapping the fluorescent signal intensity along the depth of an AF specimen, it was observed that HAMA Aldehyde product penetrated into the tissue evenly, with highest signal intensities localizing at the interfaces between lamellae. (FIG. 19B) Cross-sections of HAMA Aldehyde-treated AF tissue demonstrated that the biomaterial was retained within 850 μm from the tissue surface and that a considerable number of cells in the AF are exposed to this biomaterial at the working concentration (60 μM) and lower, which is proportional to fluorescent signal intensity. (FIG. 5C)

Example 19—Assessment of Cytocompatibility

Figure 20A:
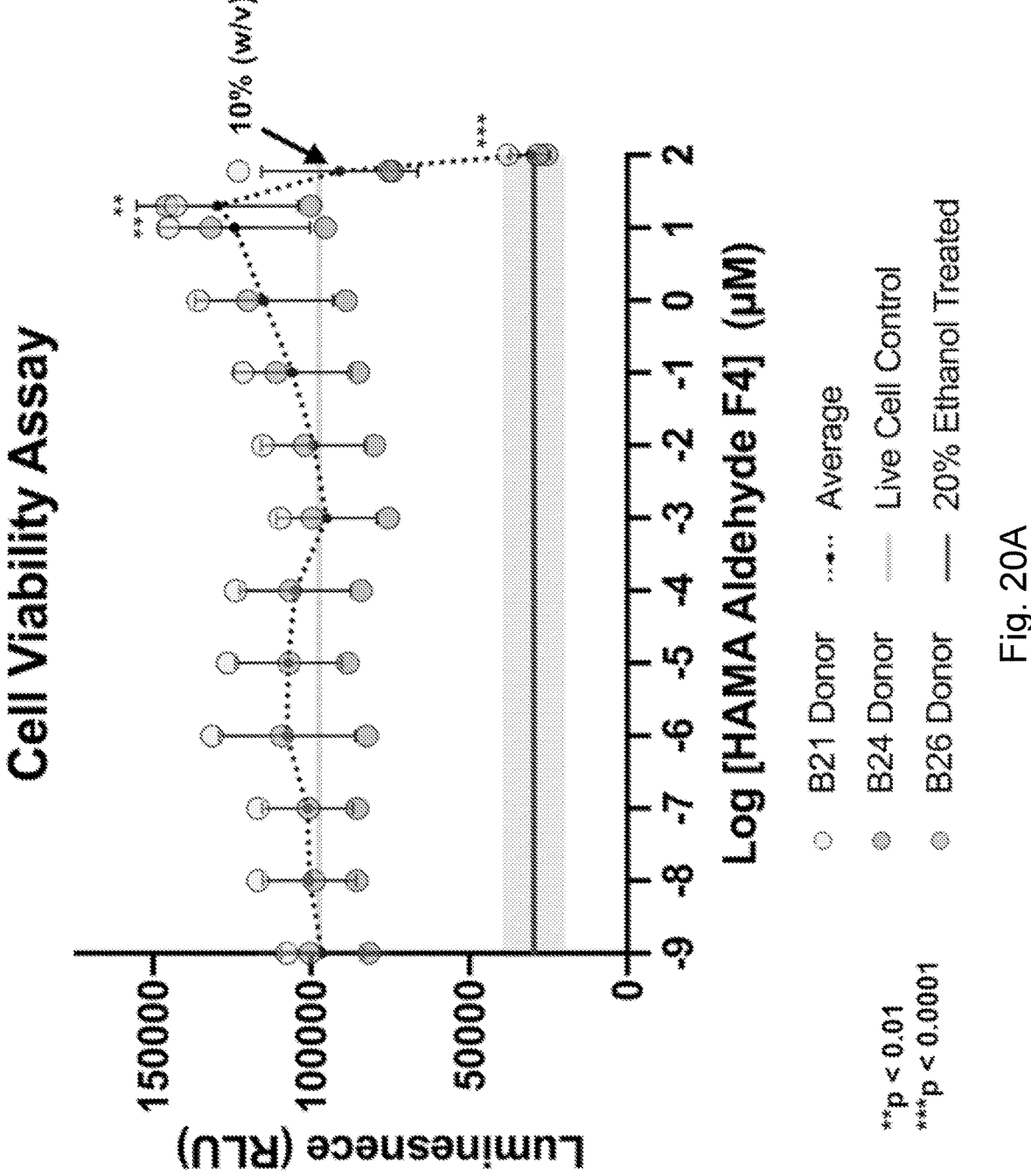
FIGS. 20A and 20B collectively show that dual-modified HA, in accordance with some embodiments of the present disclosure, does not exhibit cytotoxicity at or below the working concentration used to repair AF defects. (A) Cell-Titer-Glo® 2.0 cell viability assay to assess AF cytocompatibility to HAMA Aldehyde. Average=dotted line; live cell control=top unbroken line; 20% ethanol treated=bottom unbroken line. (B) Phase-contrast images of HAMA Aldehyde treated AF cells compared to untreated and ethanol treated controls.
Figure 20B:
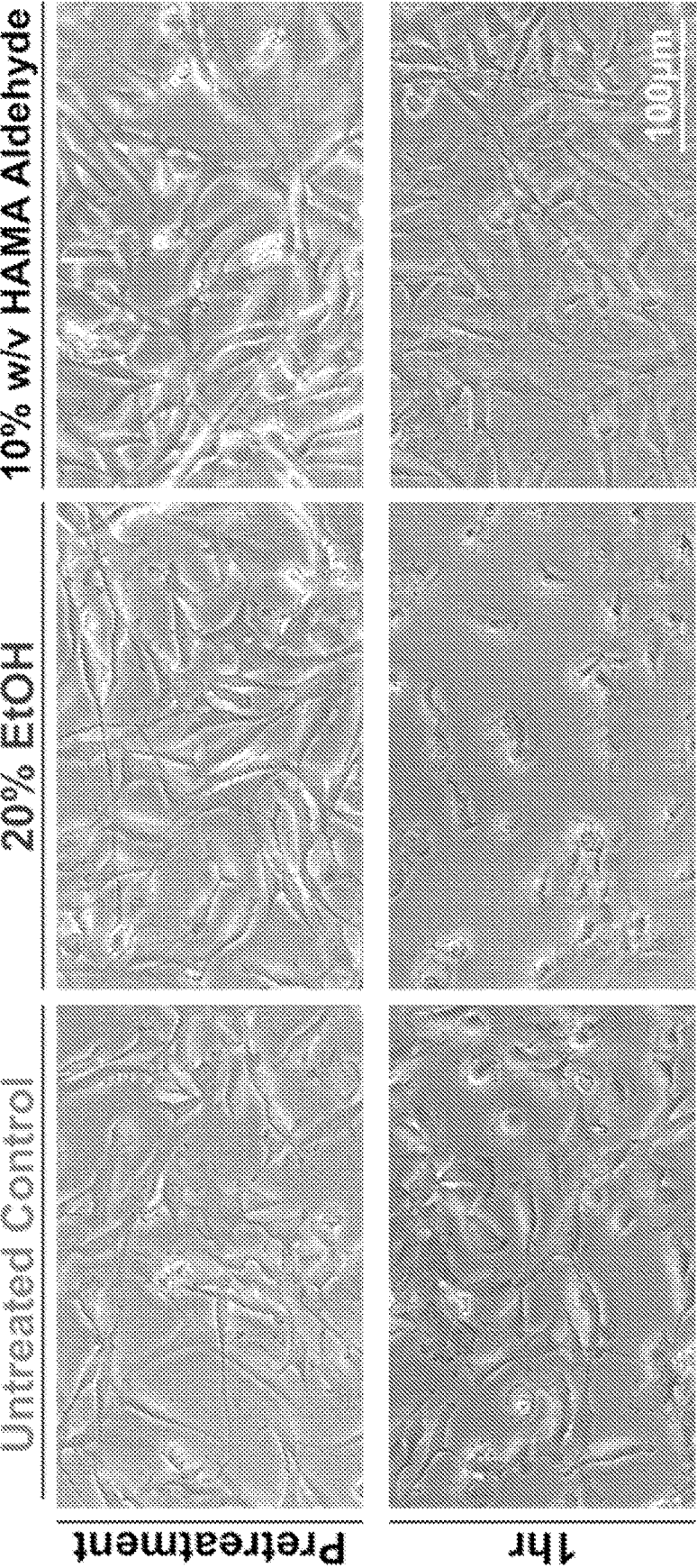

Cell viability was screened after exposing AF cells to HAMA Aldehyde product for 1 hour across a concentration range of $10^{-9}$ to $10^2$ μM (as described in Example 10). At a concentration of 1 μM and below, AF cell viability was not significantly different than the untreated controls (p>0.05). Most notably, cell viability at the working concentration applied to AF defects (60 μM, equivalently 10% w/v HAMA Aldehyde) was not different than untreated controls (p>0.05). When cells were exposed to 10 μM and 20 μM of HAMA Aldehyde product, there was a significant increase in RLU output compared to the untreated controls ($p_{10 \ \mu m}$=0.0291; $p_{20 \ \mu M}$=0.0042). Lastly, when cells were exposed to a concentration of HAMA Aldehyde product above the working concentration applied to AF defects (100 μM), there was a significant decrease in cell viability compared to the untreated controls (p<0.0001) and no significant difference when compared to the 20% v/v ethanol treated control (p>0.05). (FIG. 20A) Cell viability measurements were cross-validated with morphological observations through phase contrast microscopy. At 60 μM HAMA Aldehyde (and lower), AF cells exhibited a healthy spindle-like fibroblast morphology comparable to the live cells in the untreated controls. In contrast, the 20% v/v ethanol treated control group exhibited an aberrant morphology that is representative of poor cell health and distinctly different than the HAMA Aldehyde treated AF cells at 60 μM. (FIG. 20B)

Example 20—In Situ Histological Assessments

Figure 21A:
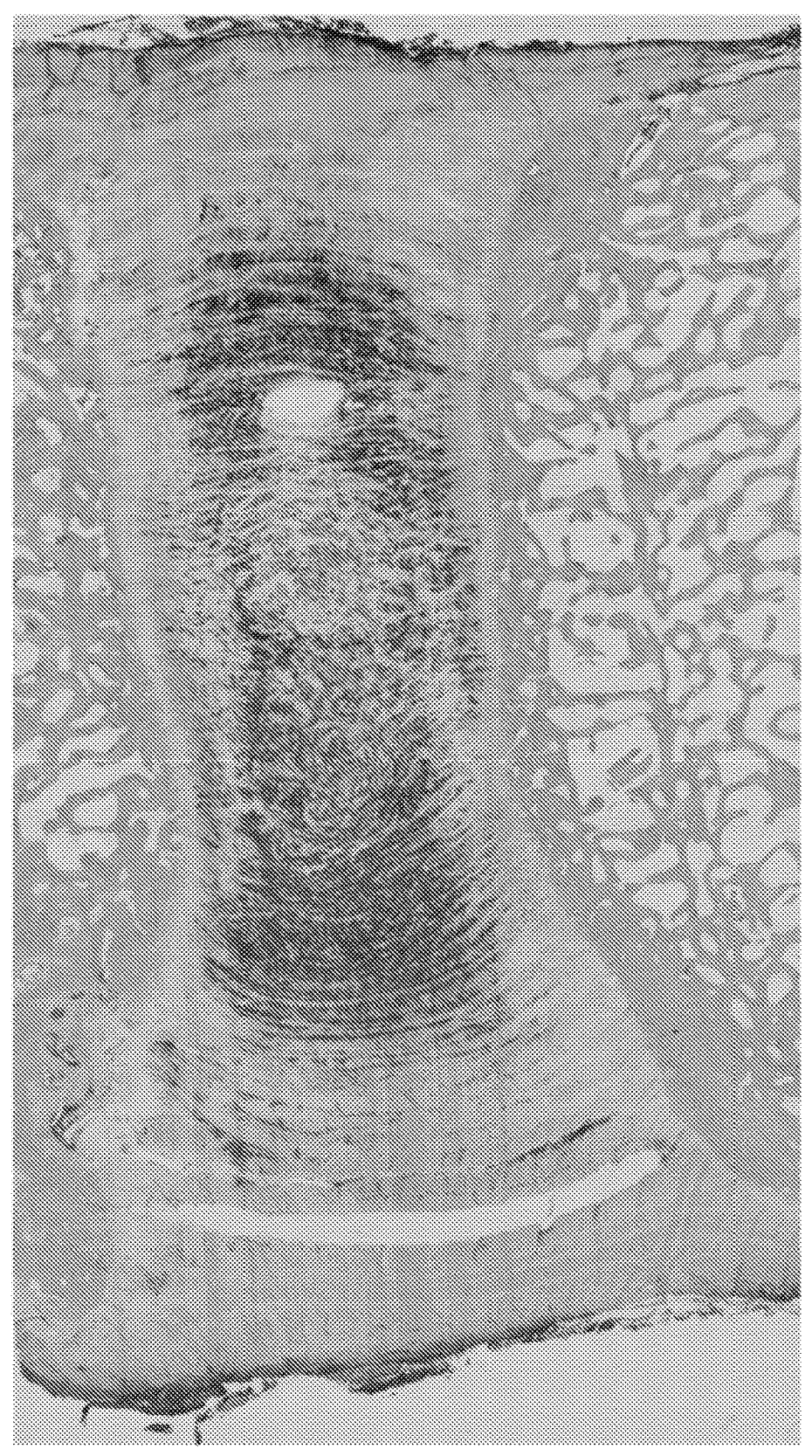
FIGS. 21A, 21B, and 21C collectively show that application of a two-part biomaterial repair strategy, in accordance with some embodiments of the present disclosure, leads to successful integration with AF tissue in an ex vivo bovine model of simulated discectomy. Picrosirius red/alcian blue staining of an (A) intact IVD, (B) IVD that underwent simulated discectomy, and (C) IVD that was repaired with the two-part strategy. Arrow points to adhesive interface between AF tissue and IPN hydrogel.
Figure 21B:
Figure 21C:
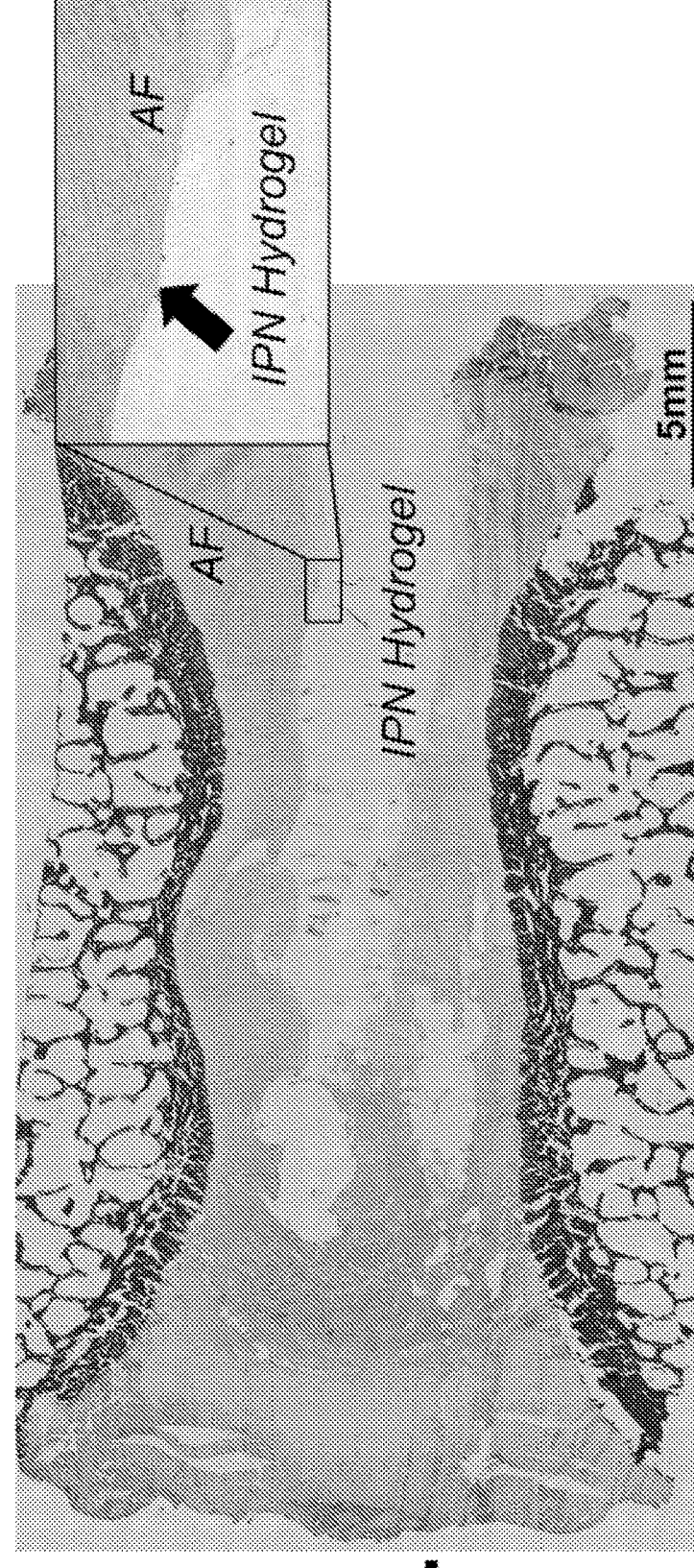

Picrosirius red and alcian blue staining indicated collagen and proteoglycan content, respectively, as well as overall tissue architecture of bovine IVDs that were either intact, injured with a clinically-relevant AF defect (4 mm biopsy punch with 200 mg NP removal) that simulates discectomy, or repaired with the two-part strategy developed herein. In the intact condition, the lamellar structure of collagenous AF fibers is present and contains a proteoglycan-rich NP. (FIG. 21A) In the simulated discectomy model, mid-sagittal sections indicate the removal of NP along with complete disruption of AF integrity on the IVD's posterolateral side. (FIG. 21B) Repair of clinically-relevant AF defects with the two-part repair strategy developed herein corroborates with the histological findings indicated by lap shear specimens when scaling this approach up to a large animal model of simulated discectomy. The injectable hydrogel implant was able to volumetrically fill the void space of AF defects and featured a contiguous boundary between AF tissue and hydrogel implant at the interface, suggesting that the tissue and biomaterial are adsorbed to one another via GAG-mediated covalent bonds. (FIG. 21C)

Example 21—Assessment of IVD Herniation Risk

Figure 22A:
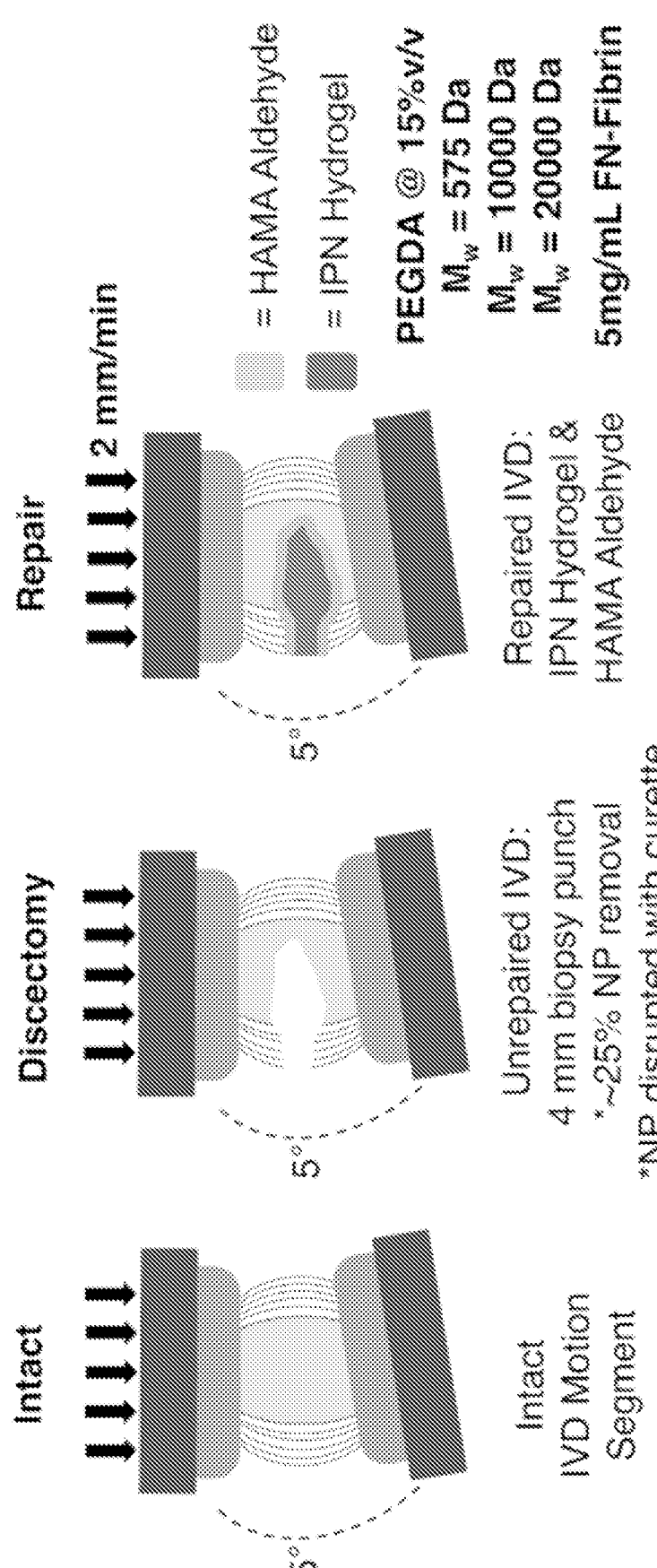
Figure 22C:
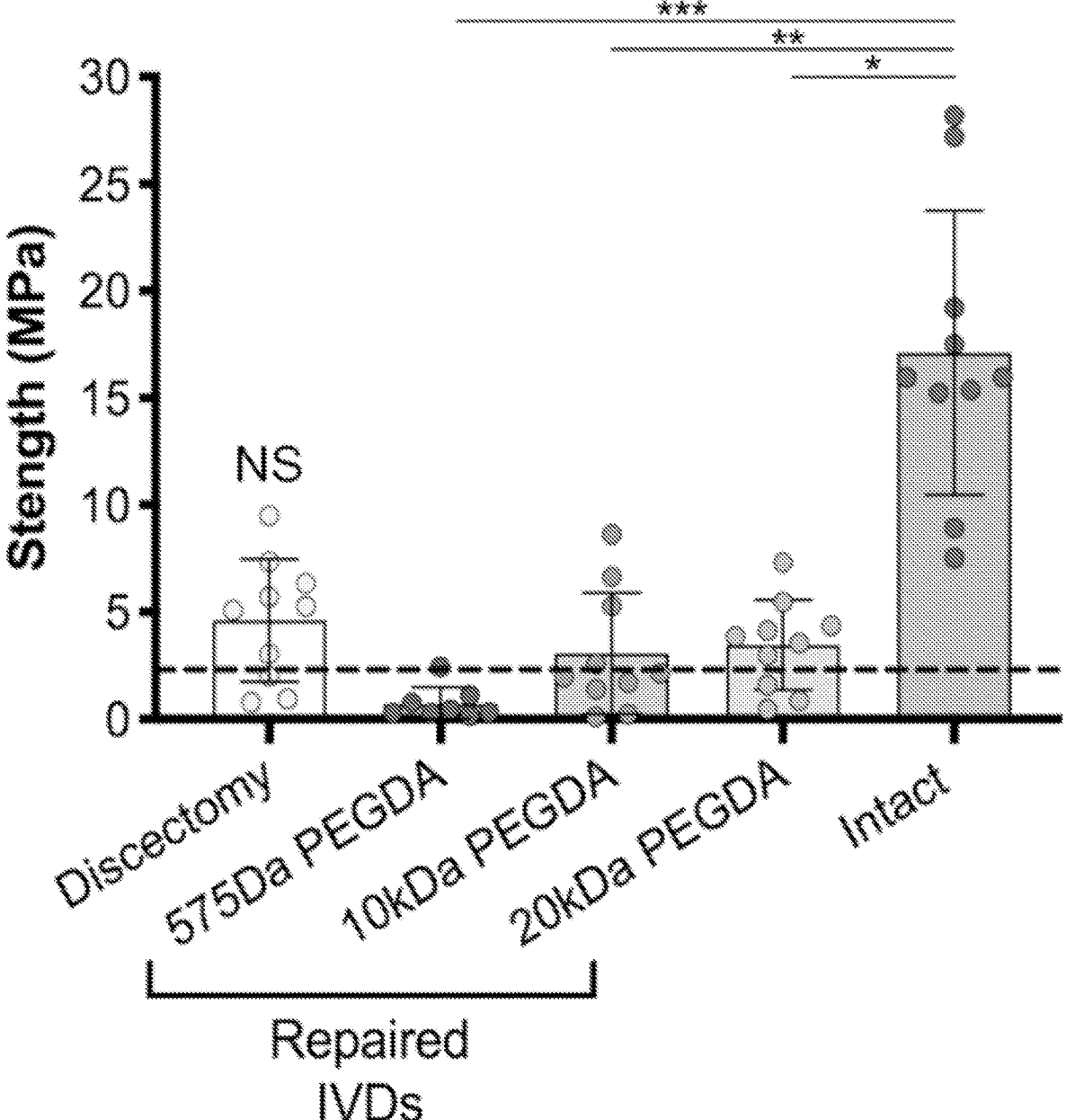
Figure 22D:
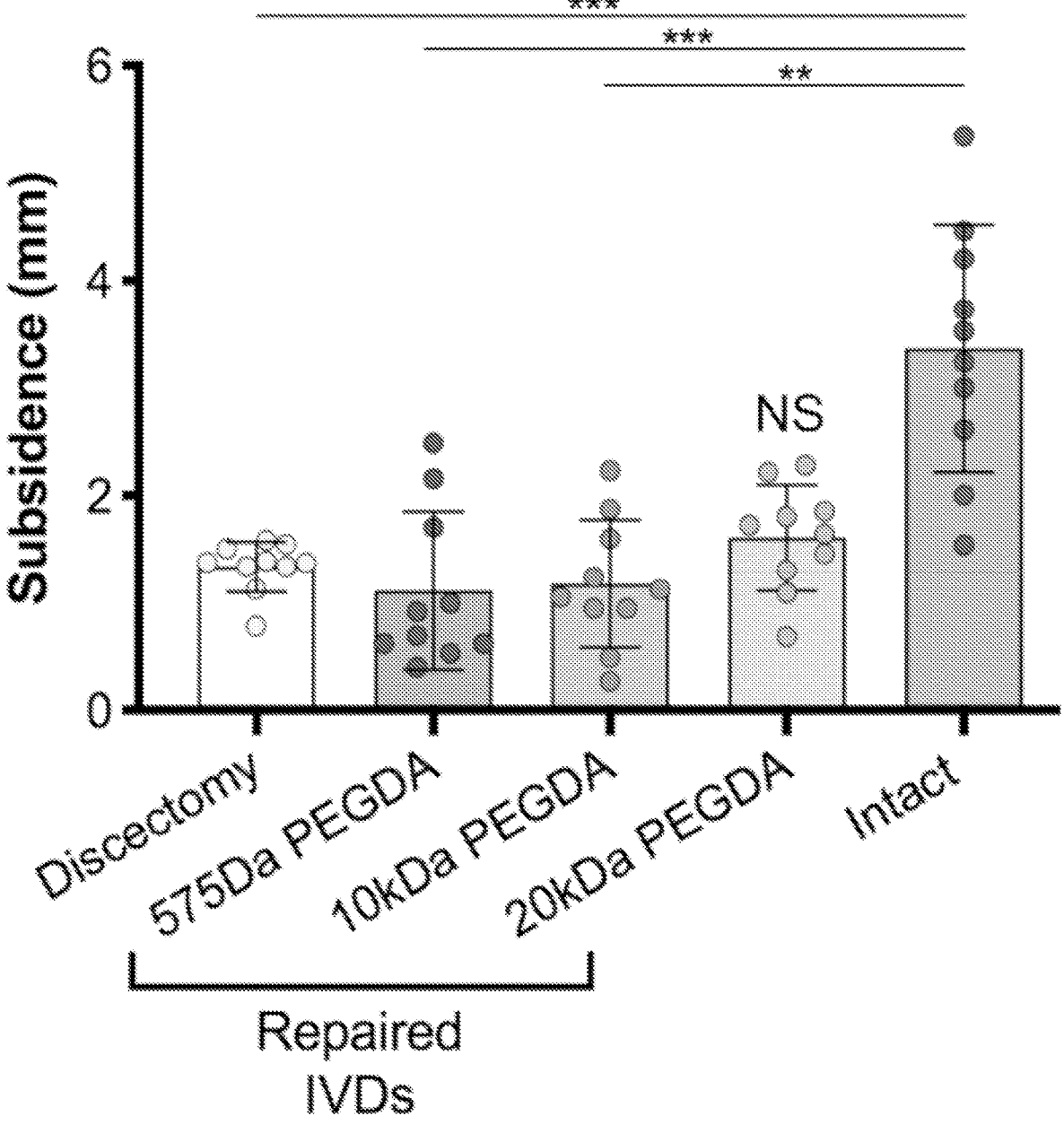
Figure 22E:
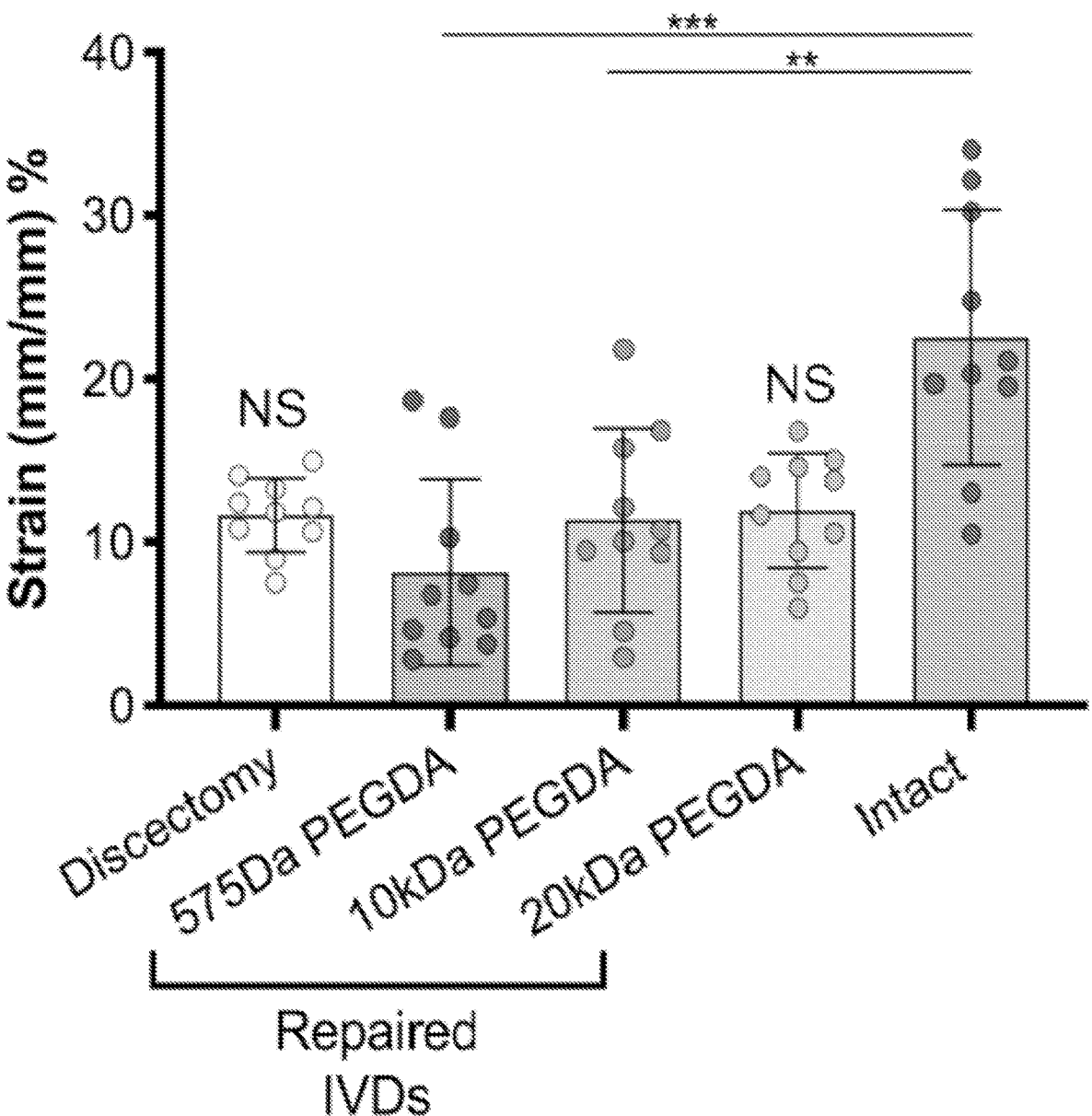
Figure 22F:
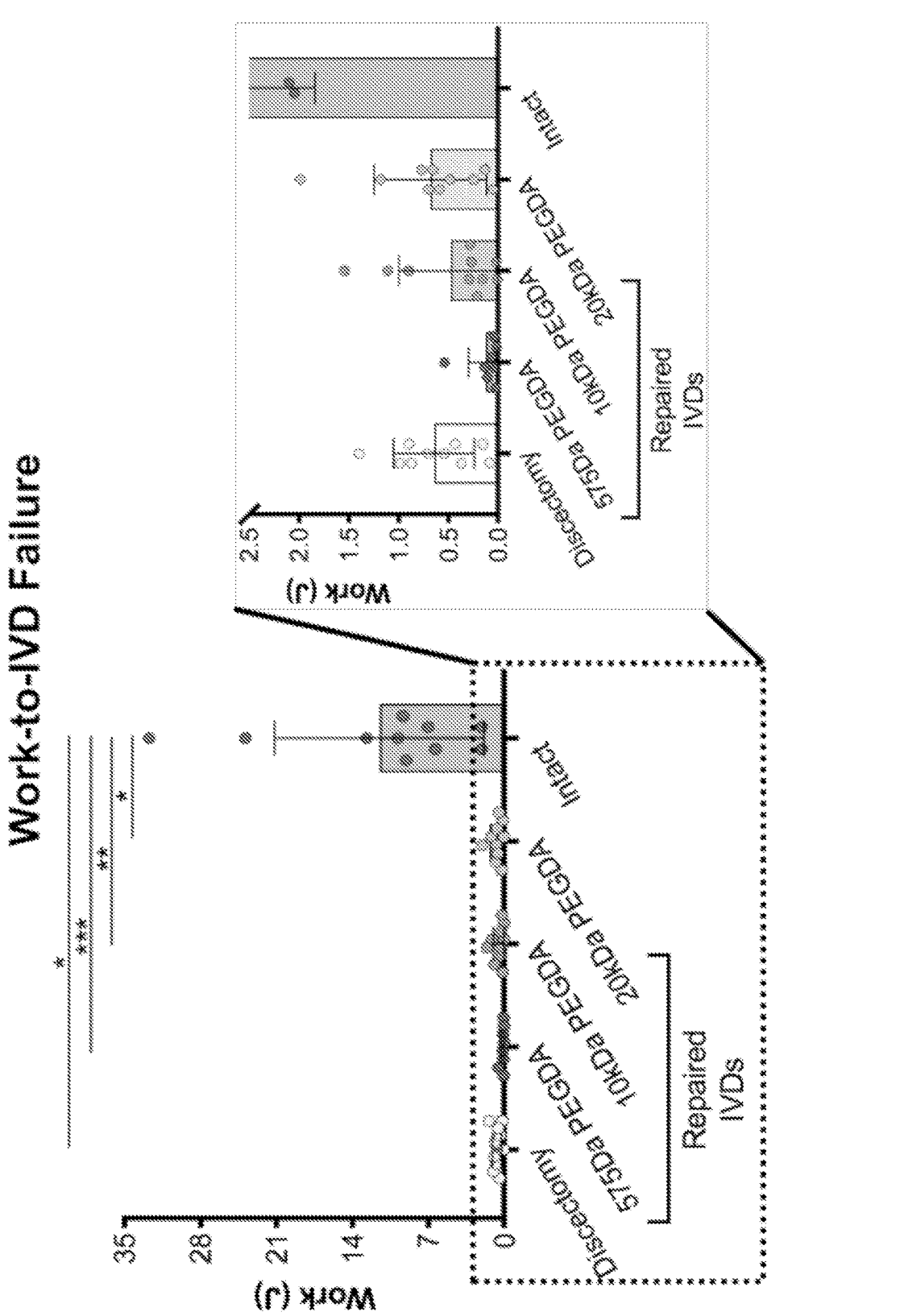
Figure 22G:
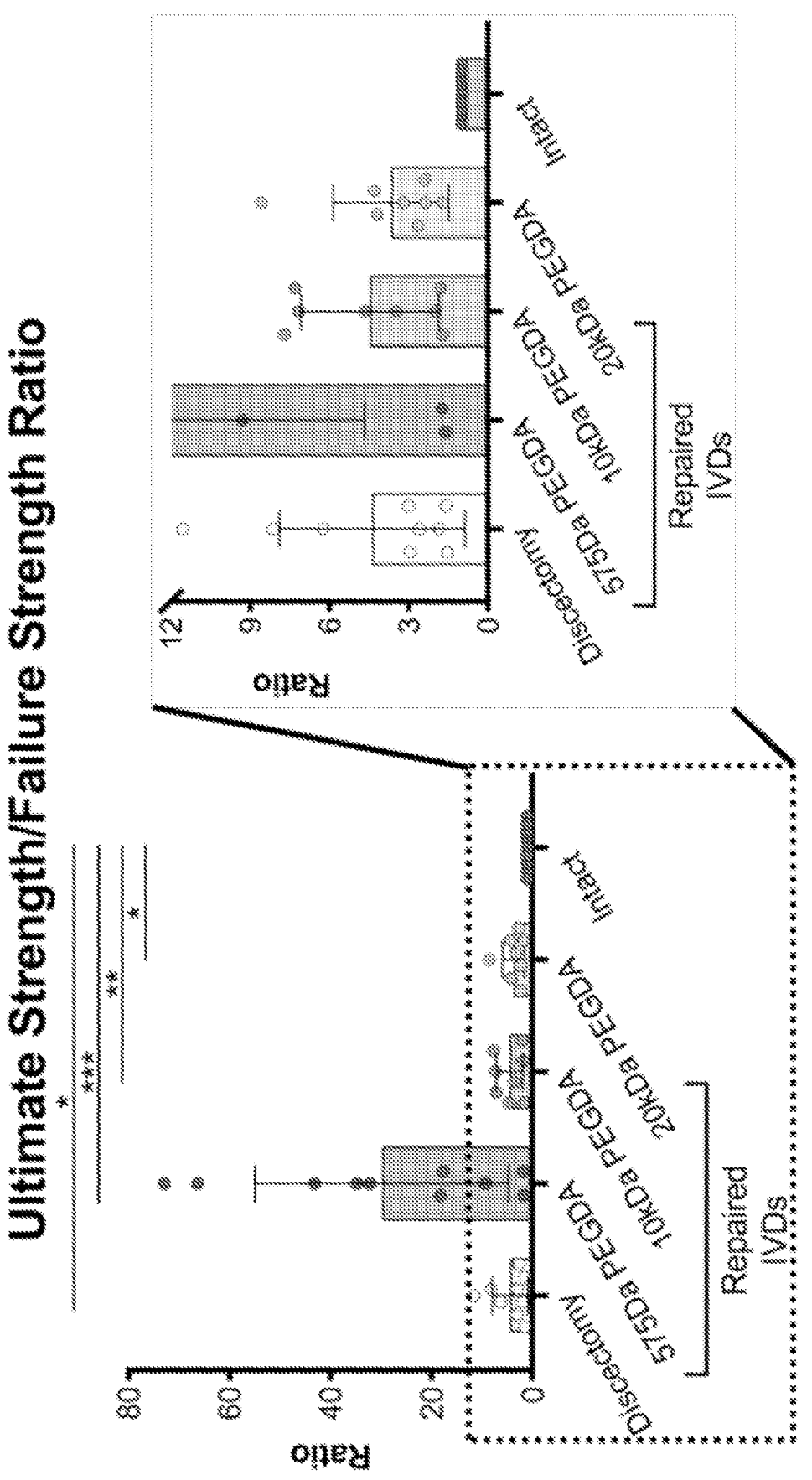

The herniation risk of this two-part repair strategy was characterized against the IVD model of simulated discectomy and intact IVD controls ex vivo in a displacement-controlled ramp-to-failure test (as described in Example 13). Within the repair cohort, AF defects were sealed with IPN hydrogels composed of 575 Da, 10 kDa, or 20 kDa PEGDA, while holding all concentrations of the prepolymer solution constant. (FIG. 22A) Representative force-displacement traces indicate two modes of motion segment failure: endplate fracture or NP herniation. Notably, all intact motion segments failed by endplate fracture, whereas all motion segments in the discectomy and repair groups failed by NP protrusion, exhibited by a discontinuous drop in force prior to reaching the ultimate strength of the motion segment specimen. (FIG. 22B) IVD failure strength was significantly decreased compared to the intact condition for all IVDs that were repaired ($p_{575 \ Da}$<0.0001; $p_{10 \ kDa}$=0.0013; $p_{20 \ kDa}$=0.0089), however only a trend towards a decrease in failure strength was observed for the discectomy group (p=0.0631). Notably, 70% of specimens in both the discectomy group and 20 kDa PEGDA repair group endured supraphysiological stresses (≥2.3 MPa) before failure. (FIG. 22C) Subsidence-to-IVD failure was significantly lower than intact levels for the discectomy condition (p=0.0087) as well as the 575 Da (p=0.0002) and 10 kDa PEGDA (p=0.0009) repair conditions, however there was no difference between the intact group and 20 kDa PEGDA repair group (p=0.1603). (FIG. 22D) IVD failure strain was significantly lower than intact levels for the 575 Da (p=0.0002) and 10 kDa PEGDA (p=0.0323) repair conditions, however there was no difference between the intact group and 20 kDa PEGDA repair group (p=0.1089) or discectomy group (p=0.0912). (FIG. 22E) Work-to-IVD failure was significantly decreased compared to the intact condition for all IVDs that were repaired ($p_{575 \ Da}$<0.0001; $p_{10 \ kDa}$=0.0009;

$p_{20\ kDa}$=0.0148) as well as unrepaired in the discectomy group (p=0.0241). (FIG. 22F) The ultimate strength to failure strength ratio was significantly higher for all IVDs that were repaired ($p_{575\ Da}$<0.0001; $p_{10\ kDa}$=0.0155; $p_{20\ kDa}$=0.0266) or unrepaired in the discectomy group (p=0.0295). (FIG. 22G) Nonlinear semi-log correlations were used to assess empirical exponential relationships between herniation risk parameters and indicated a strong negative correlation between IVD failure strength and hydrogel tensile modulus ($R^2$=0.82), as well as subsidence-to-IVD failure and hydrogel tensile modulus ($R^2$=0.88). (FIG. 22H)

Example 22—Future Studies

Although higher degrees of HA oxidation lead to greater hydrogel adhesion to AF tissue, it is known that higher degrees of polysaccharide oxidation can lead to faster bio-degradation rates. [38,66] Since the dual-modified HA described in the Examples is an interfacial primer applied to tissue surfaces in liquid form, the only way to assess biodegradation is to histologically examine the presence/retention of these biomaterials over time in the AF repair site using a large in vivo animal model. Future large animal in vivo investigations are necessary to assess biomaterial degradation kinetics and examine implant durability. Additionally, the FN-Fibrin natural polymer network within this hydrogel system incorporates integrin recognition sequences to enable cellular migration into the repair site, however this secondary hypothesis regarding endogenous cell recruitment and remodeling was considered beyond the scope of the current studies which focused on integration and herniation risk as the prime surgical design constraint. [67,68] Moreover, despite the presence of biochemical cues that permit cell attachment and motility, the current hydrogel system does not incorporate chemoattractants to stimulate resident cell migration or contain other bioactive factors to promote IVD healing, which may pose a limitation to long-term repair using this strategy in its current state. One potential avenue of advanced development is incorporating a bioactive component that directs biological repair responses after in situ application. Future work to address the aforementioned limitations and further demonstrate advanced pre-clinical validation, durability, safety, and effectiveness in an in vivo model are warranted following the successful integration and biomechanical optimizations achieved herein.

CONCLUSION

The foregoing description, for purposes of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

Dulebohn S C, Ngnitewe Massa R, Mesfin F B. Disc Herniation. StatPearls, Treasure Island (FL): StatPearls Publishing; 2019.

[2] Hartvigsen J, Hancock M J, Kongsted A, Louw Q, Ferreira M L, Genevay S, et al. What low back pain is and why we need to pay attention. Lancet 2018; 391: 2356-67. doi:10.1016/S0140-6736(18)30480-X.

[3] Schroeder G D, Guyre C A, Vaccaro A R. The epidemiology and pathophysiology of lumbar disc herniations. Semin Spine Surg 2016; 28:2-7. doi:10.1053/j.semss.2015.08.003.

[4] Schoenfeld A J, Weiner B K. Treatment of lumbar disc herniation: Evidence-based practice. Int J Gen Med 2010; 3:209-14.

[5] Lurie J D, Tosteson T D, Tosteson A N A, Zhao W, Morgan T S, Abdu W A, et al. Surgical versus nonoperative treatment for lumbar disc herniation: eight-year results for the spine patient outcomes research trial. Spine 2014; 39:3-16. doi:10.1097/BRS.0000000000000088.

[6] Tosteson A N A, Tosteson T D, Lurie J D, Abdu W, Herkowitz H, Andersson G, et al. Comparative effectiveness evidence from the spine patient outcomes research trial: surgical versus nonoperative care for spinal stenosis, degenerative spondylolisthesis, and intervertebral disc herniation. Spine 2011; 36:2061-8. doi:10.1097/BRS.0b013e318235457b.

[7] Hlubek R J, Mundis G M. Treatment for recurrent lumbar disc herniation. Curr Rev Musculoskelet Med 2017; 10:517-20. doi:10.1007/s12178-017-9450-3.

[8] Atlas S J, Keller R B, Wu Y A, Deyo R A, Singer D E. Long-term outcomes of surgical and nonsurgical management of sciatica secondary to a lumbar disc herniation: 10 year results from the maine lumbar spine study. Spine 2005; 30:927-35.

[9] Ambrossi G L G, McGirt M J, Sciubba D M, Witham T F, Wolinsky J-P, Gokaslan Z L, et al. Recurrent lumbar disc herniation after single-level lumbar discectomy: incidence and health care cost analysis. Neurosurgery 2009; 65:574-8; discussion 578. doi:10.1227/01.NEU.0000350224.36213.F9.

[10] Oh J T, Park K S, Jung S S, Chung S Y, Kim S M, Park M S, et al. Surgical results and risk factors for recurrence of lumbar disc herniation. Korean J Spine 2012; 9:170-5. doi:10.14245/kjs.2012.9.3.170.

[11] Shepard N, Cho W. Recurrent lumbar disc herniation: A review. Global Spine J 2019; 9:202-9. doi:10.1177/2192568217745063.

[12] Carragee E J, Han M Y, Suen P W, Kim D. Clinical outcomes after lumbar discectomy for sciatica: the effects of fragment type and anular competence. J Bone Joint Surg Am 2003; 85:102-8.

[13] McGirt M J, Eustacchio S, Varga P, Vilendecic M, Trummer M, Gorensek M, et al. A prospective cohort study of close interval computed tomography and magnetic resonance imaging after primary lumbar discectomy: factors associated with recurrent disc herniation and disc height loss. Spine 2009; 34:2044-51. doi: 10.1097/BRS.0b013e3181b34a9a.

[14] Bron J L, Helder M N, Meisel H-J, Van Royen B J, Smit T H. Repair, regenerative and supportive therapies of the annulus fibrosus: achievements and challenges. Eur Spine J 2009; 18:301-13. doi:10.1007/s00586-008-0856-x.

[15] Sloan S R, Lintz M, Hussain I, Hartl R, Bonassar U. Biologic annulus fibrosus repair: A review of preclinical in vivo investigations. Tissue Eng Part B Rev 2018; 24:179-90. doi:10.1089/ten.TEB.2017.0351.

[16] Iatridis J C, Nicoll S B, Michalek A J, Walter B A, Gupta M S. Role of biomechanics in intervertebral disc degeneration and regenerative therapies: what needs repairing in the disc and what are promising biomaterials for its repair?Spine J 2013; 13:243-62. doi: 10.1016/j.spinee.2012.12.002.

[17] Wilke H-J, Ressel L, Heuer F, Graf N, Rath S. Can prevention of a reherniation be investigated?Establishment of a herniation model and experiments with an anular closure device. Spine 2013; 38:E587-93. doi: 10.1097/BRS.0b013e31828ca4bc.

[18] Long R G, Torre O M, Hom W W, Assael D J, Iatridis J C. Design requirements for annulus fibrosus repair: review of forces, displacements, and material properties of the intervertebral disk and a summary of candidate hydrogels for repair. J Biomech Eng 2016; 138:021007. doi:10.1115/1.4032353.

[19]D'Este M, Eglin D, Alini M. Lessons to be learned and future directions for intervertebral disc biomaterials. Acta Biomater 2018; 78:13-22. doi:10.1016/j.actbio.2018.08.004.

[20] Hegewald A A, Ringe J, Sittinger M, Thome C. Regenerative treatment strategies in spinal surgery. Front Biosci 2008; 13:1507-25. doi:10.2741/2777.

[21] Bowles R D, Setton L A. Biomaterials for intervertebral disc regeneration and repair. Biomaterials 2017; 129:54-67. doi:10.1016/j.biomaterials.2017.03.013.

[22] Foyt D A, Norman M D A, Yu T T L, Gentleman E. Exploiting advanced hydrogel technologies to address key challenges in regenerative medicine. Adv Healthc Mater 2018; 7:e1700939. doi:10.1002/adhm.201700939.

[23] Ghobril C, Grinstaff M W. The chemistry and engineering of polymeric hydrogel adhesives for wound closure: a tutorial. Chem Soc Rev 2015; 44:1820-35. doi:10.1039/c4cs00332b.

[24] Annabi N, Yue K, Tamayol A, Khademhosseini A. Elastic sealants for surgical applications. Eur J Pharm Biopharm 2015; 95:27-39. doi:10.1016/j.ejpb.2015.05.022.

[25] Guterl C C, See E Y, Blanquer S B G, Pandit A, Ferguson S J, Benneker L M, et al. Challenges and strategies in the repair of ruptured annulus fibrosus. Eur Cell Mater 2013; 25:1-21. doi:10.22203/eCM.v025a01.

[26] Buckley C T, Hoyland J A, Fujii K, Pandit A, Iatridis J C, Grad S. Critical aspects and challenges for intervertebral disc repair and regeneration-Harnessing advances in tissue engineering. JOR Spine 2018; 1:e1029. doi:10.1002/jsp2.1029.

[27] Li J, Mooney D J. Designing hydrogels for controlled drug delivery. Nat Rev Mater 2016; 1. doi:10.1038/natrevmats.2016.71.

[28] Nicodemus G D, Bryant S J. Cell encapsulation in biodegradable hydrogels for tissue engineering applications. Tissue Eng Part B Rev 2008; 14:149-65. doi:10.1089/ten.teb.2007.0332.

[29] Slaughter B V, Khurshid S S, Fisher O Z, Khademhosseini A, Peppas N A. Hydrogels in regenerative medicine. Adv Mater Weinheim 2009; 21:3307-29. doi:10.1002/adma.200802106.

[30] Li X, Sun Q, Li Q, Kawazoe N, Chen G. Functional hydrogels with tunable structures and properties for tissue engineering applications. Front Chem 2018; 6:499. doi:10.3389/fchem.2018.00499.

[31] Guan X, Avci-Adali M, Alargin E, Cheng H, Kashaf S S, Li Y, et al. Development of hydrogels for regenerative engineering. Biotechnol J 2017; 12. doi:10.1002/biot.201600394.

[32] Wang D-A, Varghese S, Sharma B, Strehin I, Fermanian S, Gorham J, et al. Multifunctional chondroitin sulphate for cartilage tissue-biomaterial integration. Nat Mater 2007; 6:385-92. doi:10.1038/nmat1890.

[33] Purcell B P, Lobb D, Charati M B, Dorsey S M, Wade R J, Zellars K N, et al. Injectable and bioresponsive hydrogels for on-demand matrix metalloproteinase inhibition. Nat Mater 2014; 13:653-61. doi:10.1038/nmat3922.

[34] Burdick J A, Chung C, Jia X, Randolph M A, Langer R. Controlled degradation and mechanical behavior of photopolymerized hyaluronic acid networks. Biomacromolecules 2005; 6:386-91. doi:10.1021/bm049508a.

[35] Bryant S J, Davis-Arehart K A, Luo N, Shoemaker R K, Arthur J A, Anseth K S. Synthesis and Characterization of Photopolymerized Multifunctional Hydrogels: Water-Soluble Poly(Vinyl Alcohol) and Chondroitin Sulfate Macromers for Chondrocyte Encapsulation. Macromolecules 2004; 37:6726-33. doi:10.1021/ma0499324.

[36] Su W-Y, Chen Y-C, Lin F-H. Injectable oxidized hyaluronic acid/adipic acid dihydrazide hydrogel for nucleus pulposus regeneration. Acta Biomater 2010; 6:3044-55. doi:10.1016/j.actbio.2010.02.037.

[37] Jeon O, Alt D S, Ahmed S M, Alsberg E. The effect of oxidation on the degradation of photocrosslinkable alginate hydrogels. Biomaterials 2012; 33:3503-14. doi:10.1016/j.biomaterials.2012.01.041.

[38] Jeon O, Samorezov J E, Alsberg E. Single and dual crosslinked oxidized methacrylated alginate/PEG hydrogels for bioadhesive applications. Acta Biomater 2014; 10:47-55. doi:10.1016/j.actbio.2013.09.004.

[39] Villanueva I, Gladem S K, Kessler J, Bryant S J. Dynamic loading stimulates chondrocyte biosynthesis when encapsulated in charged hydrogels prepared from poly(ethylene glycol) and chondroitin sulfate. Matrix Biol 2010; 29:51-62. doi:10.1016/j.matbio.2009.08.004.

[40] Steinmetz N J, Bryant S J. Chondroitin sulfate and dynamic loading alter chondrogenesis of human MSCs in PEG hydrogels. Biotechnol Bioeng 2012; 109:2671-82. doi:10.1002/bit.24519.

[41] Loebel C, Rodell C B, Chen M H, Burdick J A. Shear-thinning and self-healing hydrogels as injectable therapeutics and for 3D-printing. Nat Protoc 2017; 12:1521-41. doi:10.1038/nprot.2017.053.

[42] ASTM F2150—19 Standard Guide for Characterization and Testing of Biomaterial Scaffolds Used in Regenerative Medicine and Tissue-Engineered Medical Products n.d. https://www.astm.org/Standards/F2150.htm (accessed Mar. 4, 2020).

[43] Costi J J, Stokes I A, Gardner-Morse M G, Iatridis J C. Frequency-dependent behavior of the intervertebral disc in response to each of six degree of freedom dynamic loading: solid phase and fluid phase contributions. Spine 2008; 33:1731-8. doi:10.1097/BRS.0b013e31817bb 116.

[44] Hom W W, Tschopp M, Lin H A, Nasser P, Laudier D M, Hecht A C, et al. Composite biomaterial repair strategy to restore biomechanical function and reduce herniation risk in an ex vivo large animal model of intervertebral disc herniation with varying injury severity. PLoS One 2019; 14:e0217357. doi:10.1371/journal.pone.0217357.

[45] Cruz M A, Hom W W, DiStefano T J, Merrill R, Torre O M, Lin H A, et al. Cell-Seeded Adhesive Biomaterial for Repair of Annulus Fibrosus Defects in Intervertebral Discs. Tissue Eng Part A 2018; 24:187-98. doi:10.1089/ten.TEA.2017.0334.

[46] Vergroesen P-P A, Bochyn Ska A I, Emanuel K S, Sharifi S, Kingma I, Grijpma D W, et al. A biodegradable glue for annulus closure: evaluation of strength and endurance. Spine 2015; 40:622-8. doi:10.1097/BRS.0000000000000792.

[47] Lin H A, Varma D M, Hom W W, Cruz M A, Nasser P R, Phelps R G, et al. Injectable cellulose-based hydrogels as nucleus pulposus replacements: Assessment of in vitro structural stability, ex vivo herniation risk, and in vivo biocompatibility. J Mech Behav Biomed Mater 2019; 96:204-13. doi:10.1016/j.jmbbm.2019.04.021.

[48] Long R G, Rotman S G, Hom W W, Assael D J, Illien-Jünger S, Grijpma D W, et al. In vitro and biomechanical screening of polyethylene glycol and poly(trimethylene carbonate) block copolymers for annulus fibrosus repair. J Tissue Eng Regen Med 2018; 12:e727-36. doi:10.1002/term.2356.

[49] Liu Y, Wu Y, Zhou L, Wang Z, Dai C, Ning C, et al. A Dual-Bonded Approach for Improving Hydrogel Implant Stability in Cartilage Defects. Materials (Basel) 2017; 10. doi:10.3390/ma10020191.

[50] Sharma B, Fermanian S, Gibson M, Unterman S, Herzka D A, Cascio B, et al. Human cartilage repair with a photoreactive adhesive-hydrogel composite. Sci Transl Med 2013; 5:167ra6. doi:10.1126/scitranslmed.3004838.

[51] Gullbrand S E, Smith L J, Smith H E, Mauck R L. Promise, progress, and problems in whole disc tissue engineering. JOR Spine 2018; 1:e1015. doi:10.1002/jsp2.1015.

[52] Ahsan T, Sah R L. Biomechanics of integrative cartilage repair. Osteoarthr Cartil 1999; 7:29-40. doi:10.1053/joca.1998.0160.

[53] Kristiansen K A, Potthast A, Christensen B E. Periodate oxidation of polysaccharides for modification of chemical and physical properties. Carbohydr Res 2010; 345:1264-71. doi:10.1016/j.carres.2010.02.011.

[54] Schek R M, Michalek A J, Iatridis J C. Genipin-crosslinked fibrin hydrogels as a potential adhesive to augment intervertebral disc annulus repair. Eur Cell Mater 2011; 21:373-83. doi:10.22203/ecm.v021a28.

[55] Jiang E Y, Sloan S R, Wipplinger C, Kirnaz S, Hartl R, Bonassar U. Proteoglycan removal by chondroitinase ABC improves injectable collagen gel adhesion to annulus fibrosus. Acta Biomater 2019; 97:428-36. doi:10.1016/j.actbio.2019.08.024.

[56] Wiltsey C, Christiani T, Williams J, Scaramazza J, Van Sciver C, Toomer K, et al. Thermogelling bioadhesive scaffolds for intervertebral disk tissue engineering: preliminary in vitro comparison of aldehyde-based versus alginate microparticle-mediated adhesion. Acta Biomater 2015; 16:71-80. doi:10.1016/j.actbio.2015.01.025.

[57] Mehdizadeh M, Yang J. Design strategies and applications of tissue bioadhesives. Macromol Biosci 2013; 13:271-88. doi:10.1002/mabi.201200332.

[58] Canonico S. The use of human fibrin glue in the surgical operations. Acta Biomed 2003; 74 Suppl 2:21-5.

[59] Li Y, Meng H, Liu Y, Lee B P. Fibrin gel as an injectable biodegradable scaffold and cell carrier for tissue engineering. ScientificWorldJournal 2015; 2015: 685690. doi:10.1155/2015/685690.

[60] Drury J L, Mooney D J. Hydrogels for tissue engineering: scaffold design variables and applications. Biomaterials 2003; 24:4337-51. doi:10.1016/s0142-9612(03)00340-5.

[61] Murakami T, Otsuki S, Okamoto Y, Nakagawa K, Wakama H, Okuno N, et al. Hyaluronic acid promotes proliferation and migration of human meniscus cells via a CD44-dependent mechanism. Connect Tissue Res 2019; 60:117-27. doi:10.1080/03008207.2018.1465053.

[62] Jordan A R, Racine R R, Hennig M J P, Lokeshwar V B. The role of CD44 in disease pathophysiology and targeted treatment. Front Immunol 2015; 6:182. doi:10.3389/fimmu.2015.00182.

[63] Carragee E J, Spinnickie A O, Alamin T F, Paragioudakis S. A prospective controlled study of limited versus subtotal posterior discectomy: short-term outcomes in patients with herniated lumbar intervertebral discs and large posterior anular defect. Spine 2006; 31:653-7. doi:10.1097/01.brs.0000203714.76250.68.

[64] Varma D M, Lin H A, Long R G, Gold G T, Hecht A C, Iatridis J C, et al. Thermoresponsive, redox-polymerized cellulosic hydrogels undergo in situ gelation and restore intervertebral disc biomechanics post discectomy. Eur Cell Mater 2018; 35:300-17. doi:10.22203/eCM.v035a21.

[65] Aichmair A, Du J Y, Shue J, Evangelisti G, Sama A A, Hughes A P, et al. Microdiscectomy for the treatment of lumbar disc herniation: an evaluation of reoperations and long-term outcomes. Evid Based Spine Care J 2014; 5:77-86. doi:10.1055/s-0034-1386750.

[66] Artzi N, Zeiger A, Boehning F, bon Ramos A, Van Vliet K, Edelman E R. Tuning adhesion failure strength for tissue-specific applications. Acta Biomater 2011; 7:67-74. doi:10.1016/j.actbio.2010.07.008.

[67] To W S, Midwood K S. Plasma and cellular fibronectin: distinct and independent functions during tissue repair. Fibrogenesis Tissue Repair 2011; 4:21. doi:10.1186/1755-1536-4-21.

[68] Janmey P A, Winer J P, Weisel J W. Fibrin gels and their clinical and bioengineering applications. J R Soc Interface 2009; 6:1-10. doi:10.1098/rsif.2008.0327.

What is claimed:

1. A method for repairing a fibrocartilage defect in a subject, comprising: contacting the fibrocartilage defect with a first composition comprising an oxidized and methacrylated non-sulfated glycosaminoglycan, wherein the glycosaminoglycan is hyaluronic acid, to form an imine bond between the glycosaminoglycan and the fibrocartilage defect, thereby coating the fibrocartilage defect with the glycosaminoglycan; and contacting the fibrocartilage defect coated with the glycosaminoglycan with a pre-polymer hydrogel composition comprising a first crosslinking unit that is capable of bonding to methacrylate, wherein the first crosslinkinq unit comprises poly(ethylene glycol) diacrylate (PEGDA) having an average molecular weight of from 15 kDa to 25 kDa, wherein the pre-polymer hydrogel composition forms an interpenetrating network (IPN) hydrogel or a single network hydrogel, and wherein the hydrogel is covalently bonded to the glycosaminoglycan through methacrylate.

2. The method of claim 1, wherein the fibrocartilage defect coated with the glycosaminoglycan is contacted with a mixture of (i) a pre-polymer hydrogel composition comprising a first crosslinking unit that, when polymerized, is capable of bonding to methacrylate and (ii) a hydrogel polymerization initiator composition, thereby forming a hydrogel that is covalently bonded to the glycosaminoglycan through methacrylate.

3. The method of claim 1, wherein the fibrocartilage defect is an annulus fibrosus defect in an intervertebral disk.

4. The method of claim 1, wherein contacting the fibrocartilage defect with the first composition comprises:

filling a cavity comprising the fibrocartilage defect with the first composition comprising the glycosaminoglycan;

waiting for a sufficient time to allow formation of imine bonds between the glycosaminoglycan and the fibrocartilage defect; and aspirating excess glycosaminoglycan that has not bonded to the fibrocartilage defect from the cavity.

5. The method of claim 1, wherein the degree of oxidation of the oxidized and methacrylated non-sulfated glycosaminoglycan is from 20% to 45% and the degree of methacrylation of the oxidized and methacrylated non-sulfated glycosaminoglycan is from 30% to 80%.

6. The method of claim 1, wherein contacting the fibrocartilage defect coated with the glycosaminoglycan comprises using a dual-barrel syringe and volumetric mixing tip to inject a newly formed mixture of the pre-polymer hydrogel composition and hydrogel polymerization initiator composition into the coated fibrocartilage defect.

7. The method of claim 1, wherein the pre-polymer hydrogel composition forms an interpenetrating network hydrogel and wherein the interpenetrating network hydrogel comprises a fibronectin-conjugated fibrin network.

8. The method of claim 2, wherein the hydrogel polymerization initiator composition comprises ammonium persulfate (APS) and N,N,N',N'-tetramethylethylenediamine (TEMED).

9. A kit for repairing a fibrocartilage defect, the kit comprising: a first container holding a first composition comprising an oxidized and methacrylated non-sulfated glycosaminoglycan, wherein the glycosaminoglycan is hyaluronic acid; and a second container holding a pre-polymer hydrogel composition comprising a first crosslinking unit that is capable of bonding to methacrylate, wherein the first crosslinking unit comprises poly(ethylene glycol) diacrylate (PEGDA) having an average molecular weight of from 15 kDa to 25 kDa, wherein the pre-polymer hydrogel composition forms a single network hydrogel or an interpenetrating network hydrogel (IPN).

10. The kit of claim 9, further comprising a third container holding a hydrogel polymerization initiator composition.

11. The kit of claim 9, wherein the kit is for repairing an annulus fibrosus defect in an intervertebral disk.

12. The kit of claim 9, wherein the degree of oxidation of the oxidized and methacrylated non-sulfated glycosaminoglycan is from 20% to 45% and the degree of methacrylation of the oxidized and methacrylated non-sulfated glycosaminoglycan is from 30% to 80%.

13. The kit of claim 9, wherein the first container comprises a syringe that is pre-loaded with the first composition.

14. The kit of claim 9, wherein the pre-polymer hydrogel composition forms an interpenetrating network hydrogel comprising a fibronectin-conjugated fibrin network.

15. The kit of claim 10, wherein the hydrogel polymerization initiator composition comprises ammonium persulfate (APS) and N,N,N',N'-tetramethylethylenediamine (TEMED).

16. The kit of claim 10, wherein the second and third containers comprise a dual-barrel syringe and volumetric mixing tip.

* * * * *